(12) United States Patent
Lagasse

(10) Patent No.: US 11,191,785 B2
(45) Date of Patent: Dec. 7, 2021

(54) LYMPH NODE AS A SITE FOR TRANSPLANTATION, ORGANOGENESIS AND FUNCTION FOR MULTIPLE TISSUES AND ORGANS

(71) Applicant: UNIVERSITY OF PITTSBURGH-OF THE COMMONWEALTH SYSTEM OF HIGHER EDUCATION, Pittsburgh, PA (US)

(72) Inventor: Eric Lagasse, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 25 days.

(21) Appl. No.: 14/810,064

(22) Filed: Jul. 27, 2015

(65) Prior Publication Data

US 2016/0058794 A1    Mar. 3, 2016

Related U.S. Application Data

(63) Continuation of application No. PCT/US2014/021420, filed on Mar. 6, 2014, and a continuation-in-part of application No. 12/921,001, filed as application No. PCT/US2009/036506 on Mar. 9, 2009, now Pat. No. 9,125,891.

(60) Provisional application No. 61/773,625, filed on Mar. 6, 2013, provisional application No. 61/068,548, filed on Mar. 7, 2008.

(51) Int. Cl.

| A61K 35/26 | (2015.01) |
| A61K 35/22 | (2015.01) |
| A61K 35/55 | (2015.01) |
| A61K 35/42 | (2015.01) |
| A61K 35/30 | (2015.01) |
| A61K 35/38 | (2015.01) |
| A61K 35/39 | (2015.01) |
| A61K 35/12 | (2015.01) |

(52) U.S. Cl.
CPC .............. *A61K 35/26* (2013.01); *A61K 35/22* (2013.01); *A61K 35/30* (2013.01); *A61K 35/38* (2013.01); *A61K 35/39* (2013.01); *A61K 35/42* (2013.01); *A61K 35/55* (2013.01); *A61K 2035/122* (2013.01)

(58) Field of Classification Search
None
See application file for complete search history.

(56) References Cited

U.S. PATENT DOCUMENTS

| 9,125,891 B2 * | 9/2015 | Lagasse ................. A61K 35/26 |
| 2007/0087029 A1 * | 4/2007 | Pakala ................. A61K 9/0004 424/423 |
| 2009/0324607 A1 * | 12/2009 | Reisner ................. A61K 31/00 424/158.1 |

FOREIGN PATENT DOCUMENTS

WO    WO 2009111778 A2 *   9/2009   ............. A61K 35/26

OTHER PUBLICATIONS

Kim et al., 2007, Stem Cell. vol. 25: 1393-1401.*
Orlando et al., 2010, Transp. Int. vol. 24: 223-232.*
Rogers et al., 1998, Kidney International. vol. 54: 27-37.*
Hammerman, 2003, Kidney International. vol. 63: 1195-1204.*
Francipane et al., "The Lymph Node as a New Site for Kidney Organogenesis," Stem Cells Translational Medicine 4:295-307 (2015).

* cited by examiner

*Primary Examiner* — Amy E Juedes
(74) *Attorney, Agent, or Firm* — Baker Botts L.L.P.

(57) ABSTRACT

The present invention relates to methods and compositions for transplanting non-lymphoid tissues into lymphoid organs. It may be used to cultivate organ tissues including for the purpose of supplementing or reconstituting organ function. Tissues that may be propagated in this manner include but are not limited to lung, kidney, thyroid, intestine, and brain.

22 Claims, 93 Drawing Sheets

Specification includes a Sequence Listing.

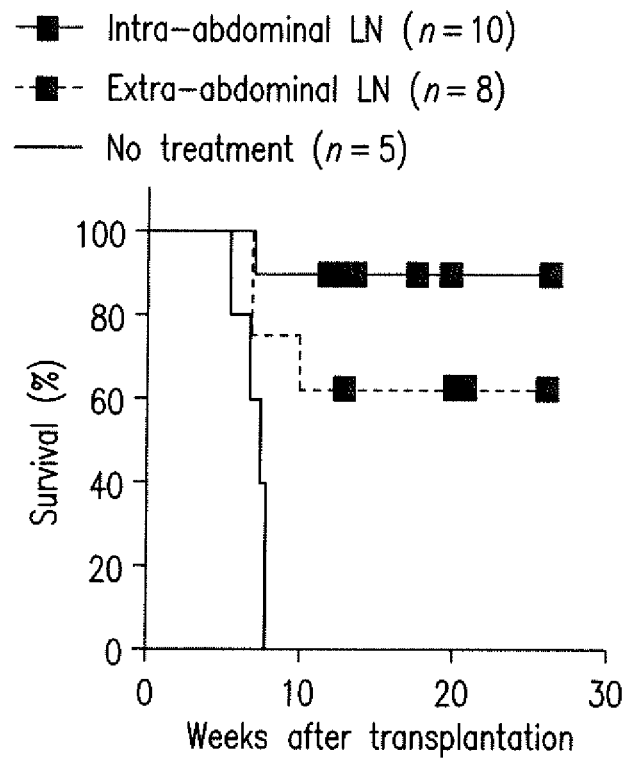
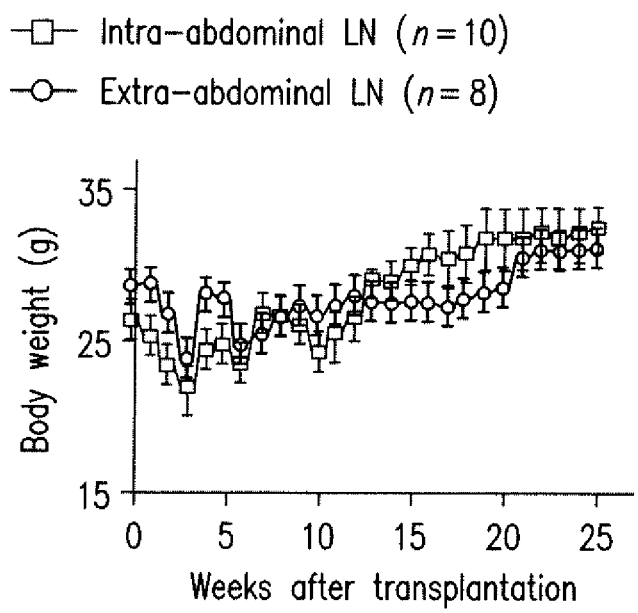
FIG. 2C

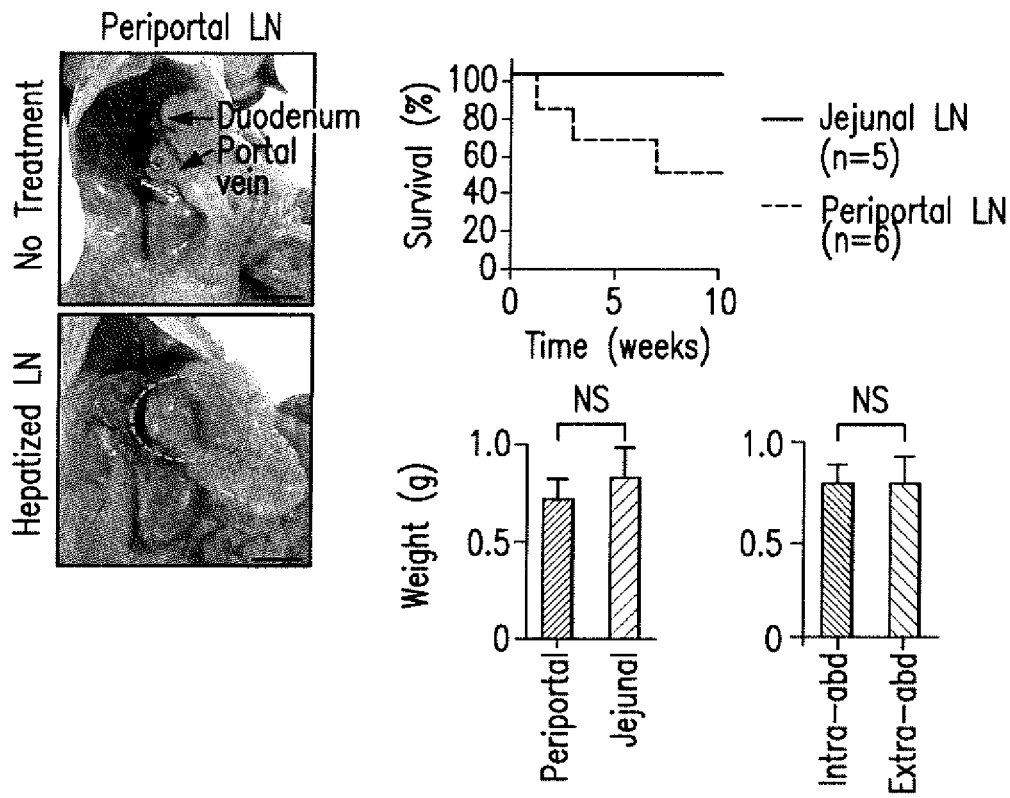
FIG. 2D
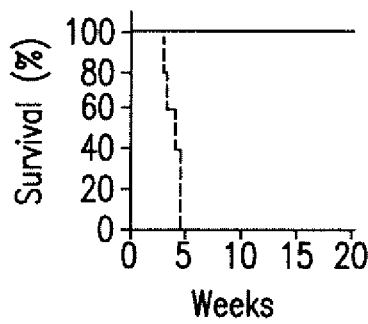 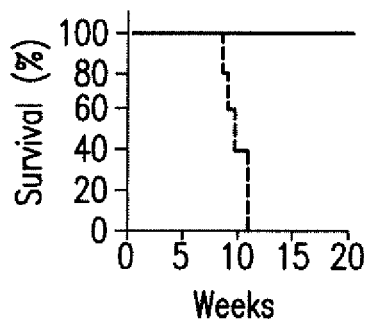
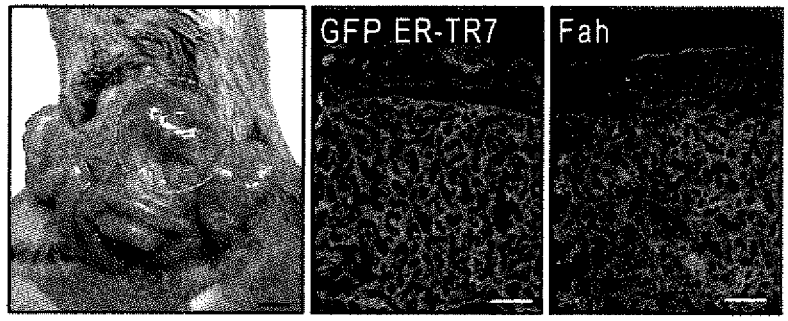
FIG. 2E

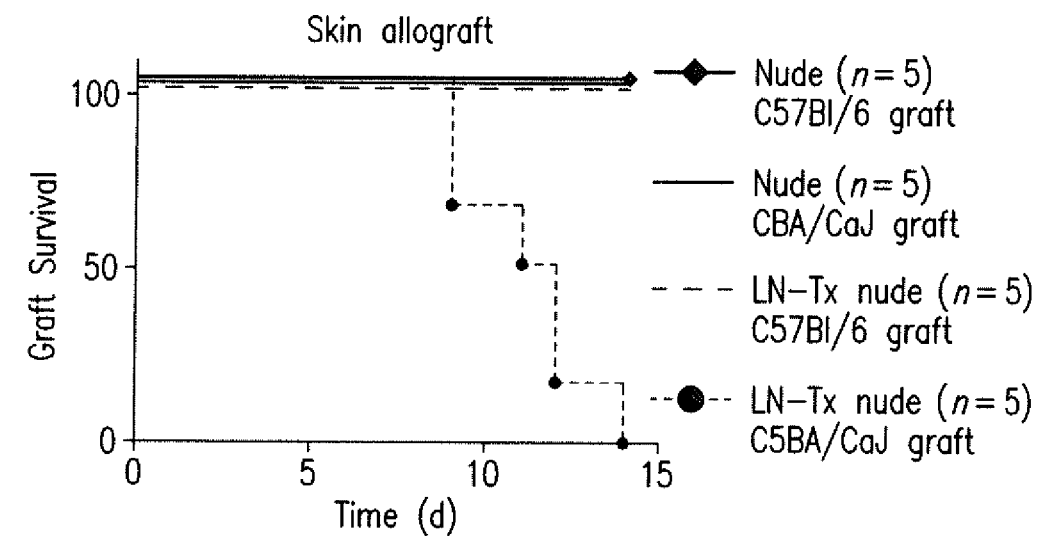
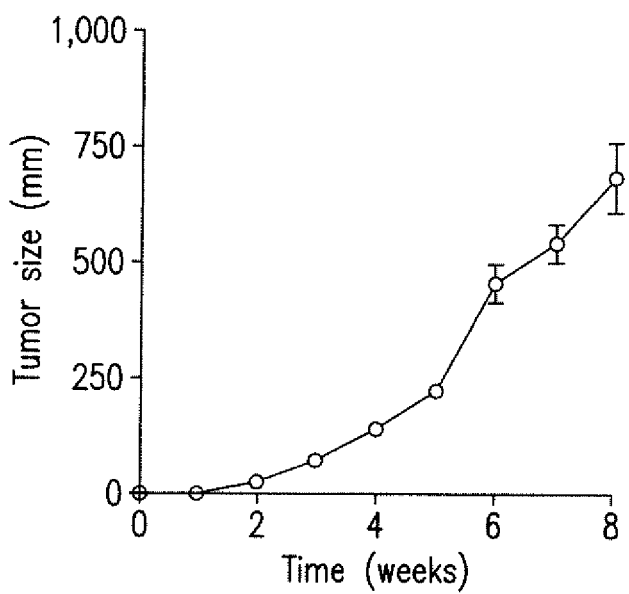
| Xenograft Tumor growth | | | |
|---|---|---|---|
| | Mice (n) | Tumor growth | |
| | | + | − |
| LN-Tx nude | 9 | 1 | 8 |
| Nude | 16 | 16 | 0 |
| WT | 6 | 0 | 6 |
FIG. 3E

|      | CD4 T Cells | CD8 T Cells |
|------|-------------|-------------|
| L083 | 7.06        | 5.2         |
| L084 | 21.9        | 5.24        |
| L085 | 18.3        | 4.79        |

|  | | CD4 T Cells | CD8 T Cells |
|---|---|---|---|
|  | C57Bl/6 | 18.9 | 3.48 |
|  | L039 | 2.97 | 0.28 |
|  | L040 | 1.21 | 0.48 |
|  | L041 | 0.25 | 0.14 |
|  | L042 | 5.62 | 4.40 |
|  | L043 | 0.15 | 0.30 |
| Ep-Cam Enriched | L044 | 0.01 | 0.22 |
|  | L045 | 0.05 | 0.17 |
|  | L046 | 0.06 | 0.16 |

FIG. 9

Figure 1. A Harvest of the uterine items from a pregnant mouse, and removal of placentas and fetal membranes from an embryo. Sagittal and transversal paraffin sections of an embryo stained with Hematoxylin and Eosin.
B. Scheme of the jejunal lymph node injection procedure using different mouse fetal tissues.

Engraftment and Maturation of Fetal Tissues into the Lymph Node
LUNG
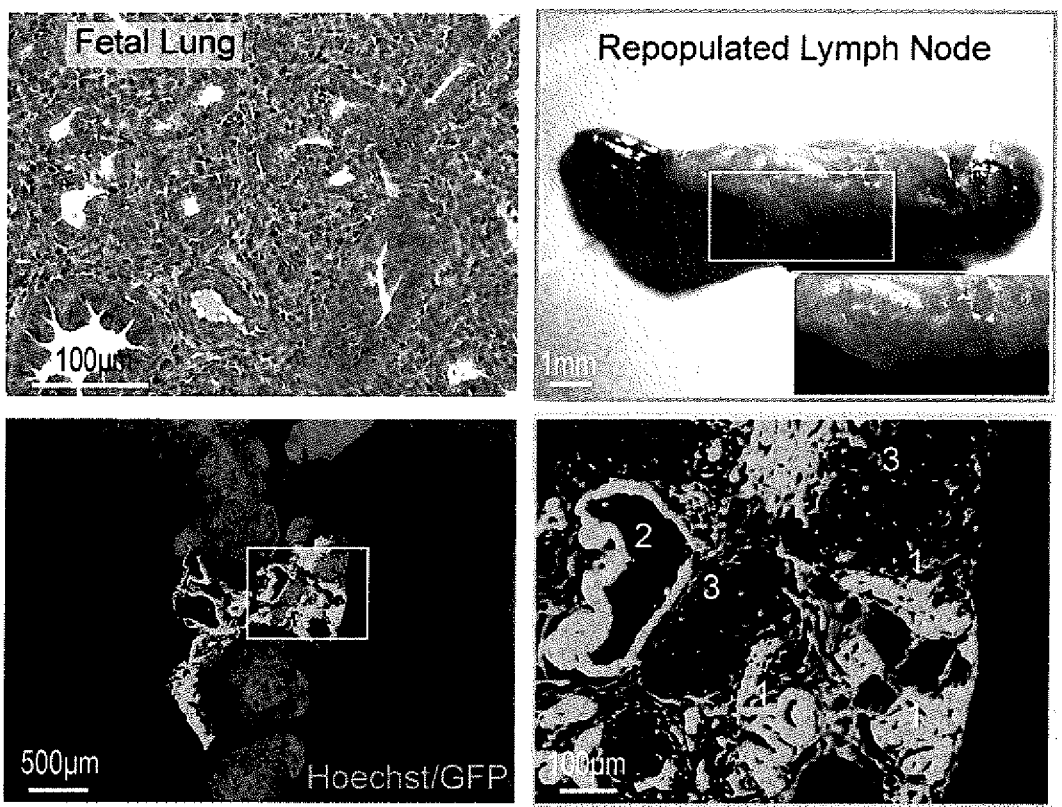
1 Canalicular-like structures,
2 Lumen of the Bronchus, 3 Alveols
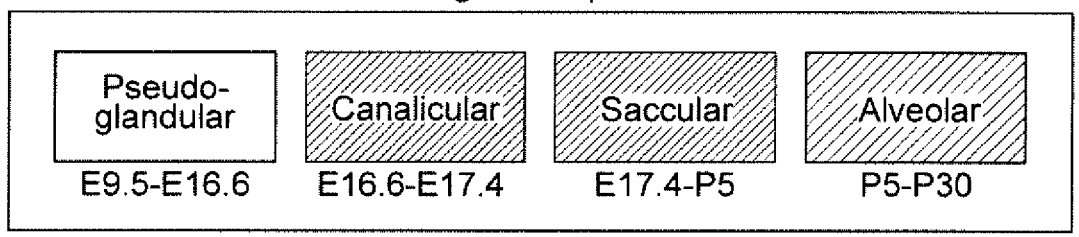
Mouse Lung Development Timeline
FIG. 12B

Figure 12A:
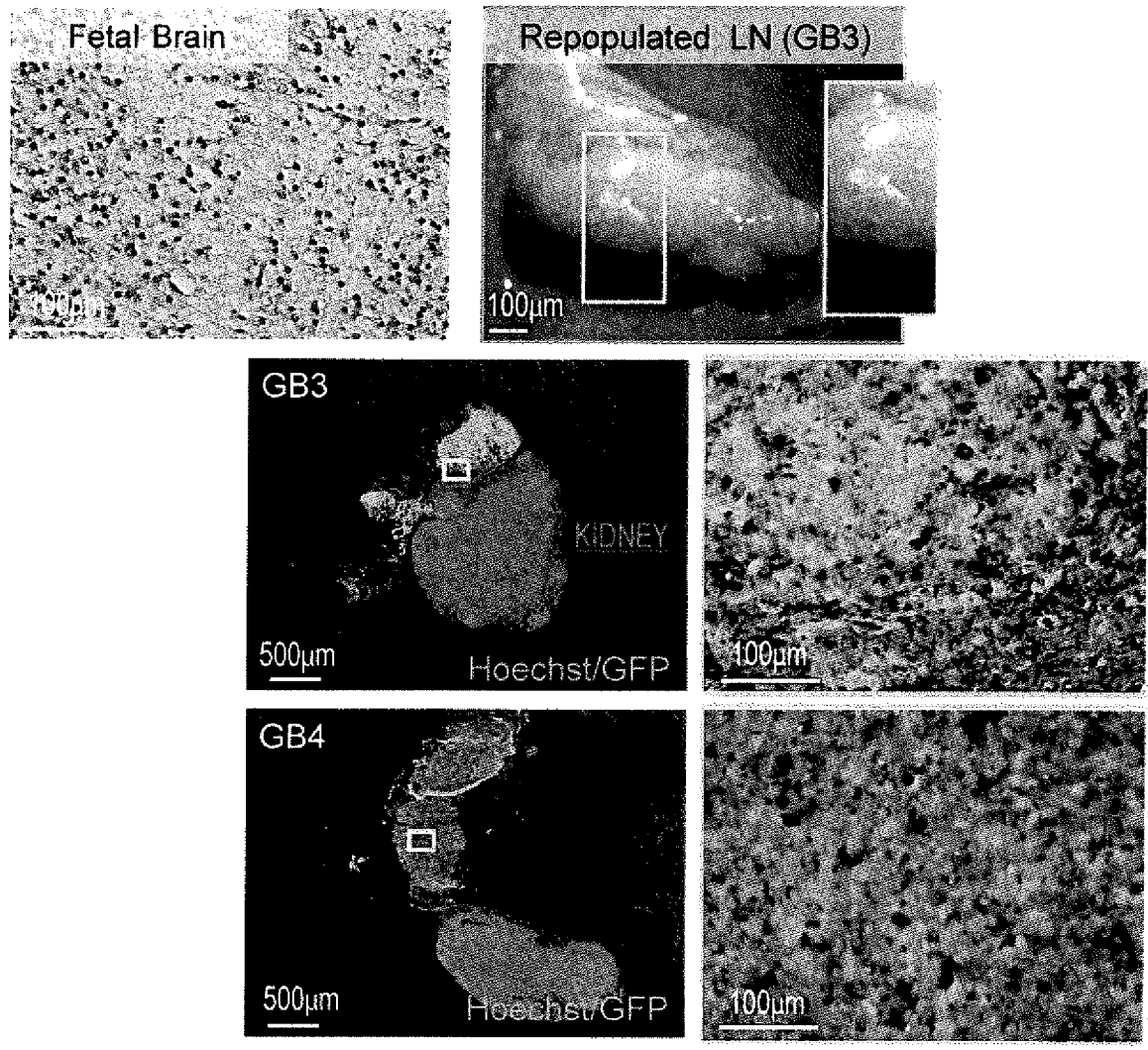
Figure 12C:
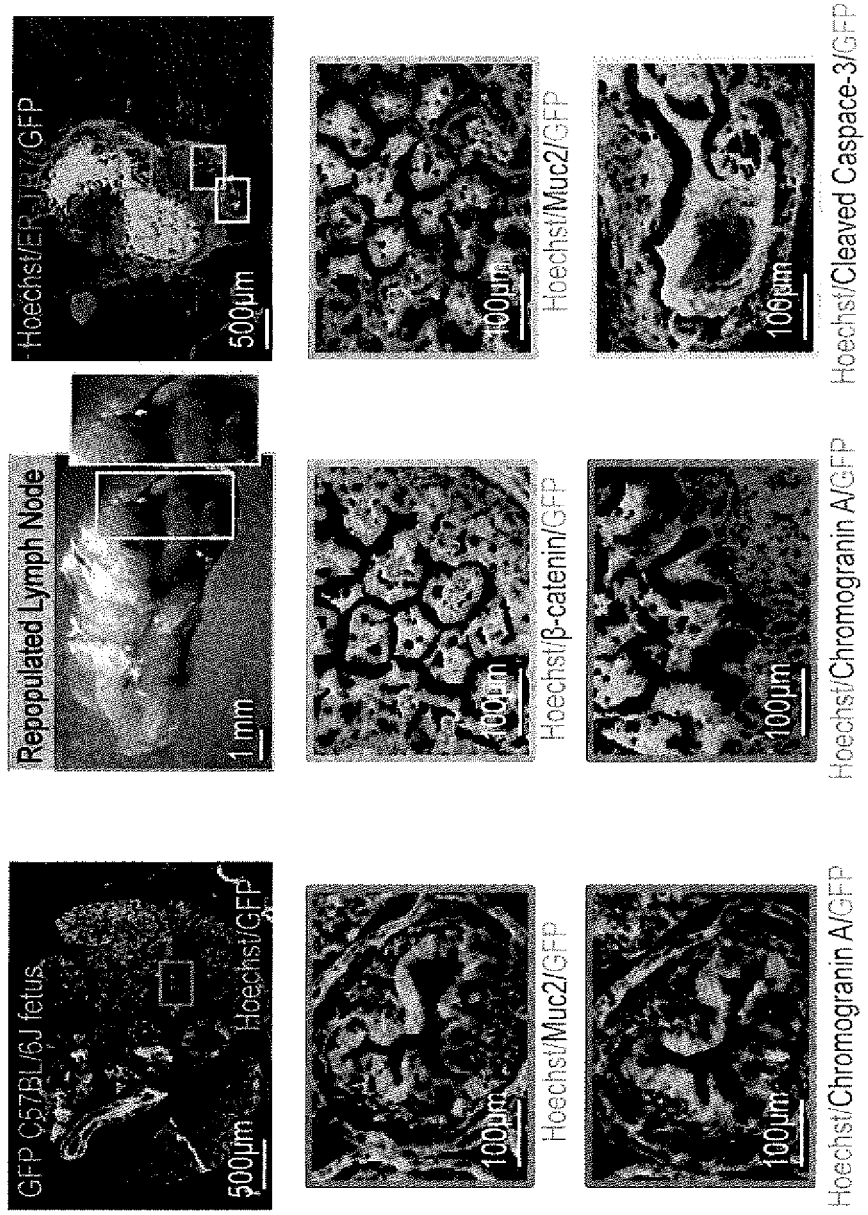
Figure 12D:
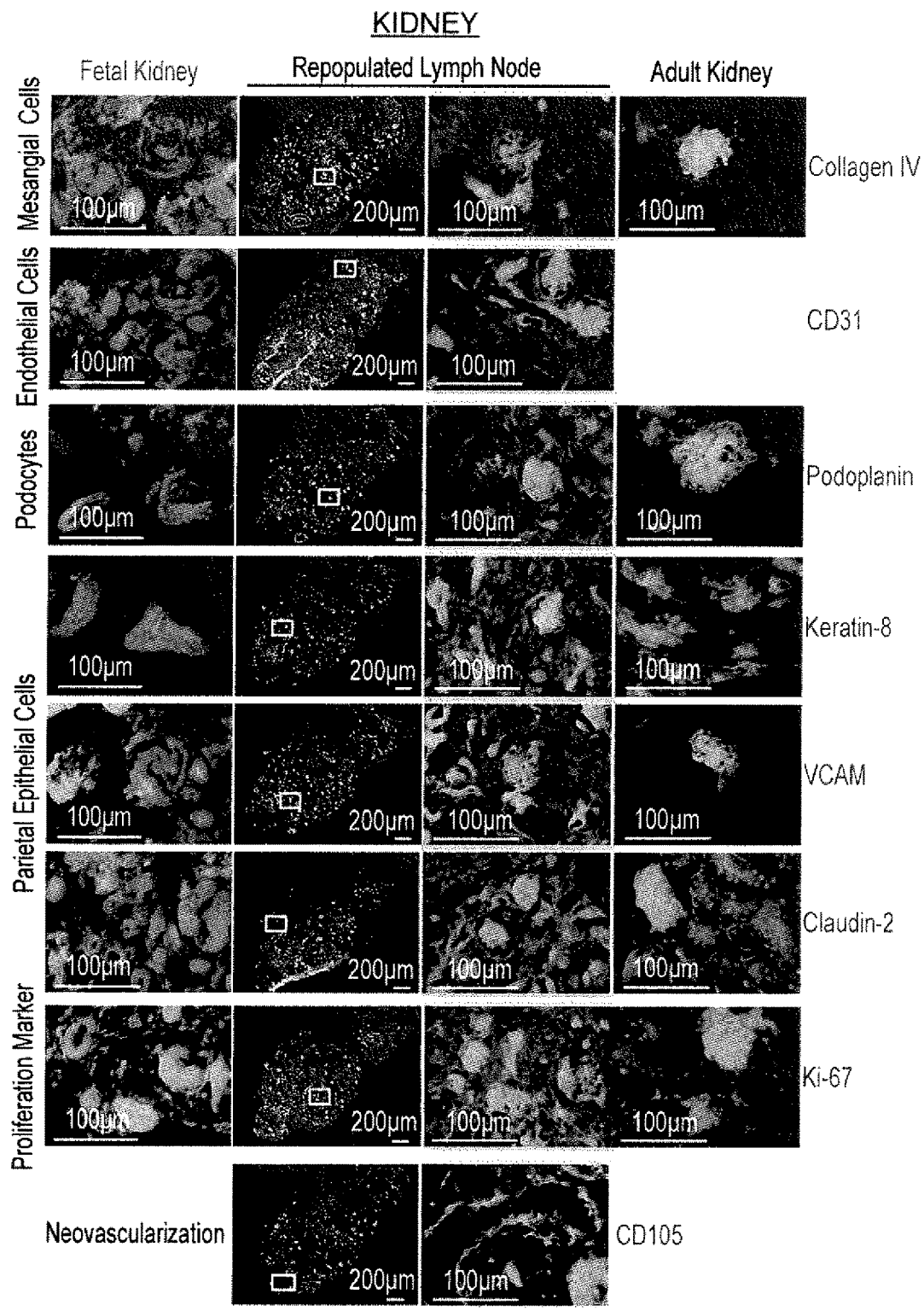

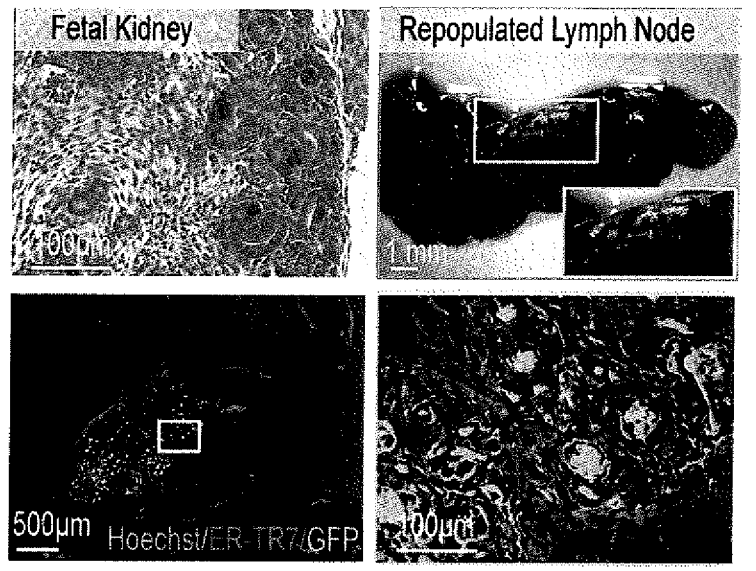
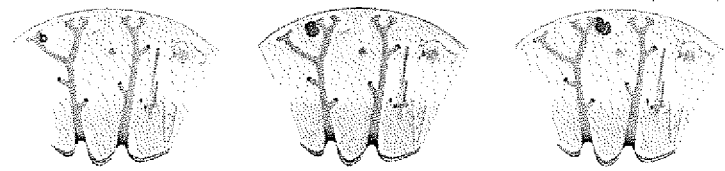
Mouse Kidney Development
renal vesicle (stage I nephron)   comma-shaped body   s-shaped body (stage II nephron)
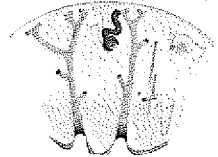 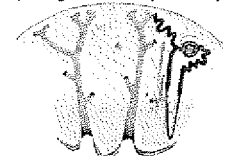
capillary loop nephron (stage III nephron)   maturing nephron (stage IV nephron)
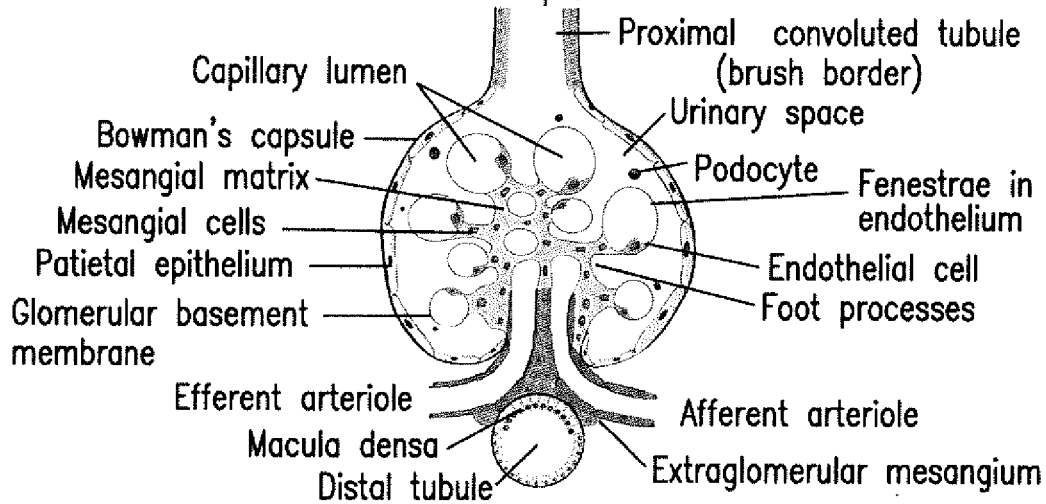
FIG. 12D Each panel shows paraffin (A, B, and D) ar frozen (C) sections of donor C57BL/6 GFP' tissues stained with Hemetoxytin and Eosin or Hoechst, respectively, white-mount jeusal lymph nodes of C57BL/6 mice 3 weeks after transplantation, and immusofluresence staining of frozen lymph node serial sections with the presence of GFP' cells.

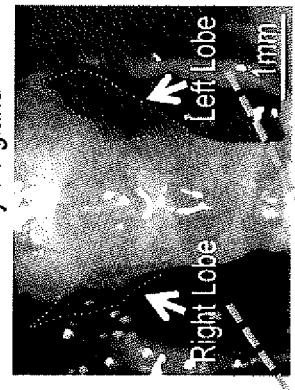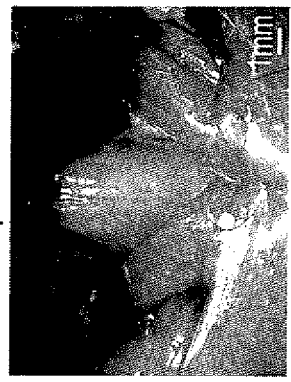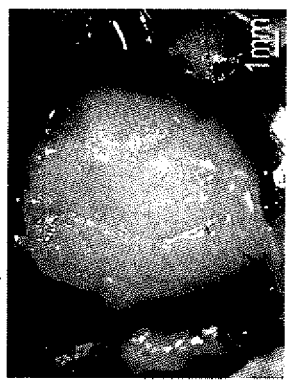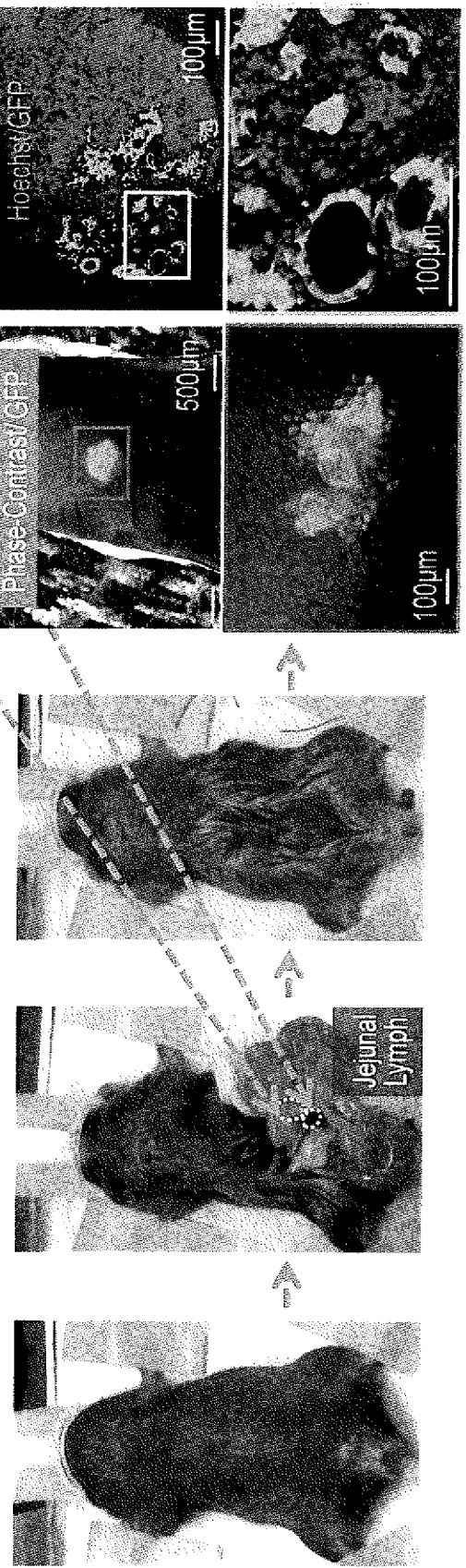
Fig. 13

Problems associated with determination of gestational age

There are 2 phases of murine neurogenesis. The first phase spans from embryonic day E8.5 to 10.5, during which neural progenitor population expands. The second phase commences around E11.5, reaches peak by E15.5, and then diminishes by E17.5, generating most of cortical neurons.

The mouse thyroid gland begins to develop at E8.5 as an endodermal thickening in the floor of the primitive pharynx. After losing all connections with the pharynx, the thyroid bud migrates caudally, reaching its final position in front of the trachea E13. Activation of the TSH/TSHR pathway occurs in mice at E15.

Initiation of thymus development begins around E10.5 with the outgrowth of epithelial cells from the third pharyngeal pouch endoderm into the underlying mesenchyme. The colonization of by T-lymphoid progenitor cells in the fetal thymus begins at E11.5.

Lung development begins on the tenth day of mouse development. By 11 days pc, the lung consists of five distinct lung buds, which form the five lobes that are characteristic of the adult mouse lung. Histologically, lung development has been divided into four chronological stages in mouse: (1) pseudoglandular stage (E9.5-16.6), the bronchial and respiratory tree develops and an undifferentiated primordial system forms; (2) canalicular stage (E116.6-17.4), terminal sacs and vascularization develop in the period; (3) terminal sac stage (E17.4 to postnatal day 5 (p5)), the number of terminal sacs and vascularization increase and type I and II cells differentiate; and (4) alveolar stage (P5-30, terminal sacs develop into mature alveolar ducts and alveoli.

  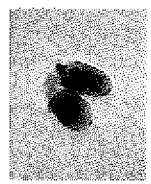 

FIG.14A

Problems associated with determination of gestational age

The heart is the first organ to develop and function in the embryo. Cardiomyocytes differentiate from precursor cells in the primitive streak and move anterior-laterally to form bilateral paired cardiogenic plates (myocardial primordial) in the mouse embryo at E7.5. Most morphogenetic processes are completed by E15.5 and are basically followed by a growth process from E15.5 to E18.5 in the ventricular chambers.

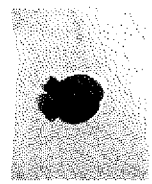

Bud of the stomach is apparent at E10.5. Although the stomach region is enlarged at E11.5, the greater curvature of the fore-stomach becomes obvious from around E12.

The mammalian small intestine undergoes dramatic developmental changes during the last third of embryogenesis. In mice, this period begins at E13.5, when the small intestine is lined on its inner surfaced by a pseudo-stratified, uniformly proliferative endoderm. From E15.5 to E18.5, a proximal-to distal wave of cyto-differntiation converts the epithelium.

The liver diverticulum forms by E9 and expands into an obvious liver bud by E10. The liver grows, and by E15 hepatoblasts are differentiating into hepatocyte and biliary cells. Final maturation of the liver is gradual and continues into the postnatal period.

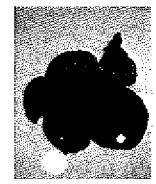

FIG. 14B

Problems associated with determination of gestational age

The mouse adrenal gland starts its development at E11.5, when the anlage of the adrenal cortex is first formed. The cortical cells are found close to the adrenal medulla sympathoblasts at 12.5 dpc, and the capsule surrounding the adrenal gland and cortical capillaries is formed at E14.5. Both the cortex and the capsule have completed their development by E15. The medulla also starts its development at E11.5, when the two chains of sympathoblasts are observed on either side of the aorta. These sympathoblasts then migrate along the sympathetic nerves towards the cortical anlage, were they can be found at E12. Two days later, at E14, the medullary cells are located in the centre of the adrenal gland, which is fully functional at birth.

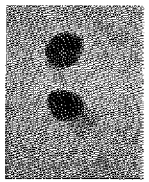

Development of kidney nephrons begins on E11.5 in the mouse when the ureteric bud first contacts the metanephric mesenchyme. This interaction induces small groups of nonpolarized mesenchymal cells surrounding the ureteric bud to adhere tightly to one another and begin to differentiate into polarized epithelial cells.

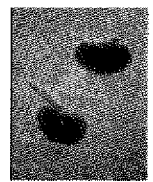

FIG. 14C

- 65 mice injected so far (3 died).

| Organ(s) | # of mice injected | # of LNs repopulated | # of good injections |
|---|---|---|---|
| Brain | 7 | 7/7 | 5/7 |
| Trachea/Thyroid | 1 | to assess | 1/1 |
| (Adult) Thyroid | 6 | 1/5 | 4/6 |
| Thymus | 3 | 2 to assess | 2/3 |
| Lung | 2 | 1/2 | 1/2 |
| Heart | 4 | 1 + 2 to assess | 4/4 |
| Heart + Lung + Thymus | 3 | 1/3 | 2/3 |
| Stomach | 4 | 2 to assess | 2/4 |
| Gut | 7 | 4/7 | 5/7 |
| Liver | 8 | 2 + 2 to assess | 6/8 |
| Adrenal Gland | 2 | 2 to assess | 2/2 |
| Kidney | 15 | 4 + 10 to assess | 8/15 |

FIG. 15

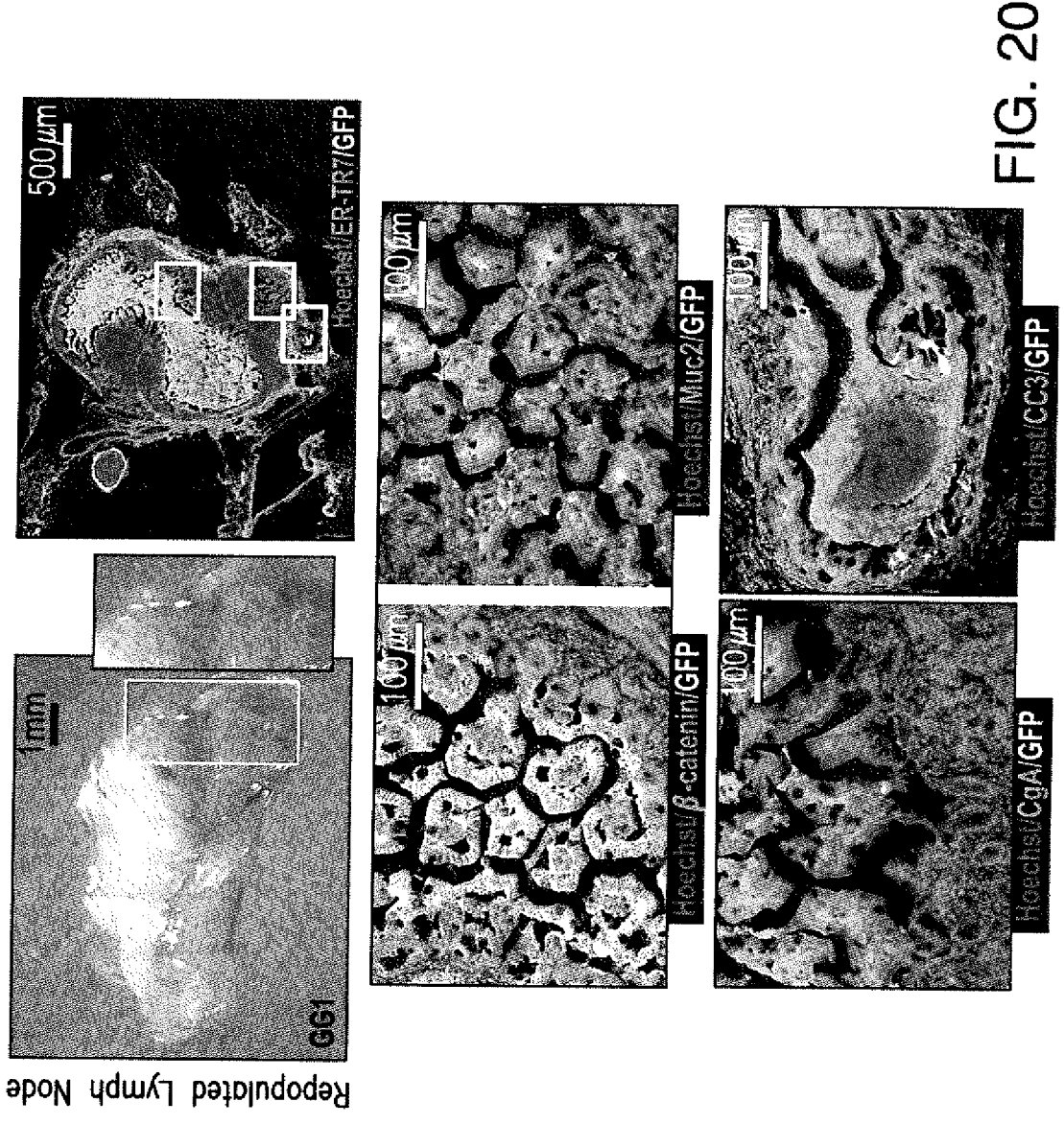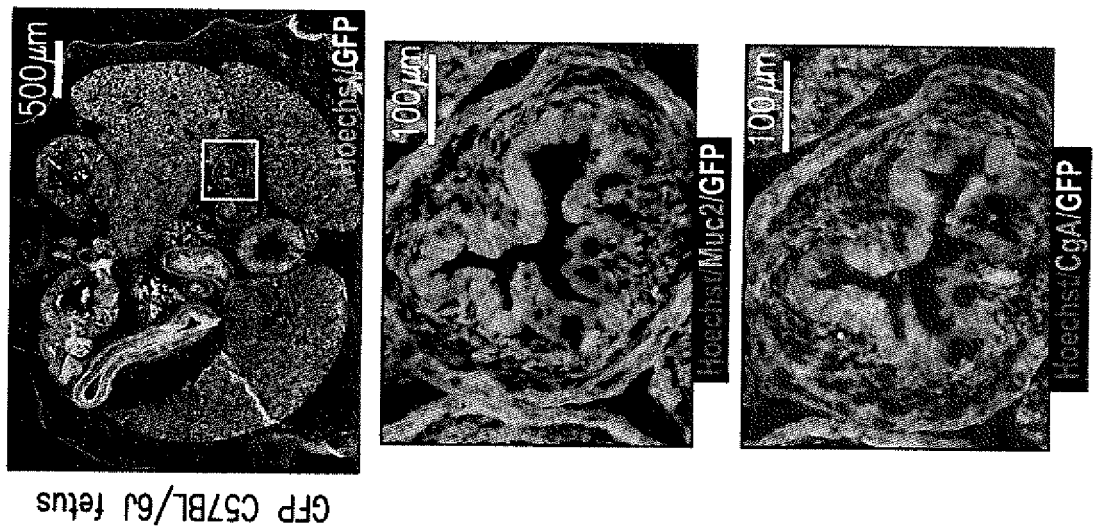
FIG. 20

Transplantation of kidneys in lymph node

The glomerulus consists of three cell types: mesangial cells, endothelial cells, and epithelial cells. There are two types of epithelial cell: podocytes, also known as the visceral epithelial cells (VECs), and the parietal epithelial cells (PECs).

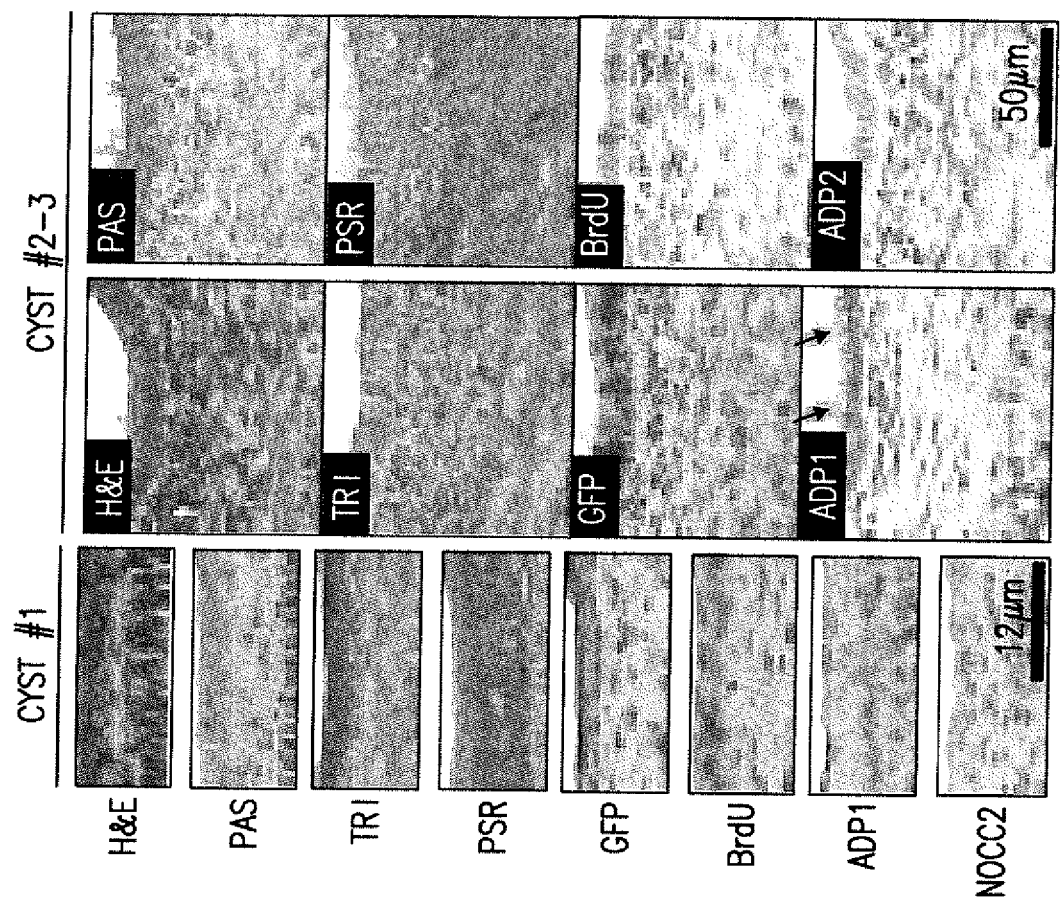
FIG. 26B
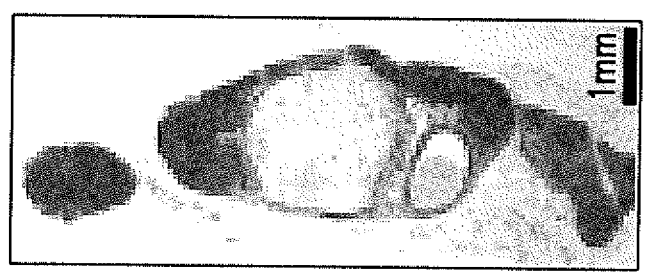
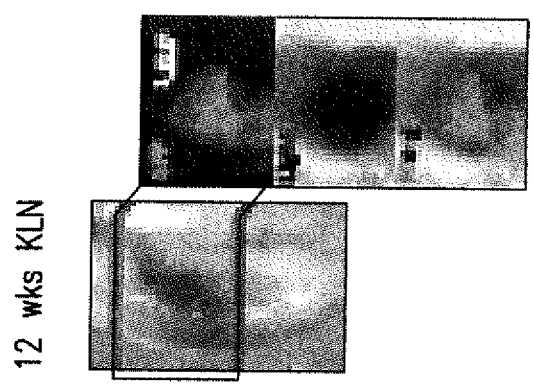
FIG. 26A

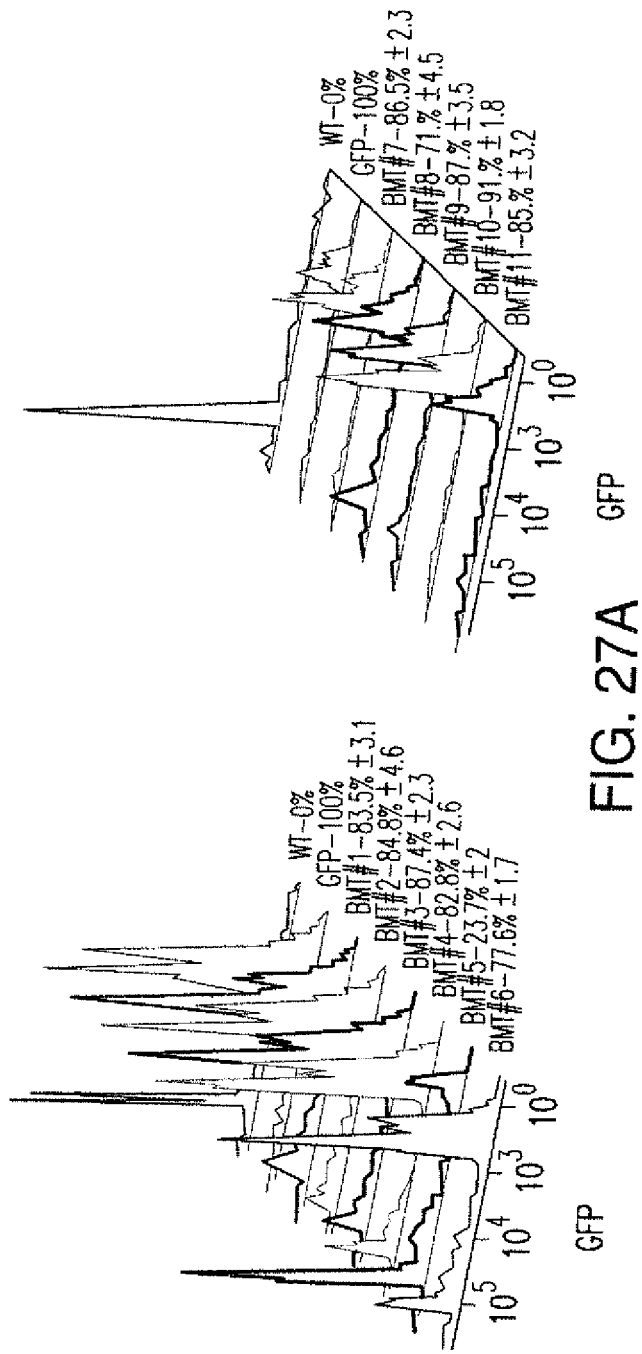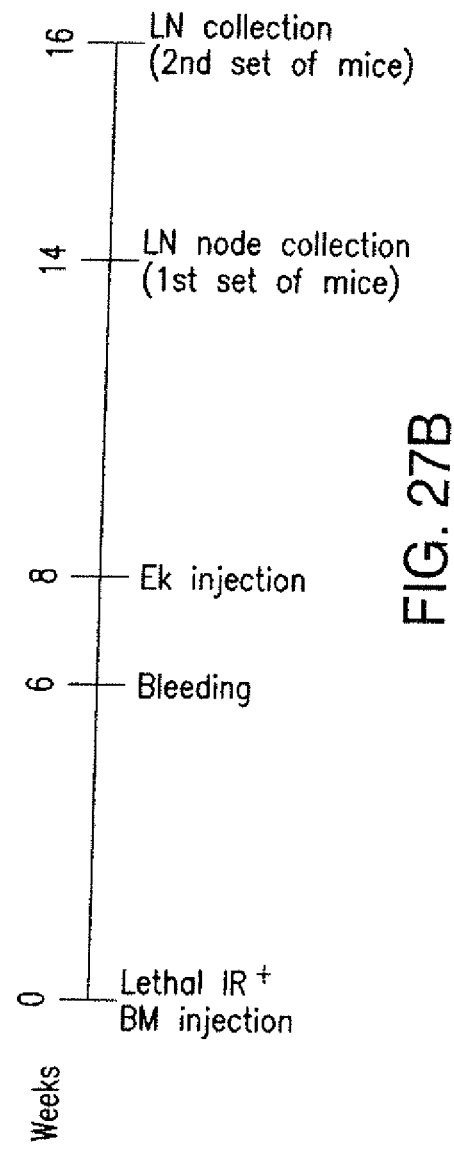
FIG. 27A
FIG. 27B

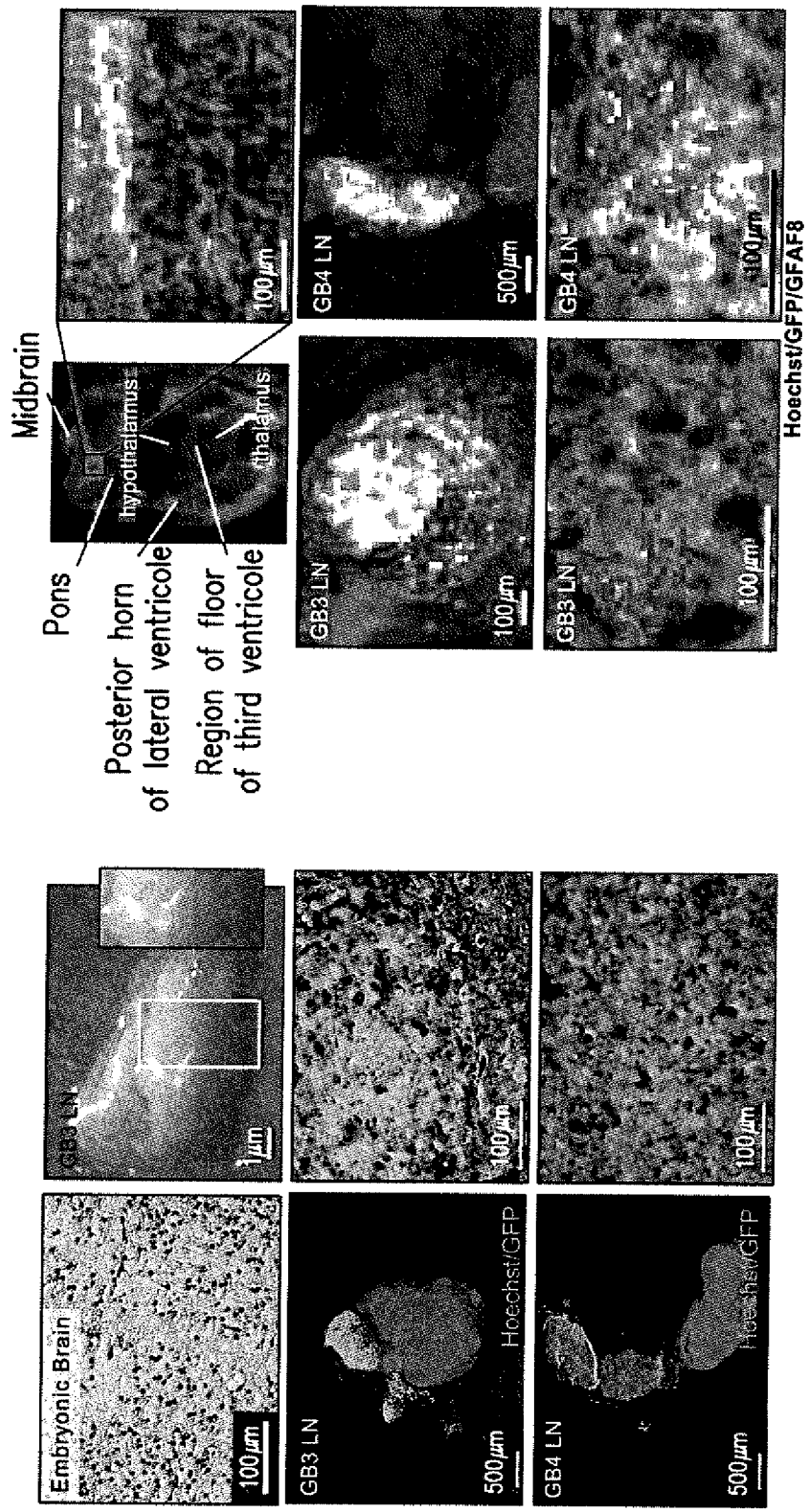
FIG. 32C2
FIG. 32C1

Figure 37:
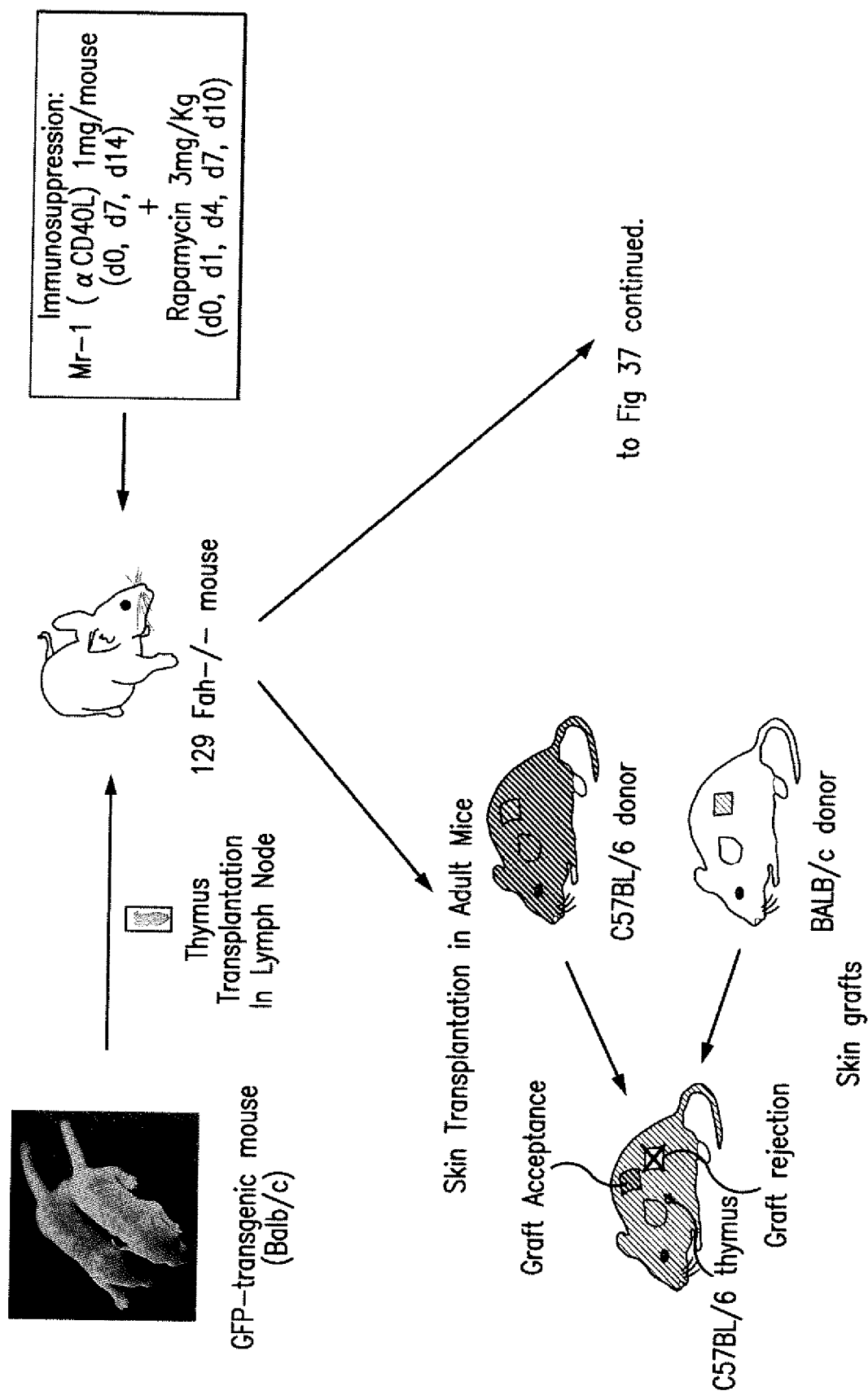

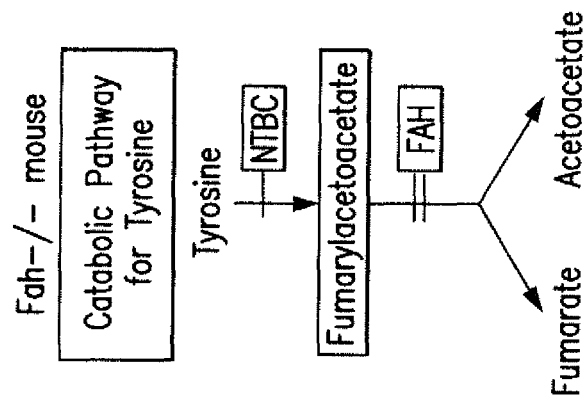
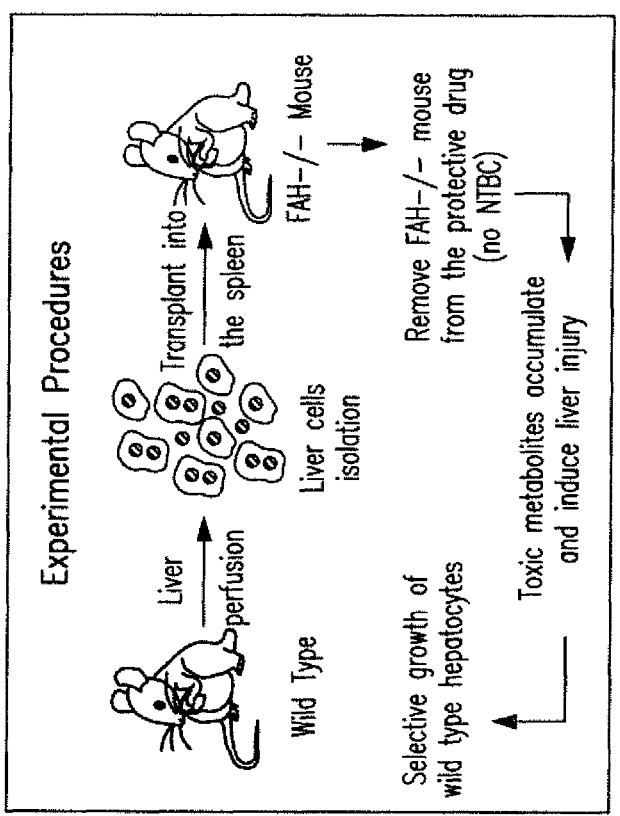
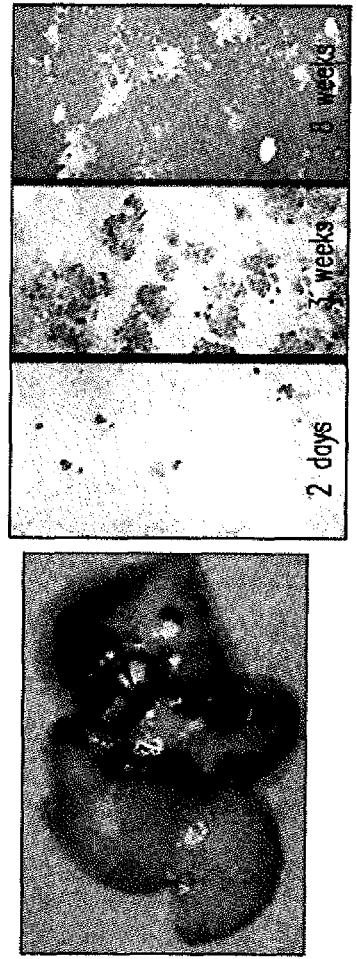
FIG. 37 continued

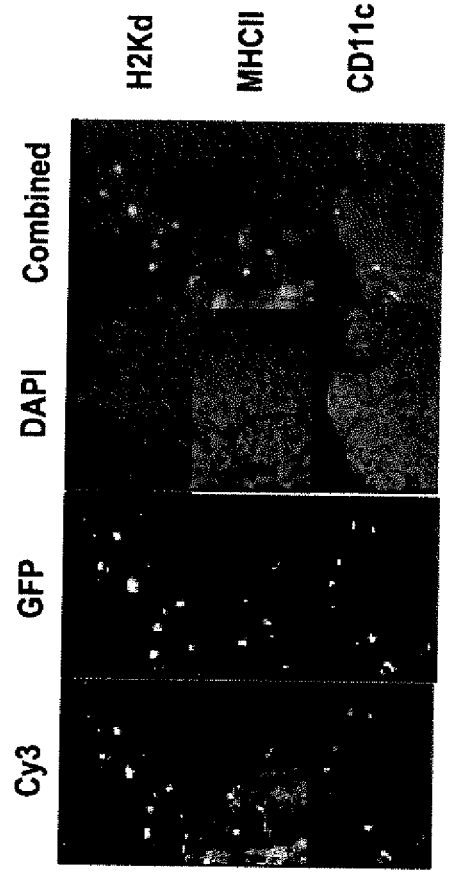
FIG. 41B
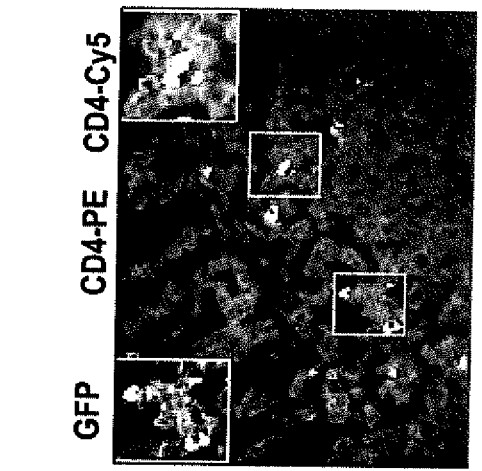
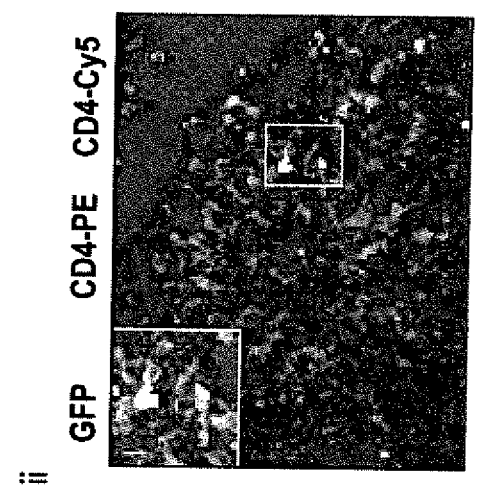
FIG. 41C
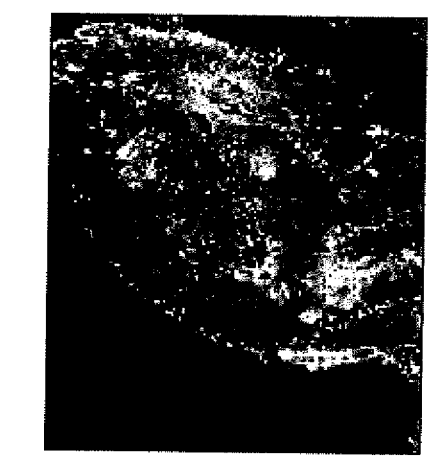
FIG. 41A
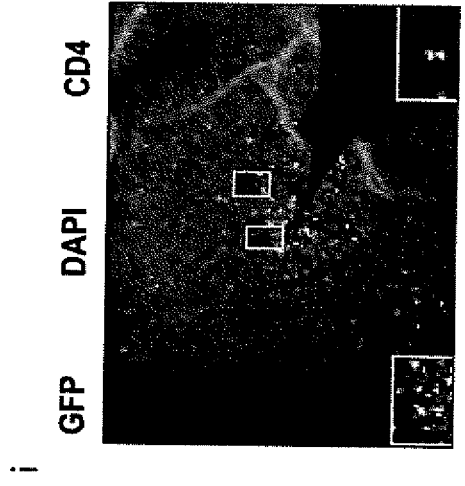

LYMPH NODE AS A SITE FOR TRANSPLANTATION, ORGANOGENESIS AND FUNCTION FOR MULTIPLE TISSUES AND ORGANS

CROSS-REFERENCE TO RELATED APPLICATIONS

This application is a continuation of International Application Serial No. PCT/US2014/021420 filed Mar. 6, 2014, which claims priority to U.S. Application Ser. No. 61/773,625 filed Mar. 6, 2013; and is also a continuation in part of U.S. application Ser. No. 12/921,001 filed Sep. 3, 2010, which is a U.S. National Stage Patent Application under 35 U.S.C. § 371 of International Application Serial No. PCT/US2009/036506 filed Mar. 9, 2009, which claims priority to U.S. Application Ser. No. 61/068,548, filed Mar. 7, 2008, the contents of each of which are incorporated by reference in their entireties herein, and priority to each of which is claimed.

GRANT INFORMATION

This invention was made with government support under grant number Grant Nos. DK085711 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 28, 2015, is named 072396.0601_SL.txt and is 3,422 bytes in size.

1. INTRODUCTION

The present invention relates to methods and compositions for transplanting non-lymphoid tissues into lymphoid organs. It may be used to cultivate organ tissues for purposes including supplementing or reconstituting organ function. Tissues that may be propagated in this manner include but are not limited to lung, kidney, thyroid, intestine, and brain.

2. BACKGROUND OF THE INVENTION

The shortage of organs available for transplant to terminally ill patients represents a major worldwide medical, social and economic challenge. An alternative approach to whole-organ transplant involves the transplantation of cells to regenerate failing organs (1,2). However, orthotopic cell-based therapy directed at a diseased organ may not be feasible for many reasons, ranging from a possible lack of an appropriate environment in cirrhotic and fibrotic liver during end-stage disease to the lack of a thymus in complete DiGeorge syndrome (3-5). Consequently, a crucial requirement of cell-based therapy for these patients is to establish an optimal in vivo site for cell and tissue transplantation to restore organ functions (6,7).

The lymph node is a key organ of the mammalian immune system that has evolved to mount an immediate and orchestrated response against invading pathogens. The lymph node acts as a checkpoint where migrating T and B cells may encounter foreign antigens (8,9). If a foreign antigen is identified, T cells undergo rapid cell division and also signal for help and recruit additional T cells (8,9). To accommodate this sudden increase in cell number, lymphocytes need a special environment, which the lymph node provides.

Interestingly, the lymph node is also one of the first clinically observed sites of most cancer metastasis. Selected cancer cells will often migrate away from a primary tumor and colonize the lymph node (10). Lymphatic vessels are designed to facilitate the uptake of surrounding fluid and cells, which are then transported to a nearby lymph node (10). Therefore, malignant tumor cells take advantage of this route normally traveled by immune cells. On arrival in the lymph node, tumor cells can survive, perhaps because the architecture of the lymph node provides direct access through the high endothelial venules to essential nutrients and growth factors found in the blood. The lymph node also contains fibroblastic reticular cells and other stromal cells that secrete chemokines to enhance cell recruitment and survival (8, 9, 11).

3. SUMMARY OF THE INVENTION

The present invention relates to the use of the lymph node environment to promote the survival and expansion of healthy cells and tissues. Healthy cell and tissue growth in lymph nodes would provide a new approach for cell therapies in regenerative medicine.

The present invention is based, at least in part, on the discoveries that (i) hepatocytes injected directly into a single jejunal, popliteal, axillary or periportal lymph node generate an ectopic hepatic mass and rescue mice from lethal liver failure; (ii) thymic tissue injected into single jejunal lymph nodes of athymic nude mice generates functional ectopic thymuses; (iii) pancreatic islets transplanted into single jejunal lymph nodes of streptozotocin-induced diabetic mice engraft and secrete insulin to normalize glucose concentrations; (iv) additional fetal tissues including brain, lung, intestine, kidney and thyroid could also be successful engrafted into lymph nodes, and in various cases produced a histologic resemblance to the native organ.

In certain embodiments, the present invention provides for methods of inducing tolerance in a subject to transplantation of allograft tissue. In certain embodiments, the method of inducing tolerance comprises conditioning a transplant recipient with cells immune-matched to a donor of a subsequent allograft. In certain embodiments, the immune-matched cells are thymic cells. In certain embodiments, the thymic cells are transplanted into the lymph node of the recipient.

In certain embodiments, the method of inducing tolerance comprises increasing regulatory T cell (Treg) induction associated with cross-talk between donor thymus tissue and recipient thymus tissue. In certain embodiments, the Treg cells are CD4+, CD25+ and/or FoxP3+ Treg cells.

In certain embodiments, the present invention also provides a method of transplanting allograft tissue to a subject comprising (i) introducing non-lymphoid cells in a lymphoid tissue of the subject under conditions such that the cells are able to proliferate; and (ii) introducing allograft tissue to the subject after the non-lymphoid cells have been introduced into the lymphoid tissue of the subject.

In certain embodiments, the non-lymphoid cells are immune-matched to the allograft tissue.

In certain embodiments, the non-lymphoid cells are thymus cells.

4. BRIEF DESCRIPTION OF THE FIGURES

FIG. 1A-E Direct injection of hepatocytes into a single lymph node of a C57BL/6 wild-type mouse. (a) Jejunal lymph node (LN, yellow dotted oval) not transplanted (top) and just after transplantation (bottom) with primary hepatocytes, which were mixed with 3% Evans blue dye and Matrigel before injection. Scale bars, 1 mm. (b) In vivo optical imaging of mice into which primary hepatocytes from luciferase transgenic mice were injected into a single jejunal or popliteal lymph node, into the spleen (SP) or intraperitoneally (IP). Signals (blue to red) depict different concentrations of donor hepatocytes at day 1 (top) and 1 week (bottom) after transplant. (c) Top left, whole-mount imaging of a jejunal lymph node 1 week after injection of donor GFP+ hepatocytes. Shown is the bright-field image merged with the fluorescence. Top middle to bottom right, immunofluorescent staining of frozen lymph node serial sections with monoclonal antibodies (mAbs) (red) to ER-TR7 (reticular fibroblasts), LYVE-1 (lymphatic vessels), PNAd (high endothelial venules), B220 (B cells) and CD4/CD8 (CD4 T and CD8 T cells) with the presence of GFP+ hepatocytes (green). Dotted lines indicate the lymph node boundary. Scale bars, 100 μm. (d) Immunofluorescent staining of donor GFP+ hepatocytes (green) in jejunal lymph nodes 1 week after transplantation. Shown are serial sections stained with mAbs (red) to E-cadherin (E-Cad), C-C chemokine receptor type 7 (CCR7) and S1PR1, as well as native liver sections stained as controls (right). In native liver, CCR7 (red) was co-stained with dipeptidyl peptidase-4 (DPPIV) (green). All sections were counterstained with Hoechst 33342 (blue). Scale bars, 100 μm. (e) Proliferation of engrafted hepatocytes in lymph nodes after partial hepatectomy (PHx). Paraffin sections of injected lymph nodes and corresponding native liver 1 and 2 weeks (1W and 2W, respectively) after transplantation stained for GFP (1 and 2 weeks after transplantation) and BrdU (2 weeks after transplantation) and revealed by peroxidase (brown cytoplasmic and brown nuclei staining, respectively). Sections were counterstained with hematoxylin. Yellow outlines mark small populations of GFP+ hepatocytes. The bar graphs show the number of GFP+ hepatocytes and the percentage of BrdU+ hepatocytes per section after immunostaining at 2 weeks after transplantation in mice with or without PHx.*$P<0.05$, **$P<0.0001$. Data (mean±s.e.m.) are representative of one experiment with three to five mice per group. The experiment was repeated twice. Scale bars, 100 μm.

FIG. 2A-E Direct injection of hepatocytes into a single lymph node of a Fah−/− mouse. (a) Macroscopic appearances of nontransplanted and transplanted (hepatized) lymph nodes (lymph nodes are marked by yellow dotted ovals). For nontransplanted axillary and popliteal lymph nodes, the presence of the lymph node is highlighted by injected Evans blue. Shown are representative images of the jejunal, axillary and popliteal hepatized lymph nodes captured at 12, 22 and 25 weeks after transplantation, respectively. Scale bars, 5 mm. (b) Histology of hepatized jejunal lymph nodes in rescued Fah−/− mice. Left, serial sections of hepatized lymph nodes stained with hematoxylin and eosin (H&E) (top left), Fah (brown) and counterstained with hematoxylin (blue) (middle left). The immunofluorescence shows lymphatic vessels (LYVE1, red) and hepatocytes (GFP+, green) (bottom left). Right, higher magnification of H&E staining showing typical cuboidal hepatocytes. Reticular fibroblasts stain with antibodies specific for ER-TR7 (red), whereas hepatocytes are GFP+ and stain with antibodies specific for DPPIV (red). Glutamine synthetase (GS, red) expression shows unique zonal restriction surrounding terminal hepatic venules. Sections were counterstained with Hoechst 33342 (blue). Scale bars, left, 1 mm; middle and right, 100 μm. (c) Kaplan-Meier survival curves (top) and body weight (bottom) of Fah−/− mice transplanted in intra- and extra-abdominal lymph nodes compared to mice given no treatment. Error bars show the standard error. (d) Left, macroscopic appearances of normal and hepatized lymph nodes (yellow dotted ovals) in the periportal area. Top right, Kaplan-Meier survival curves of Fah−/− mice transplanted into the jejunal or periportal lymph node. Bottom right, average weights of periportal and jejunal lymph nodes and intra-(intra-abd) and extra-abdominal (extra-abd) lymph nodes. No statistical difference (NS) was observed. Error bars show s.e.m. Scale bars, 5 mm. (e) Top, lymph node injection (LN-Tx) and splenic injection (SP-Tx) of GFP+ hepatocytes (C57BL/6 background) into Fah−/− mice (129sv background) after removal of 2-(2-nitro-4-trifluoromethylbenzoyl)-1,3-cyclohexanedione (NTBC) (lack of NTBC in drinking water induces liver failure in Fah−/− mice). Where indicated, mice were injected with the immunosuppressive agents CTLA4-Ig and MR1 on days 0, 2, 4 and 6 after transplantation. The experiment was repeated twice. The images n the bottom show one representative LN-Tx mouse injected with CTLA4-Ig and MR1. Also shown are the macroscopic appearances of hepatized jejunal lymph nodes (yellow dotted ovals) and immunostaining of the hepatized lymph nodes for the presence of GFP+ (green) and Fah+ (red) hepatocytes, as well as reticular fibroblasts (ER-TR7, red). Sections were counterstained with Hoechst 33342 (blue). Scale bars, left, 5 mm; middle and right, 100 μm.

FIG. 3A-E Functional ectopic thymus in the jejunal lymph node. (a) Flow cytometric analysis of T cells in the peripheral blood. Top, representative analysis of the gating strategy for CD4 and CD8 T cells in wild-type C57BL/6 (WT), BALB/c nude (Nude) and BALB/c nude mice into which C57BL/6 GFP+ thymic cells were injected into a jejunal lymph node (LN-Tx nude). The number values assigned to the gates and quadrants represent the percentage of total live cells within that gate or quadrant. All contour plots display 10% probability contours. Bottom, the percentage of CD3+, CD3+CD4+ and CD3+CD8+ live T cells in the blood of each mouse analyzed (each symbol represents one mouse); the mice were WT, nude, KC-Tx nude (BALB/c nude mice transplanted under the kidney capsule) and LN-Tx nude. The thin black line indicates the mean±s.e.m. No statistical significance (NS) was observed between kidney capsule and lymph node transplantation in each of the three groups. (b) Left, representative flow cytometric analysis of cells present in wild-type C57BL/6 (WT) and LN-Tx nude mouse tissues. The number values assigned to the gates and quadrants represent the percentage of total live cells within that gate or quadrant. Bottom, whole-mount jejunal lymph node of a nude mouse engrafted in the lymph node with GFP+ thymic cells (top left). The bright-field image was merged with the fluorescence. Top right, a frozen section with GFP+ donor thymic cells. Bottom right, immunostaining of cytokeratin 5 (K5) (blue) and cytokeratin 8 (K8) (red) and counterstaining with Hoechst (white). Bottom left, WT native thymus stained for K5 (red) and K8 (green). Scale bars, 200 μm. (c) Flow cytometric analysis of TCR Vβ segment expression in splenocytes from wild-type C57BL/6 mice (WT C57BL/6), heterozygous BALB/c nude mice (Het nude) or LN-Tx mice. The bar graphs show the mean percentage of the particular Vβ receptor. Individual symbols represent data from a single mouse (n=4-5). (d) Dot plots and histograms show the gating strategy to detect regulatory T cells (FoxP3+ fraction of CD4+CD25+ T cells) and naive (CD44+CD62L+), central memory (CD44+CD62L+) and effector memory (CD44+CD62L−) T cells in splenocytes. Graphs show the data from individual mice, labeled as in panel c. The thin black line indicates the mean. (e) Top, Kaplan-Meier curves showing the survival of skin grafts from C57BL/6 or CBA/CaJ donor mice transplanted onto BALB/c nude recipients that had previously undergone transplantation of C57BL/6 thymic cells into the lymph node (LN-Tx nude) or into unmanipulated nude mice. Middle, graph of tumor growth in athymic BALB/c nude (nu/nu) mice. Values are mean±s.e.m. n=10. Bottom, presence (+) or absence (−) of tumor growth after a single subcutaneous injection of 300,000 human colorectal cancer cells into LN-Tx nude, BALB/c nude (Nude) or C57BL/6 wild-type (WT) recipients.

Figure 4A:
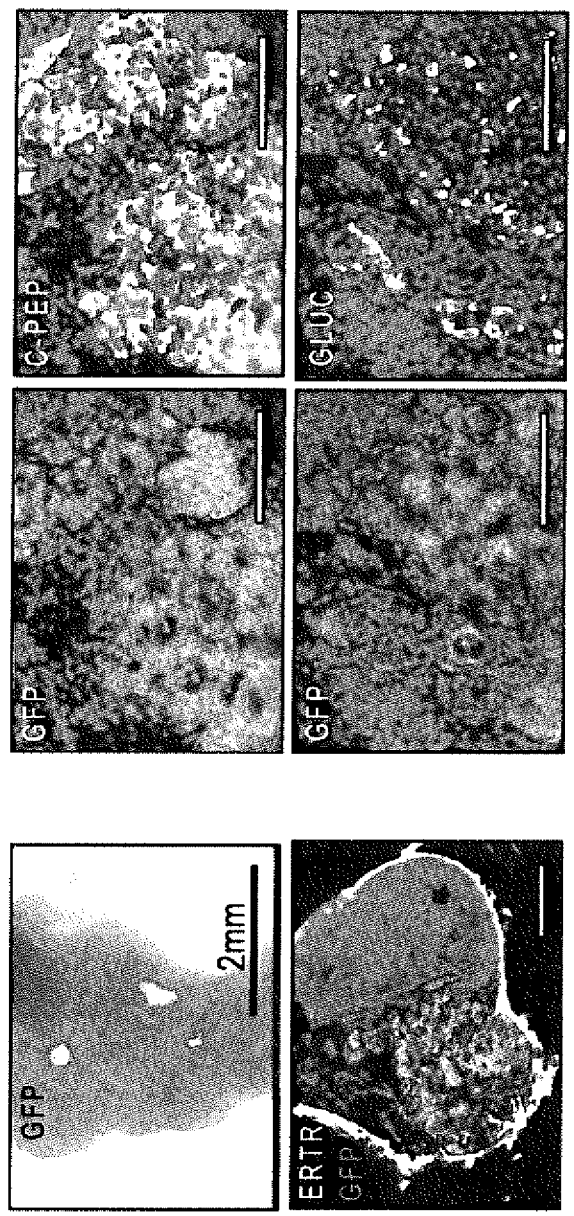
Figure 4B:
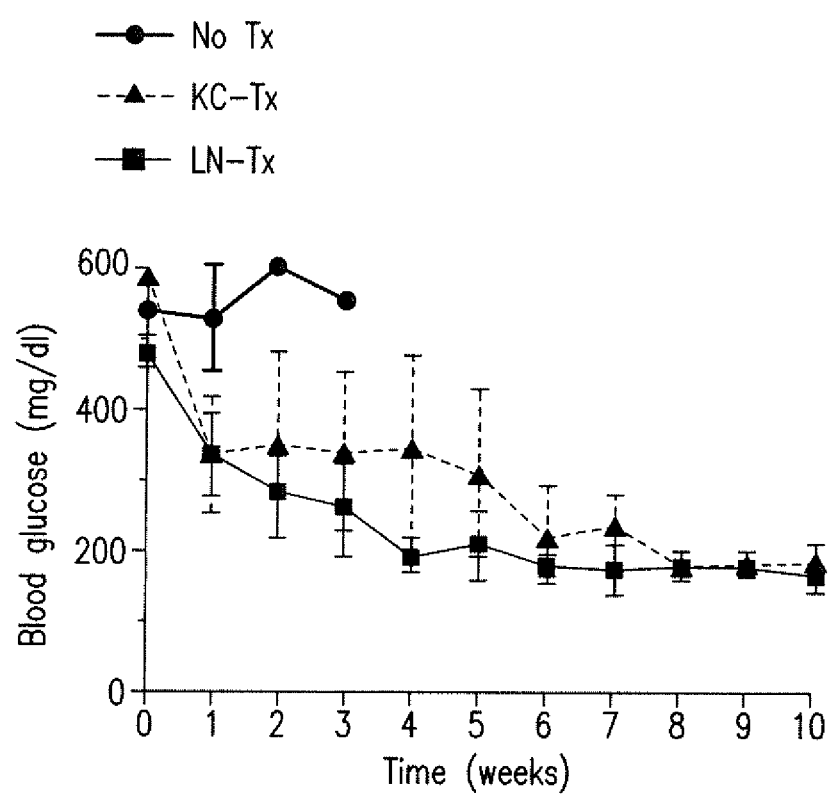
Figure 4C:
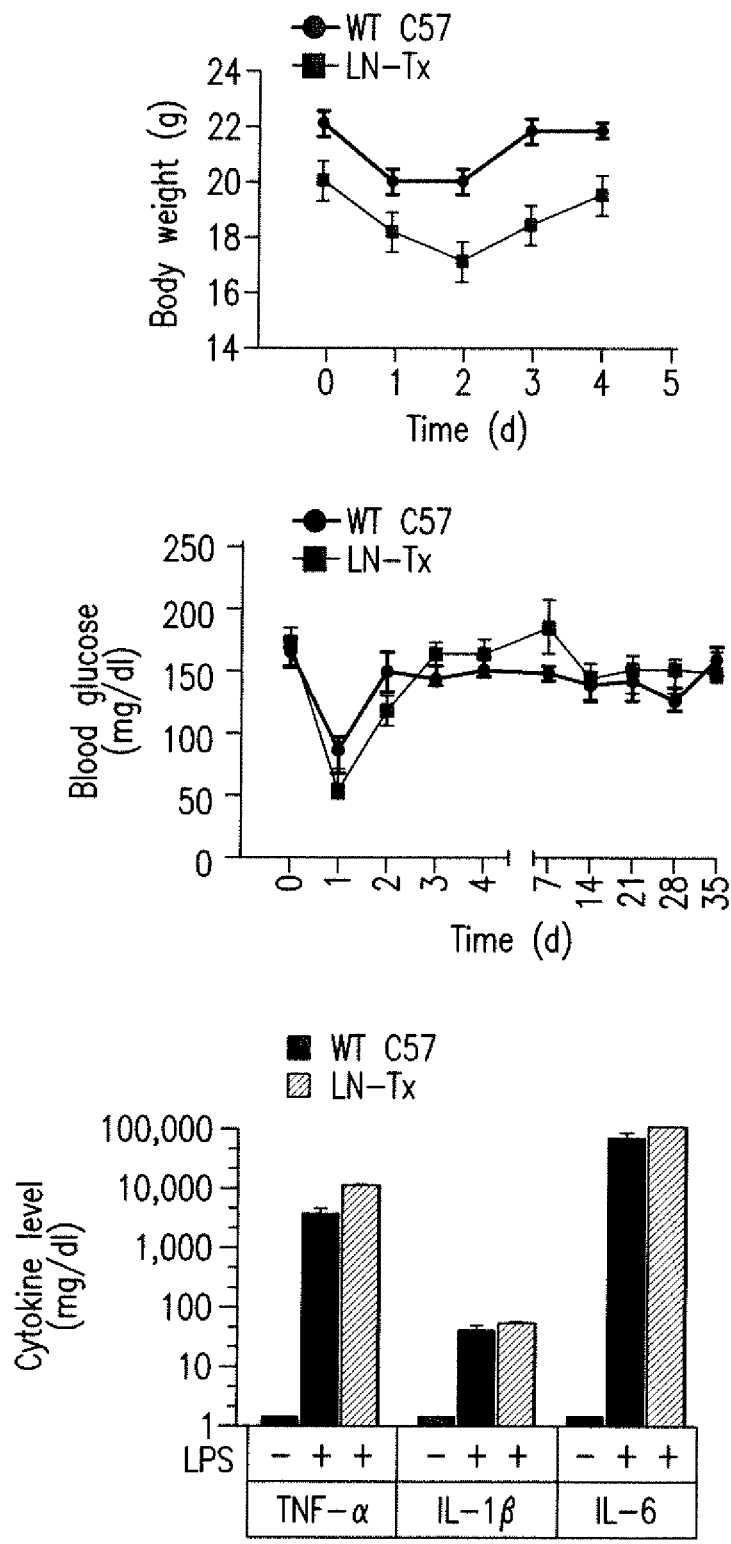

FIG. 4A-C Ectopic pancreas generation in the jejunal lymph node after islet transplantation. (a) Top, whole-mount lymph node of a streptozotocin-treated diabetic C57BL/6 mouse engrafted with C57BL/6 GFP+ pancreatic islets. The bright-field image was merged with the fluorescence. Other images show immunofluorescence of lymph nodes removed 6 weeks after engraftment. Staining with antibodies specific for ERTR7 (reticular fibroblasts), C-peptide (C-PEP) and glucagon (GLUC) is shown in red, GFP is shown in green, and Hoechst counterstain is shown in blue. (b) Average blood glucose concentrations in diabetic recipient mice over the course of 10 weeks after transplantation of islets into the jejunal lymph nodes (LN-Tx, n=5), under the kidney capsule (KC-Tx, n=3) or in diabetic mice with no transplantation (No Tx, n=6). The data are presented as means±s.e.m. (c) Average body weight (left) and blood glucose concentrations (middle) of C57BL/6 wild-type (WT C57) mice or C57BL/6 LN-Tx mice after LPS injection (1 mg per kg of body weight). Right, average serum concentrations of TNF-α, IL-1β and IL-6 2 h after LPS injection. All error bars show standard error. All immunofluorescent image scale bars are 100 µm unless otherwise indicated.

Figure 5A:
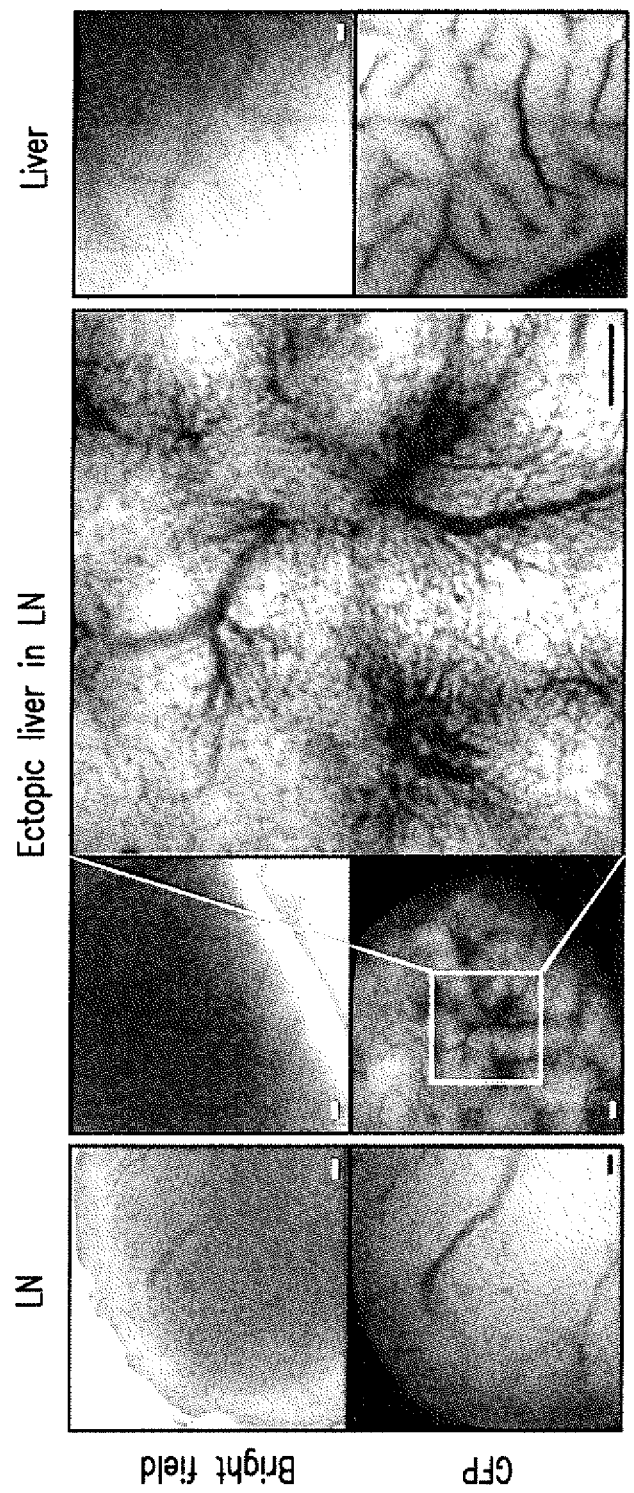
Figure 5B:
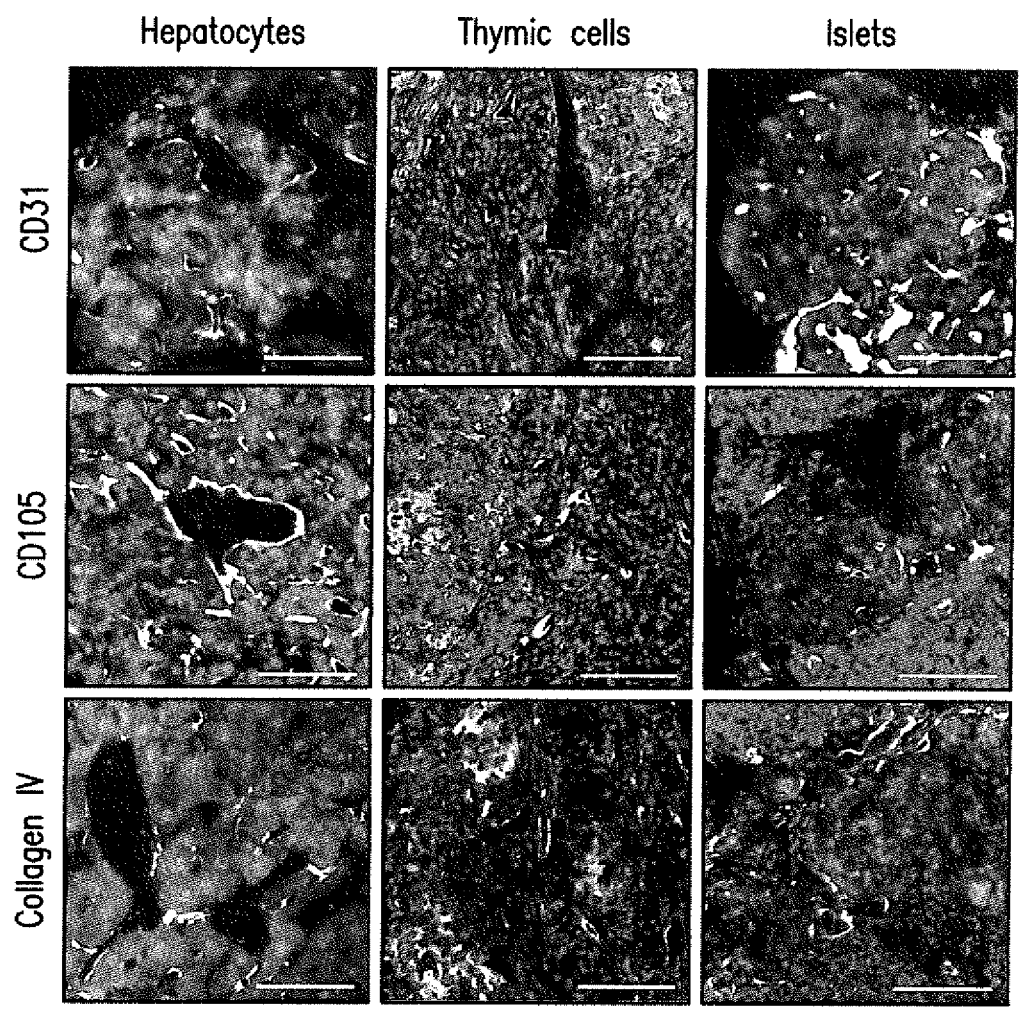

FIG. 5A-B. Neovascularization of ectopic tissue. (a) Vascular trees are shown in a native lymph node and native liver of a GFP transgenic mouse and in mice after hepatocyte transplantation into the lymph node. (b) Immunostaining of lymph nodes injected with hepatocytes, thymic cells and pancreatic islets. Images were captured 12, 15 and 6 weeks after the transplant of each tissue, respectively. CD31 is a marker for blood vessels, and CD105 and Collagen IV are markers for neovascularization. Vasculature markers are shown in red, and ectopic tissue is shown in green. All sections were counterstained with Hoechst 33342 in blue. All scale bars are 100 µm.

Figure 6:
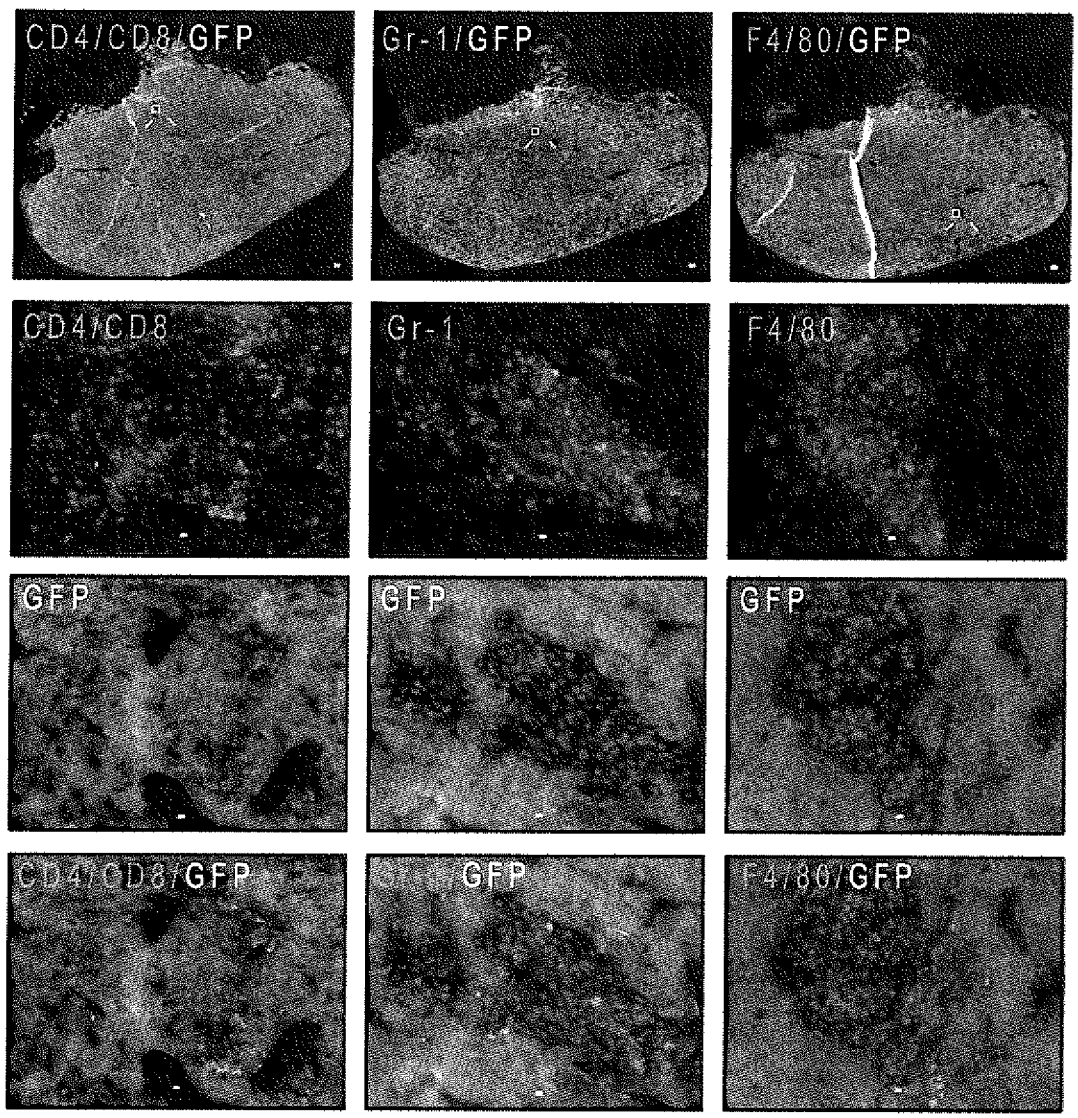

FIG. 6. Distribution of immune cells in the hepatized jejunal LN of a rescued C57BL/6 Fah−/− mice at 12 weeks after transplantation. Left to right panels, immunostaining of frozen LN serial sections with mAbs (red) against CD4/CD8 (CD4 and CD8 T cells), Gr-1 (granulocytes) and F4/80 (macrophages) with the presence of C57BL/6 GFP+ hepatocytes (green). All sections were counterstained with Hoechst 33342 (blue). Scale bar: 100 mm.

Figure 7:
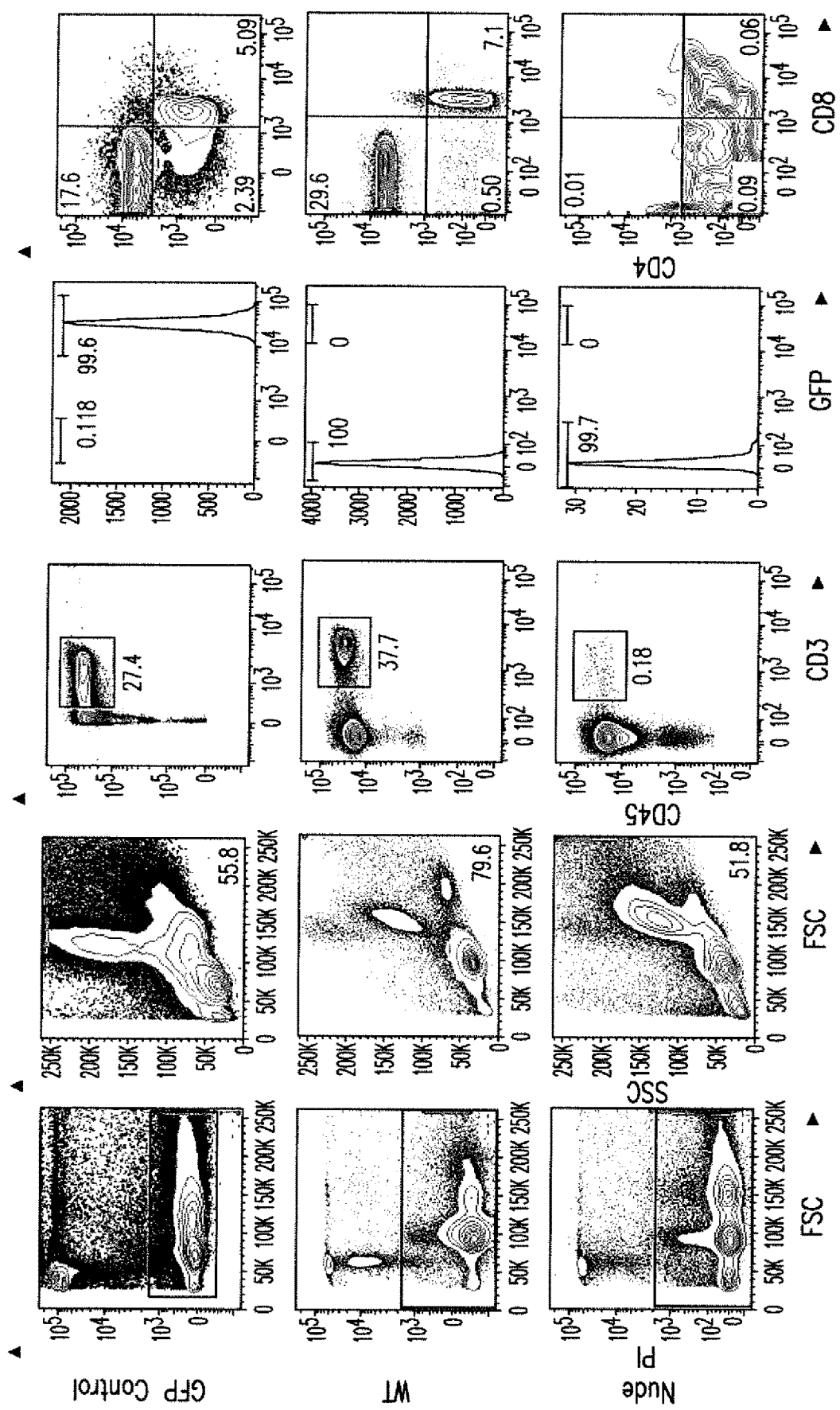
Figure 7:
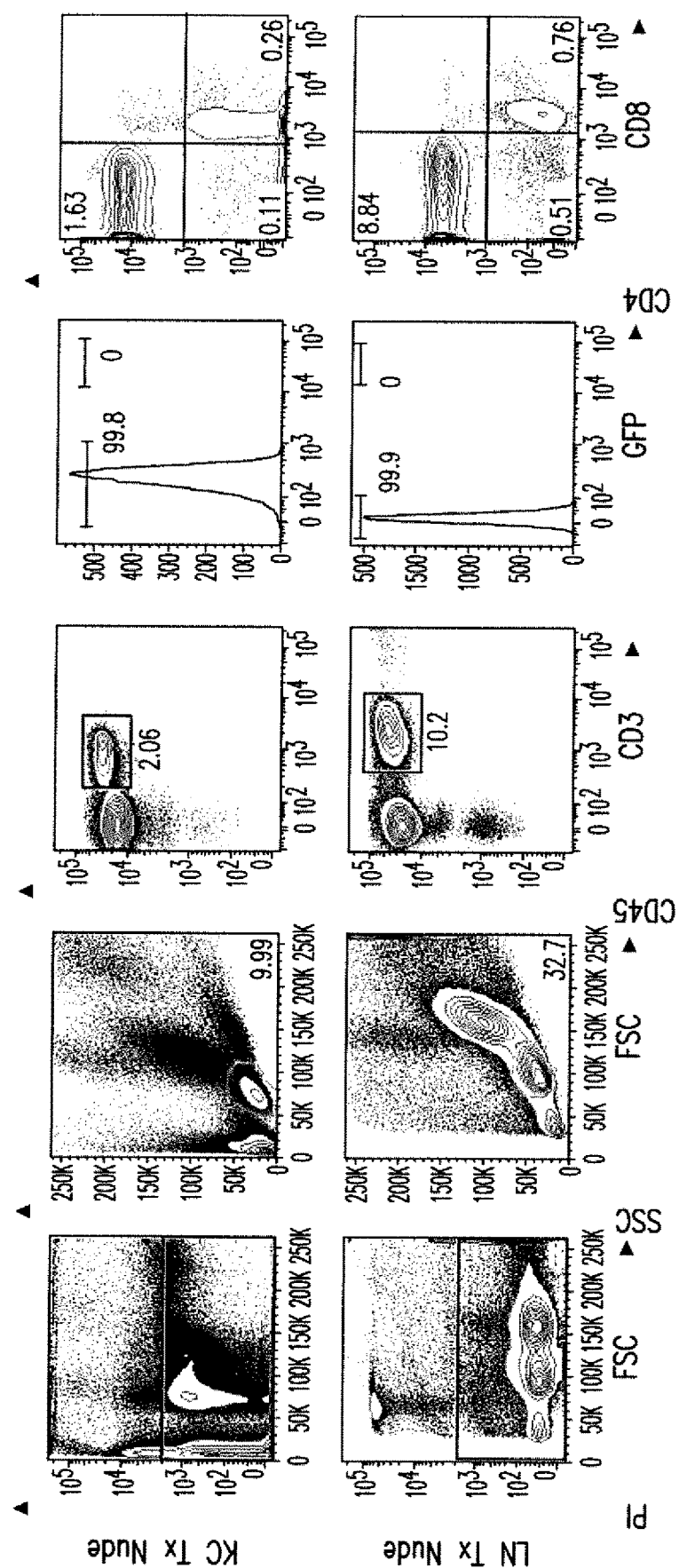

FIG. 7. Representative flow cytometry analysis of peripheral blood T cells. Analysis of CD4 and CD8 T cells from C57BL/6 GFP+ mice, wild type C57BL/6, BALB/c Nude, kidney capsule (KC) transplanted (Tx) BALB/c Nude, and lymph node (LN) transplanted BALB/c Nude mice. The number values assigned to the gates and quadrants represent the percentage of total live cells within that gate or quadrant. All contour plots display 10% probability contours.

Figures 8A, 8B:
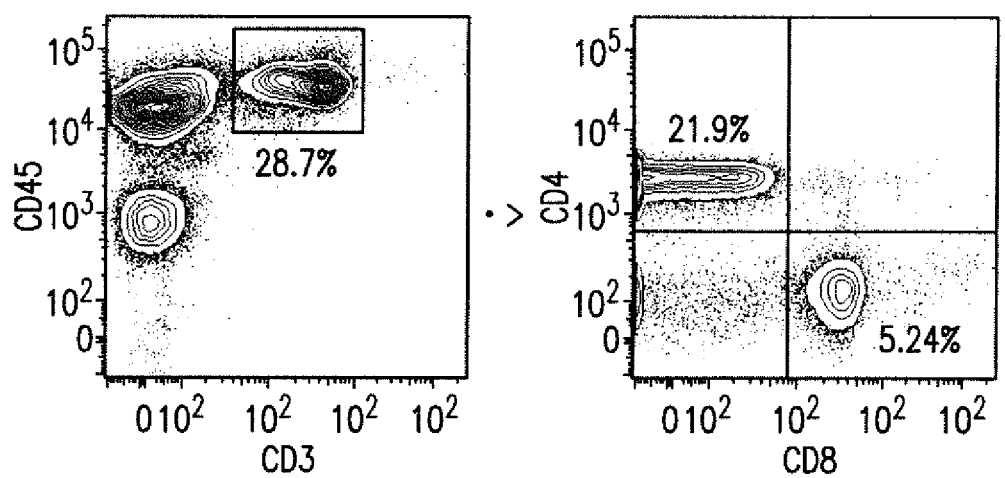

FIG. 8A-B. Presence of peripheral T cells 10 months after C57BL/6 GFP+ thymic transplantation in BALB/c Nude LN. (a) Blood analysis of 3 mice; the number values assigned represent the percentage of total live CD4 and CD8 T cells. (b) Flow cytometric analysis of mouse L084. The number values assigned to the gates and quadrants represent the percentage of total live cells within that gate or quadrant. All contour plots display 10% probability contours.

FIG. 9. Table 1.

Figure 10A:
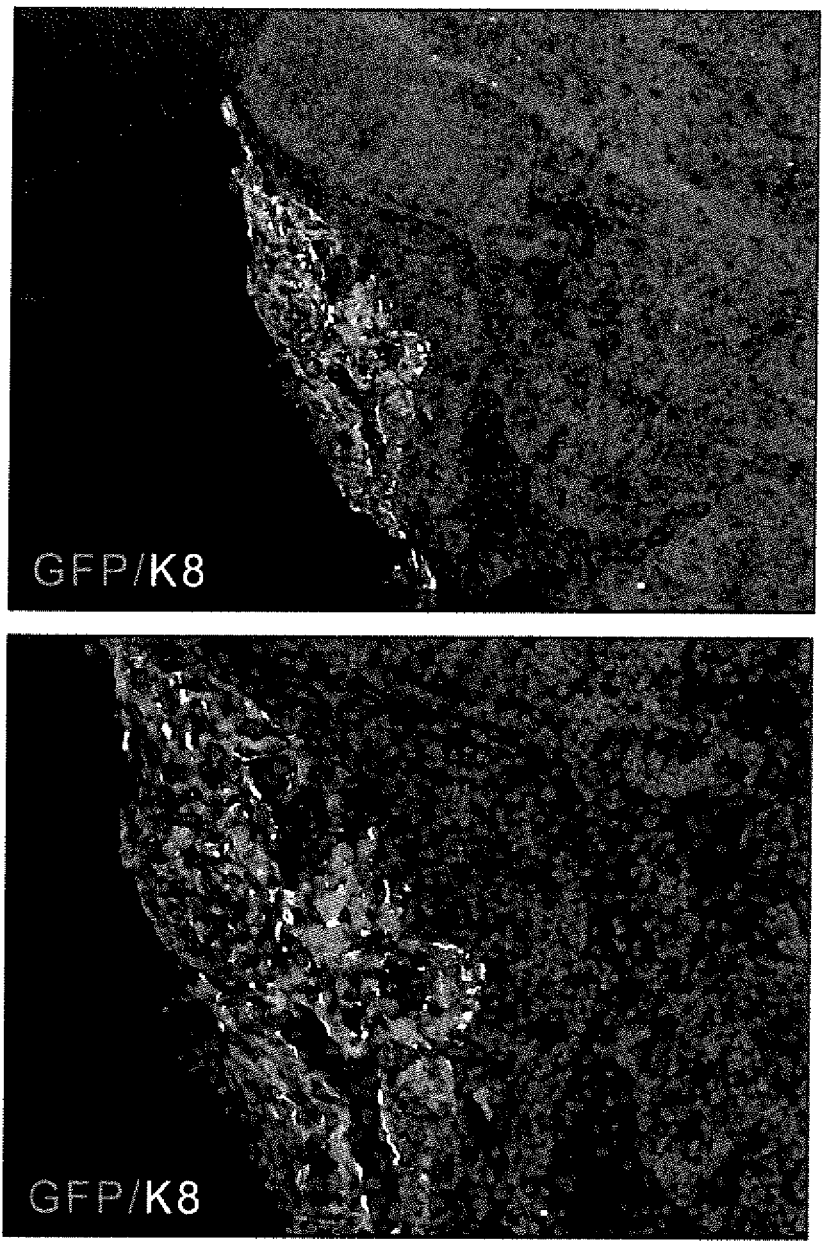
Figure 10B:
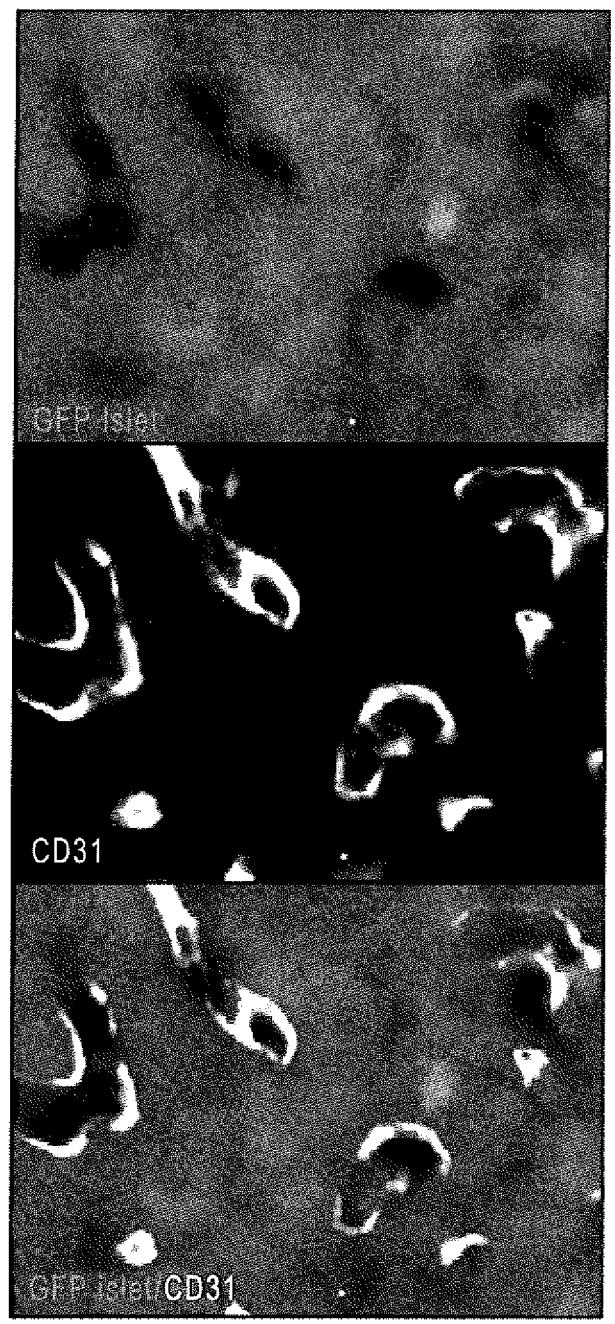

FIG. 10A-B. A. C57BL/6 GFP+ thymic tissue engrafts in the subcapsular space of the jejunal BALB/c Nude LN. Frozen section of an ectopic thymus with GFP+ donor thymic cells and stained with cytokeratin 8 (K8) in red. Hoechst counterstain is shown in blue. Scale bar: 100 mm. B. Engrafted C57BL/6 GFP+ islet vasculature is derived from the recipient C57BL/6 mouse 6 weeks after transplantation. Immunostaining against CD31 (red) does not co-stain with the GFP+ donor derived islets (green). Scale bar: 50 mm.

Figure 11A:
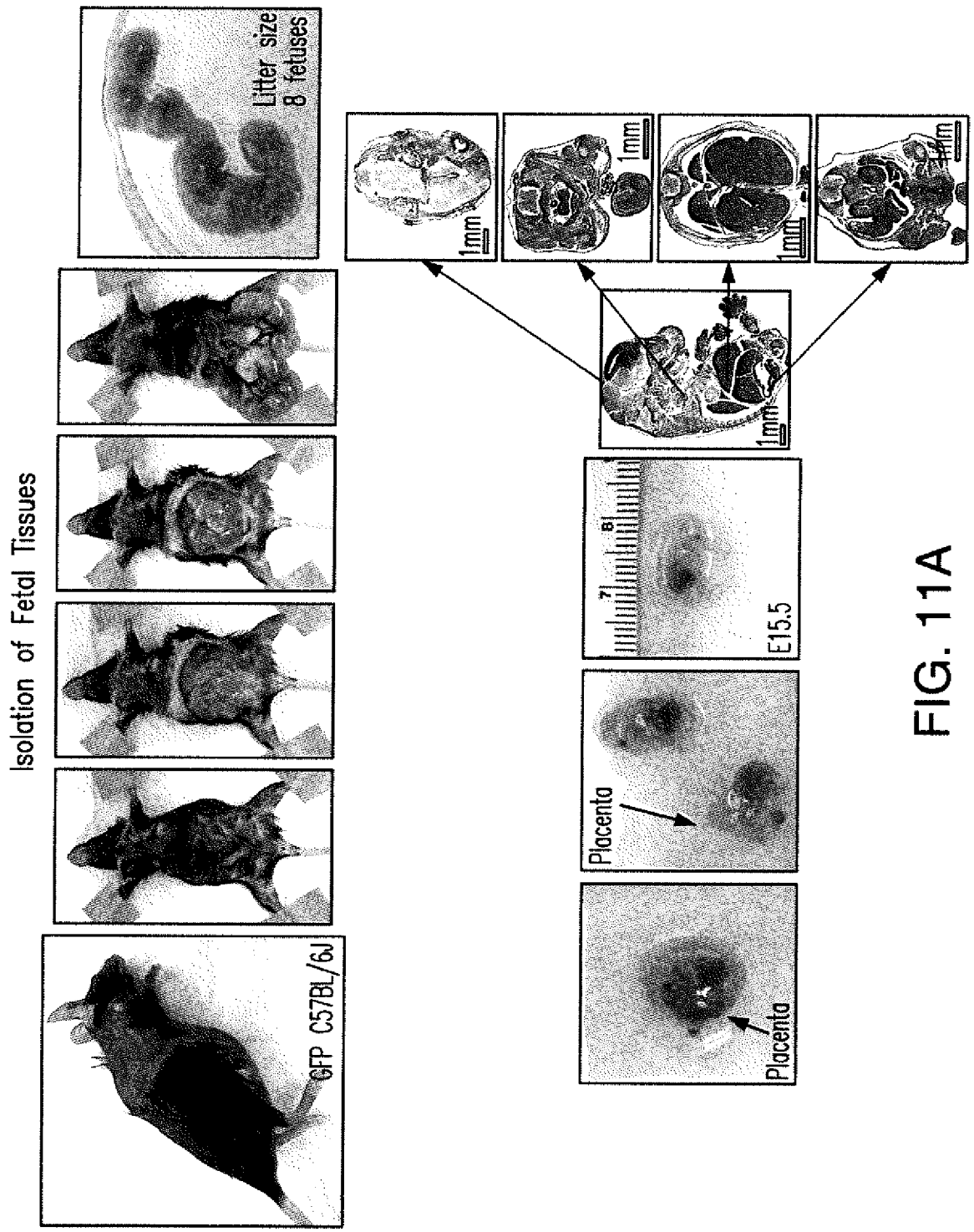
Figure 11B:
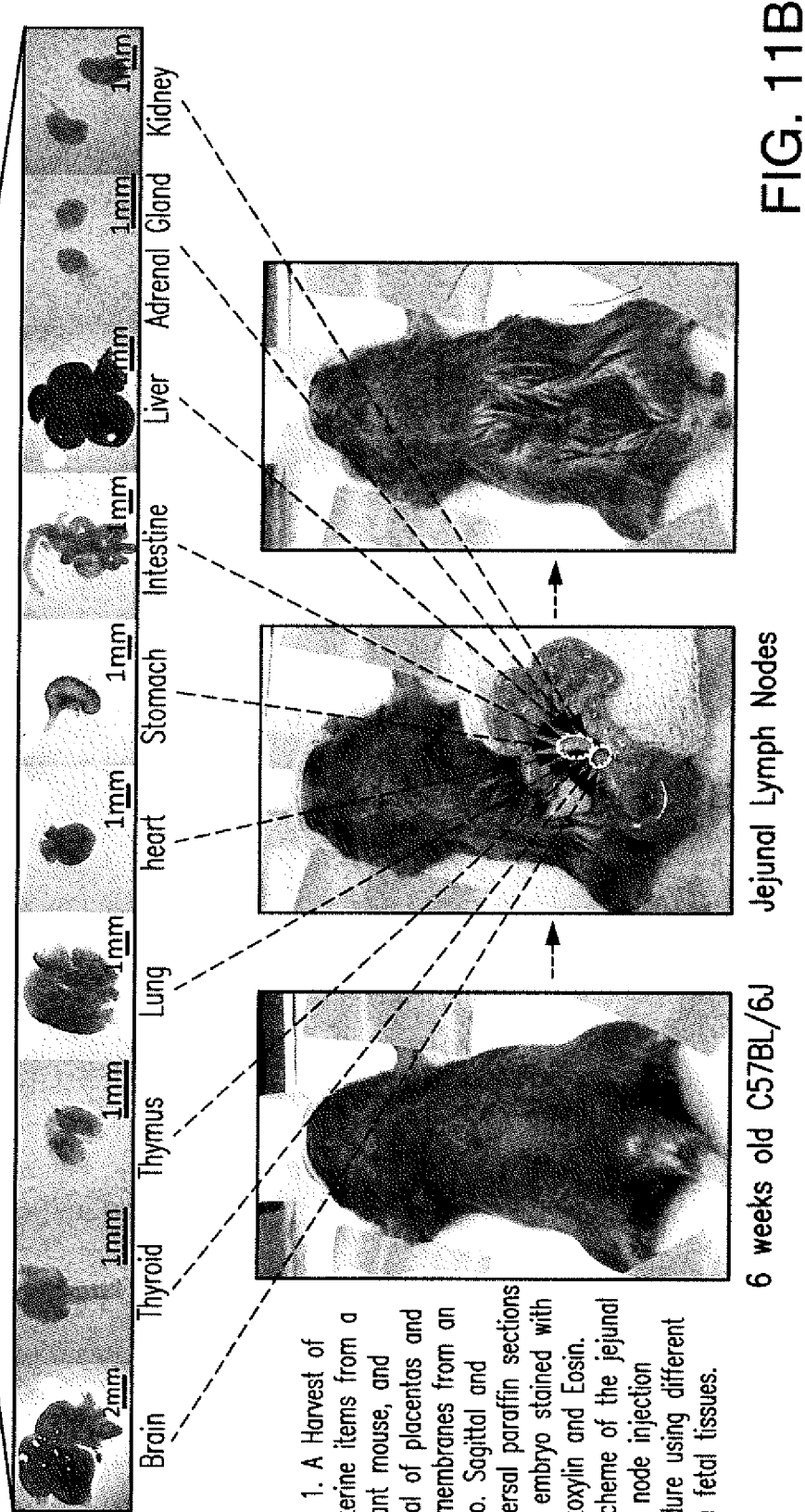

FIG. 11A-B. A, Harvest of the uterine horns from a pregnant mouse, and removal of placenta and fetal membranes from an embryo. Sagittal and transversal paraffin sections of an embryo stained with Hematoxylin and Eosin. B, Scheme of the jejunal lymph node injection procedure using different mouse fetal tissues.

FIG. 12A-D. Each panel shows paraffin (A, B and D) or frozen (C) sections of donor C57BL/6 GFP+ tissues stained with Hematoxylin and Eosin or Hoechst, respectively, whole-mount jejunal lymph nodes of C57BL/6 mice 3 weeks after transplantation, and immunofluorescence staining of frozen lymph node serial sections with the presence of GFP+ cells.

FIG. 13. (Upper) Dissection of mouse thyroid gland. (Bottom) Scheme of the jejunal lymph node injection procedure, whole-mount jejunal lymph node 3 weeks after transplantation, and immunofluorescence staining of a frozen lymph node section with the presence of GFP+ cells.

FIG. 14A-C. Problems associated with determining gestational age.

FIG. 15. Table showing mice injected and lymph nodes repopulated for various organ types.

Figure 16:
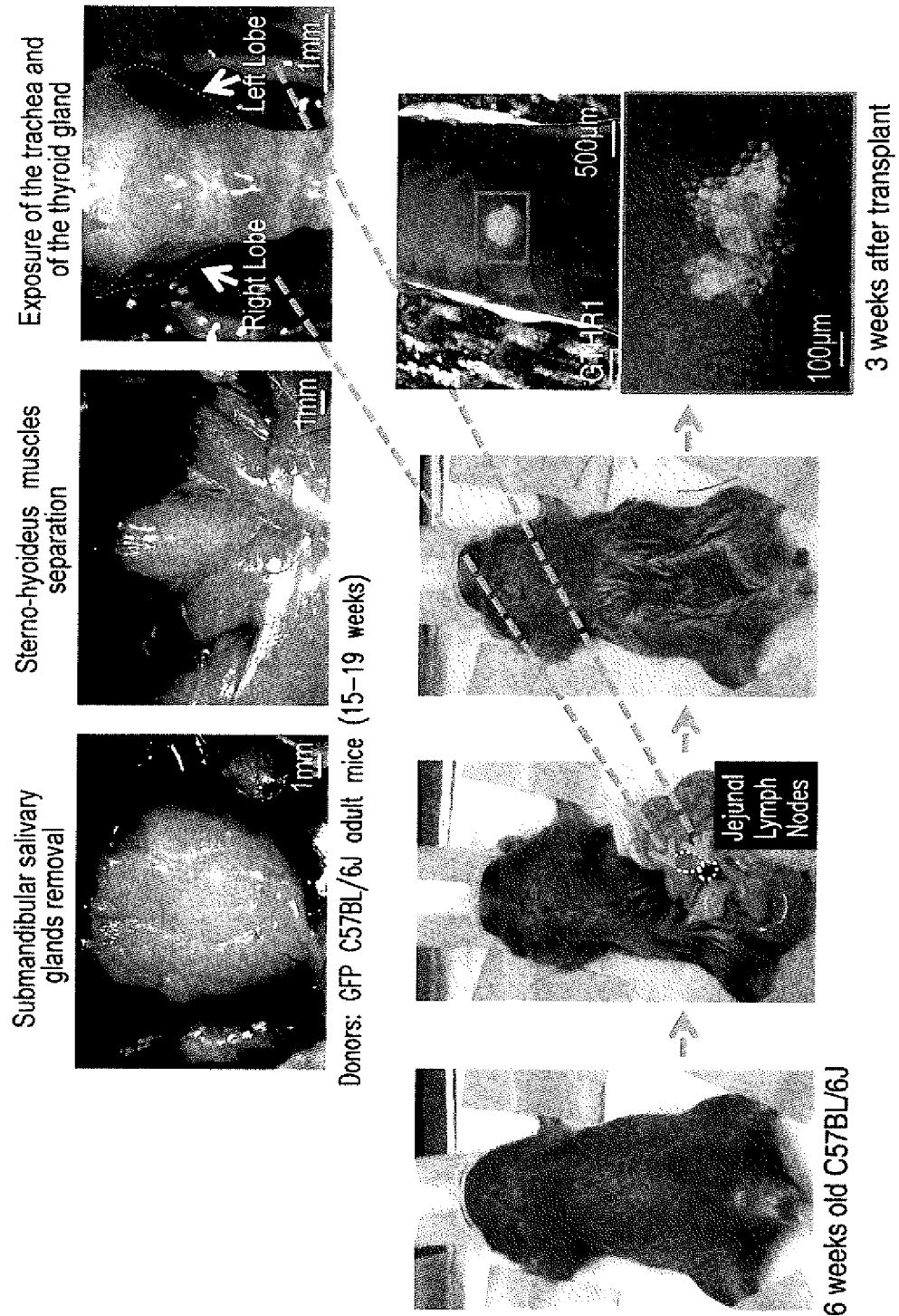

FIG. 16. Transplantation of thyroid gland into lymph node.

Figure 17:
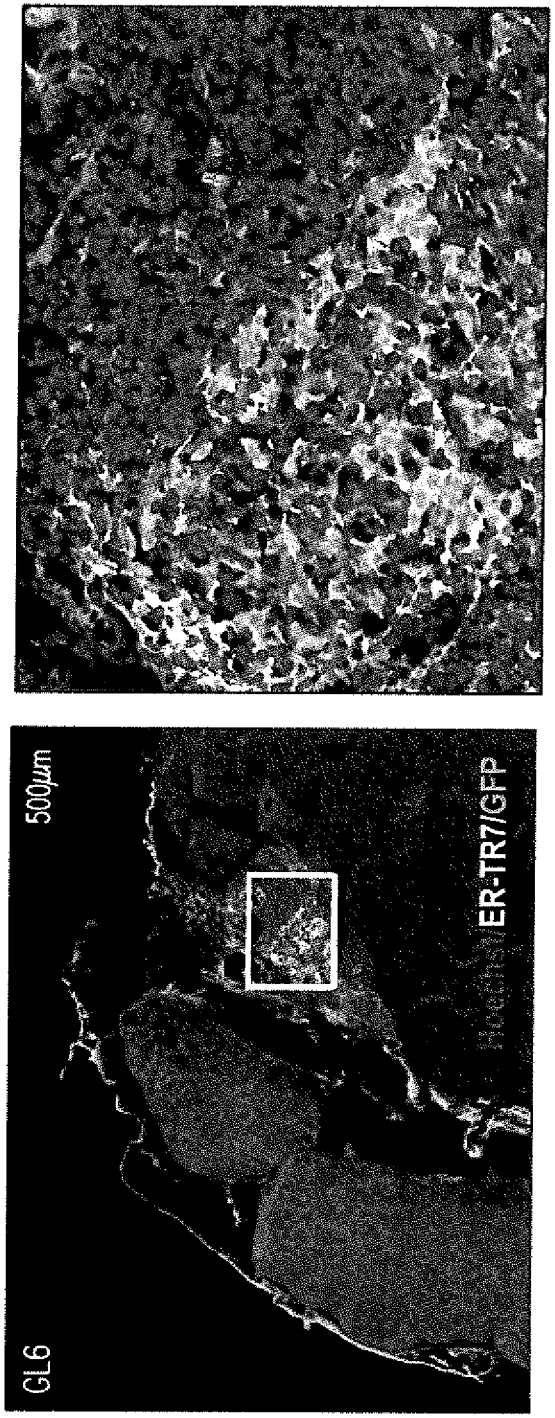

FIG. 17. Transplantation of liver into lymph node.

Figure 18:
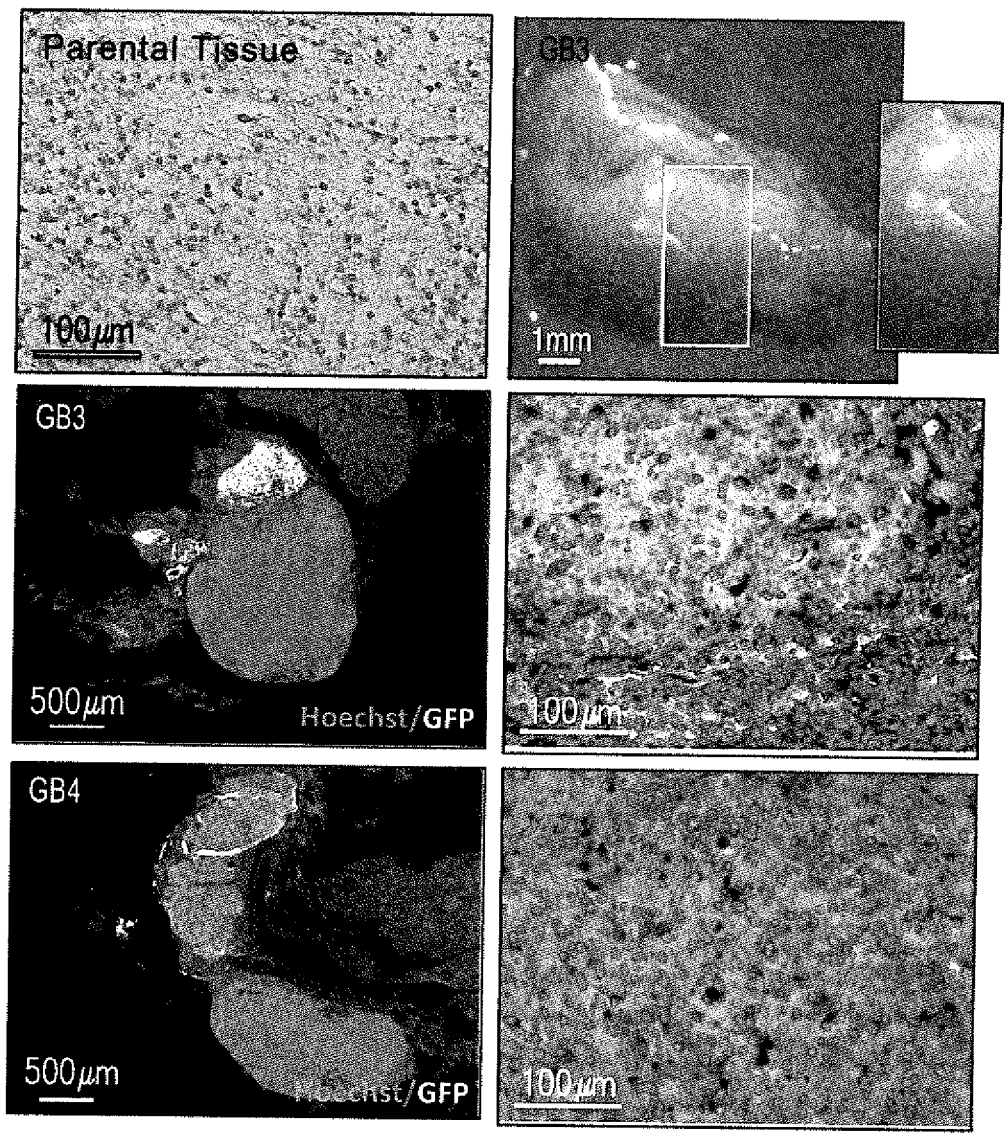

FIG. 18. Transplantation of brain tissue into lymph node.

Figure 19:
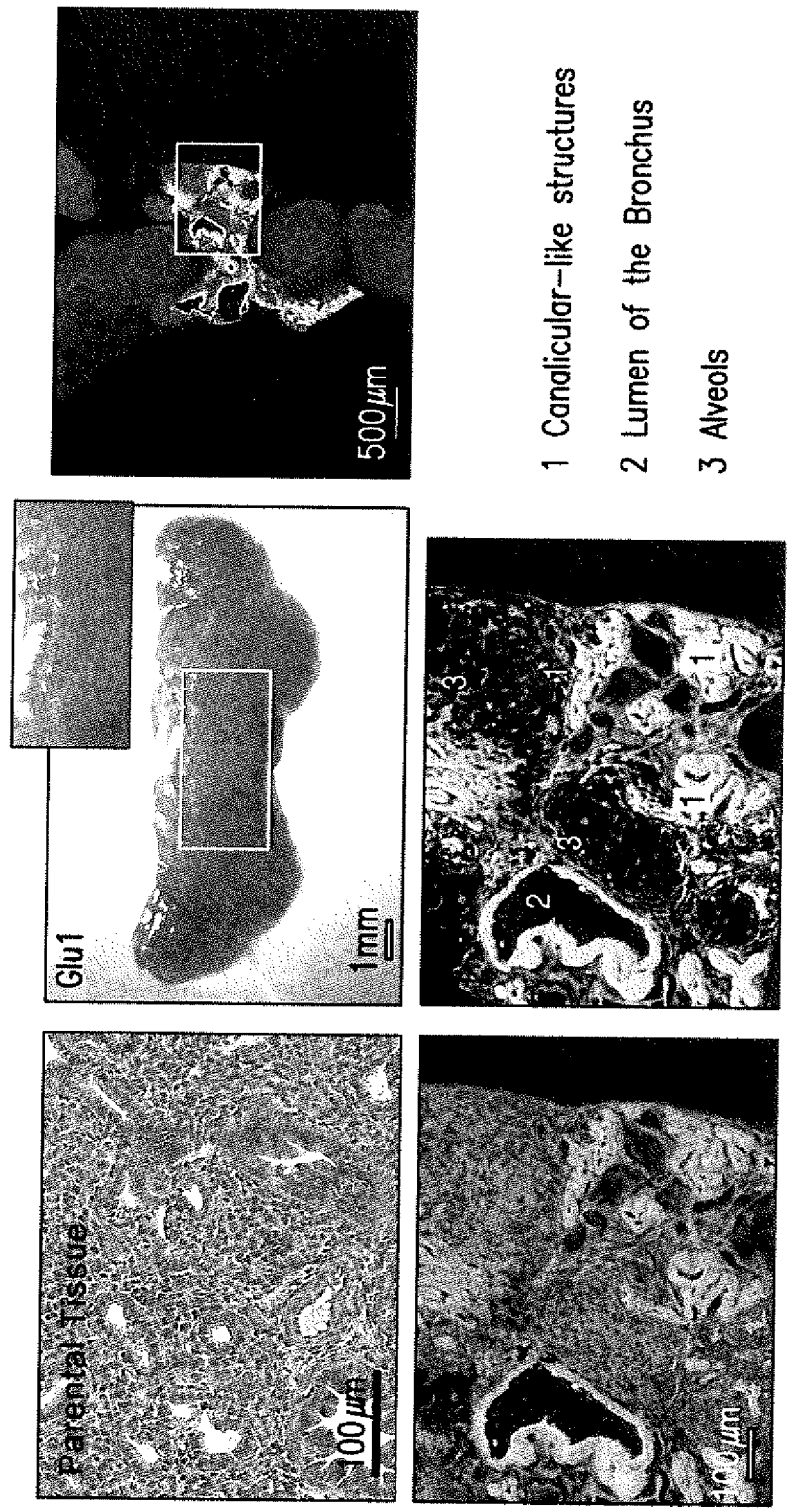

FIG. 19. Transplantation of lung tissue into lymph node.

FIG. 20. Transplantation of intestinal tissue into lymph node.

Figure 21A:
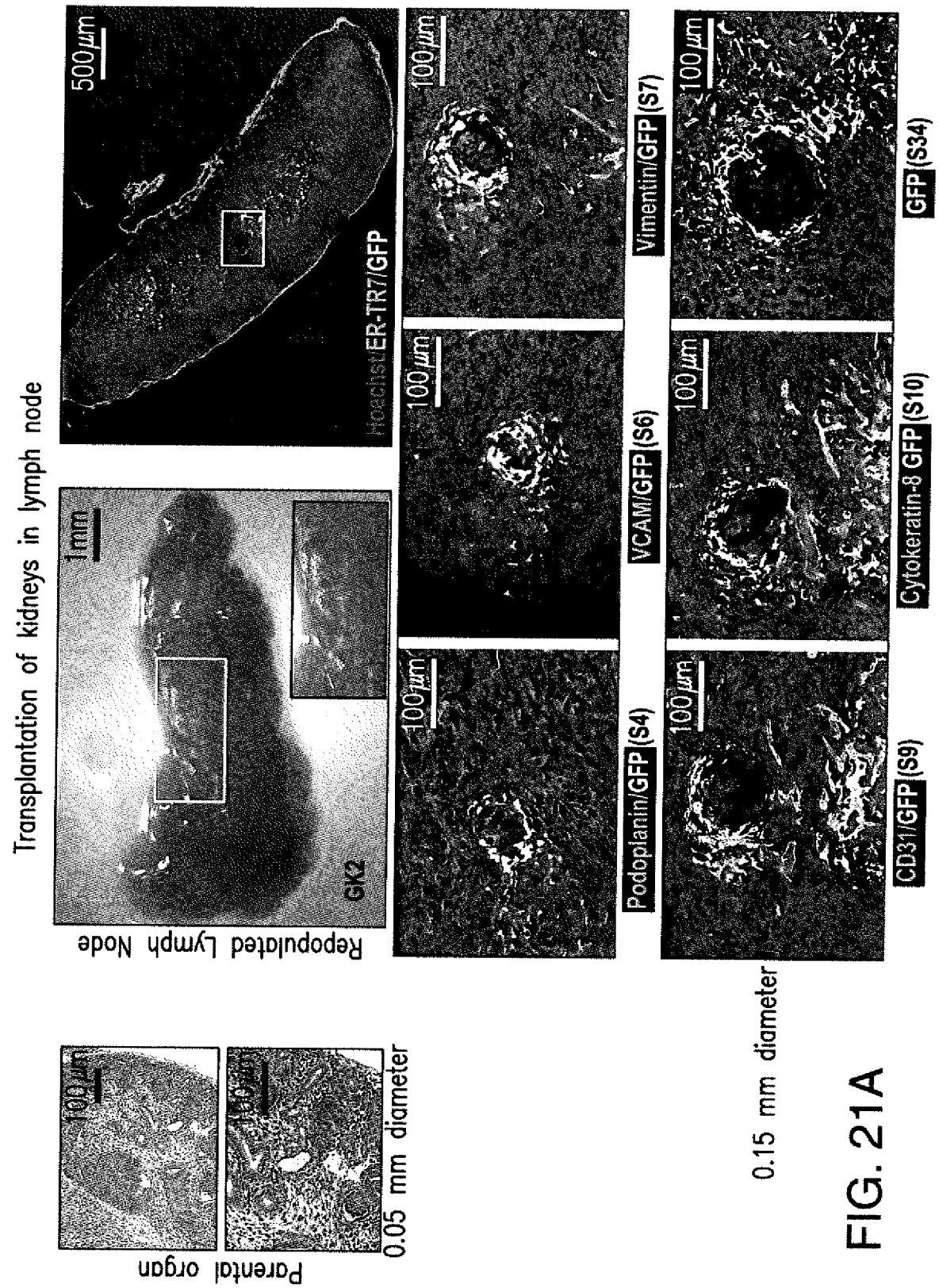
Figure 21B:
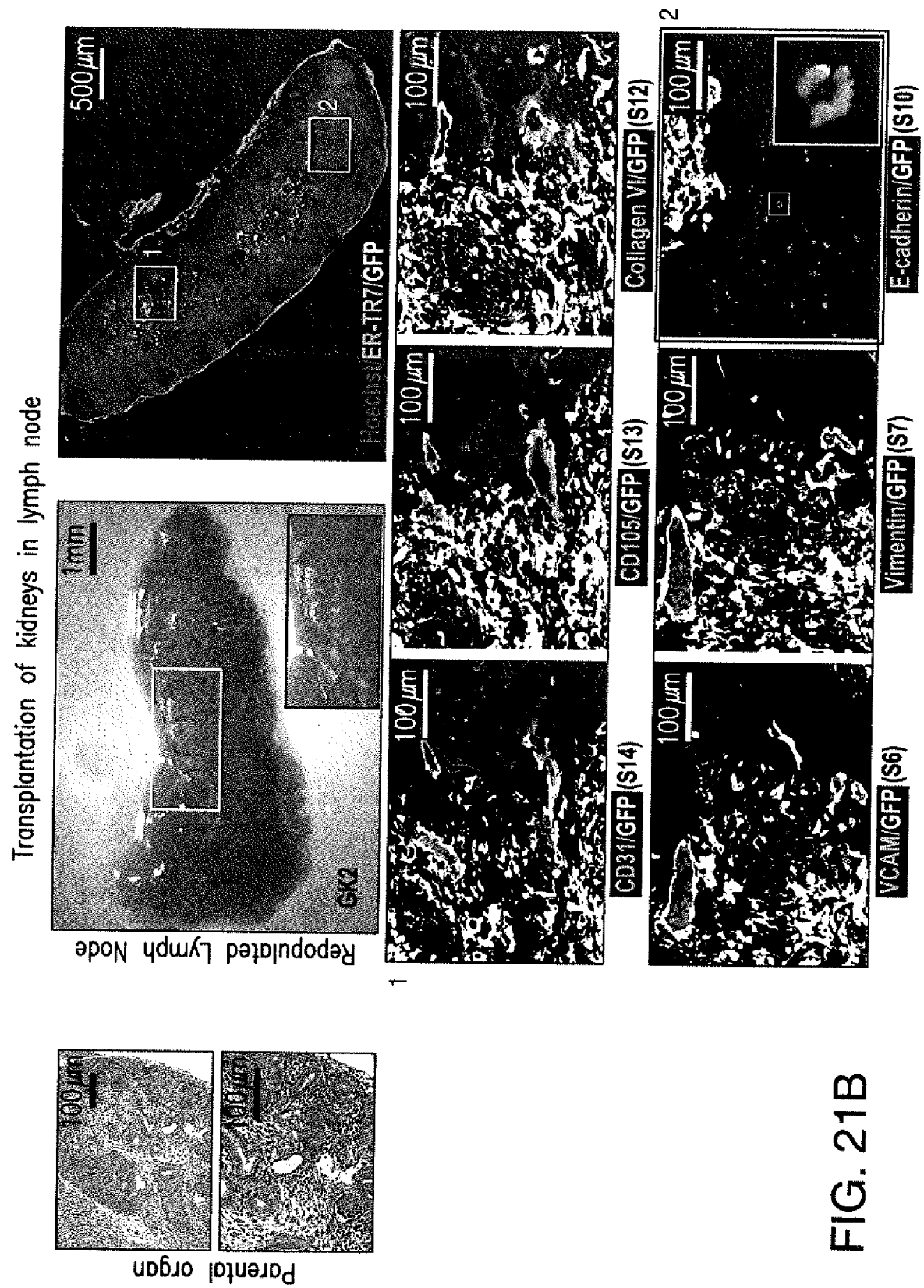
Figure 21C:
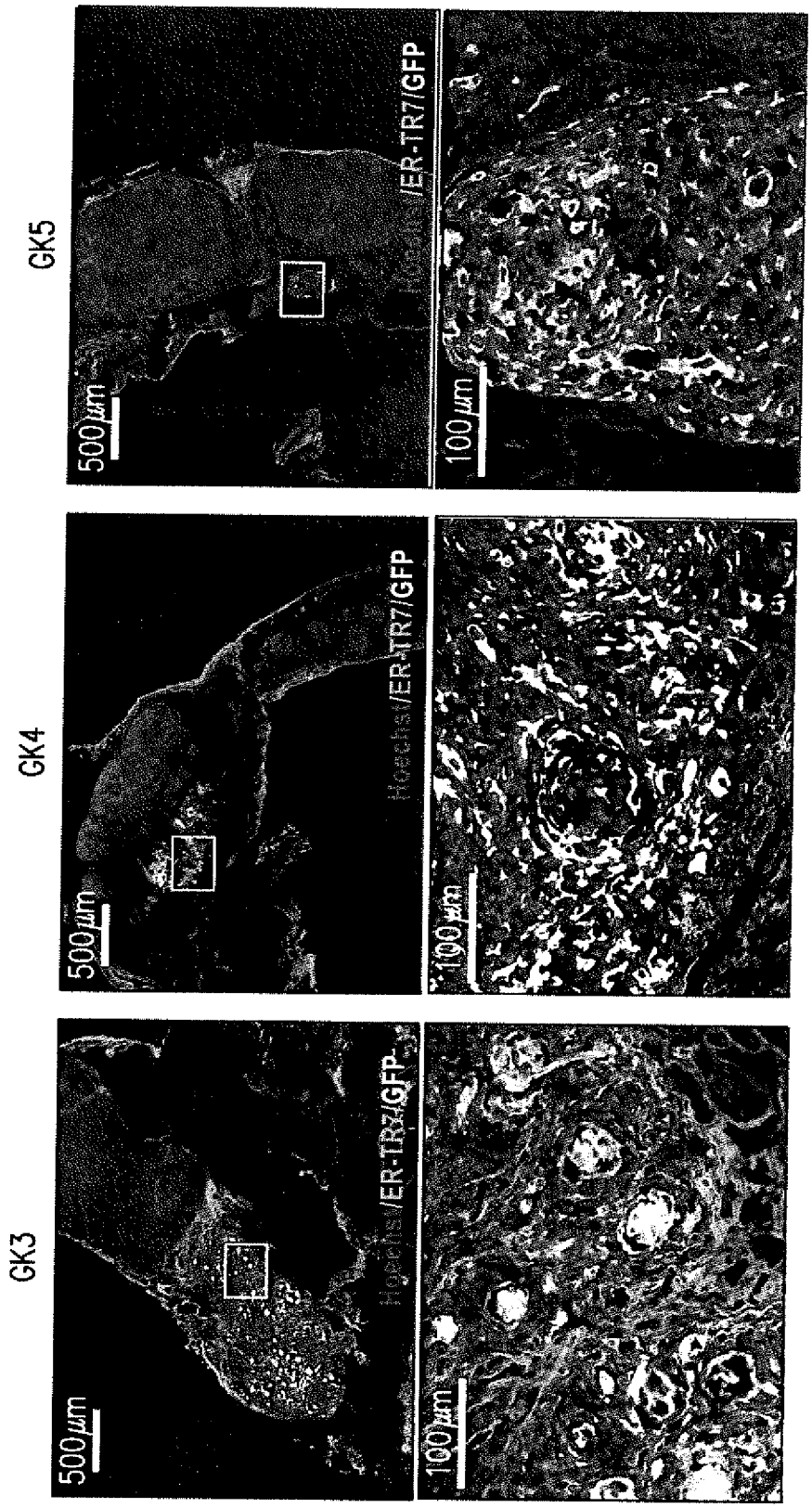
Figure 22A:
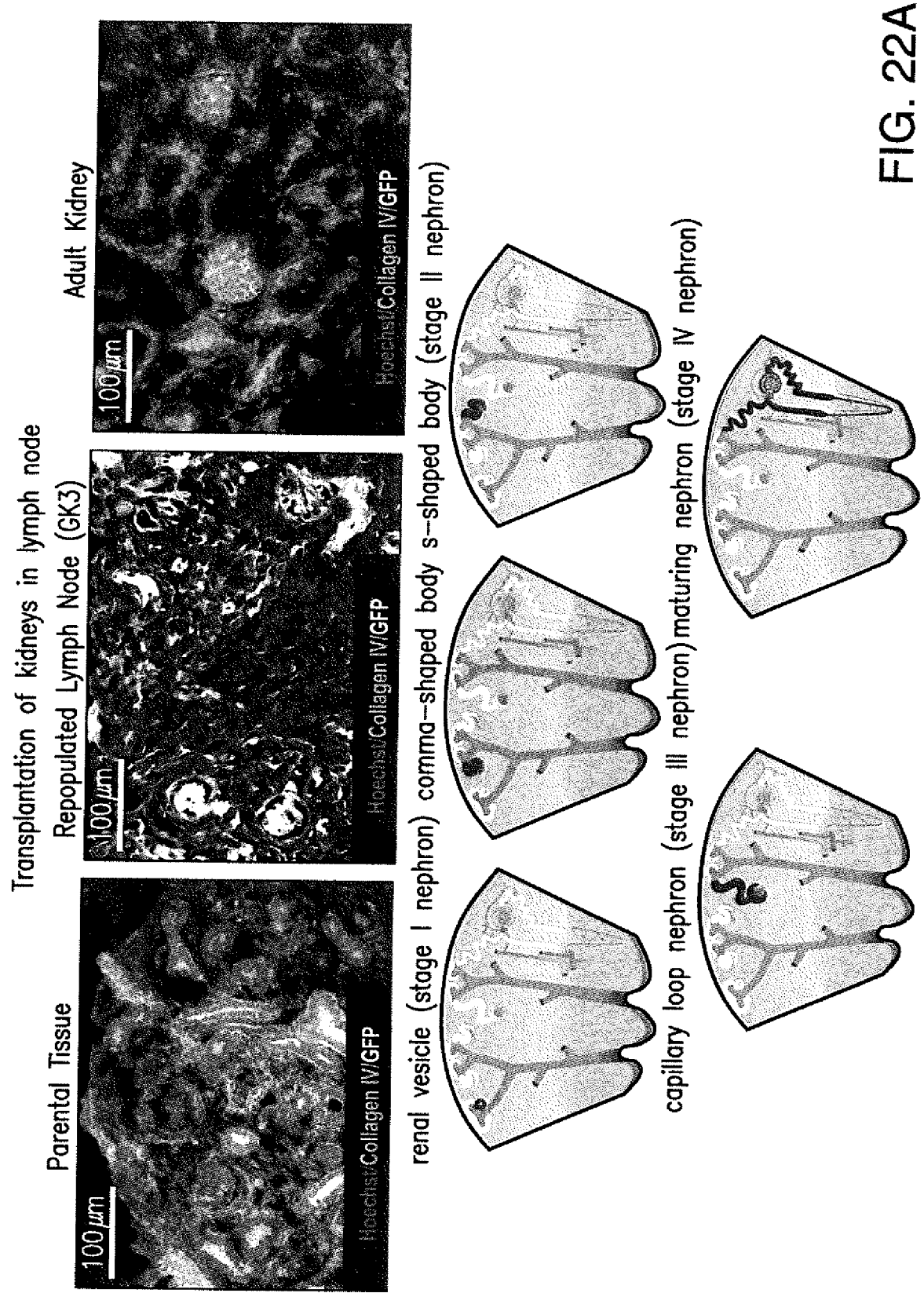
Figure 22B:
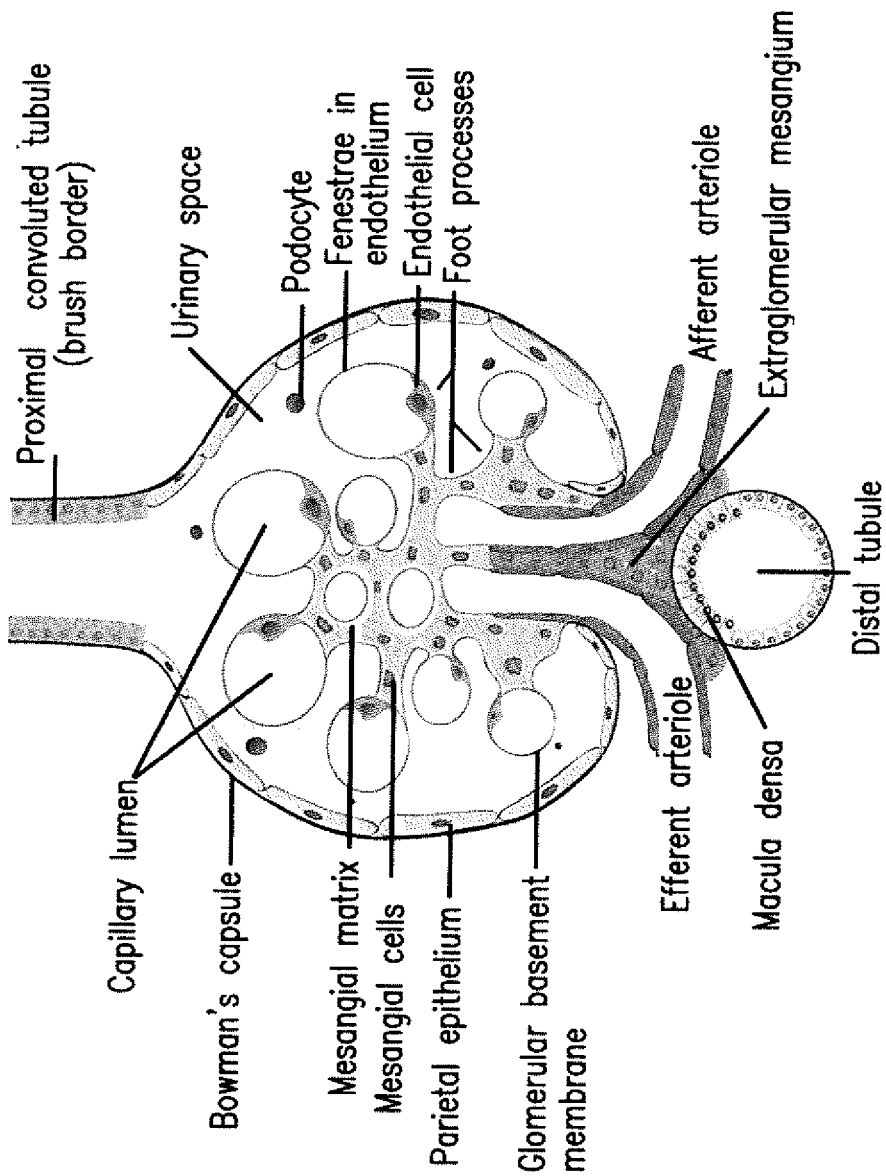
Figure 22C:
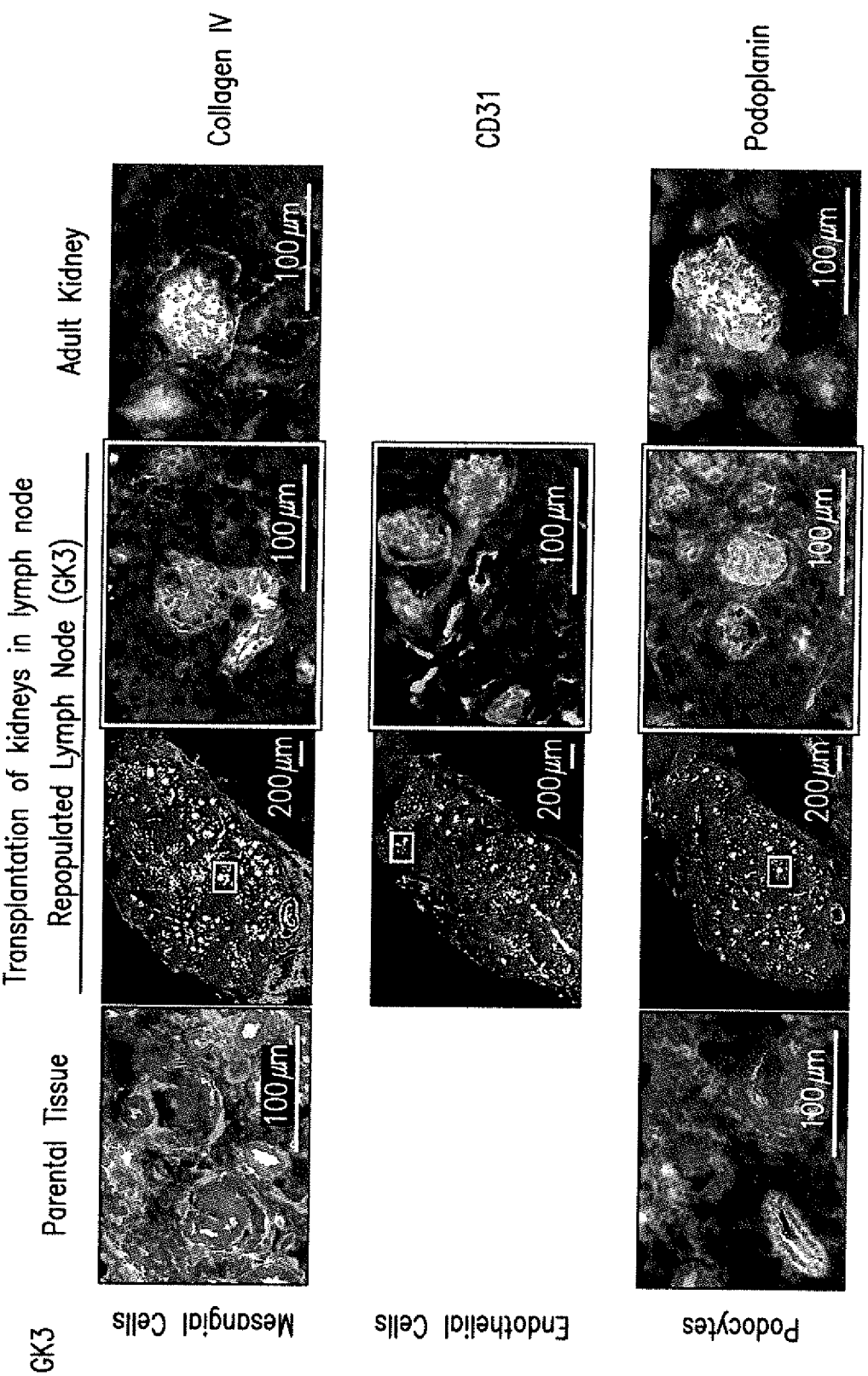
Figure 22D:
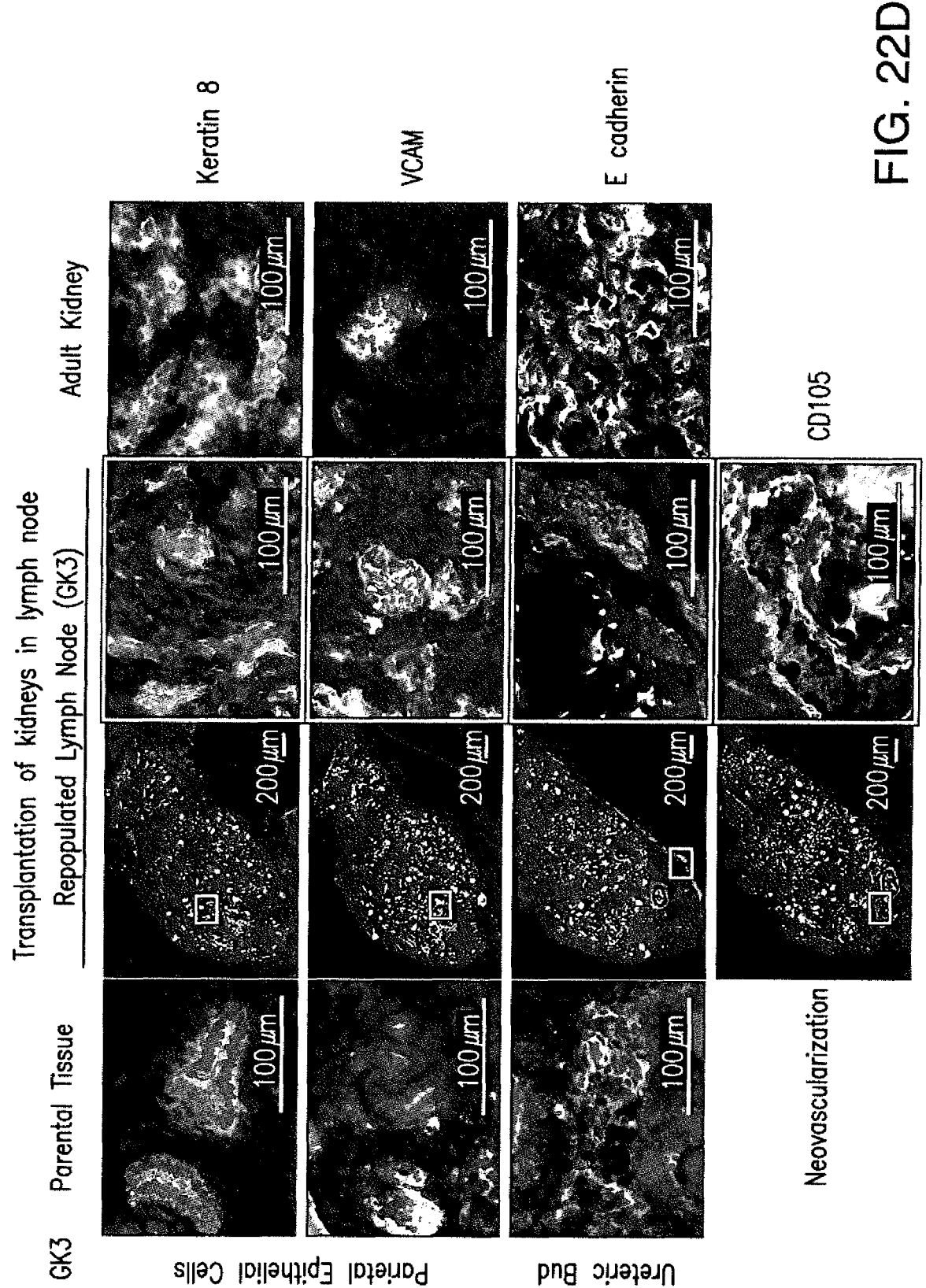

FIG. 21A-C. Transplantation of kidney tissue into lymph node.

FIG. 22A-D. Transplantation of kidney tissue into lymph node.

FIG. 23A-D. The lymph node is a permissive site for kidney organogenesis. (A). Schematic view of kidney transplantation into the lymph node. (B). Hematoxylin and Eosin (H&E) staining of a paraffin section of donor C57BL/6 GFP+ embryonic kidney showing S-shaped bodies (upper left); whole-mount jejunal lymph node of a C57BL/6 mouse 3 weeks after embryonic kidney transplantation (upper right), and picture of a frozen lymph node section stained for reticular fibroblasts and reticular fibers (ER-TR7), with the presence of GFP+ cells (lower). Nuclei were counterstained using Hoechst. (C). Picture of a frozen lymph node section with the presence of GFP+ cells (upper). Enlarged views of the collagen IV-stained boxed regions are shown (lower). Nuclei were counterstained using Hoechst. (D). Immunofluorescence staining for CD31, podoplanin, claudin-2, keratin-8, and erythropoietin (Epo) of frozen sections of a 3-week repopulated lymph node with the presence of GFP+ cells. Nuclei were counterstained using Hoechst.

Figure 24A:
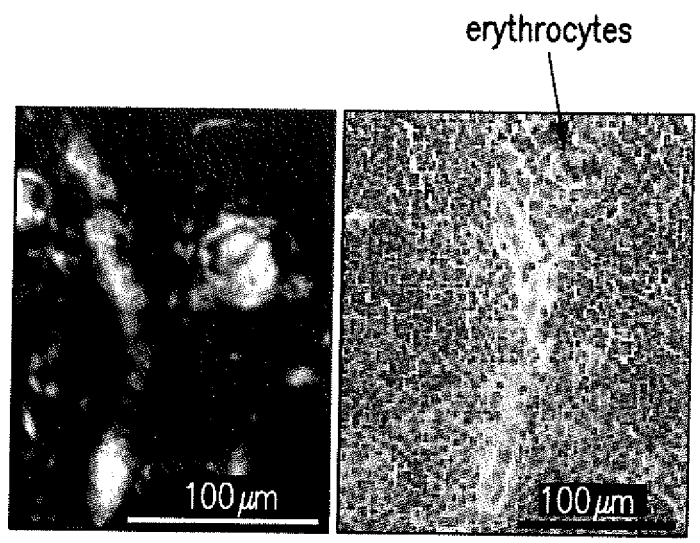
Figure 24B:
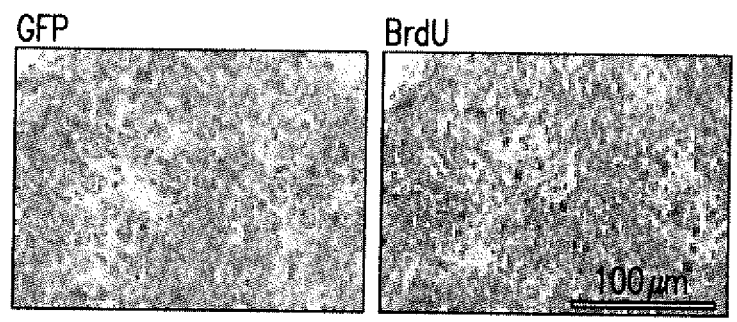
Figure 24C:
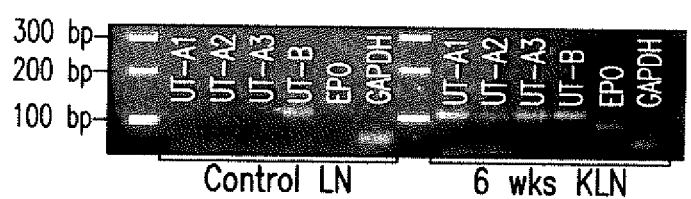

FIG. 24A-C. Proliferative and urine-concentrating ability of 6-week ectopic grafts. (A). GFP positivity (left) and H&E staining (right) of a frozen or paraffin section of a jejunal lymph node 6 weeks after transplantation. (B). Picture of paraffin lymph node sections stained for GFP or BrdU (AEC, red color). (C). Representative RT-PCR analysis for different urea transporters and erythropoietin (Epo) in lymph node 6 weeks after embryonic kidney injection as compared to a control lymph node.

Figure 25:
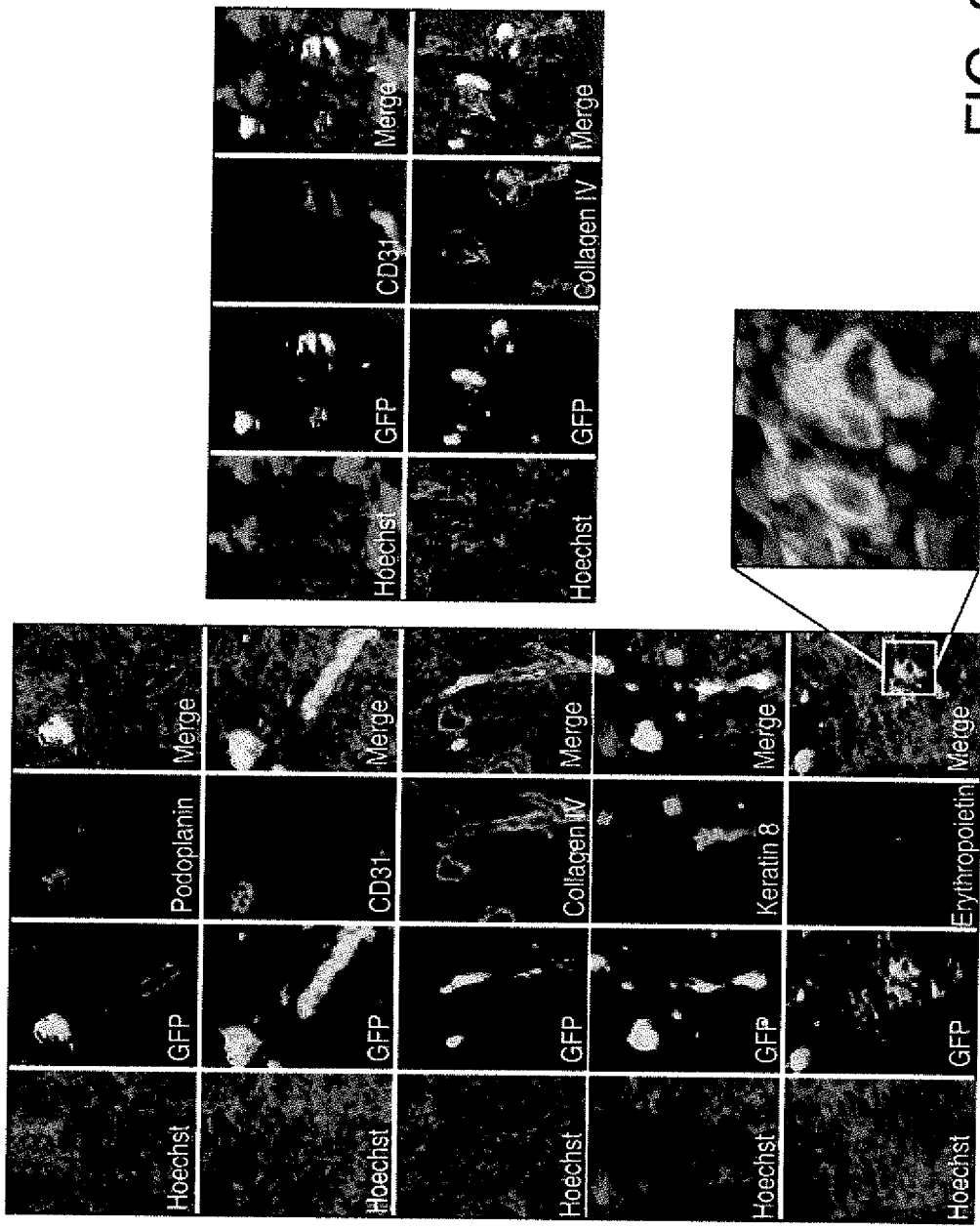

FIG. 25. Host cells vascularize the developing tissue. Immunofluorescence staining for podoplanin, CD31, collagen IV, keratin-8, and erythropoietin of lymph node frozen sections with the presence of GFP+ cells. Nuclei were counterstained using Hoechst.

FIG. 26A-F. Renal cyst development in repopulated lymph nodes. (A). Whole-mount jejunal lymph node of a C57BL/6 mouse 12 weeks after embryonic kidney transplantation showing GFP positivity (left), and hematoxylin and eosin (H&E) staining showing cysts (right). (B). Detail of cyst #1 epithelium stained with H&E, periodic acidschiff (PAS), masson's trichrome (TRI), picro-sirius red (PSR), GFP, BrdU, aquaporin-1 (AQP1), and sodium-potassium-chloride transporter 2 (NKCC2) (left), and of cyst #2-3 epithelium stained with H&E, PAS, TRI, PSR, GFP, BrdU, AQP1 and 2 (right, yellow arrows indicates vacuoles). (C). Details of proteinaceous material and fibers found inside cyst #1 (left) and of round globules found inside cyst #2 and 3 (right), after staining with H&E, PAS, TRI, and PSR. (D). Pictures of urinary crystals found inside cyst #1 (left), and Blood Urea Nitrogen (BUN) levels in serum and lymph node fluid of a transplanted mouse versus a control mouse (right). (E). Detail of cyst #3 epithelium stained with GFP. (F). Details of repopulated lymph node stained with H&E, PAS, TRI, and PSR, BrdU, or collagen IV showing glomerular and tubular alterations (black arrows indicate BrdU+ nuclei; yellow arrows indicates vacuoles).

FIG. 27A-D. Bone marrow-derived host cells contribute to mesangial cells and podocyte regeneration. (A). Fluorescence intensity profiles of GFP expressing leukocytes in peripheral blood of bone marrow chimeric mice. Blood of a wild type and a GFP+ mouse were used as negative and positive control, respectively. (B). Overview of experimental plan (IR, irradiation; EK, embryonic kidney; LN, lymph node). (C). Representative ectopic glomerulus grown inside lymph nodes of bone marrow chimeric mice, showing bone marrow-derived cell contribution to glomerular mesangium. Sections were stained with collagen IV antibody and nuclei were counterstained using Hoechst. (D). (left) I-III, pictures of a lymph node section from bone marrow chimeric mouse showing localization of bone marrow-derived cells in the kidney graft; IV-VI, enlarged view of pictures I-III. (right) Representative ectopic glomeruli as in C. Sections were stained with collagen IV, CD45, CD106, CD3, CD4, CD8, CD45R/B220, Ly6C/G, F4/80, CD31, podoplanin, WT-1 or Epcam. Nuclei were counterstained using Hoechst. Insets show the presence of GFP+CD45-, GFP+CD106+, or GFP+ WT1+ cell subsets inside the ectopic glomeruli.

Figure 28A:
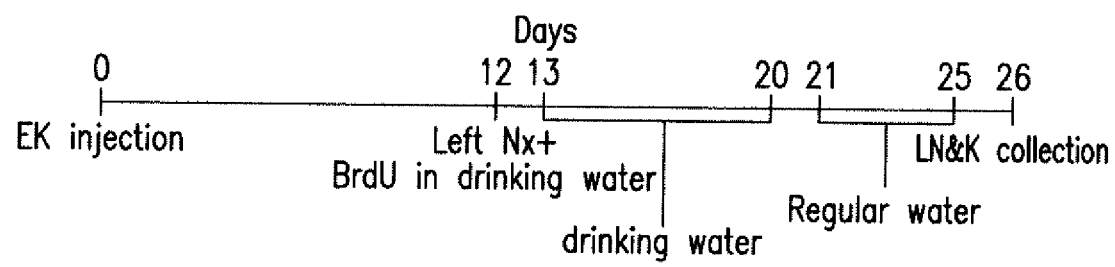
Figure 28B:
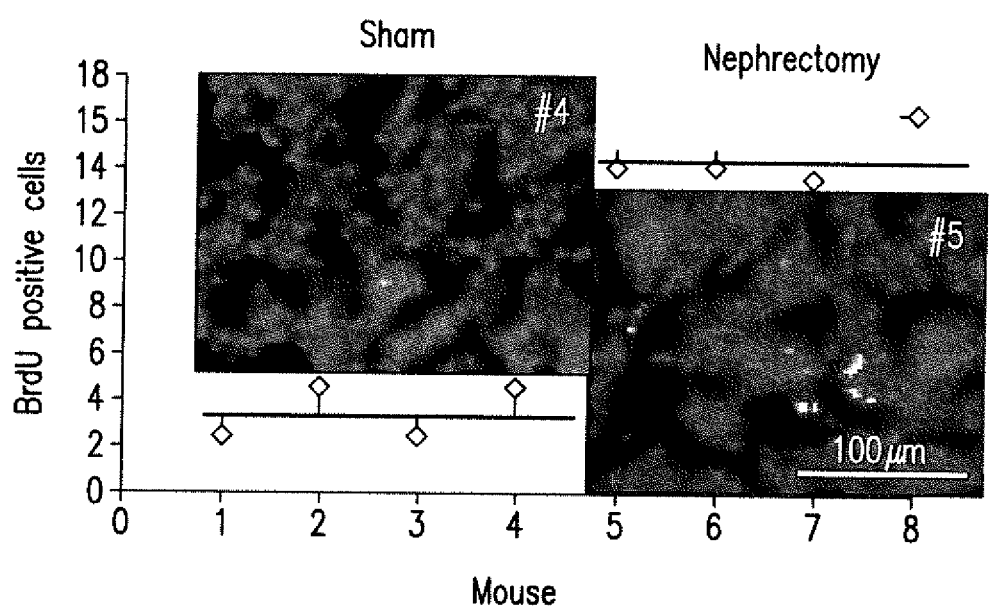
Figure 28C:
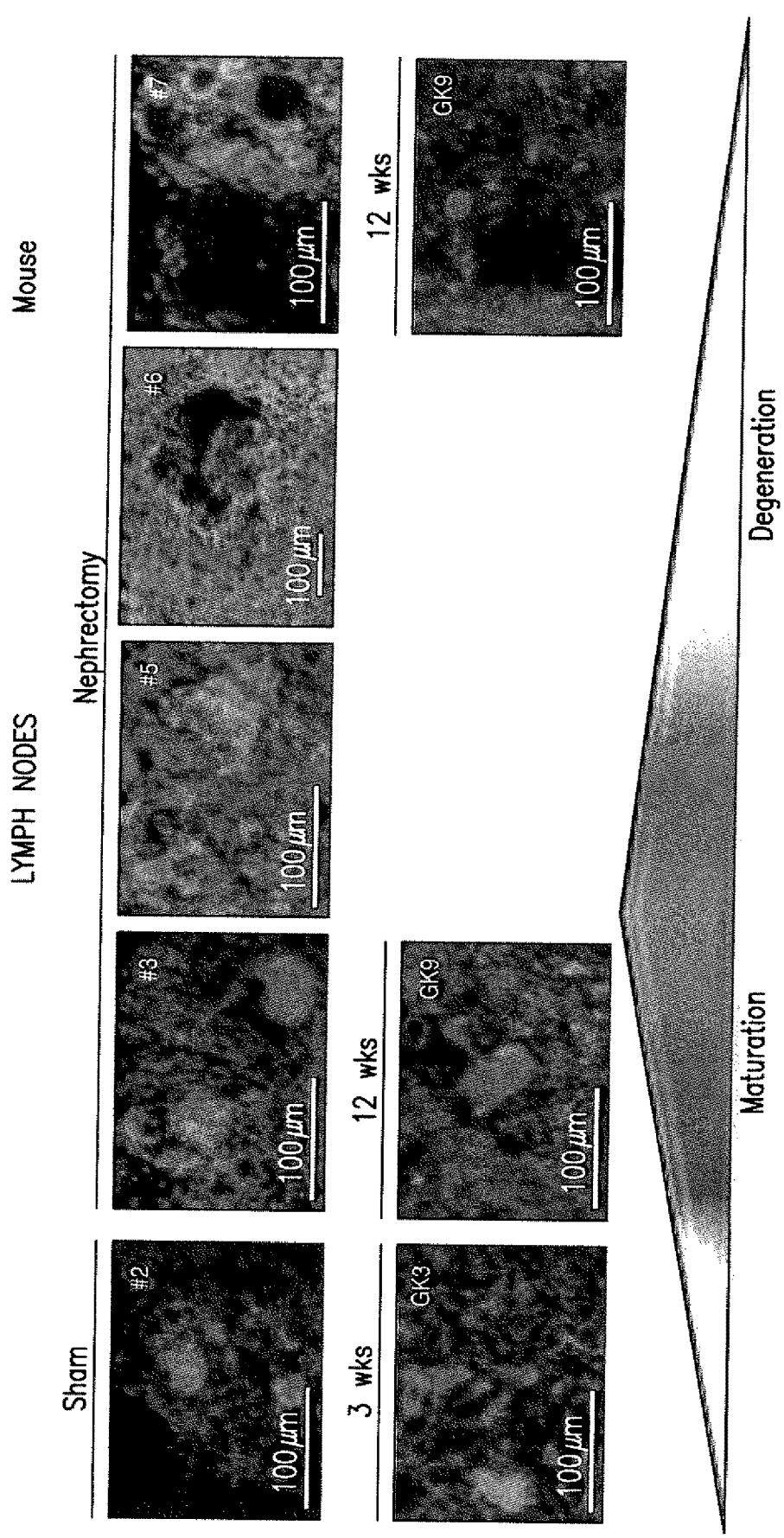

FIG. 28A-C. Nephrectomy accelerates kidney organogenesis and degeneration. (A). Overview of experimental plan (EK, embryonic kidney; Nx, nephrectomy; LN, lymph node; K, kidney; see Materials and Methods section for details). (B). Renal cell proliferation shown by bromodeoxyuridine (BrdU) incorporation. (C). Representative ectopic grafts of nephrectomized mice and sham-operated controls (upper) as compared to 3 or 12 weeks ectopic grafts (bottom).

Figure 29:
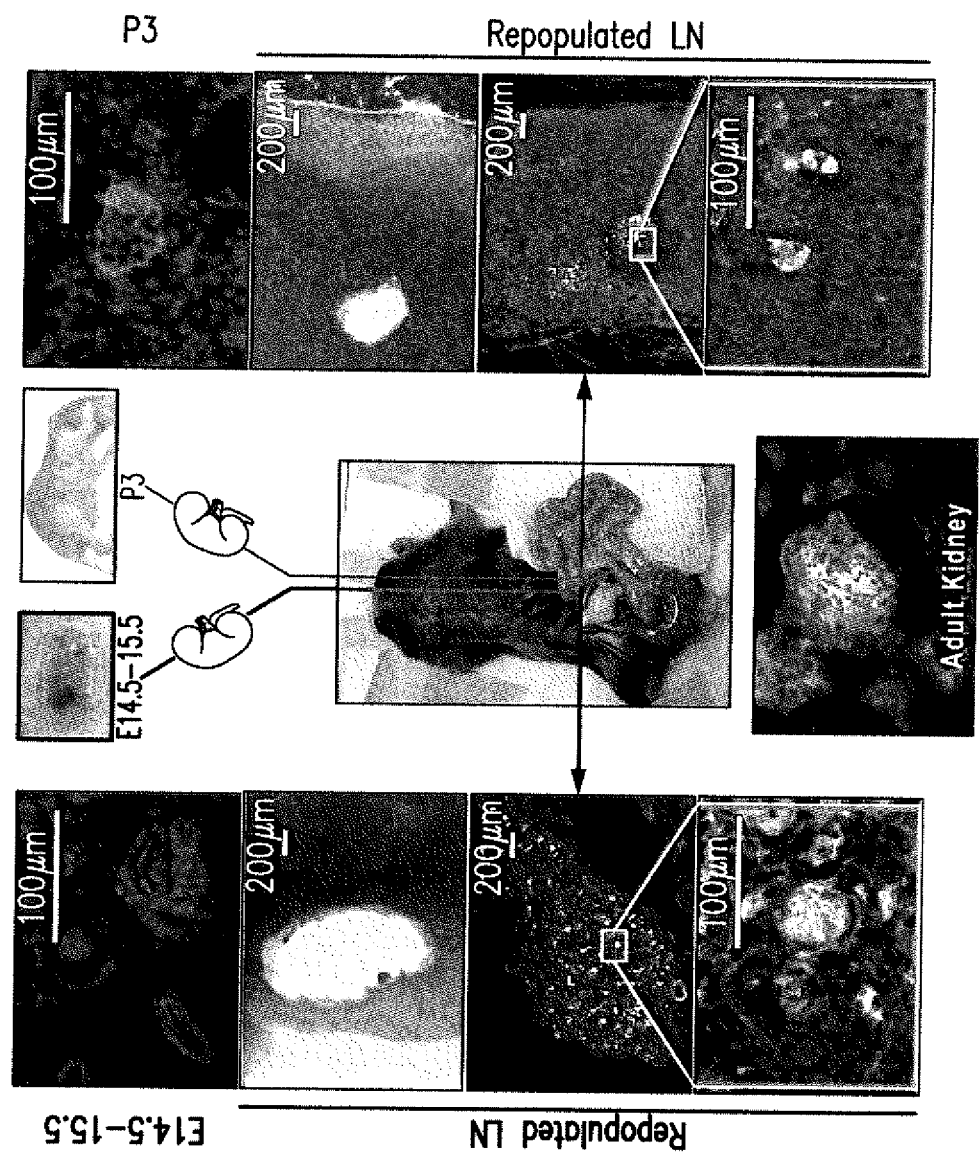

FIG. 29. Middle Panel: Schematic view of transplantation of E14.5-15.5 or P3 kidney into the lymph node, and immunofluorescence staining for podoplanin of an adult kidney section isolated from a GFP+ mouse (lower). Left and Right Panels, from the top to the bottom: immunofluorescence staining for podoplanin of frozen sections of embryonic (left) or new born (right) kidney showing different maturity; whole-mount mouse jejunal lymph node 3 weeks after embryonic (left) or new born (right) kidney transplantation, showing different engraftment; immunofluorescence staining for podoplanin of lymph node frozen sections 3 weeks after transplantation of embryonic (left) or new born (right) kidney. Nuclei were counterstained using Hoechst.

Figure 30A:
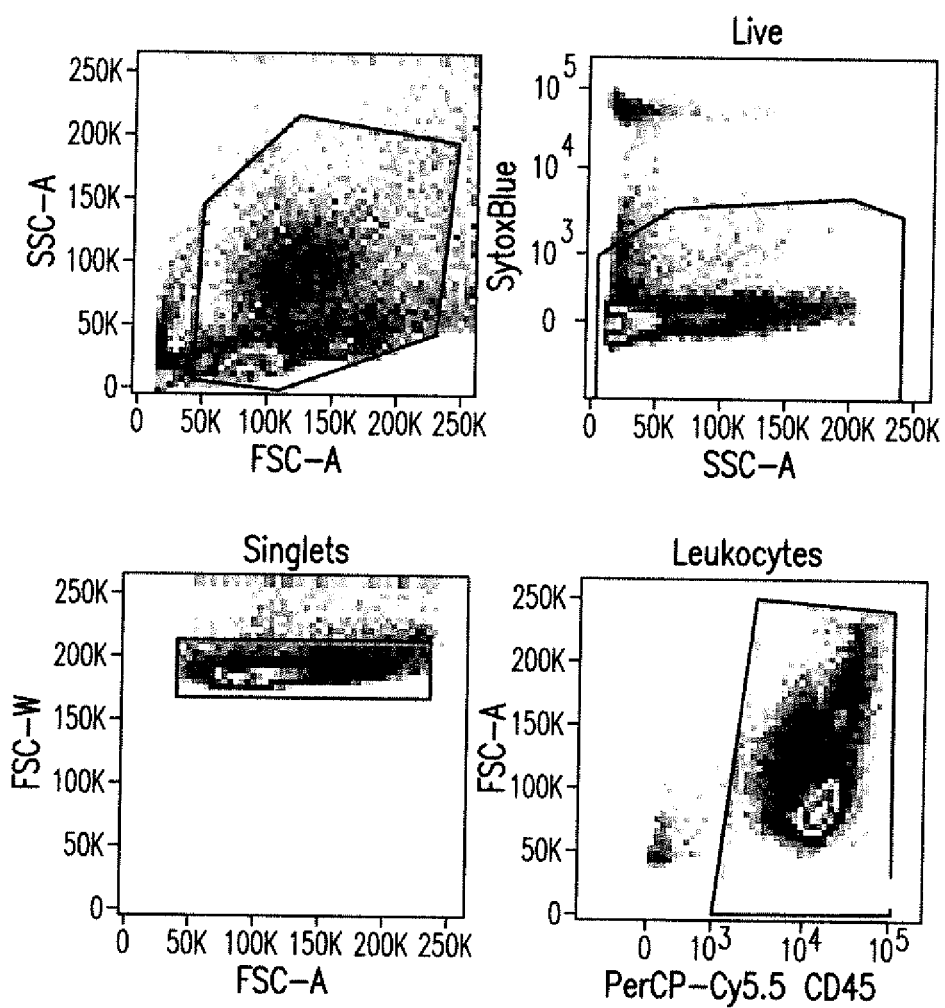
Figure 30A:
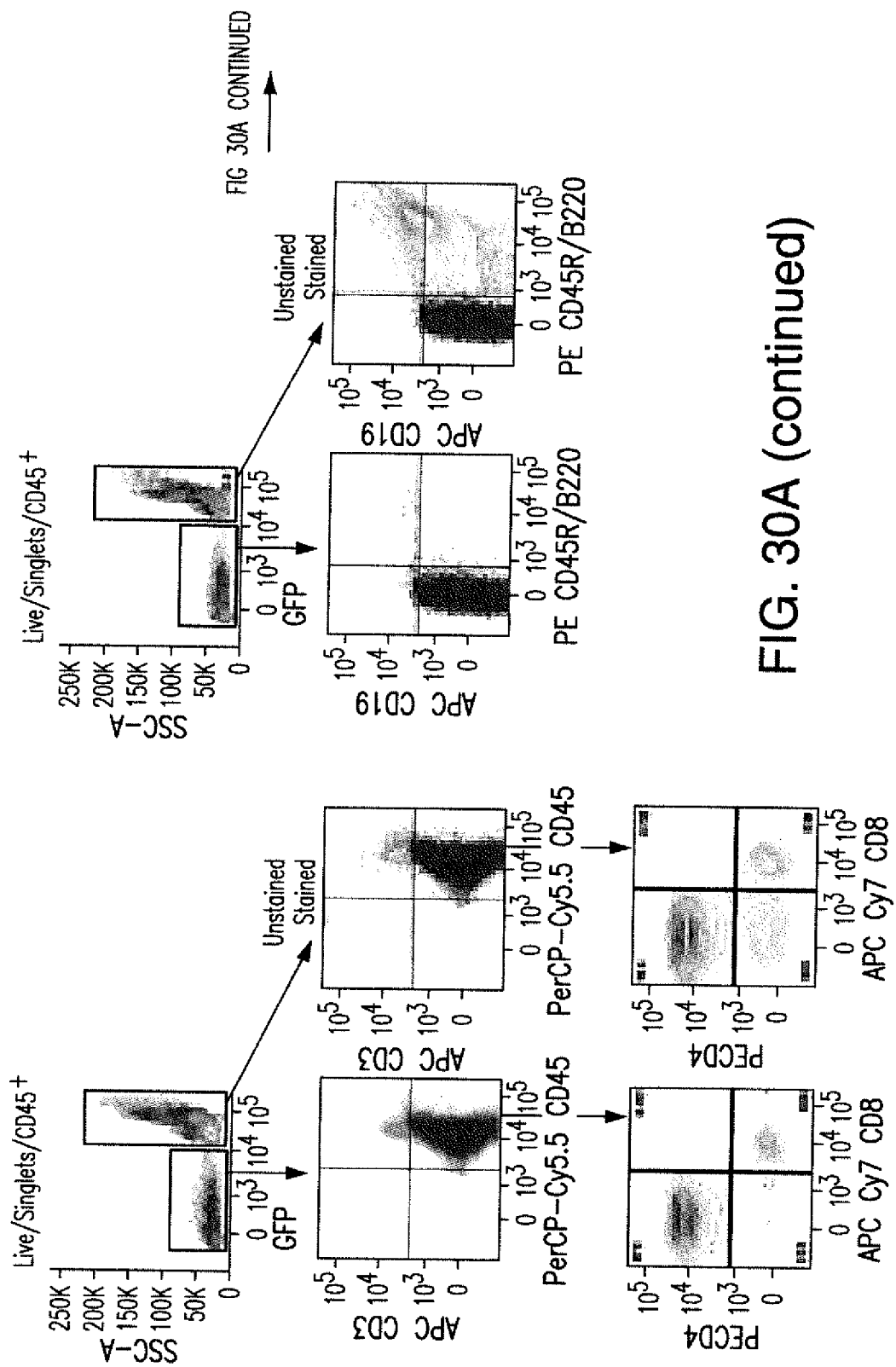
Figure 30A:
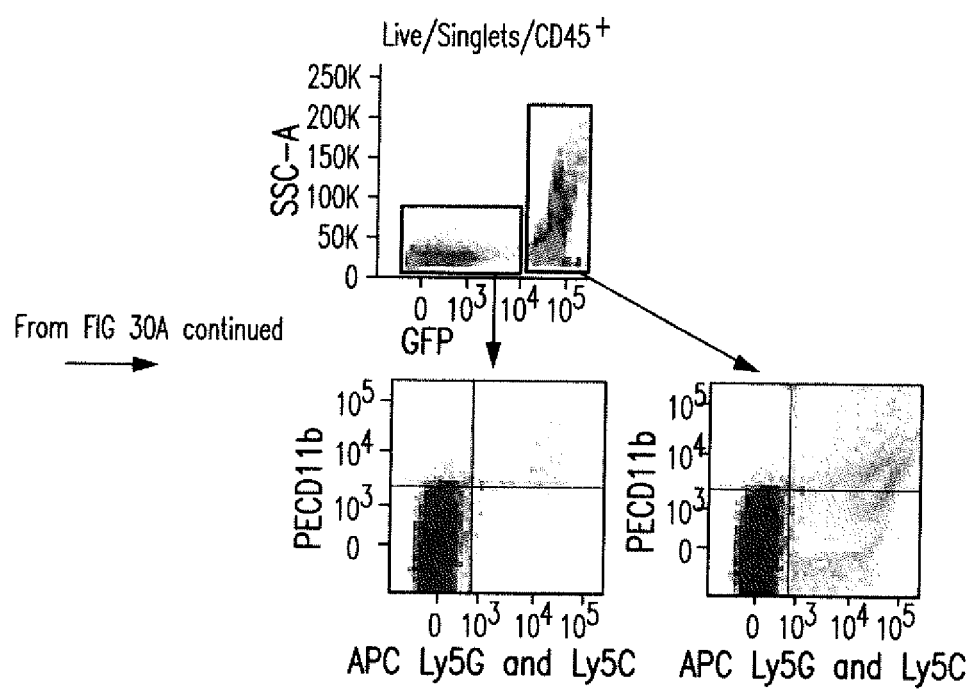
Figure 30B:
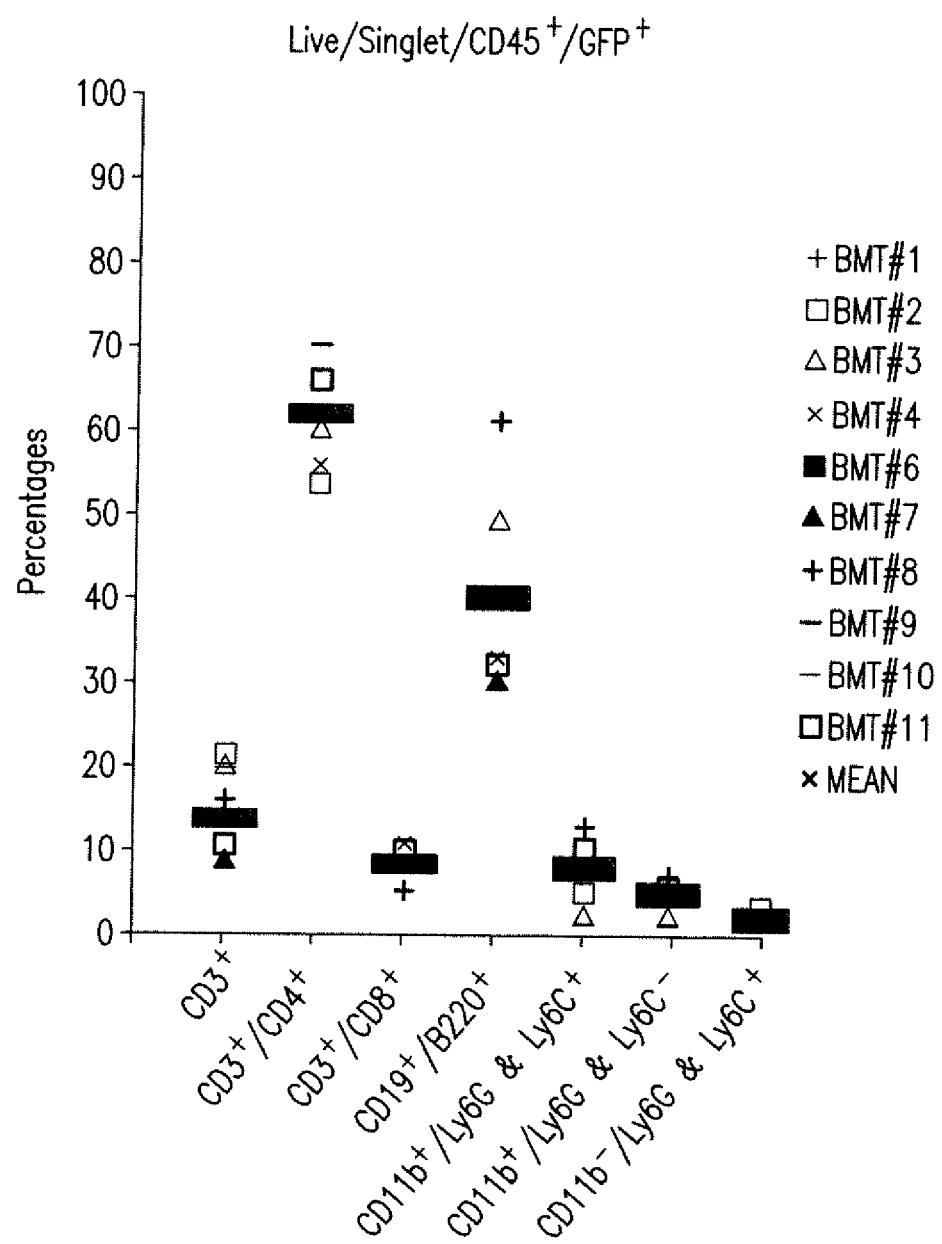
Figure 30C:
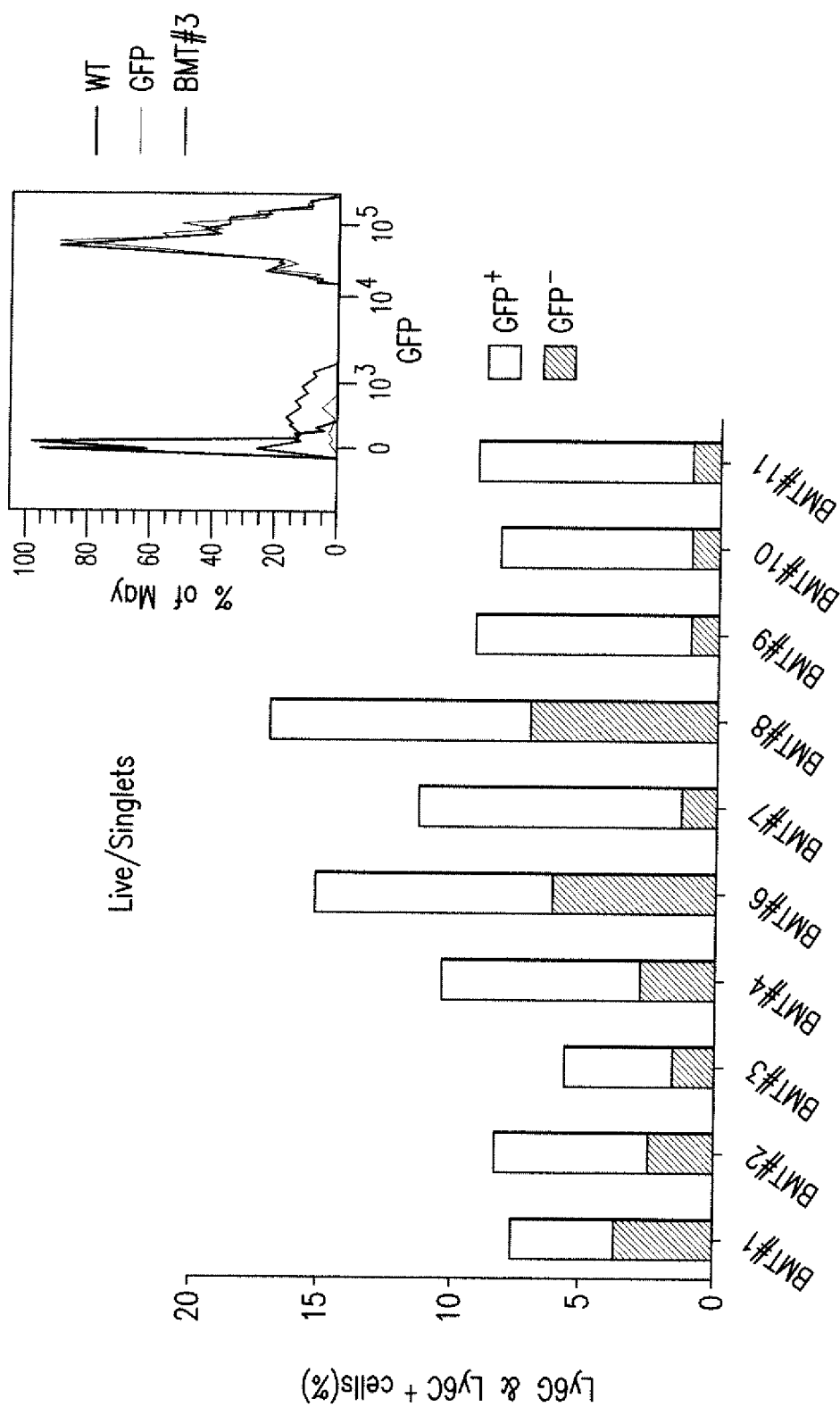

FIG. 30A-C. (A). Gating strategy for fluorescence-activated cell sorting (FACS) analysis of peripheral blood of chimeric mice 6 weeks after bone marrow transplant. Blood cells were gated on live cells, singlets, leukocytes (upper). Both GFP+ and GFP-leukocyte subsets were analyzed for CD3, CD19/CD45R or CD11b/Ly6G-LY6C (middle). The CD3+ cell population was further analyzed for CD4/CD8 (lower). (B). Dot plot graph showing percentages of different GFP+ leukocyte populations from bone marrow chimeric mice. C. Stacked bar graph showing percentages of donor GFP+/Ly6G-LY6C+ versus host GFP-/Ly6G-LY6C+ cells. Cells were gated on live, Ly6G-LY6C, GFP. A representative histogram profile is shown. Blood from a wild type and a GFP+ mouse were used as control.

Figure 31:
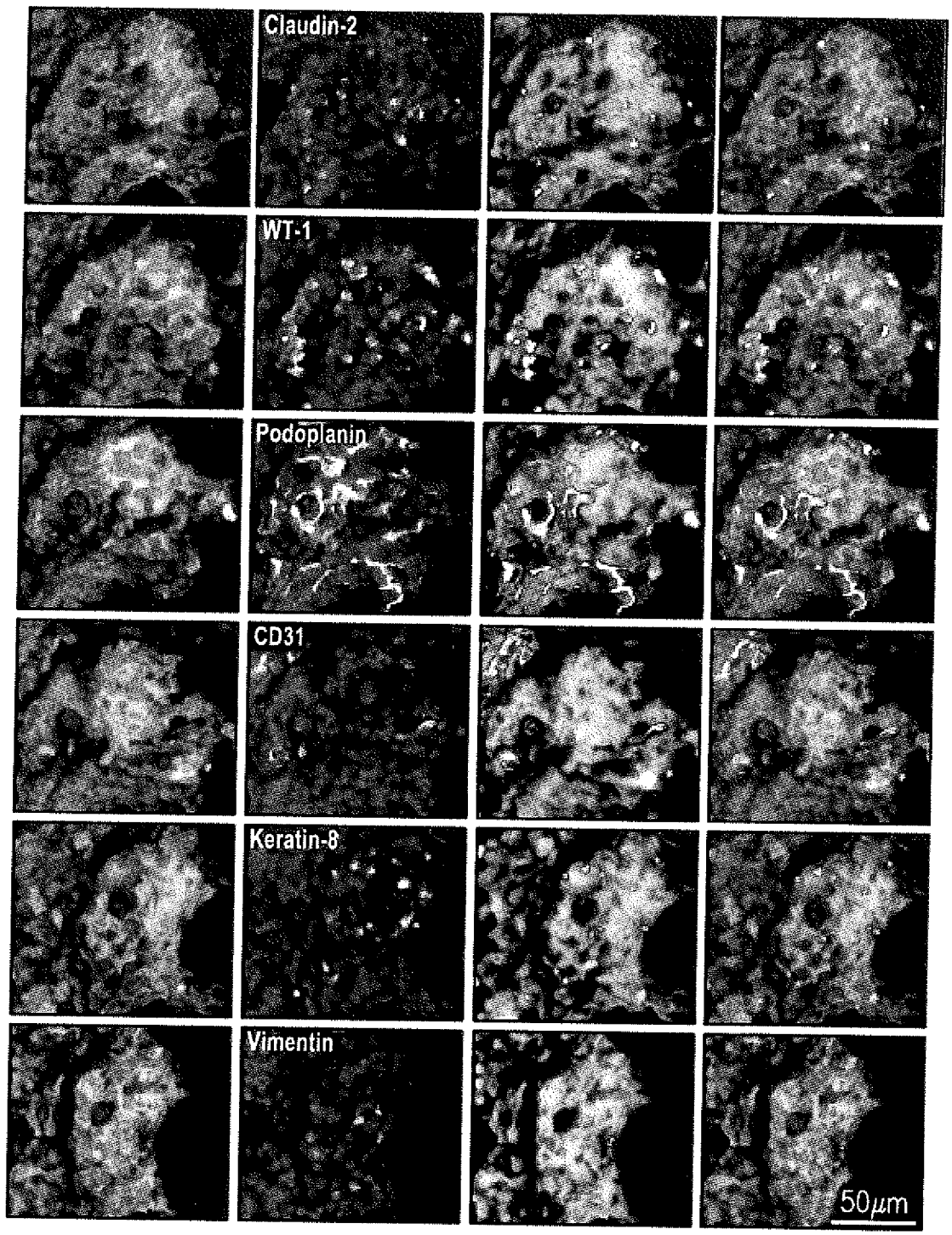

FIG. 31. Representative ectopic glomerulus grown inside lymph nodes of bone marrow chimeric mice 10 weeks after transplantation showing nodular lesion. Sections were stained with claudin-2, WT-1, podoplanin, CD31, keratin-8, and vimentin. Nuclei were counterstained using Hoechst.

Figures 32A, 32B:
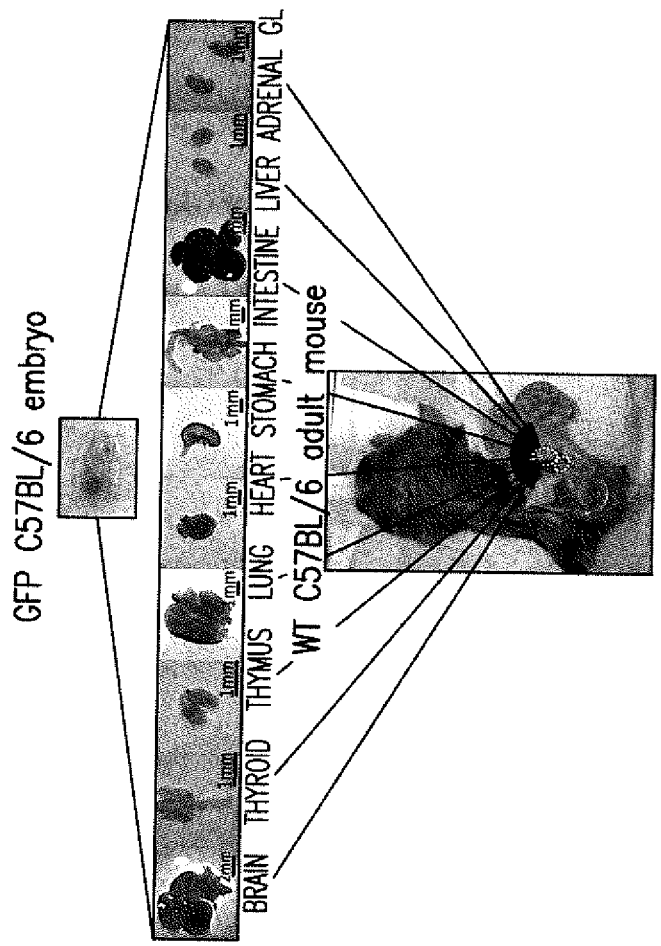

FIG. 32A-C. Astrogenesis in the developing ectopic brain. (A). Schematic view of transplantation of multiple embryonic tissues into the lymph node (scale bar, 1 mm). (B). Table shows percentages of engraftment into the mouse lymph node for different tissues. (C1). Hematoxylin and Eosin (H&E) staining of a paraffin section of donor embryonic brain (upper left); whole-mount jejunal lymph node 3 weeks after embryonic brain transplantation (GB3 LN, upper right), and pictures of frozen lymph node (GB3 and GB4 LN) sections with the presence of GFP+ cells (lower). Nuclei were counterstained using Hoechst. (C2). Mouse embryonic brain transversal section (upper), and pictures of GB3 and GB4 LN sections stained for GFAPδ with the presence of GFP+ cells (lower). Nuclei were counterstained using Hoechst.

FIG. 33A-D. Granulocyte/macrophage progenitor accumulation following embryonic thymus transplantation into the lymph node (LN), and host contribution in the generation of the ectopic thymic cortex. (A). Gating strategy for FACS analysis of peripheral blood of mice (M1-M5) receiving thymus transplant into their lymph nodes. Blood cells were gated on live cells, leukocytes, singlets, granulocyes/myeloid cells or lymphocytes. (B). Representative fluorescence intensity histograms of granulocyes/myeloid cells from M2 analyzed for Ly6G-Ly6C (upper) or CD11b (lower) at 0, 3, 6, 12, or 21 weeks after thymus transplant. (C). Representative flow cytometric contour plots of granulocyes/myeloid cells from M2 stained for Ly6G-Ly6C and CD11b, and gated on CD11b+/Ly6G-Ly6C-/low, CD11b+/Ly6G-Ly6Cint, and CD11b+/Ly6G-Ly6Chigh at 0, 3, 6, 12, or 21 weeks after thymus transplant. (D). Dot plots showing frequency of CD11b+/Ly6G-Ly6C-/low, CD11b+/Ly6G-Ly6Cint, and CD11b+/Ly6G-Ly6Chigh at 0, 3, 6, 12, or 21 weeks after thymus transplant. Each symbol represents one mouse, and the horizontal bars represent the median values. * $p<0.05$,  $p<0.01$, * $p<0.001$.

Figure 34A:
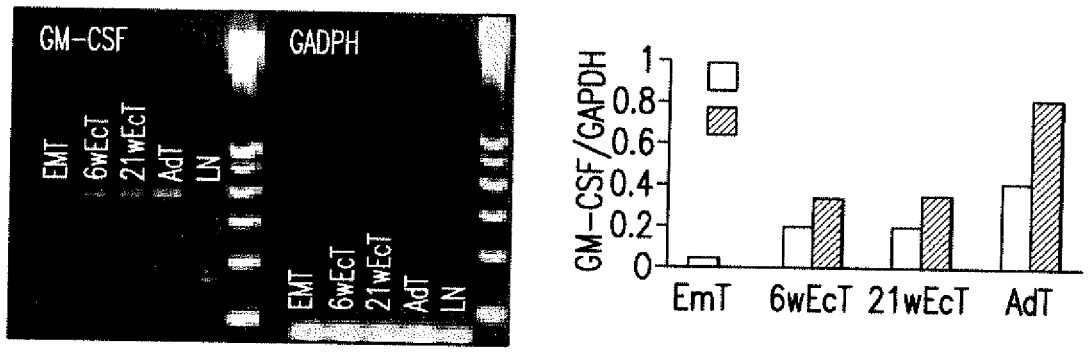
Figure 34B:
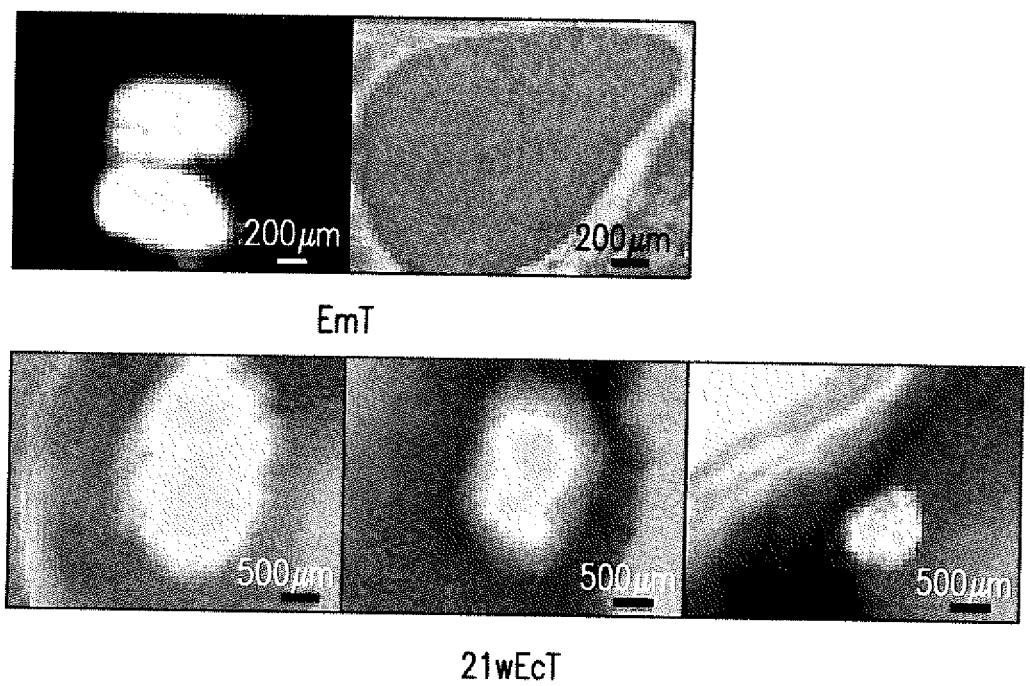
Figure 34C:
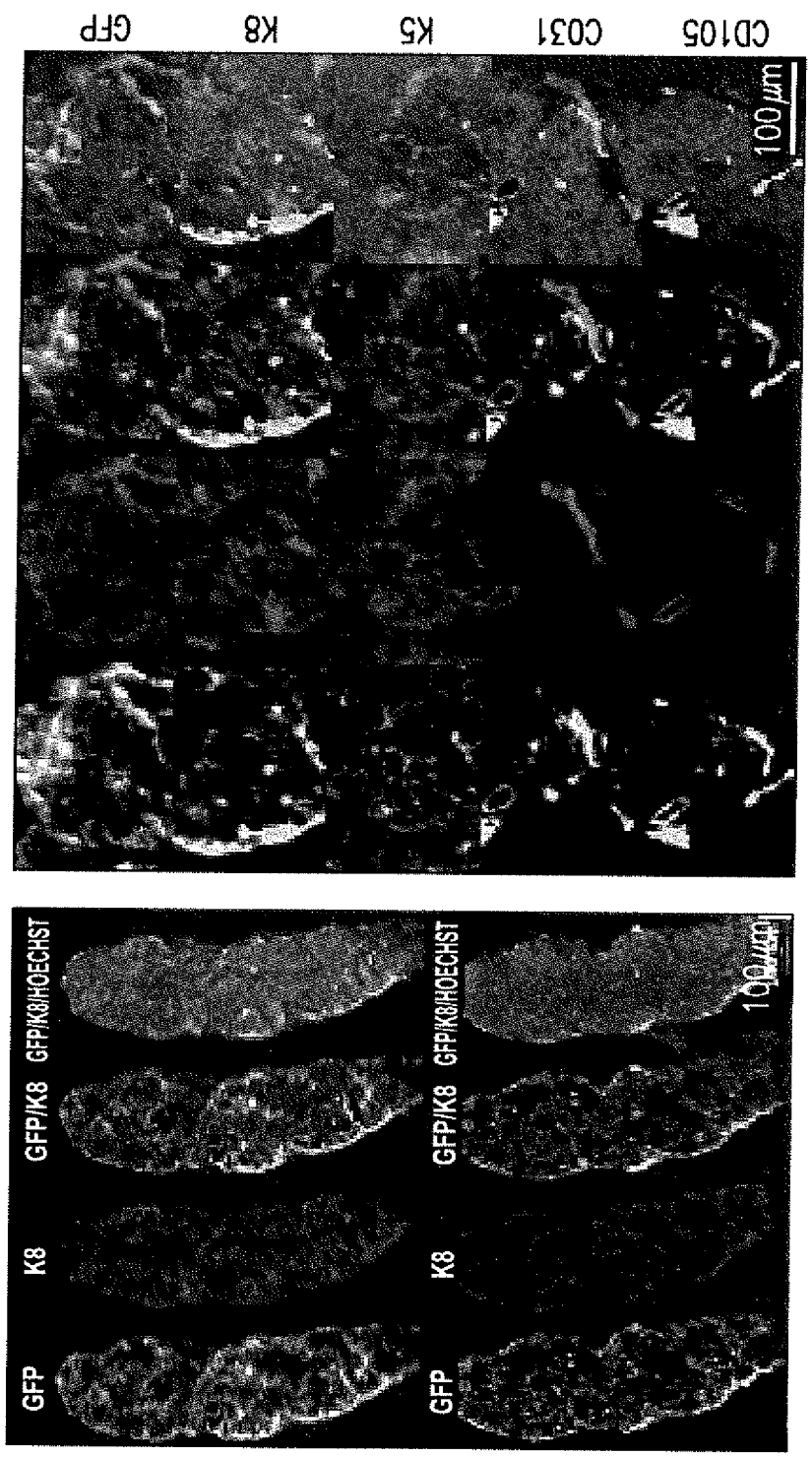

FIG. 34A-C. Contribution of the host in the generation of the ectopic thymic cortex. (A). Agarose gel electrophoresis of PCR products following semi-quantitative RT-PCR analysis for GM-CSF (expected amplicon size of 431 bp) in embryonic thymus (EmT), 6-(6wEcT) or 21-week ectopic thymus (21wEcT), and adult thymus (AdT). Wild type lymph node (LN) was used as a negative control. Amplification of GAPDH was used as an internal control. The densitometric scanning data from two experiments are shown as bar graphs of GM-CSF/GAPDH ratio on the right (6wEcTs were isolated from M4 and M5, while 21wEcTs were isolated from M1 and M3). (B). Picture of thymus glands isolated from a C57BL/6 GFP+ embryo (upper left) and H&E staining of a paraffin section of embryonic thymus (EmT, upper right); whole-mount mouse jejunal lymph nodes 21 weeks after embryonic thymus transplantation, showing different engraftment (21wEcT, lower). (C). Immunofluorescence staining for keratin 8 (K8) or keratin 5 (K5) of 21-week ectopic thymus from M2 with the presence of GFP+ cells (left). Nuclei were counterstained using Hoechst. Enlargements of K8 and K5 stainings are shown on the right, together with stainings of GFP, CD31, and CD105 (CD31 and CD105 pictures were taken from a lymph node isolated from M6).

Figure 35A:
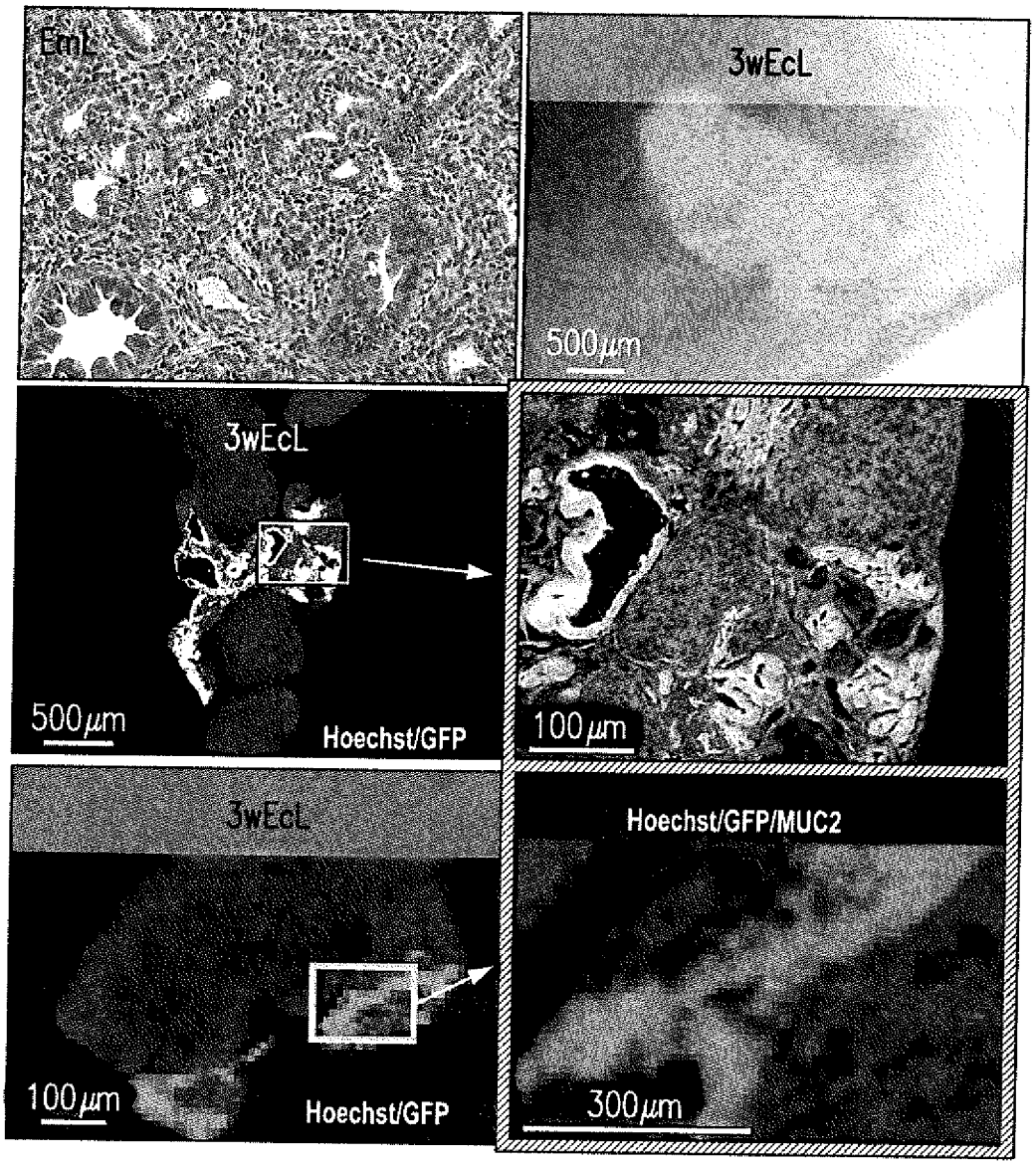
Figure 35B:
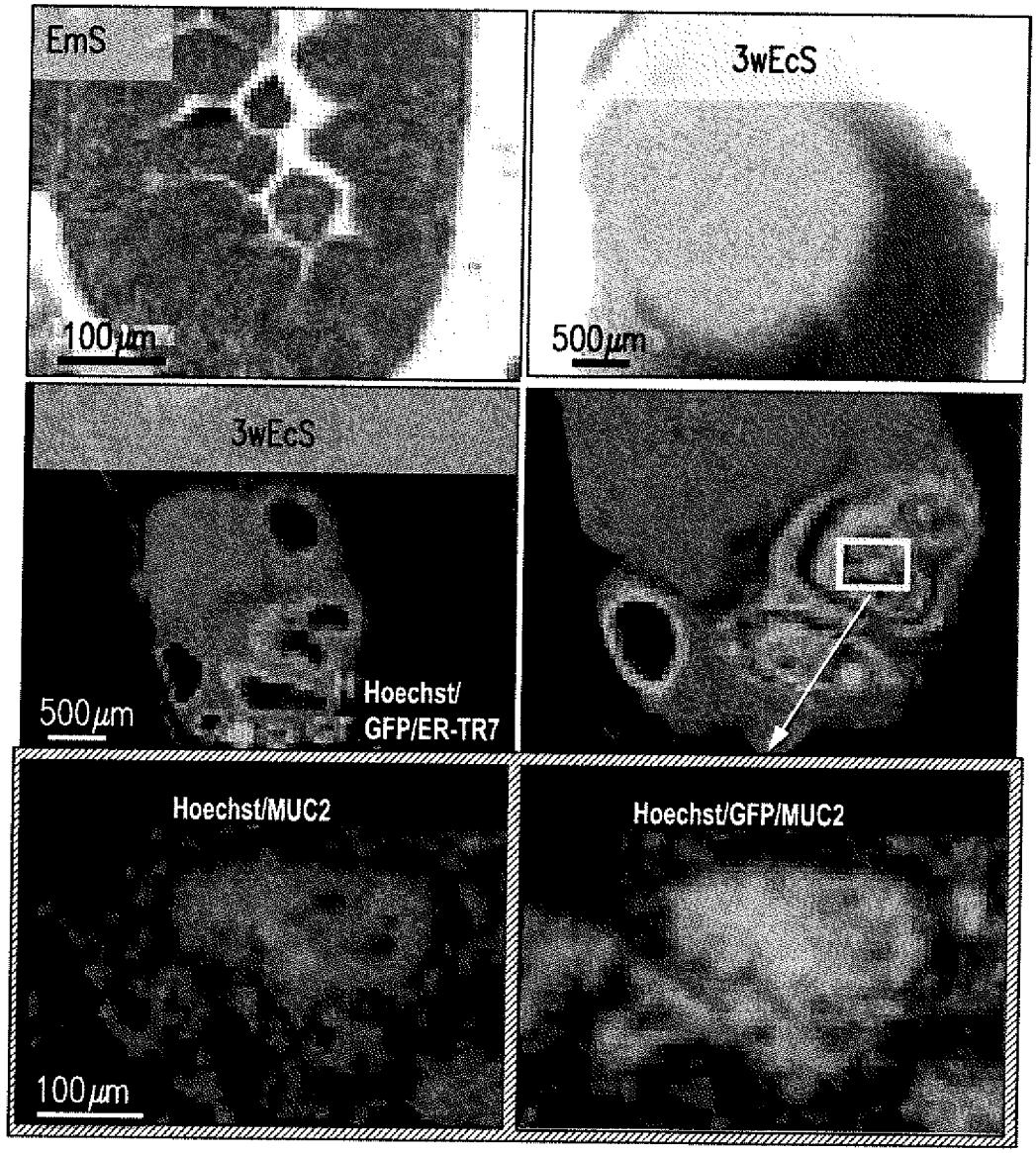
Figure 35C:
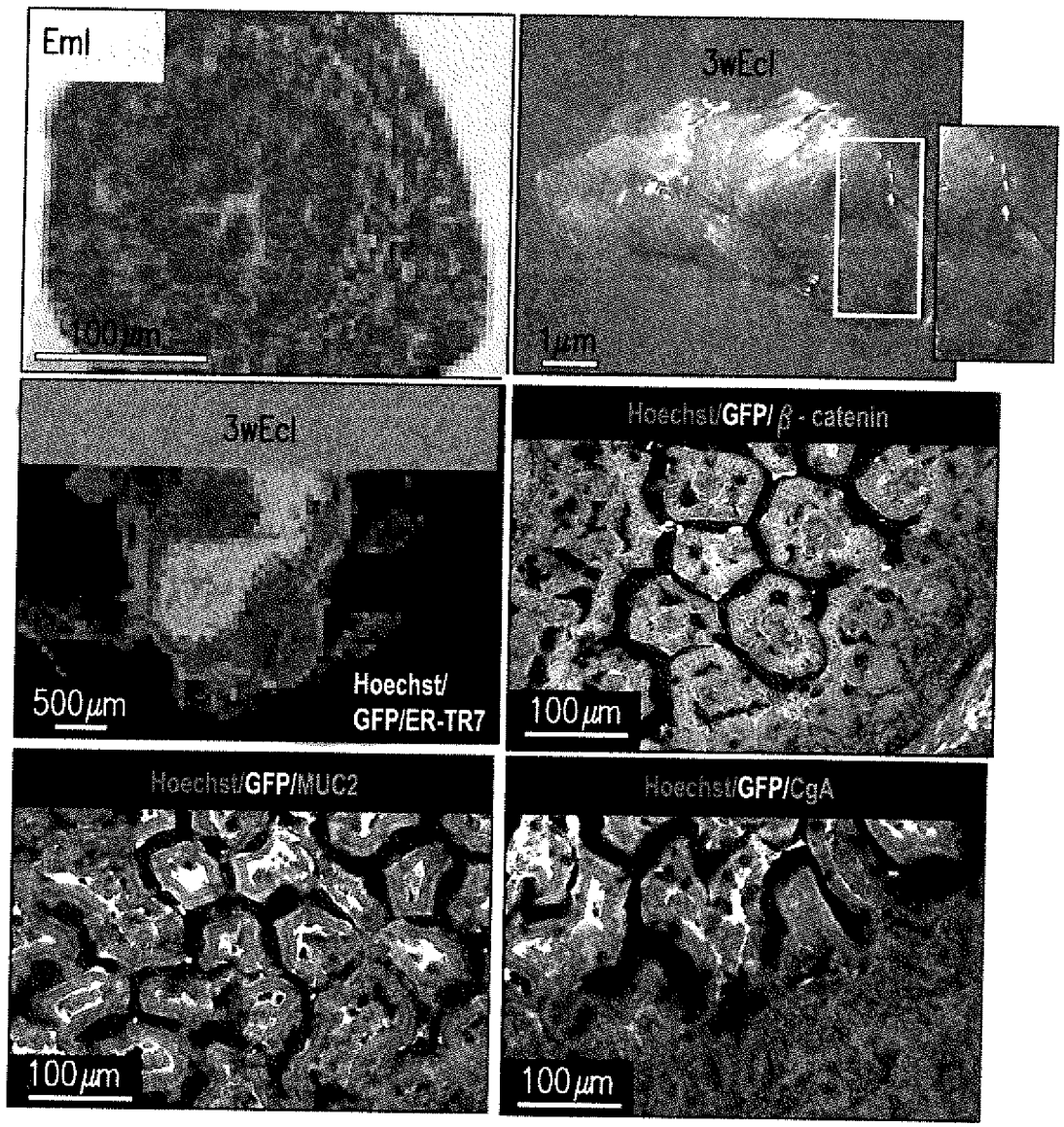

FIG. 35A-C. Presence of terminally differentiated, mucus-producing cells in ectopic lung, stomach and intestine tissues. (A-C). Each panel shows H&E staining of a paraffin section of donor embryonic lung (EmL), stomach (EmS) or intestine (EmI); whole-mount jejunal lymph node 3 weeks after transplantation of embryonic lung (3wEcL), stomach (3wEcS) or intestine (3wEcI), and pictures of frozen lymph node sections stained with specific markers with the presence of GFP+ cells. Nuclei were counterstained using Hoechst (ER-TR7, Reticular Fibroblasts and Reticular Fibres; CgA, chromogranin A).

Figure 36:
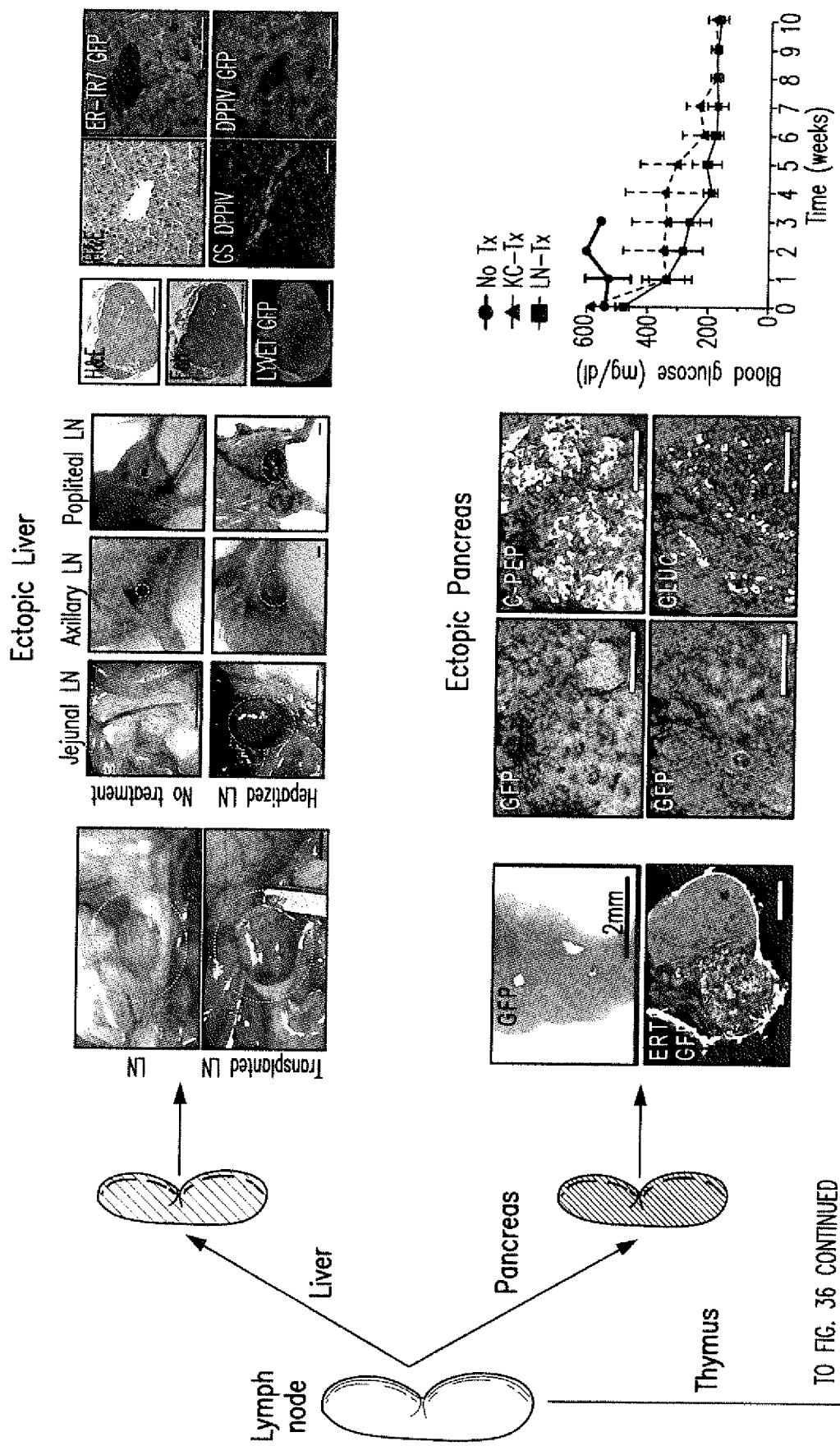
Figure 36:
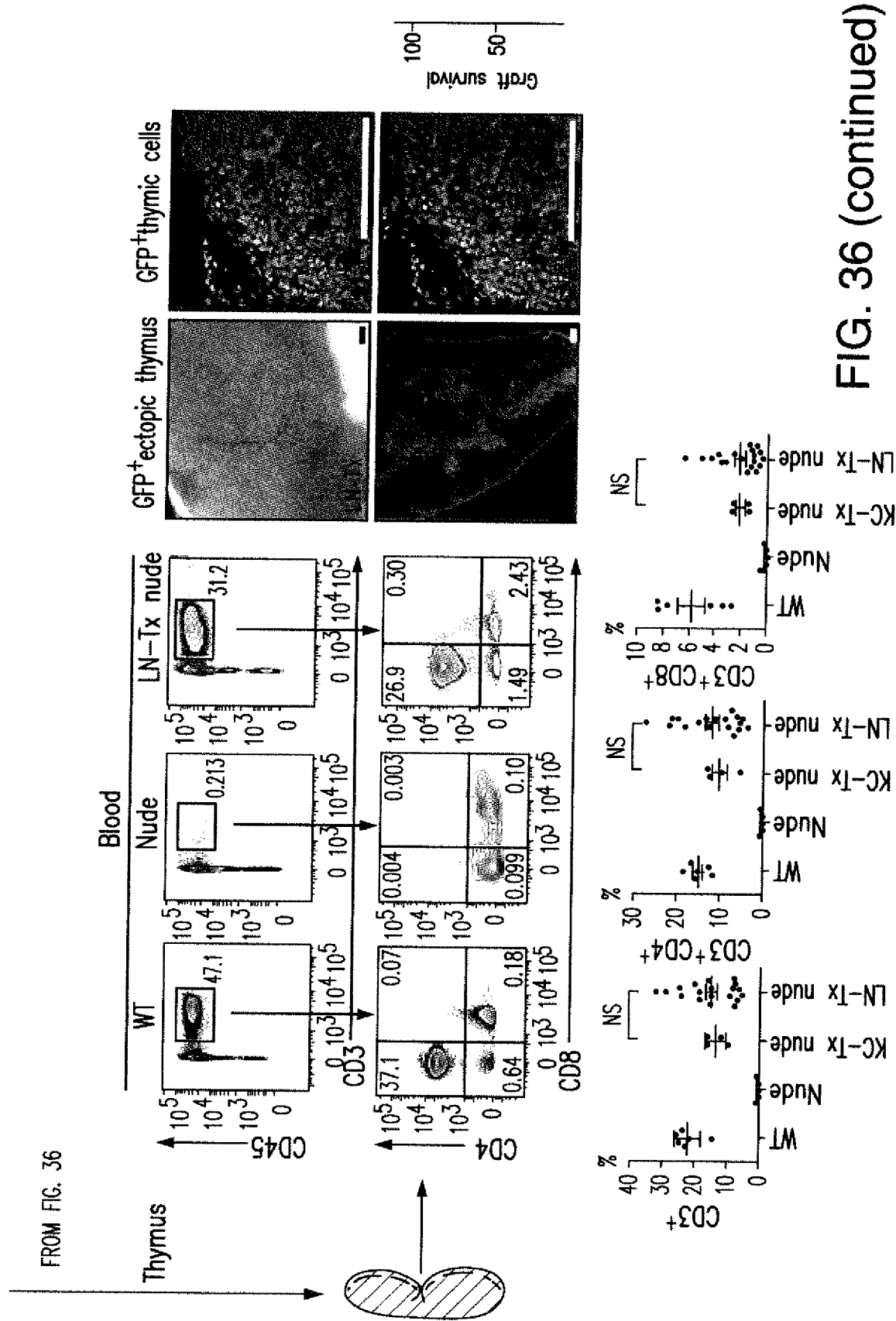

FIG. 36. Ectopic liver, pancreas and thymus has been successfully grown in lymph node tissue.

FIG. 37. Experimental plan for assessing the utility of transplanted thymus in mediating acceptance of allografts. 129 Fah−/− mice were transplanted with neonatal (d2-4) Balb/c GFP thymus in the lymph node (LN). An immunosuppression regiment consisting of MR-1 and rapamycin was started concomitantly. 6 weeks after thymus transplant, mice were either given skin grafts or hepatocyte transfers to assess ability of thymus to mediate acceptance of subsequent allogeneic grafts. Mice receiving just immunosuppression (IS controls) were used as controls.

Figure 38A:
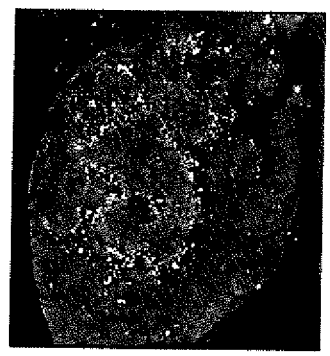
Figure 38B:
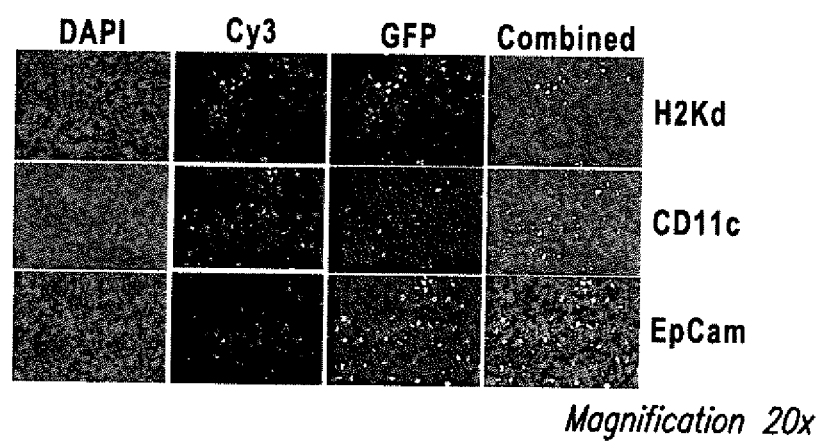
Figure 38C:
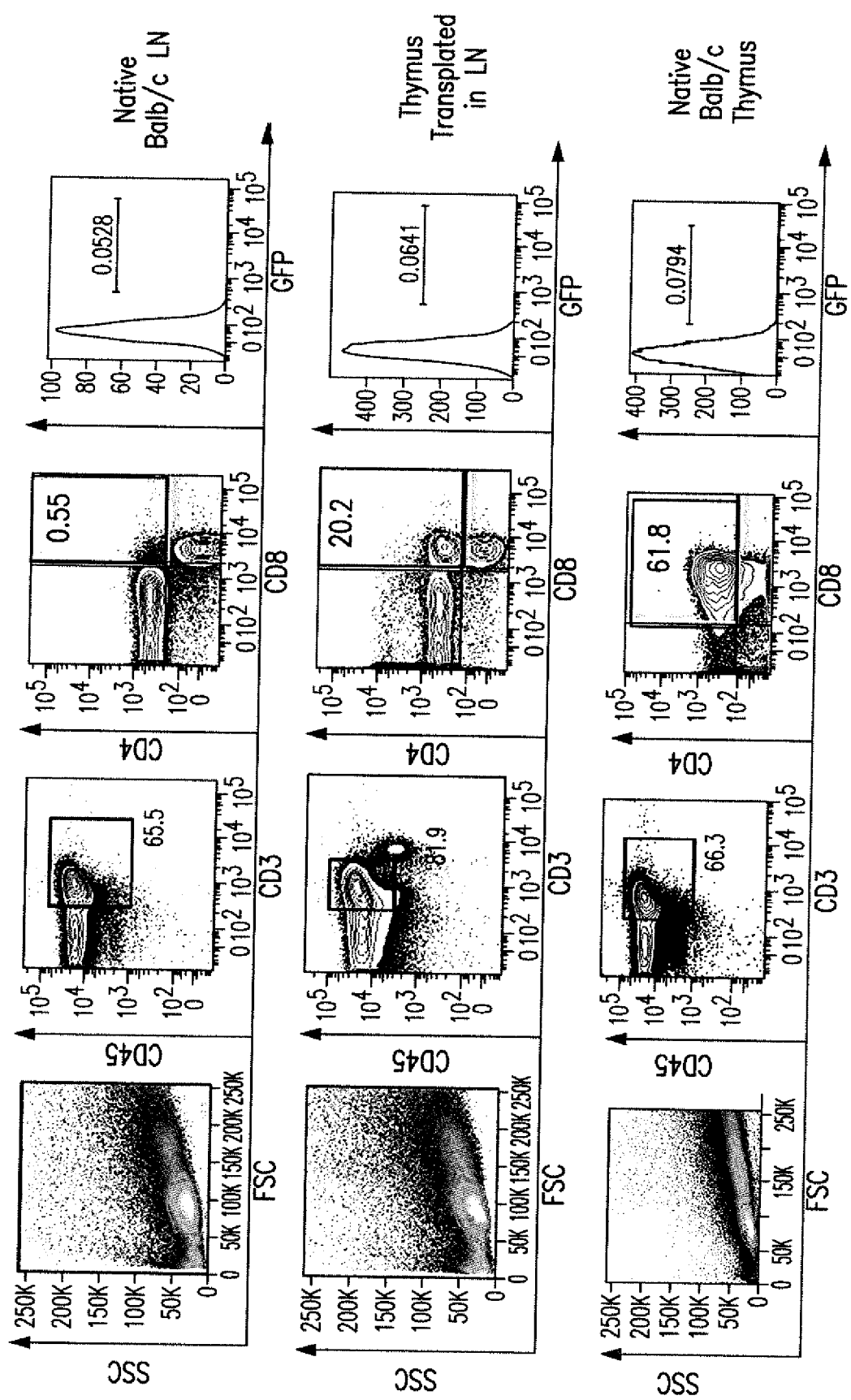
Figure 39B:
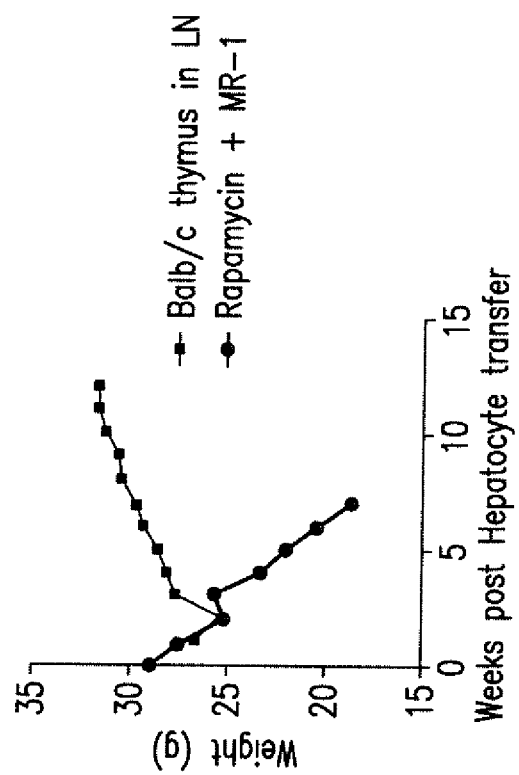
Figure 39A:
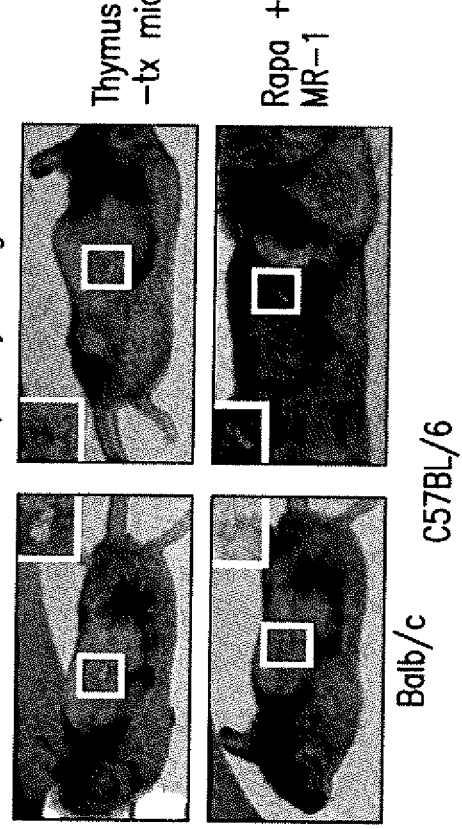
Figure 39C:
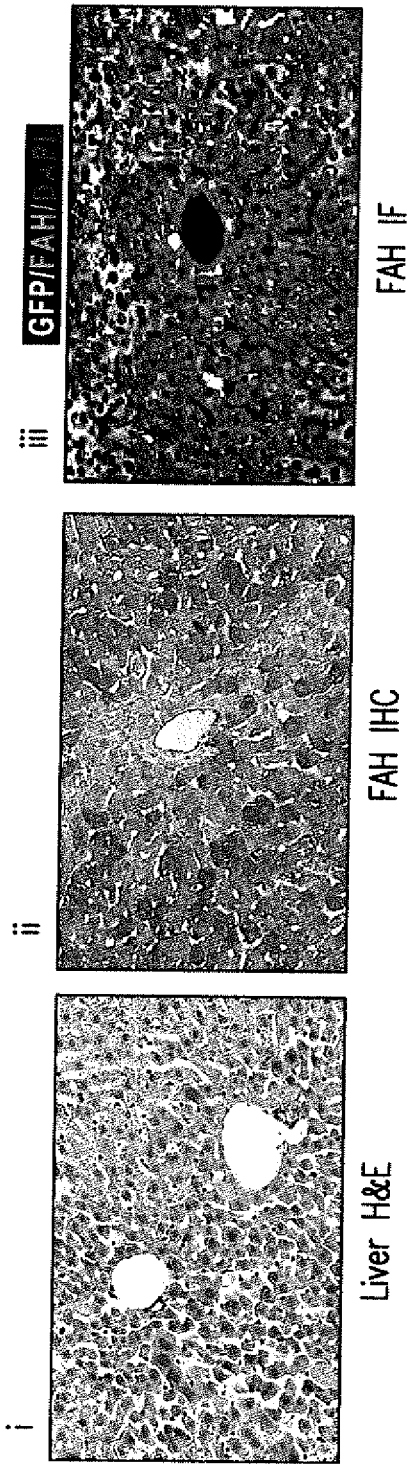
Figure 39D:
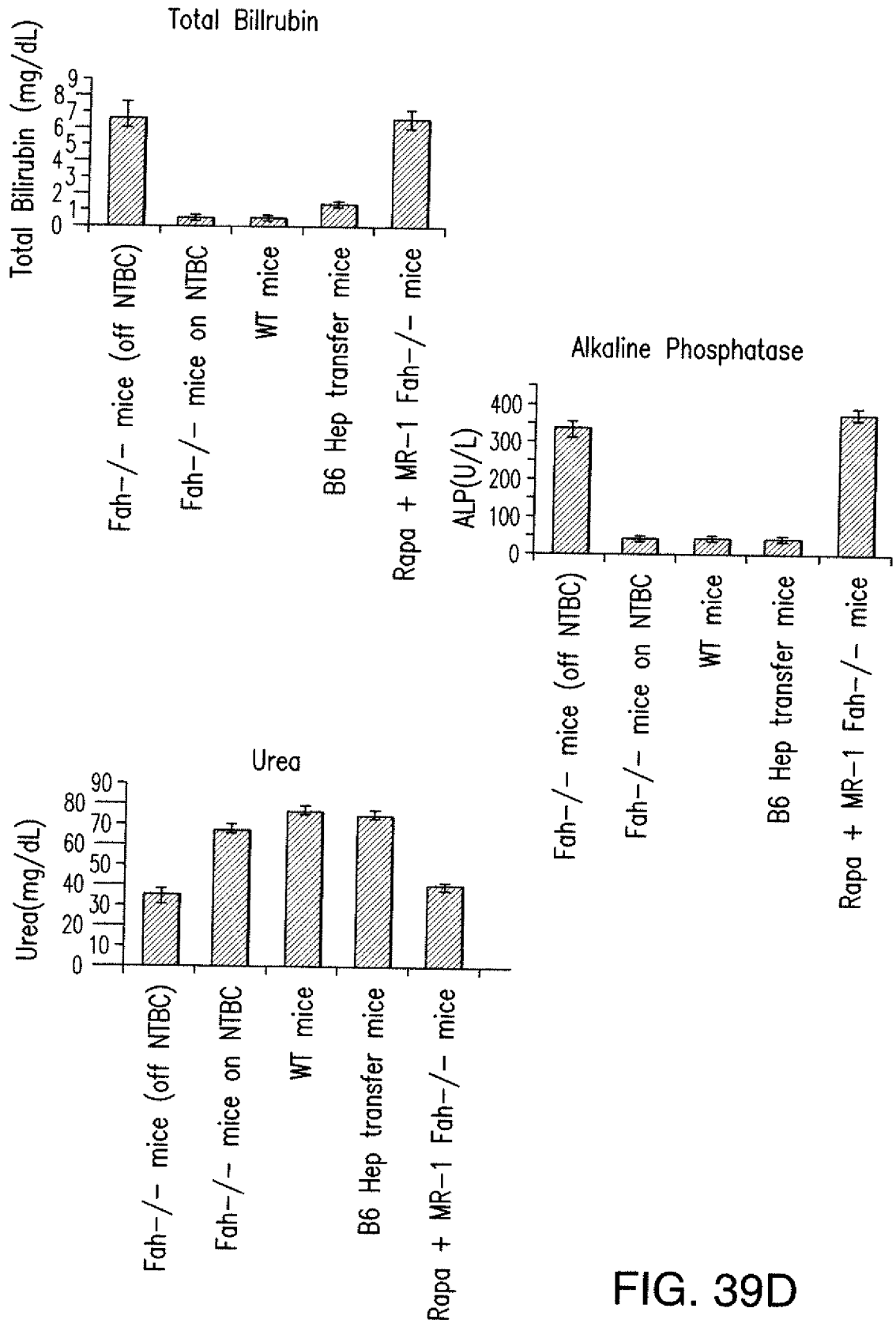

FIG. 38A-C. (A) Presence of donor-specific GFP+ cells in the lymph node (LN) of 129sv mice transplanted with Balb/c-GFP neonatal thymus in the lymph node. (B) GFP+ cells in thymus-transplanted LN were positive for CD11c and EpCam, markers of thymic dendritic cells (DCs) and epithelial cells, respectively. (C) Thymus-transplanted LN showed presence of CD4/CD8 double-positive (DP) T cells (a marker of T cell development), similar to a regular thymus. No presence of DP T cells in a nontransplanted LN.

FIG. 39A-D. Long-term acceptance of allogeneic hepatocytes mediated by ectopic thymus in the lymph node. (A) C57BL6/J and Balb/c skin grafts in 129.Fah−/− mice receiving Balb/c thymus (B) Rescue of liver failure as evidenced by weight gain and survival in Balb/c thymus-transplanted 129.Fah−/− mice receiving Balb/c hepatocytes. (C) Liver in Balb/c hepatocyte transferred mice showed normal liver morphology by hematoxylin and eosin (H&E) staining (i) and positivity for FAH by immunohistochemistry (IHC) (ii). (iii) shows the presence of transplanted GFP+ Balb/c hepatocytes that are also positive for FAH by immunofluorescence (IF). (D) Balb/c thymus-transplanted mice show normal levels of liver enzymes in the serum after Balb/c hepatocyte transfer.

Figure 40A:
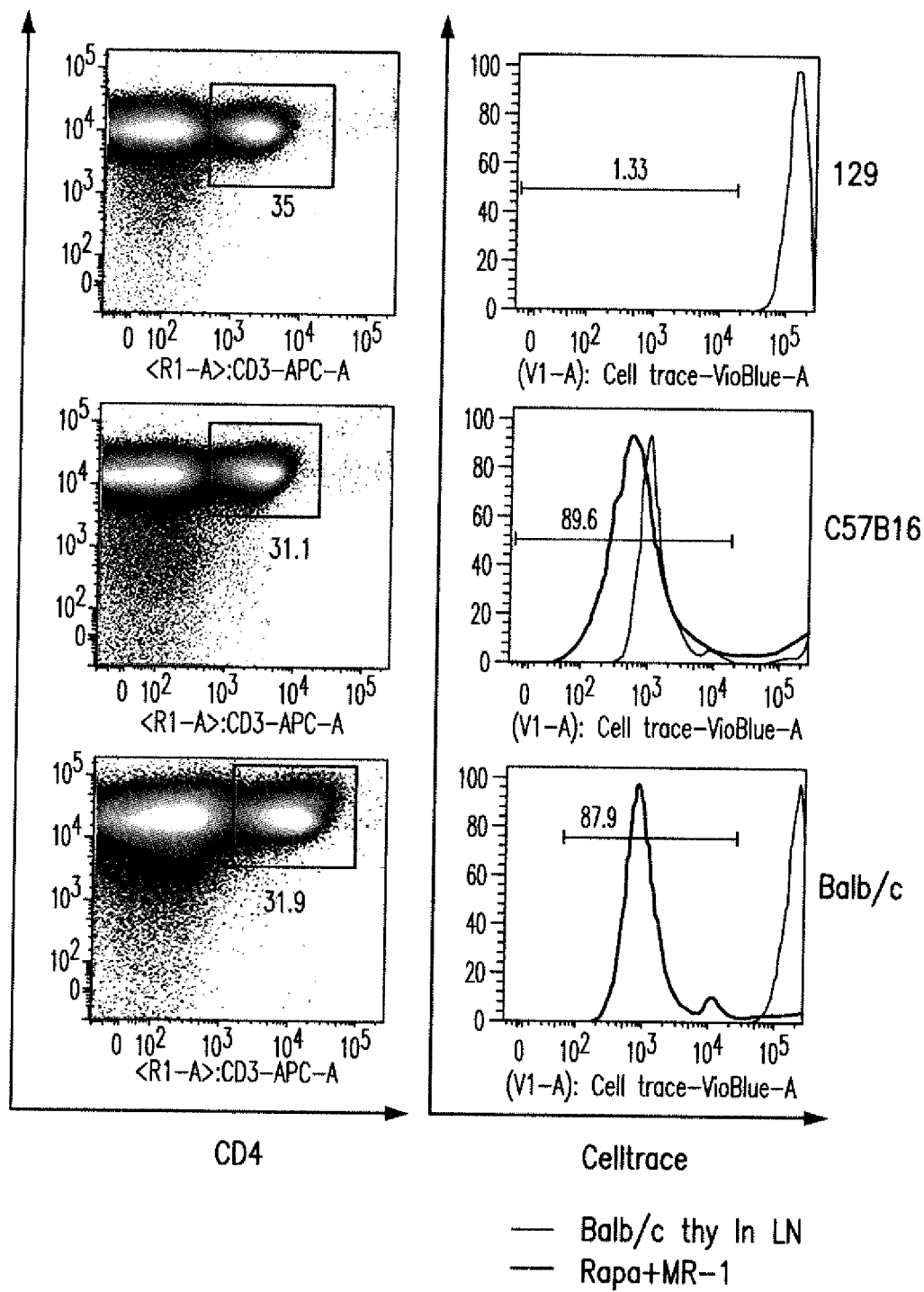
Figure 40B:
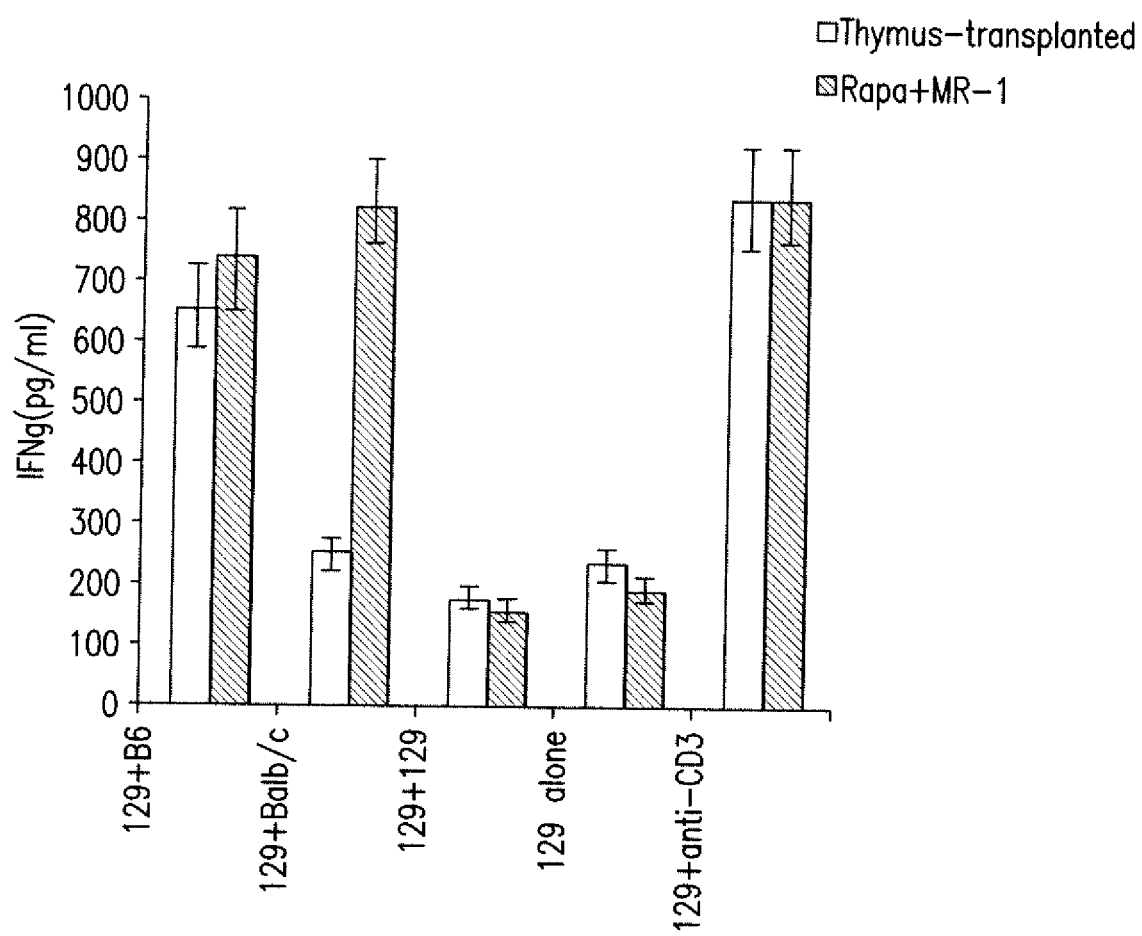
Figure 40C:
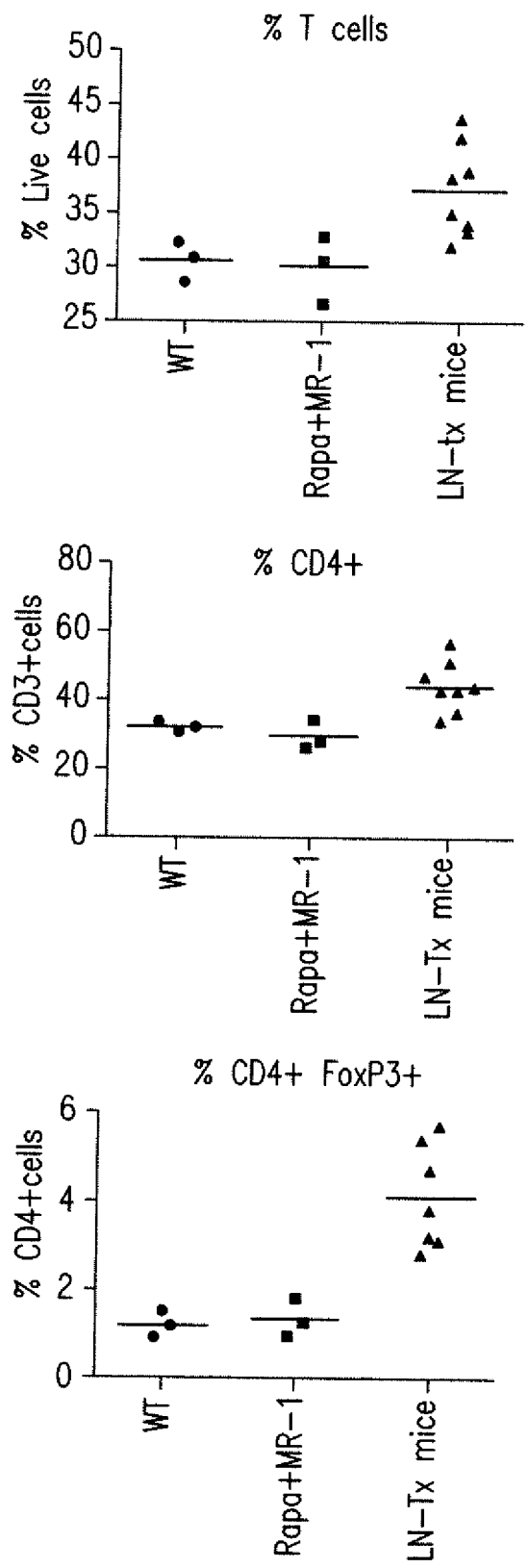

FIG. 40A-C. Ectopic thymus induces donor-specific tolerance and increased incidence of Tregs in recipients. (A) Splenocytes from Balb/c thymus-transplanted mice were labeled with CellTrace™ and co-cultured with naive 129.sv (top panel), C57BL6/J (middle panel) or Balb/c splenocytes (bottom panel). After 72 hours, cells were analyzed for CellTrace™ dilution by flow cytometry. (B) IFNγ levels from cell culture supernatants in (A). (C) Total percentages of T cells, CD4+ T cells and Tregs in the blood of thymus-transplanted mice (and controls) were determined by flow cytometry.

FIG. 41A-C. Characterization of cells migrating from ectopic to native thymus. (A) Presence of GFP+ cells in the native thymus of mice transplanted with Balb/c mice (top panel, 4× magnification). (B) GFP+ cells present in the native thymus were MHC-II+(middle panel) and CD11c+ (bottom panel). (C) GFP+ cells in the native thymus of mice transplanted with Balb/c-GFP thymus in the LN are observed to be interacting with CD4+ cells (i, inset) and CD4+CD25+ cells (ii and iii, inset). Images in C (i) and C (ii, iii) are at 10× and 40× magnification, respectively.

Figure 42A:
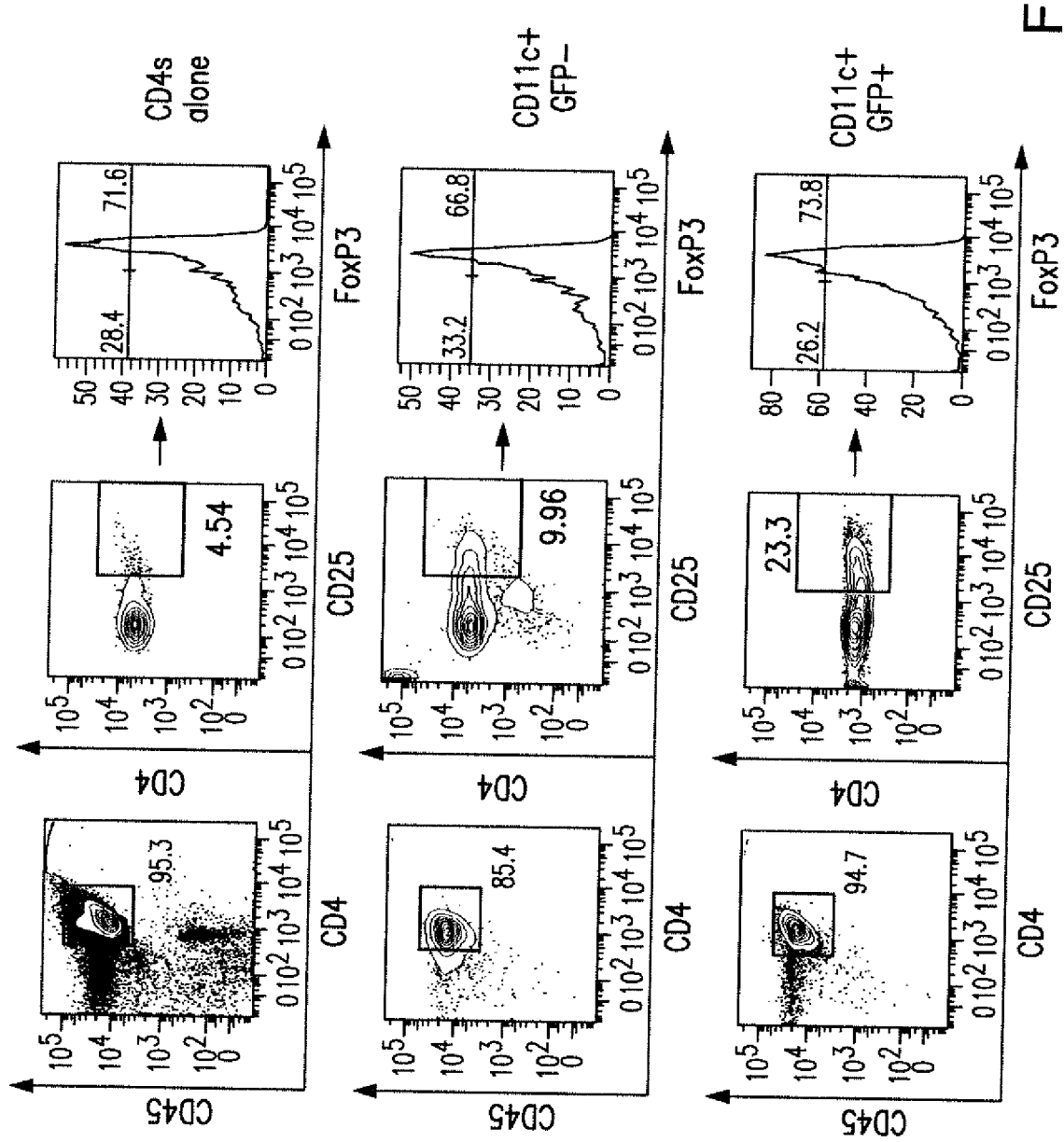
Figure 42B:
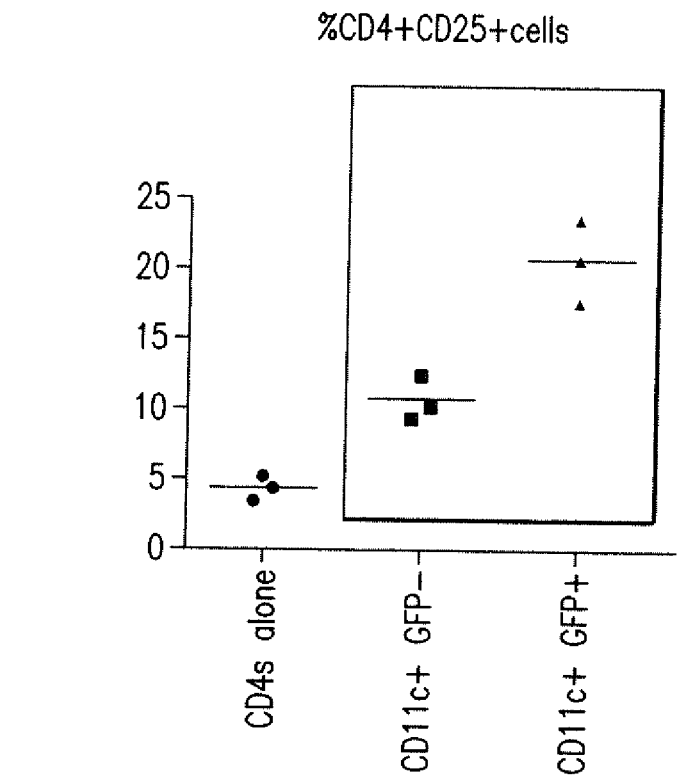
Figure 42C:
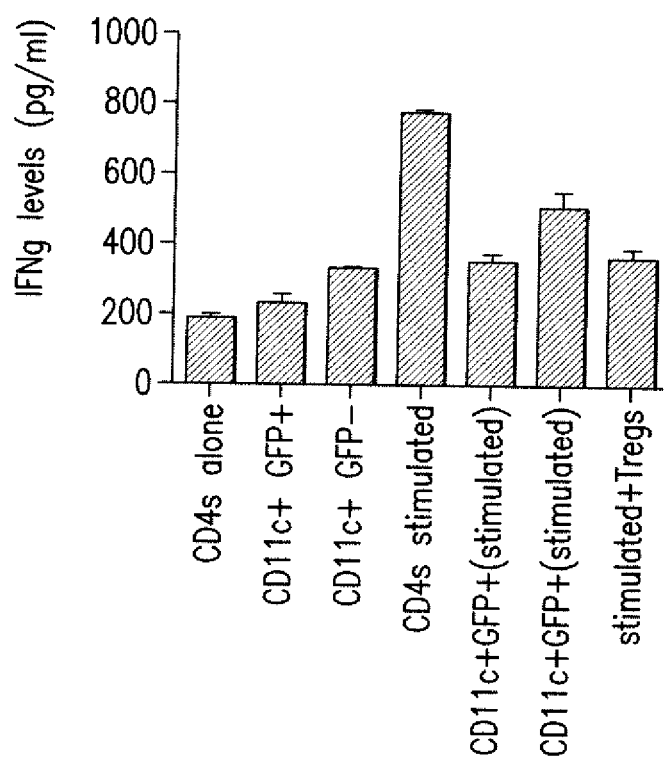

FIG. 42A-C. Migrating DCs induce Tregs capable of suppressing T cell activation. (A) CD11c+ GFP+ cells from native thymus were co-cultured with naive CD4+ thymocytes. After 72 hours, the culture was analyzed for proportion of CD4+CD25+ cells (Tregs) in culture. (B) Summarized data for Treg percentages in cultures described in (A). (C) Tregs generated in culture in (B) are efficient in suppressing CD4+ T cell proliferation, as determined by IFNγ levels. Results representative of one of three independent experiments.

Figure 43:
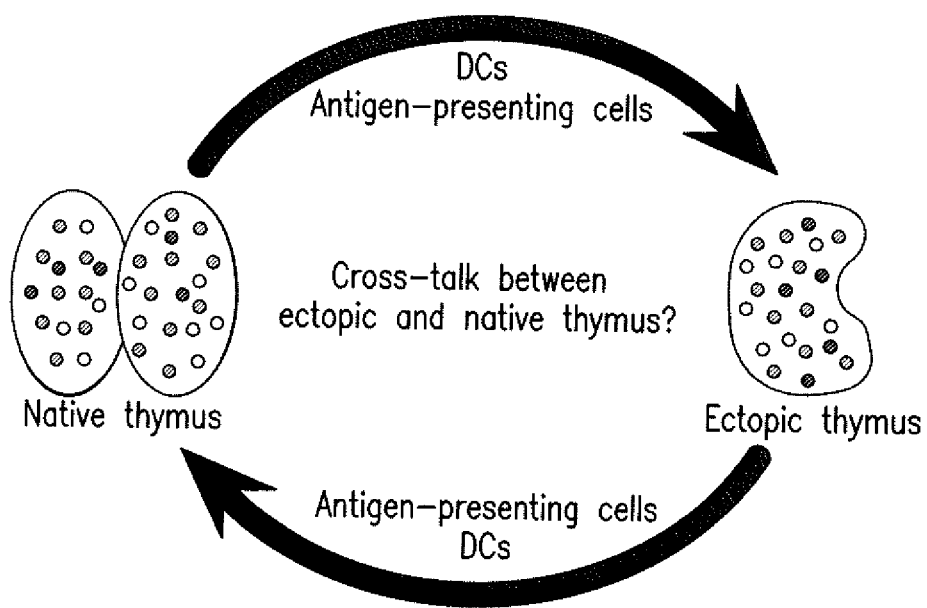

FIG. 43. Model depicting cross-talk between ectopic and native thymus in transplant recipient showing migration of antigen-presenting cells which induce Tregs.

5. DETAILED DESCRIPTION OF THE INVENTION

The present invention provides for methods of propagating non-lymphoid cells in a lymphoid tissue for the purpose of producing a non-lymphoid tissue and or/providing a desirable biological function.

Suitable cells include but are not limited to embryonal cells, non-embryonal cells, progenitor cells, and reprogrammed somatic cells (47). Cells may be human or non-human cells (eg non-human primate, dog, cat, pig, cow, horse, sheep, goat, mouse, rat, rabbit, etc.). Cells may be autologous, allogeneic, or xenogeneic. Suitable cells include but are not limited to a kidney cell or a partially differentiated kidney cell or a kidney progenitor cell, a lung cell or a partially differentiated lung cell or a lung progenitor cell, a thyroid cell or a partially differentiated thyroid cell or a thyroid precursor cell, a brain cell or a partially differentiated brain cell or a brain progenitor cell, an intestinal cell or a partially differentiated intestinal cell or an intestinal precursor cell; a thymus cell or a partially differentiated thymus cell or a thymic progenitor cell, a pancreas cell or a partially differentiated pancreas cell or a pancreas precursor cell (in the foregoing, including islet cells), a liver cell a partially differentiated liver cell and a liver precursor cell, a stomach cell or a partially differentiated stomach cell or a stomach precursor cell and so forth.

Cells can be implanted into a lymph node or multiple lymph nodes. Such methods are intended to encompass implantation into any lymph node, including, but not limited to: abdominal lymph nodes, celiac lymph nodes, paraaortic lymph nodes, splenic hilar lymph nodes, porta hepatis lymph nodes, gastric lymph nodes (left and right), gastroomental (gastroepiploic) lymph nodes (left and right), retroperitoneal lymph nodes, pyloric lymph nodes (suprapyloric, subpyloric, retropyloric), pancreatic lymph nodes (superior pancreatic, inferior pancreatic, splenic lineal lymph nodes), hepatic lymph nodes (cystic, foraminal—including foramen of Winslow), pancreaticoduodenal lymph nodes (superior pancreaticoduodenal, inferior pancreaticodoudenal), superior mesenteric lymph nodes, ileocolic lymph nodes, prececal lymph nodes, retrocecal lymph nodes, appendicular lymph nodes, mesocolic lymph nodes (paracolic, left colic, middle colic, right colic, inferior mesenteric lymph nodes, sigmoid, superior rectal), common iliac lymph nodes (medial common ilic, intermediate common iliac, lateral common iliac, subaortic common iliac, common iliac nodes of promontory), and external iliac lymph nodes (medial external iliac, intermediate external iliac, lateral external iliac, medial lacunar—femoral, intermediate lacunar—femoral, lateral lacunar—femoral, interiliac external iliac, obturator—external iliac obturatory). In certain embodiments, the cells are injected into a recipient's lymph node from a donor's tissue. In certain embodiments, it is important for the lymph node to be able to swell as the graft expands, and thus lymph nodes that are present in the peritoneal cavity are particularly useful, especially where the lymph nodes are not closely associated with arteries or large veins.

In certain embodiments, the present invention provides for a method of propagating non-lymphoid cells in a lymphoid tissue for the purpose of producing a non-lymphoid tissue and or/providing or supplementing a desirable biological function, comprising introducing, into a lymph node in a host, non-lymphoid cells, under conditions such that the cells are able to proliferate.

The host may be a human or non-human (eg non-human primate, dog, cat, pig, cow, horse, sheep, goat, mouse, rat, rabbit, etc).

In one particular embodiment, the present invention provides for a method of providing or supplementing a biological function in a host comprising introducing, into a lymph node of a host, a non-lymphoid cell of an organ where the cell or organ normally provides said function; for example, but without limitation, introducing an islet cell to provide insulin production, or, introducing a thyroid cell to provide thyroxin, or introducing a kidney cell to provide kidney function (filtering, etc.), or introducing a thymus cell to provide immune function, etc.

In certain embodiments, the present invention provides for methods of inducing tolerance in a subject to transplantation of allograft tissue.

In certain embodiments, the method of inducing tolerance comprises conditioning a transplant recipient with cells immune-matched to a donor of a subsequent allograft. In certain embodiments, the immune-matched cells are thymic cells. In certain embodiments, the thymic cells are transplanted into the lymph node of the recipient.

In certain embodiments, the allograft tissue comprises a liver cell or tissue. In certain embodiments, the allograft tissue comprises a skin cell or skin tissue.

In certain embodiments, the method of inducing tolerance comprises increasing regulatory T cell (Treg) induction associated with cross-talk between donor thymus tissue and recipient thymus tissue. In certain embodiments, the Treg cells are CD4+, CD25+ and/or FoxP3+ Treg cells.

In certain embodiments, the present invention also provides a method of transplanting allograft tissue to a subject comprising (i) introducing non-lymphoid cells in a lymphoid tissue of the subject under conditions such that the cells are able to proliferate; and (ii) introducing allograft tissue to the subject after the non-lymphoid cells have been introduced into the lymphoid tissue of the subject.

In certain embodiments, the non-lymphoid cells are immune-matched to the allograft tissue.

In certain embodiments, the non-lymphoid cells are thymus cells.

6. EXAMPLE 1

The Mouse Lymph Node as an Ectopic Transplantation Site for Multiple Tissues

6.1 Materials and Methods

Mice and Tissues.

Donor 129sv mice and recipient 129sv Fah−/− mice were a kind gift from M. Grompe (Oregon Health and Science University). For allogeneic experiments, donor hepatocytes were isolated from C57BL/6 GFP+ mice (GFP transgene under the control of the human ubiquitin C promoter, C57BL/6-Tg(UBC-GFP)30Scha/J, Jackson Laboratory) and transplanted into 129sv Fah−/− mice. For syngeneic experiments using C57BL/6 GFP+ hepatocytes, 129sv Fah−/− mice were backcrossed for more than eight generations with C57BL/6 mice (Jackson Laboratory) to generate C57BL/6 Fah−/− mice. Luciferase C57BL/6 transgenic mice (Luc+) expressing firefly luciferase under the control of the broadly expressed β-actin promoter were kindly provided by S. Thorne (University of Pittsburgh). Donor primary hepatocytes were isolated from adult (5- to 8-week-old) mice. Donors and recipients were not matched according to gender. Newborn (1- to 3-day-old) C57BL/6 GFP+ mice were used as donors of thymic cells. Athymic BALB/c nude Foxn1nu (Harlan) mice were used as recipients of thymic cells. Blood collection (100 μl) was performed using the submandibular bleeding technique. Adult (5- to 8-week-old) C57BL/6 GFP+ mice were used as the donors of pancreatic islets. Adult (5- to 8-week-old) C57BL/6 mice were used as recipients of pancreatic islets. Mice were bred and housed in the Division of Laboratory Animal Resources facility at the University of Pittsburgh Center for Biotechnology and Bioengineering. Experimental protocols followed US National Institutes of Health guidelines for animal care and were approved by the Institutional Animal Care and Use Committee at the University of Pittsburgh.

Hepatocyte Transplantation.

Primary hepatocytes were isolated using the two-step collagenase perfusion technique. The number and viability of the cells were determined by trypan blue exclusion. For each recipient, 100,000-500,000 viable cells were suspended in 20 μl Matrigel (BD Biosciences) and kept on ice until transplantation. Recipient mice were anesthetized with 1-3% isoflurane and laparotomized. The jejunal lymph node was exposed, and cells were injected using a 28 G needle under a dissecting scope (Leica). Just after injection, the contact site was clipped for 5 min by micro clamp to prevent cell leakage. In the experiments with Fah−/− mice, the mice were kept on NTBC-containing drinking water at a concentration of 8 mg/l until transplantation. NTBC was discontinued just after surgery. For extra-abdominal lymph node injections, we injected 3% Evans blue solution intradermally into the footpad of the hindlimb or forelimb before cell transplant to visualize the small popliteal or axillary lymph node.

Thymic Transplantation.

Thymuses were harvested from newborn GFP+ transgenic mice and cut into small fragments. The jejunal lymph nodes were exposed, and cells were injected with minced thymus tissue through a 20 G needle. Thymus tissue was also grafted beneath the kidney capsule as a positive control. For the kidney capsule experiments, an incision was made on the left side of the peritoneal cavity, and the kidney was exposed. A small hole was made in the capsule, and the thymus was inserted between the kidney capsule and the arenchyma. Light cauterization was used to seal the opening. The wound was closed with surgical sutures.

Pancreatic Islet Transplantation.

Recipient C57BL/6 mice were injected with 190 mg per kg of body weight streptozotocin (Sigma) intraperitoneally to induce diabetes. Diabetes (blood glucose concentration greater than 300 mg/dl) was confirmed 3 d after injection using a Contour Blood Glucose Meter (Bayer). The pancreases from adult C57BL/6 GFP+ transgenic mice were perfused with Collagenase P (Roche) through the bile duct. Digested islets were washed in Hanks Balanced Salt Solution and fetal bovine serum (HBSS/FBS) and placed in a 70-μm cell strainer. The contents collected in the cell strainer were transferred to a Petri dish, and individual islets were picked and counted under a dissecting microscope. Approximately 200-300 islets were mixed with 10 μl of Matrigel and loaded into a 27 G insulin syringe on ice. For lymph node transplantation, a small incision was made in the abdomen to expose the jejunal lymph node. The syringe containing the islets was inserted into the lymph node, and the islets were slowly injected. For kidney capsule transplantation, a small incision over the left kidney was made to expose the kidney. A hole was made in the capsule, and the islets were delivered in a manner similar to that used for the lymph node. Light cauterization was used to seal the opening.

The wound was then closed with surgical sutures. If a decrease in glucose concentration was not observed after 1 week, a second islet transplant was performed in the same lymph node.

In Vivo Imaging.

To detect donor luciferase-positive C57BL/6 hepatocytes, we used an IVIS200 system (Caliper LifeScience) after intraperitoneal injection of 200 μl of 30 mg/ml luciferin substrate into recipient C57BL/6 mice and anesthesia with 3% isoflurane. Images were analyzed using LivingImage software (Caliper LifeScience).

Proliferation Assay.

Primary hepatocytes from C57BL/6 GFP+ mice were transplanted into 11 mice, as described above. Recipient mice were given drinking water containing 0.8 mg/ml BrdU immediately after surgery. After 1 week, we euthanized three mice for analysis. Partial hepatectomy (PHx), in which two-thirds of the liver of a mouse is removed, was then performed on 5 of the 11 mice, and the remaining 3 mice were used for controls. One week later, all eight mice were euthanized for analysis. Using histological sections, we determined the amount of hepatocyte engraftment in the lymph nodes by counting GFP+ hepatocytes and determined the ratio of proliferating hepatocytes by counting BrdU+ hepatocytes.

Allogeneic Transplantation.

Primary hepatocytes from C57BL/6 GFP+ mice were transplanted into ten 129sv Fah−/− mice by lymph node or splenic injection. Five out of ten mice from each group were intraperitoneally injected with the immunosuppressive drugs CTLA4-Ig (0.25 mg) and MR1 (0.25 mg), a kind gift from F. Lakkis (University of Pittsburgh), on days 0, 2, 4 and 6 after transplantation.

Antibodies.

Antibodies specific to the following antigens were purchased for immunohistochemistry: ER-TR7, LYVE1, GFP, glutamine synthetase, CCR7, S1PR1 (EDG1), F4/80 (Abcam), PNAd, B220, CD4, CD8, CD31, CD105 and Gr-1 (BD Biosciences), BrdU (Santa Cruz Biotechnology), DPPIV (AbD Serotec), E-cadherin (Zymed), Collagen IV (SouthernBiotech), keratin 5 (Covance), keratin 8 (DSHB) and C-peptide and glucagon (Cell Signaling Technologies). Antibodies specific to the following antigens were purchased for flow cytometric analysis: APC mouse CD3-ε, APC-Cy7 mouse CD8-α, phycoerythrin (PE)-Cy7 mouse CD45 and PE mouse CD4, a mouse Vβ TCR screening panel, a mouse naive and memory T cell panel (Pharmingen) and a mouse regulatory T (Treg) cell detection kit (Miltenyi). Appropriate isotype control antibodies (BD Biosciences) were used to estimate background fluorescence.

Immunohistochemistry.

Tissue was fixed in 4% paraformaldehyde for 4 h, stored in 30% sucrose for 12 h and then embedded in optimal cutting temperature (OCT) medium, frozen and stored at −80° C. Sections 5-10 (5-10 (m) were mounted on glass slides and fixed in cold acetone for 10 min. For immunohistochemical staining, sections were washed with PBS and blocked with 5% bovine serum albumin (BSA) or milk for 30 min. Sections were then incubated with primary antibody for 1 h and secondary antibody for 30 min. Sections were mounted with Hoechst mounting media. Images were captured with an Olympus FluoView 1000 Confocal Microscope or an Olympus IX71 inverted microscope.

Flow Cytometry.

Whole blood was collected in K2EDTA collection tubes (Terumo Medical). One hundred microliters of blood was added to cold fluorescence-activated cell sorting (FACS) tubes. Antibodies were added at a dilution of 1/10 in blood and mixed by gentle pipetting. Reactions were incubated in the dark in an ice slurry bath for 30 min. Three milliliters of Red Blood Cell Lysing Buffer (Sigma) was added to each tube, lightly vortexed and incubated for an additional 5 min. Two milliliters of flow buffer (2% FBS in HBSS) was added to the tubes, mixed and centrifuged at 500 g for 5 min. The supernatant was aspirated, and secondary antibody was added at a dilution of 1/50 in flow buffer and mixed by gentle pipetting. Reactions were incubated in the dark in an ice slurry bath for 15 min. The red blood cell lysis and centrifuge were repeated as described. The final cell pellet was resuspended in 400 μl of flow buffer with propidium iodide. Cells were analyzed using the BD FACSVantage Cell Sorter, a BD Aria II Cell Sorter or a Miltenyi MACSQuant.

Tail Skin Graft.

Recipient mice (BALB/c nude) containing an ectopic thymus (C57BL/6) in the lymph node were anesthetized, and the tail skin (5 mm×5 mm). from CBA/CaJ or C57BL/6 mice was grafted on the left and right lateral sides of the superior dorsal region of the recipient mouse, respectively. A bandage was applied and removed 7 d after surgery. The grafts were observed daily for rejection.

Tumor Cell Transplantation.

Human metastatic colon cancer cells (Tu #12) were prepared and transplanted into mice as previously described (32). Briefly, $3\times10^5$ cells were transplanted by subcutaneous injections with Matrigel. Tumor size was recorded once per week using a caliper and calculated as (n/6)×(length (mm)× width2 ($mm^2$)).

LPS-Induced Inflammation.

LPS (1 mg per kg of body weight, Sigma) was injected intraperitoneally into C57BL/6 wild-type or normoglycemic mice that previously received an islet transplant to the lymph node. Mice were bled to determine glucose concentrations or measure serum cytokine levels. Cytokine level was determined by ELISA assay for TNF-α, IL-1β and IL-6 (eBioscience).

Statistical Analyses.

Figure 1A:
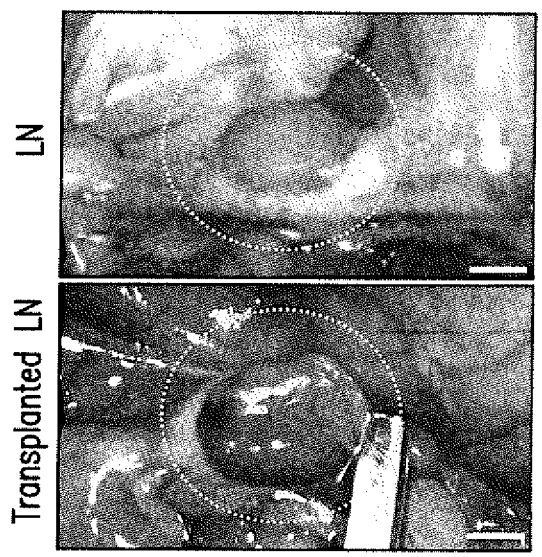
Figure 1B:
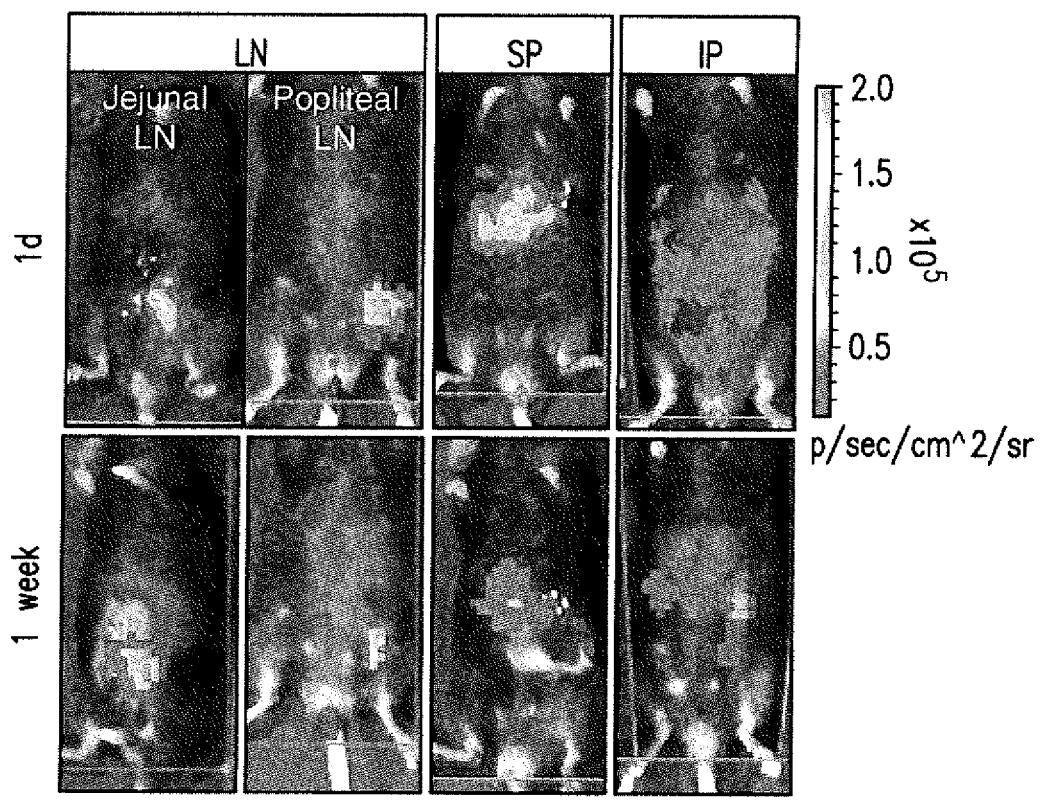
Figure 1C:
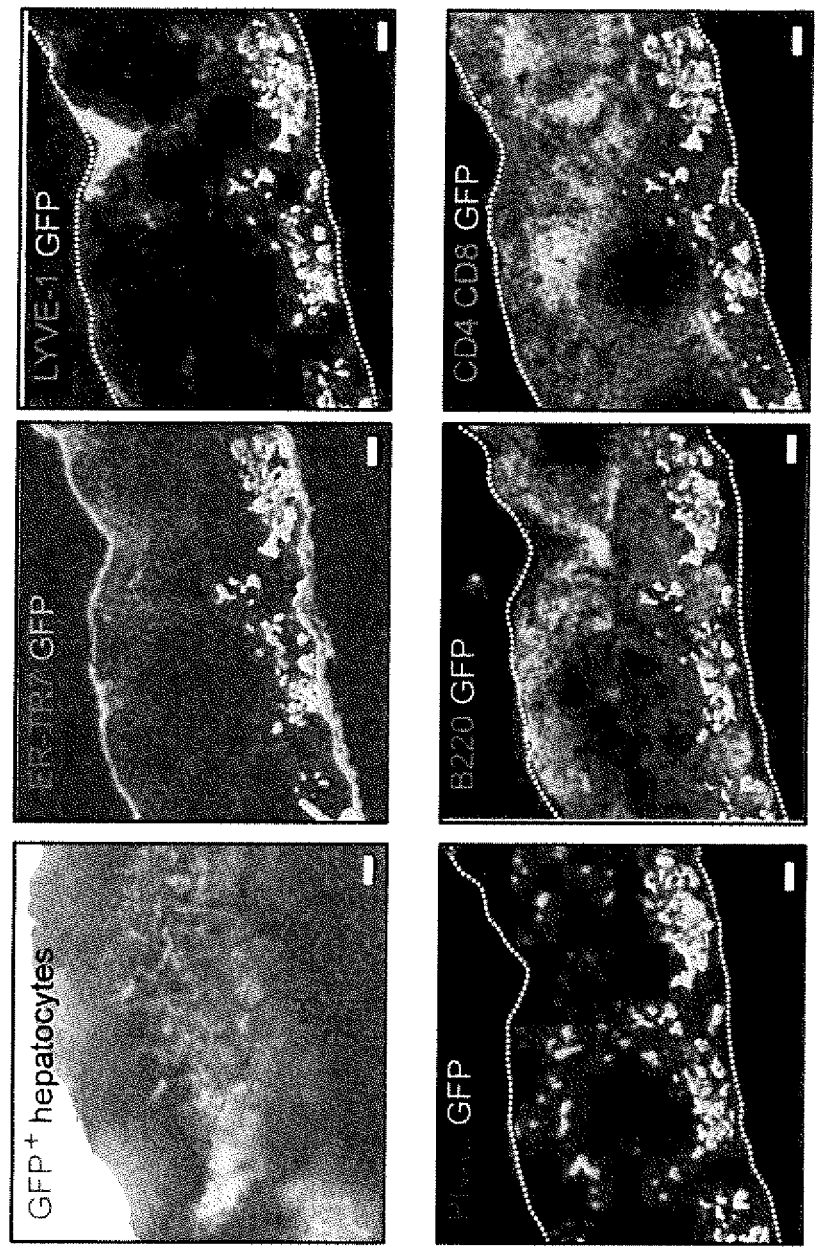
Figure 1D:
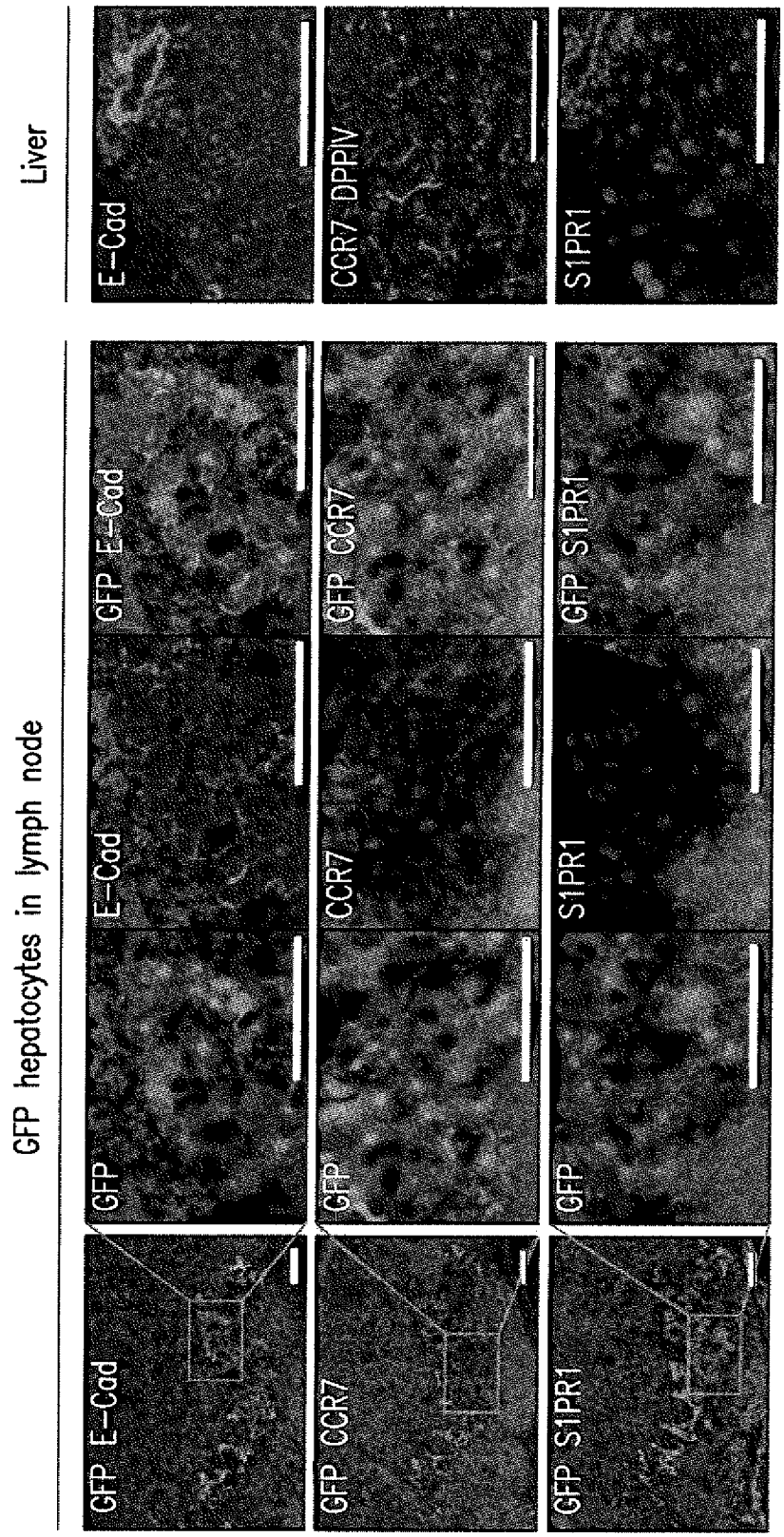
Figure 1E:
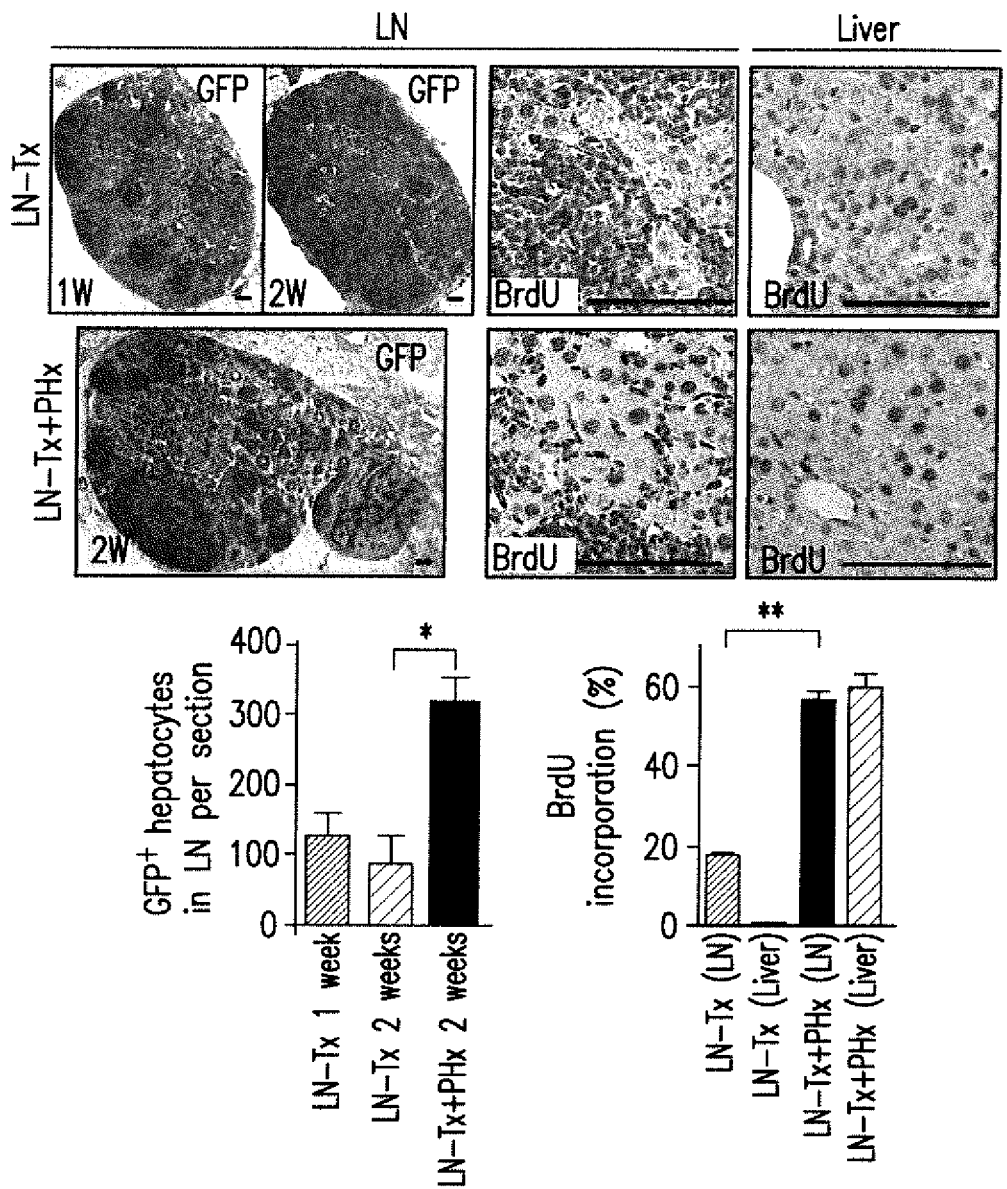
Figure 2A:
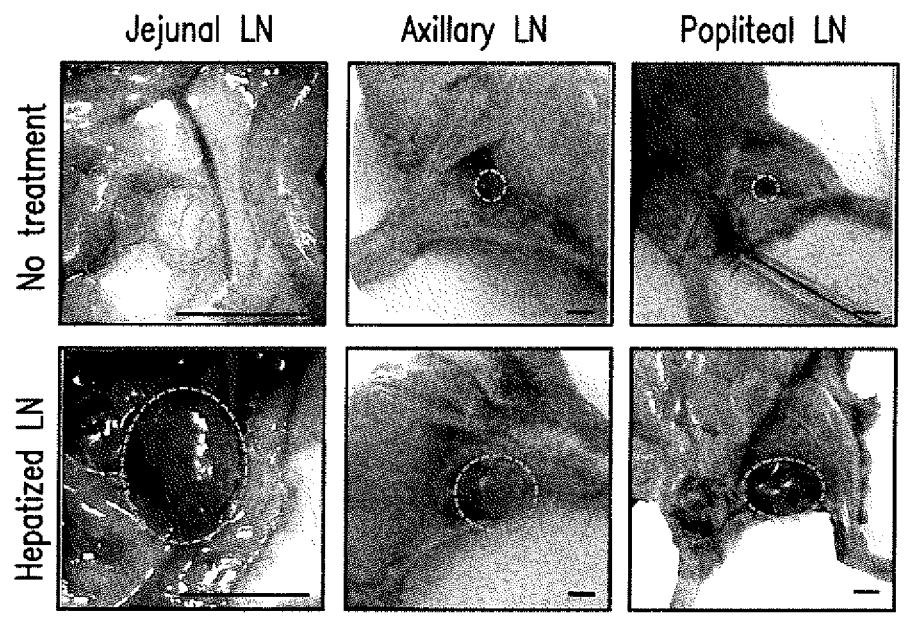
Figure 3A:
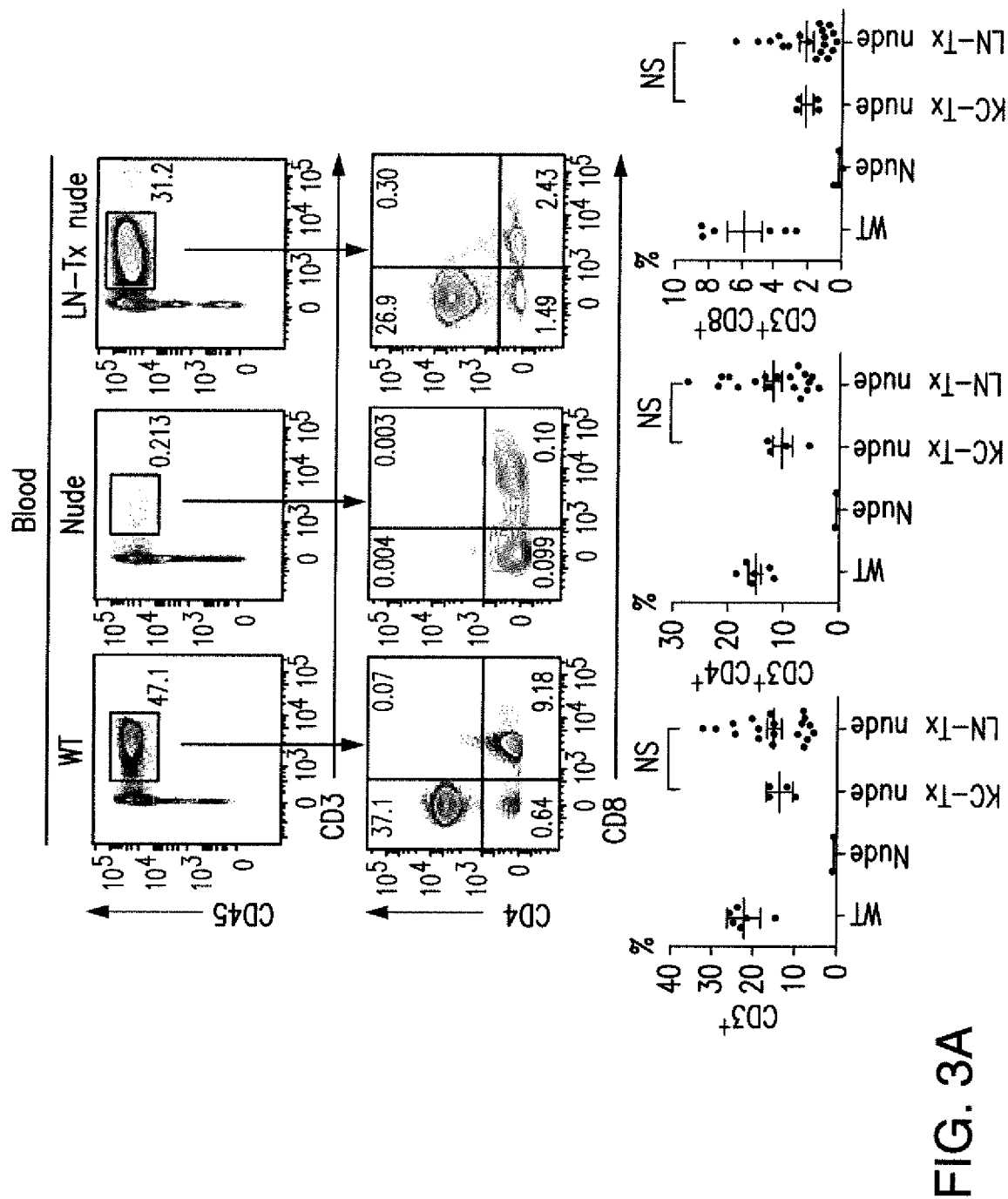

Statistical significance was determined with an unpaired two-tailed Student's t-test for the data shown in FIGS. 1e, 2d and 3a.

6.2 Results

Direct Injection of Hepatocytes into the Lymph Node

We targeted single jejunal lymph nodes in the abdominal cavities of C57BL/6 wild-type mice, an area that we selected because it is easily accessible and relatively large (13). After injection of 100,000-500,000 syngeneic primary hepatocytes, the lymph nodes enlarged slightly and had no visible leakage, as evidenced by staining with Evans blue dye (FIG. 1a). One day after injection, syngeneic luciferase-expressing hepatocytes remained in the lymph nodes, as determined by in vivo imaging of luciferase (FIG. 1b). In contrast, splenic and intraperitoneal injection of hepatocytes resulted in the rapid dispersion of cells to the liver and throughout the abdominal cavity, respectively (FIG. 1b). One week after transplant, syngeneic GFP+ hepatocytes were distributed mainly in the subcapsular sinus of the lymph nodes but were not present in the lymph node follicles or germinal centers (FIG. 1c). Additionally, the hepatocytes rapidly formed patches of hepatic tissue expressing E-cadherin (FIG. 1d). This hepatocyte-to-hepatocyte attachment may help retain hepatocytes within the site of transplantation (14).

Furthermore, the cell trafficking molecule sphingosine-1-phosphate receptor 1 (S1PR1), which is necessary for the egress of B and T cells from lymph nodes (15,16), was not present on hepatocytes in the lymph nodes. Conversely, CCR7, a molecule known to control the migration of memory T cells and/or tumor cells into the lymph nodes (17), was expressed by hepatocytes in the lymph nodes (FIG. 1d). These observations suggest a potential mechanism of retention of healthy hepatocytes in the lymph node.

To assess whether the engrafted hepatocytes in the lymph nodes proliferate in response to growth stimuli in C57BL/6 wild-type recipient mice, we performed partial hepatectomy (PHx) 1 week after syngeneic hepatocyte injection into the lymph nodes and added bromodeoxyuridine (BrdU) to the drinking water of the recipient mice. PHx is a physiologically relevant method of stimulating hepatocyte growth 18. We analyzed BrdU incorporation in the lymph node—engrafted hepatocytes 2 weeks after injection and compared the result to that in mice that were not subjected to PHx. The number of GFP-expressing hepatocytes and the percentage of BrdU+ hepatocytes in the lymph nodes of the mice subjected to PHx were significantly higher than those in the mice not subjected to PHx (FIG. 1e), indicating that hepatocytes in the lymph nodes respond to growth stimuli after PHx.

A Functional Ectopic Liver in the Lymph Node

Figure 2B:
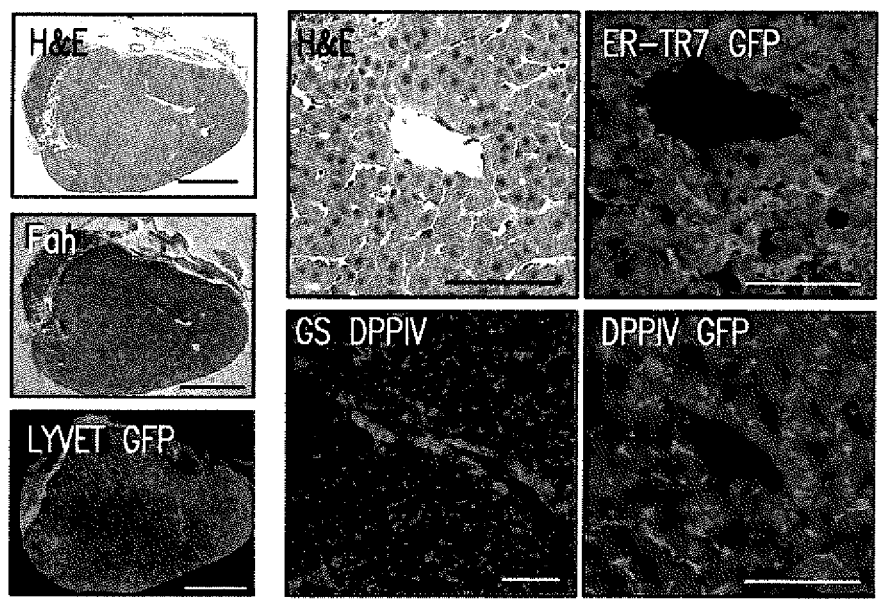

Next, we asked whether transplantation of syngeneic hepatocytes into single jejunal lymph nodes of Fah–/– tyrosinemic mice (19-21), a model of lethal metabolic liver failure, would induce hepatocyte proliferation. Twelve weeks after hepatocyte injection into the lymph nodes, the mice were rescued from lethal liver failure by the newly hepatized growth in the jejunal lymph nodes (FIG. 2). Hepatocyte engraftment was localized to the transplanted lymph nodes and was not present in other lymph nodes or the native liver (FIG. 2a), suggesting that a lymphatic distribution of hepatocytes did not occur. The 'hepatized' lymph nodes were composed mostly of newly formed liver tissue containing Fah+ GFP+ hepatocytes but also included remnants of the lymphatic system, as revealed by surrounding LYVE1+ lymphatic endothelial cells (FIG. 2b). The lymph nodes were transformed into hepatic organoids composed of characteristically cuboidal hepatocytes but with the absence of a biliary system (12). To define the hepatized lymph node microarchitecture, we stained recipient lymph nodes for ER-TR7, a marker of fibroblastic reticular cells (FRCs), dipeptidyl peptidase-4 (DPP IV), a marker for brush borders of hepatocytes and bile canaliculi organization, and glutamine synthetase, a marker of zonality for hepatocytes surrounding the terminal hepatic venules 22 (FIG. 2b). GFP+ hepatocytes resided in cellular proximity with ER-TR7+ FRCs. FRCs are known to have a crucial role in establishing the reticular network, as well as in regulating immune function (11,23). Similar to what is observed in normal liver anatomy, DPP IV was localized throughout the hepatized lymph nodes. Moreover, we identified glutamine synthetase—positive hepatocytes surrounding some of the hepatic veins in the newly formed liver tissues. Notably, we observed survival of the mice (FIG. 2c) and long-term persistence (over 25 weeks) of the graft after transplantation to the lymph nodes (FIG. 2a), and we found no immune responsiveness to the grafts, as indicated by the presence of very few lymphocytes and macrophages around the transplantation zones (FIG. 6).

We then tested whether this transplantation method is effective in other lymph nodes throughout the body, as all lymph nodes share a common histological architecture (9, 13, 24). We injected syngeneic hepatocytes into single extra-abdominal axillary or popliteal lymph nodes in Fah–/– mice (FIG. 2a). Similar to the results from the intra-abdominal jejunal lymph node injection, we observed a single, large, hepatized lymph node several weeks after cell transplantation, which subsequently rescued mice from lethal liver failure (FIG. 2c). In wild-type mice, a jejunal lymph node weighs around 5±3 mg (mean±s.d.), whereas a popliteal or axillary lymph node weighs 3±1 mg (n=5). Because the jejunal lymph node is the largest lymph node in the mouse, it was easier to inject, and injection at this site led to a higher survival rate (FIG. 2c). Furthermore, when we compared the mass of hepatic tissue generated in the intra-abdominal jejunal lymph nodes to those generated in the extra-abdominal axillary and popliteal lymph nodes, we found no statistical differences, indicating no tissue growth advantage between these three lymph nodes (FIG. 2d). Transplantation of hepatocytes into periportal lymph nodes, one of the closest lymph nodes to the liver, also resulted in large hepatized lymph nodes and rescued the recipient mice from lethal liver disease. However, transplantation of lymph nodes closer to the liver did not seem to be beneficial for the experimental outcome when compared with the other transplanted lymph nodes (FIG. 2d).

Thus far, all transplantations used syngeneic donor and recipient mice. Because lymph nodes perform a central function for allogeneic recognition (25), we next tested whether successful engraftment is possible in allogeneic lymph nodes. We injected C57BL/6 GFP+ hepatocytes into the liver (through splenic injection) or into the lymph nodes of 129sv Fah–/– recipient mice. 129sv and C57BL/6 mice share the major histocompatibility complex haplotype H2b but differ in their minor histocompatibility antigens and are considered allogeneic (26,27). Whereas C57BL/6 hepatocytes transplanted into 129sv Fah−/− recipients did not engraft (FIG. 2e), blocking the costimulation pathways CD28-B7 (blocked by CTLA4-Ig) and CD40-CD40L (blocked by MR1)(28,29) in the 129sv Fah−/− recipients facilitated successful engraftment of C57BL/6 GFP+ hepatocytes injected into either the spleen or the lymph node (FIG. 2e). This result shows that the immune reaction to transplanted cells in the lymph nodes is not stronger or faster compared to the reaction to cells transplanted in another site.

A Functional Ectopic Thymus in the Lymph Node

Using a similar approach, we asked whether de novo thymus function could be generated in the lymph nodes of athymic mice. We harvested thymuses from newborn C57BL/6 GFP+ transgenic mice and minced and injected them directly into the jejunal lymph nodes or under the kidney capsules of athymic BALB/c nude mice. After 1 month, we analyzed the blood of the recipient mice by flow cytometry for the presence of recipient (GFP−) single-positive CD4+ and CD8+ T cells. Thymic transplant into the lymph node (LN-Tx nude mice) or under the kidney capsule (KC-Tx nude mice) generated circulating recipient single-positive CD4+ and CD8+ T cells (FIG. 3a and FIG. 7). Ten months after transplantation, single-positive CD4+ and CD8+ T cells were still present in the peripheral blood, indicating long-term thymic engraftment in the lymph nodes (FIG. 8). Notably, transplantation of a thymic single-cell suspension also resulted in the presence of single-positive CD4+ and CD8+ T cells, although to a lesser degree than did transplantation of minced thymic tissues (Table 1=FIG. 9). We used newborn GFP+ mice as a source of donor thymuses because they contain a minimal amount of mature thymocytes. In fact, less than 6% (n=3/54) of the recipient mice showed any donor GFP+ T-cell contamination in the blood 1 month after transplant when measured by flow cytometry. We excluded these three mice from further studies.

Figure 3B:
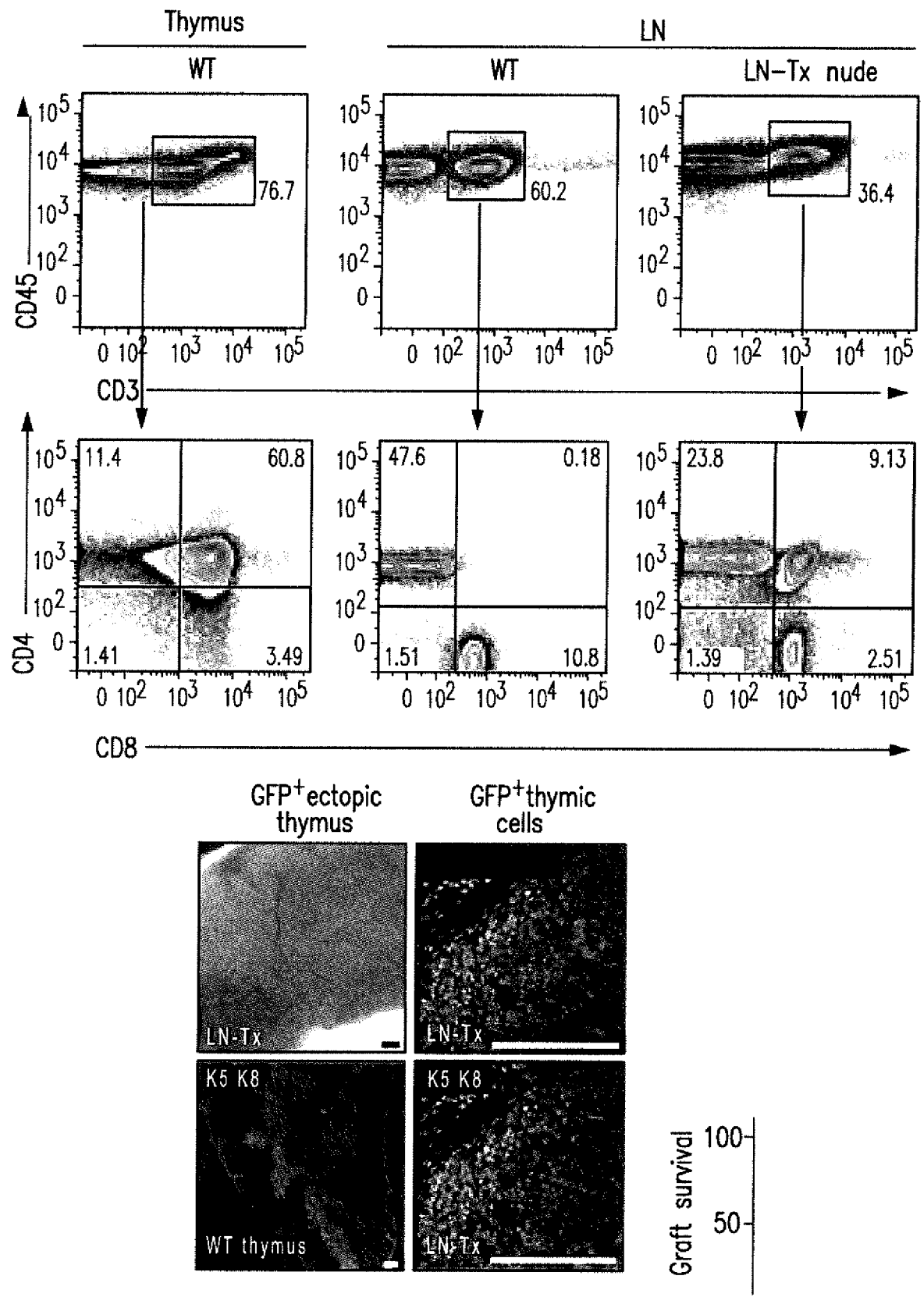

We then harvested the ectopic thymuses for further characterization of the engraftment. GFP+ epithelial thymic cells remained within the injected lymph nodes and were organized into an epithelial thymic structure (FIG. 3b). Previously, thymic epithelia have been distinguished by their cytokeratin 5 (K5) and cytokeratin 8 (K8) phenotypes (30). The ectopic thymuses were present in the subcapsular sinus of the lymph nodes (FIG. 10) and contained both K5- and K8-positive regions, which correspond with thymic medullary and cortical epithelia, respectively (FIG. 3b). We also analyzed the ectopic thymuses for the presence of recipient double-positive CD4+CD8+ thymocytes, which represent immature T cells undergoing thymic selection (31). The ectopic thymuses contained recipient double-positive thymocytes as well as single-positive CD4+ and CD8+ T cells, indicating a selective mechanism of T-cell commitment and maturation (FIG. 3b).

Figure 3C:
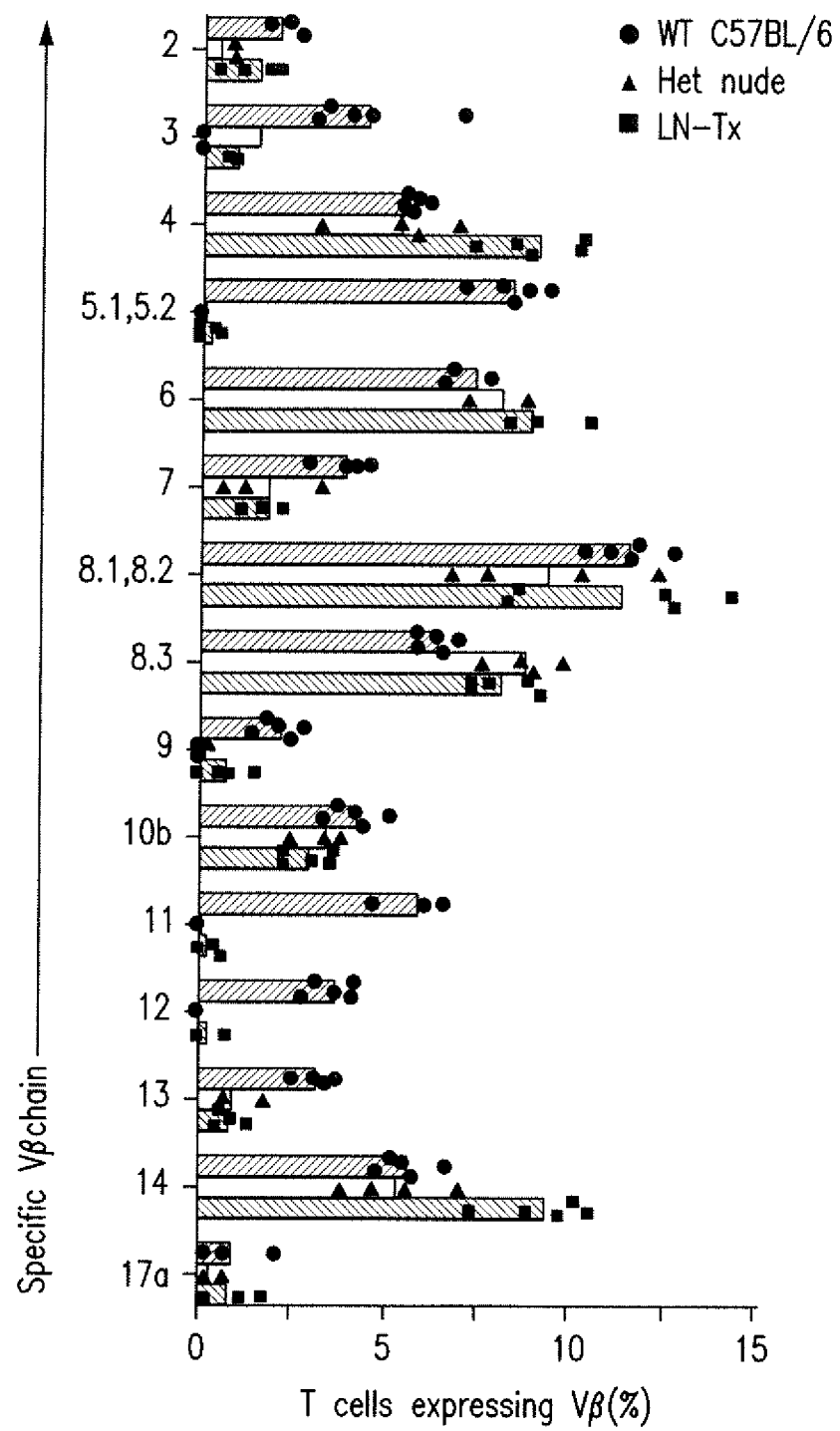
Figure 3D:
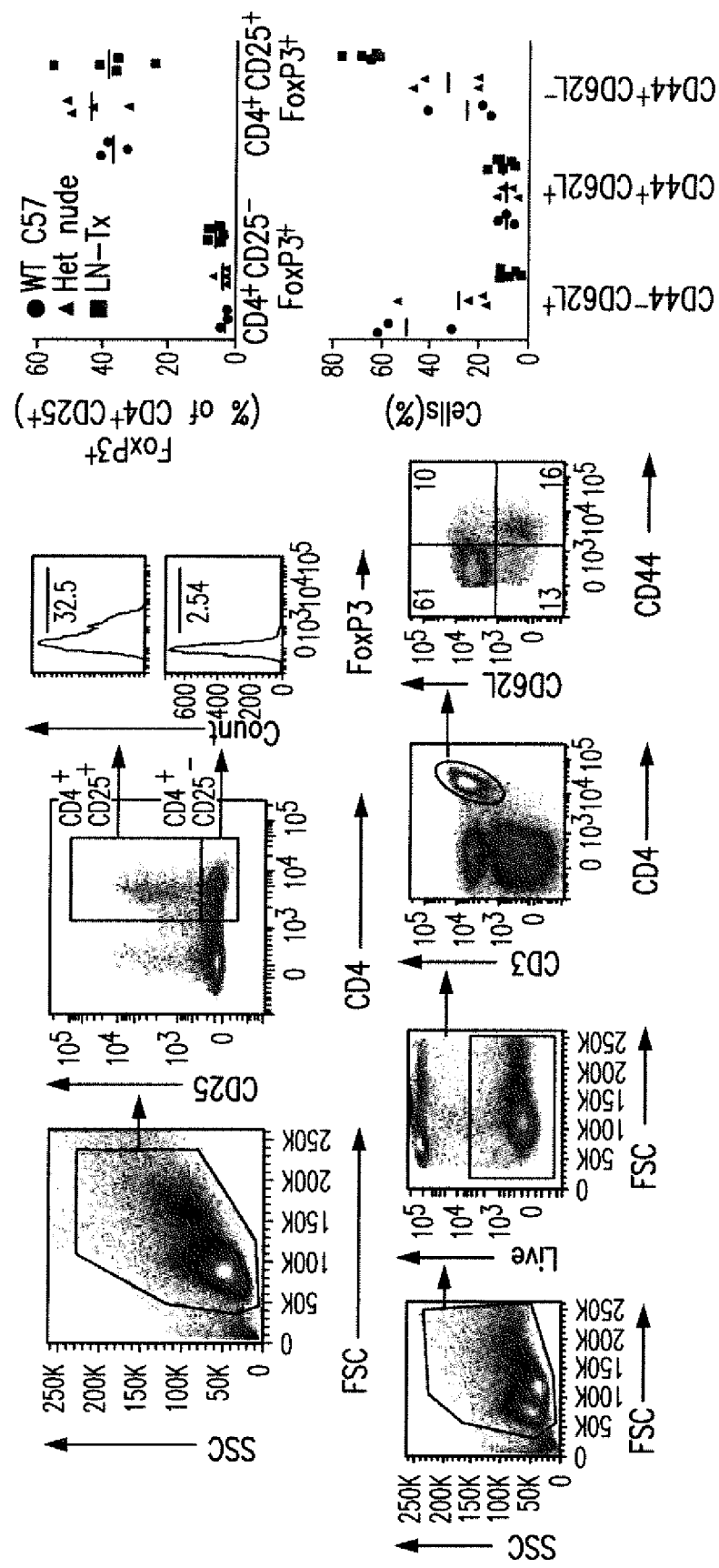

To more fully characterize the T-cell phenotypes generated in the LN-Tx nude mice, we analyzed the T-cell receptor (TCR) repertoire by flow cytometry staining with antibodies recognizing different TCR Vβ segments (Vβ2, Vβ3, Vβ4, Vβ5.1, 5.2, Vβ6, Vβ7, Vβ8.1, 8.2, Vβ8.3, Vβ9, Vβ10b, Vβ11, Vβ12, Vβ13, Vβ14 and Vβ17a). We found each Vβ segment on the CD3+ T cells of C57BL/6 wild-type splenocytes. Heterozygous BALB/c nude mouse splenocytes expressed 10 out of the 15 Vβ segments, which is consistent with known partial or complete genetic deletions of certain Vβ segments (Vβ3, Vβ5.1, 5.2, Vβ9, Vβ11 and Vβ12) in this strain. Notably, splenocytes in LN-Tx nude recipients expressed a Vβ profile similar to that of the heterozygous BALB/c nude mice (FIG. 3c). These results demonstrate that a C57BL/6 ectopic thymus promotes the development of T cells generated from the bone marrow of recipient BALB/c nude mice. We then further characterized the splenic T cells in LN-Tx nude mice by flow cytometry to determine whether regulatory, naive, central memory and effector memory T cell subsets were present. We detected regulatory T cells by analyzing FoxP3 expression in CD4+ CD25+ T cells. We observed similar percentages of regulatory T cells in splenocytes from C57BL/6, heterozygous nude and LN-Tx nude mice (FIG. 3d). We distinguished naive and memory T cells using differential expression of CD44 and CD62L (where naive cells are CD44−CD62L+, central memory cells are CD44+CD62L+, and effector memory cells are CD44+CD62L−). As with the regulatory T cells, we detected naive and memory T cell subsets among splenocytes from C57BL/6, heterozygous nude and LN-Tx nude mice (FIG. 3d). The percentage of effector memory T cells was higher and the percentage of naive T cells was lower in the LN-Tx nude mice than in the other two groups, perhaps because these mice had been previously exposed to skin grafts (see below).

As the LN-Tx nude mice contained a range of peripheral single-positive CD4+ and CD8+ T cells, we asked whether the de novo immune system in these recipient mice could mount a T cell-mediated response against a skin allograft. We transplanted tail skin from C57BL/6 (syngeneic with regard to the donor thymus) or CBA/CaJ (allogeneic with regard to the donor thymus) mice to the dorsal side of LN-Tx BALB/c nude mice. After 2 weeks, all of the LN-Tx BALB/c nude mice had rejected the allogeneic CBA/CaJ skin grafts. Conversely, the C57BL/6 skin grafts were all completely accepted after 2 weeks (FIG. 3e). We then asked whether LN-Tx BALB/c nude mice would mount an immune response against a xenogeneic tumor cell transplant. We thus injected 300,000 human colorectal cancer cells (32) into the subcutaneous space of BALB/c nude and LN-Tx BALB/c nude mice. The majority (8 of 9) of the injected LN-Tx BALB/c nude mice rejected the tumors (FIG. 3e). In contrast, xenogeneic tumors grew in the untreated BALB/c nude mice (FIG. 3e). These results suggest that the single-positive T cells present in the LN-Tx BALB/c nude mice were functional. Together, these data support the concept of using the lymph node as a site for thymic transplant to generate an ectopic thymus.

Functional Pancreatic Islets in the Lymph Node

We then hypothesized that the lymph node might also provide a suitable environment for pancreatic islet transplantation. We harvested islets from C57BL/6 GFP+ transgenic mice and transplanted them into the jejunal lymph nodes of C57BL/6 wild-type mice (LN-Tx mice) treated with streptozotocin, which induces diabetes. We monitored the blood glucose concentrations of these mice weekly, and after 6 weeks we removed the transplanted lymph nodes to analyze islet engraftment. We found GFP+ islets within the subcapsular sinus of the lymph nodes adjacent to the densely packed lymphocytes that are indicative of a typical lymph node (FIG. 4a). We detected expression of C-peptide and glucagon, markers of pancreatic β-cell and α-cell function, respectively, within the engrafted lymph nodes (FIG. 4a).

Next, we asked whether islets transplanted to the lymph nodes of diabetic mice (blood glucose concentrations greater than 300 mg/dl) are able to lower the blood glucose concentrations of the mice to a normal range (100-200 mg/dl). Similarly to islets transplanted under the kidney capsule, islets transplanted directly into the lymph nodes restored the mean blood glucose concentrations of the recipient mice to normal levels within 6 weeks after transplantation (FIG. 4b). In three of five LN-Tx mice, a second islet transplant was performed into the jejunal lymph node 1 week after the initial transplant. The mice that did not receive a transplant all died after 3 weeks. Furthermore, normoglycemia was maintained in the one mouse examined at 6 months for at least 6 months after lymph node transplantation. These results suggest that pancreatic islets transplanted in the lymph nodes survive and function in vivo with the capacity to sustain long-term normoglycemia.

Because we observed engraftment of multiple cell types in the lymph nodes, we asked whether activation of a lymph node—mediated immune response might interfere with the function of the engrafted cells. Therefore, we induced an inflammatory reaction in the intraperitoneal cavities of normoglycemic mice that had received islet transplants into their lymph nodes; to induce the inflammatory reaction, we injected the mice with lipopolysaccharide (LPS, 1 mg per kg of body weight). We confirmed the effective induction of inflammation by measuring the serum concentrations of tumor necrosis factor α (TNF-α), interleukin-1β (IL-1β) and IL-6 (FIG. 4c). Immediately after LPS injection, we noted a temporary reduction in the weight and blood glucose concentrations of the mice, which completely normalized after 4 d (FIG. 4c). We did not observe any increase in glucose concentrations above normal levels in these mice (normoglycemia was still detected 5 weeks after LPS injection).

Together, these data suggest no apparent negative effect of the lymphatic or immune systems on lymph node—grafted islets.

Vasculature of Injected Lymph Nodes

We demonstrated that cell engraftment in the lymph node is not restricted to one cell type. This result is consistent with the current concept of metastasis to the lymph node, where multiple cancer cell types are capable of residing, and suggests that the lymph node environment is exceptionally well suited to promote the survival and function of transplanted cells in general. Because abundant vasculature is required to sustain organ function (6,33), we hypothesize that the dense vascular network in the lymph node is an important contributor to sustaining long-term engraftment of normal epithelial tissue. We observed dense neovascular trees in the lymph nodes into which we injected hepatocytes (FIG. 5a). Lymph nodes injected with hepatocytes, thymic cells or islets contained many recipient-derived CD31+ endothelial cells pervading the areas of engraftment, suggesting that extensive blood-vessel remodeling took place during the ectopic tissue engraftment (FIG. 5b and Supplementary FIG. 5). Moreover, we detected CD105+ (Endoglin) cells and Collagen IV+ cells, which are markers of neovascular remodeling, in each of the engrafted lymph nodes (FIG. 5b) 34-36. These data suggest that blood vessels in the surrounding lymph node environment contribute to the neovascularization and overall function of the ectopic tissues.

6.3 Discussion

There are over 500 lymph nodes in the human body, many of which are relatively easily accessible. Although a single lymph node structurally limits the number of donor cells that can be transplanted, it is technically feasible to transplant more than one lymph node to gain sufficient organ or tissue function from the transplanted cells. The potential loss of function in a few lymph nodes does not seem to compromise the overall function of the lymphatic system. In fact, lymphedema is the most common complication after lymphadenectomy in patients with cancer and only affects a limited number of these patients (37). Compression syndrome and lymphatic spread are two of the common issues in patients with cancer that have metastatic diseases in their lymph nodes. However, we found none of these complications in any of our experiments. It is also important to note that we transplanted healthy, not transformed, cells into the lymph nodes, so the intrinsic potential of the transformed cells for widespread metastatic migration and uncontrolled growth was not present in our experiments. Large animal studies will provide further insight into the potential difficulties associated with cell transplant to the lymph node.

Lymph node biopsies by fine-needle aspiration are a routine diagnostic procedure, with lymph nodes often being readily identified by palpation or ultrasound guidance. In fact, the clinical application of lymph node injection has been validated, with patients rating the procedure as less painful than venous puncture (38). Moreover, if a less superficial node is advantageous for therapy, ultrasound guidance can be used to successfully inject the visceral mesenteric lymph nodes (39). The strong clinical precedent of ultrasound-guided lymph node injections may help make this technique readily adaptable to a clinical setting. These minimally invasive techniques may also provide a potential therapy for patients who are ineligible for a more invasive therapy because of comorbidities.

In the treatment of liver failure, transplantation of hepatocytes into ectopic sites, including the spleen, pancreas, peritoneal cavity and subrenal capsule, has been proposed. The feasibility and efficacy of these techniques have been confirmed in preclinical studies, but clinical success rates have been limited thus far, and new methods are needed to improve hepatocyte engraftment (1,7). It should be noted that our goal is not to replace a whole liver but to complement liver functions by generating functional ectopic hepatic tissue. In our Fah−/− mice, we generated around 70% of the liver mass in one lymph node. The native liver is still present but at a reduced size and, probably, reduced function. For patients with liver disease, we postulate that liver function gradually deteriorates and transplantation of several lymph nodes with hepatocytes will create enough hepatic mass to stabilize the liver disease. In addition, we hypothesize that the hepatic mass generated in the lymph node may provide enough hepatic function to facilitate regeneration of the native liver. It should also be noted that transplantation of heterotopic liver has been discussed at length in the literature as a possible alternative to orthotopic liver transplantation (34, 40, 41).

Thymus transplants have been performed exclusively in the quadriceps of pediatric patients with complete DiGeorge syndrome (4). Unfortunately, children with DiGeorge syndrome often show poor growth, and transplantation is frequently postponed to allow for further development (42). Furthermore, a lack of vascularization and the resulting ischemia after transplant are detrimental (43). Transplanting thymic cells into the lymph node may represent an advantageous site to provide thymic function.

The optimal implantation site for pancreatic islet transplantation to increase function, reduce necessary implantation mass and decrease immunogenicity is still under debate (6, 44-46). However, proximity to a good vascular supply is clearly essential for the survival of islet cells, as well as for that of hepatocytes and thymic epithelial cells.

One concern for cell transplant into the lymph node is the rapid immune response that can be initiated by the introduction of a foreign antigen into a site that is densely packed with lymphocytes. In our study, we included experiments under allogeneic conditions and blocked the T-cell response to prevent any alloreactivity. We observed that the immune reaction in the lymph nodes is not stronger or faster than the reaction in other sites and that immune suppression therapy works at a similar efficiency compared to the classic hepatocyte transplantation in the spleen. We expect that immunosuppressive therapies similar to those used in clinical organ transplants can be used with this approach.

Reprogramming somatic cells provides an exciting potential source of donor cells for regenerative medicine (47). As these cells can be derived from autologous material and are capable of being recognized as 'self' by the host immune system, they can potentially overcome immunologic barriers. However, recent studies have suggested that these autologous cells may not be entirely protected from the immune system (48). On the basis of our results, the lymph node may be an effective transplantation site for reprogrammed somatic cells that can be developed for organ regeneration purposes.

In summary, we provide the first report, to our knowledge, describing the use of a lymph node as a site for functional cellular transplant. By directly injecting the lymph node with hepatocytes, thymuses or pancreatic islets, we demonstrate engraftment of the donor cells and subsequent organ function. This new approach of using the lymph node as an in vivo bioreactor in which to regenerate functional organs may be beneficial to the field of regenerative medicine.

7. EXAMPLE 2

Multiplication of Various Tissues in the Mouse Lymph Node

The severe shortage of deceased-donor organs has driven a search for alternative methods of treating patients with failing organs. Cell-based regenerative medicine is emerging as a promising interdisciplinary field for tissue repair and restoration of organ function, able to contribute to improving health in a minimally invasive fashion. However, cellular transplantation has limitations including recapitulating the functions of structurally complex organs. One potential approach to replacing such functions is through organogenesis. Growing new organs in situ can be achieved by transplanting embryonic tissues. Renal capsule grafting is a well established method of growing embryonic or neonatal organ rudiments in vivo for extended periods. However, space limitation beneath the renal capsule has proven to be an impediment to the growth of transplants, the limitation increasing with age. Recently, the mouse jejunal lymph nodes have been identified as alternative ectopic sites able to provide a permissive environment for liver, pancreas and thymus cells. We aimed at investigating their capability in also supporting the maturation of multiple other tissues explanted from E14.5-15.5 GFP+C57BL/6 mouse embryos (FIG. 11). Our preliminary data (FIG. 12a-d) suggests that jejunal lymph nodes can favor the engraftment/maturation of several tissues. Differentiation of lung tissue from a pseudoglandular to a mixed saccular/alveolar morphology was observed (FIG. 12b). Crypt-like structures developed following injection of intestinal fragments into lymph nodes (FIG. 12c). Importantly, goblet-like cells were observed all along these structures, suggesting the presence of terminally differentiated intestinal cell types. Similarly, well-developed renal corpuscles were found in repopulated lymph nodes (12d). Further investigations are needed to understand whether these lymph nodes carry out specific functions. Our lab has previously shown that primary hepatocytes injected intraperitoneally into mice lacking fumarylacetoacetate hydrolase (a mouse model of tyrosinemia type I) migrate and colonize the host abdominal lymphatics and restore hepatic functions (1). More recently, hepatocytes and pancreatic islets injected directly into a single lymph node were shown to generate functional tissues, rescuing mice from lethal liver failure, and streptozotocin-induced diabetes, respectively (2). Similarly, de novo thymus function could be generated in athymic mice by injecting thymic tissues into lymph nodes (2). These three independent results support the proof of concept that the lymph node provides a hospitable environment for normal cell engraftment. We extended this approach to additional tissues, demonstrating lymph node capacity in supporting not only the engraftment, but also the maturation of murine fetal tissues, including lung, intestine and kidney.

Our preliminary results using fetal kidney are particularly encouraging. Morphogenesis of the S-shaped body to a structure that contains vascular loops of the glomerulus and the Bowman's capsule was observed. Engineered glomeruli contained all the different cell types present in the adult kidney. Whether the implanted tissue generates cells endowed with the ability to produce erythropoietin and exhibits physiologic functions including blood filtration and tubular reabsorption of macromolecules, will be investigated in the future.

Beyond its capacity in supporting the maturation of fetal tissues, the lymph node also provided a suitable environment for adult thyroid gland regeneration (FIG. 13). Indeed, follicle-like structures were observed in the repopulated lymph node, suggesting that the thyroid function might be restored in human patients after total thyroidectomy, by simply using their lymph nodes as bioreactors, thus avoiding thyroid hormone replacement medication for the rest of their life.

8. EXAMPLE 3

The Mouse Lymph Node as an Extopic Transplantation Site for Multiple Tissues Fetal tissues were isolated for implantation as set forth in FIG. 11. There are a number of problems associated with determining gestational age in embryonic mice (see FIGS. 14A-C). Injections of various fetal tissues were performed and in many cases resulted in lymph node repopulation (FIG. 15). FIG. 16 shows exemplary transplantation of thyroid gland tissue into lymph node. Transplantation of liver tissue in lymph node is shown in FIG. 17. FIG. 18 shows the results of transplanting brain tissue into lymph node; brain tissue was observed to grow well in lymph node. As shown in FIG. 19, transplantation of lung tissue into lymph node was observed to result in differentiation of lung tissue from a pseudoglandular to a mixed saccular/alveolar morphology. FIG. 20 shows that when intestinal tissue was transplanted into lymph node, crypt-like structures developed, and goblet-like cells were observed along the crypt-like structures, suggesting the presence of terminally-differentiated intestinal cell types. Of note, due to its size, the lymph node would not be appropriate for organogenesis. FIGS. 21A-C show the results of kidney tissue transplant into lymph node showing the presence of renal-like histology and the presence of renal cell markers. In particular, a well-developed renal corpuscle was found within GFP+ tissue inside the repopulated lymph node, and its mean volume was increased 3-fold with respect to parental tissue. Interestingly, the glomerulus-like structure was not GFP+.

GK2, GK3, and GK4 lymph nodes were injected with kidneys isolated from embryos derived from the same mother, however, well-developed renal corpuscles were observed only in the GK3 lymph node. This could reflect variability among embryos or recipient mice. Further results relating to the transplant of kidney tissue into lymph node are shown in FIGS. 22A-D. These results, inter alia, indicate that the mouse lymph node can support the maturation of kidney. Morphogenesis of the S-shaped body to a structure that contains vascular loops of the glomerulus and Bowman's capsule was observed.

REFERENCES (FOR EXAMPLES 1-3)

1. Fisher, R. A. & Strom, S. C. Human hepatocyte transplantation: worldwide results. Transplantation 82, 441-449 (2006).
2. Shapiro, A. M. et al. International trial of the Edmonton protocol for islet transplantation. N. Engl. J. Med. 355, 1318-1330 (2006).
3. Schuppan, D. & Afdhal, N. H. Liver cirrhosis. Lancet 371, 838-851 (2008).
4. Markert, M. L. et al. Transplantation of thymus tissue in complete DiGeorge syndrome. N. Engl. J. Med. 341, 1180-1189 (1999).
5. Markert, M. L., Devlin, B. H. & McCarthy, E. A. Thymus transplantation. Clin. Immunol. 135, 236-246 (2010).
6. Merani, S., Toso, C., Emamaullee, J. & Shapiro, A. M. Optimal implantation site for pancreatic islet transplantation. Br. J. Surg. 95, 1449-1461 (2008).
7. Dhawan, A., Puppi, J., Hughes, R. D. & Mitry, R. R. Human hepatocyte transplantation: current experience and future challenges. Nat. Rev. Gastroenterol. Hepatol. 7, 288-298 (2010).
8. Cyster, J. G. Chemokines and cell migration in secondary lymphoid organs. Science 286, 2098-2102 (1999).
9. von Andrian, U. H. & Mempel, T. R. Homing and cellular traffic in lymph nodes. Nat. Rev. Immunol. 3, 867-878 (2003).
10. Sleeman, J. P. & Thiele, W. Tumor metastasis and the lymphatic vasculature. Int. J. Cancer 125, 2747-2756 (2009).
11. Link, A. et al. Fibroblastic reticular cells in lymph nodes regulate the homeostasis of naive T cells. Nat. Immunol. 8, 1255-1265 (2007).
12. Hoppo, T., Komori, J., Manohar, R., Stolz, D. B. & Lagasse, E. Rescue of lethal hepatic failure by hepatized lymph nodes in mice. Gastroenterology 140, 656-666 (2011).
13. Van den Broeck, W., Derore, A. & Simoens, P. Anatomy and nomenclature of murine lymph nodes: descriptive study and nomenclatory standardization in BALB/cAnN-Crl mice. J. Immunol. Methods 312, 12-19 (2006).
14. Perl, A. K., Wilgenbus, P., Dahl, U., Semb, H. & Christofori, G. A causal role for E-cadherin in the transition from adenoma to carcinoma. Nature 392, 190-193 (1998).
15. Pham, T. H. et al. Lymphatic endothelial cell sphingosine kinase activity is required for lymphocyte egress and lymphatic patterning. J. Exp. Med. 207, 17-27 (2010).
16. Grigorova, I. L. et al. Cortical sinus probing, S1P1-dependent entry and flow-based capture of egressing T cells. Nat. Immunol. 10, 58-65 (2009).
17. Shields, J. D. et al. Autologous chemotaxis as a mechanism of tumor cell homing to lymphatics via interstitial flow and autocrine CCR7 signaling. Cancer Cell 11, 526-538 (2007).
18. Michalopoulos, G. K. & DeFrances, M. C. Liver regeneration. Science 276, 60-66 (1997).
19. Grompe, M. et al. Pharmacological correction of neonatal lethal hepatic dysfunction in a murine model of hereditary tyrosinaemia type I. Nat. Genet. 10, 453-460 (1995).
20. Overturf, K., al-Dhalimy, M., Ou, C. N., Finegold, M. & Grompe, M. Serial transplantation reveals the stem-cell—like regenerative potential of adult mouse hepatocytes. Am. J. Pathol. 151, 1273-1280 (1997).
21. Lagasse, E. et al. Purified hematopoietic stem cells can differentiate into hepatocytes in vivo. Nat. Med. 6, 1229-1234 (2000).
22. Notenboom, R. G., de Boer, P. A., Moorman, A. F. & Lamers, W. H. The establishment of the hepatic architecture is a prerequisite for the development of a lobular pattern of gene expression. Development 122, 321-332 (1996).
23. Katakai, T., Hara, T., Sugai, M., Gonda, H. & Shimizu, A. Lymph node fibroblastic reticular cells construct the stromal reticulum via contact with lymphocytes. J. Exp. Med. 200, 783-795 (2004).
24. Gretz, J. E., Anderson, A. O. & Shaw, S. Cords, channels, corridors and conduits: critical architectural elements facilitating cell interactions in the lymph node cortex. Immunol. Rev. 156, 11-24 (1997).
25. Lakkis, F. G., Arakelov, A., Konieczny, B. T. & Inoue, Y. Immunologic 'ignorance' of vascularized organ transplants in the absence of secondary lymphoid tissue. Nat. Med. 6, 686-688 (2000).
26. Siegler, E. L., Tick, N., Teresky, A. K., Rosenstraus, M. & Levine, A. J. Teratocarcinoma transplantation rejection loci: an H-2-linked tumor rejection locus. Immunogenetics 9, 207-220 (1979).
27. Dressel, R. et al. The tumorigenicity of mouse embryonic stem cells and in vitro differentiated neuronal cells is controlled by the recipients' immune response. PLoS ONE 3, e2622 (2008).
28. Bumgardner, G. L., Li, J., Heininger, M. & Orosz, C. G. Costimulation pathways in host immune responses to allogeneic hepatocytes. Transplantation 66, 1841-1845 (1998).
29. Gao, D., Li, J., Orosz, C. G. & Bumgardner, G. L. Different costimulation signals used by CD4+ and CD8+ cells that independently initiate rejection of allogenic hepatocytes in mice. Hepatology 32, 1018-1028 (2000).
30. Rodewald, H. R. Thymus organogenesis. Annu Rev. Immunol. 26, 355-388 (2008).
31. Pearse, G. Normal structure, function and histology of the thymus. Toxicol. Pathol. 34, 504-514 (2006).
32. Odoux, C. et al. A stochastic model for cancer stem cell origin in metastatic colon cancer. Cancer Res. 68, 6932-6941 (2008).
33. Ohashi, K. et al. Liver tissue engineering at extrahepatic sites in mice as a potential new therapy for genetic liver diseases. Hepatology 41, 132-140 (2005).
34. Rodeck, B., Kardorff, R., Melter, M., Schlitt, H. J. & Oldhafer, K. J. Auxiliary partial orthotopic liver transplantation for acute liver failure in two children. Pediatr. Transplant. 3, 328-332 (1999).
35. Sanz-Rodriguez, F. et al. Endoglin regulates cytoskeletal organization through binding to ZRP-1, a member of the Lim family of proteins. J. Biol. Chem. 279, 32858-32868 (2004).
36. Gerber, S. A. et al. Preferential attachment of peritoneal tumor metastases to omental immune aggregates and 37. Lawenda, B. D., Mondry, T. E. & Johnstone, P. A. Lymphedema: a primer on the identification and management of a chronic condition in oncologic treatment. CA Cancer J. Clin. 59, 8-24 (2009).
38. Senti, G. et al. Intralymphatic allergen administration renders specific immunotherapy faster and safer: a randomized controlled trial. Proc. Natl. Acad. Sci. USA 105, 17908-17912 (2008).
39. Kim, M. et al. Ultrasound-guided mesenteric lymph node iohexol injection for thoracic duct computed tomographic lymphography in cats. Vet. Radiol. Ultrasound 52, 302-305 (2011).
40. Gordon, R. D. & Starzl, T. E. Changing perspectives on liver transplantation in 1988. Clin. Transpl. 5-27 (1988).
41. Stampfl, D. A. et al. Heterotopic liver transplantation for fulminant Wilson's disease. Gastroenterology 99, 1834-1836 (1990).
42. Rice, H. E. et al. Thymic transplantation for complete DiGeorge syndrome: medical and surgical considerations. J. Pediatr. Surg. 39, 1607-1615 (2004).
43. Jiang, J., Wang, H., Madrenas, J. & Zhong, R. Surgical technique for vascularized thymus transplantation in mice. Microsurgery 19, 56-60 (1999).
44. Robertson, R. P. Islet transplantation as a treatment for diabetes—a work in progress. N. Engl. J. Med. 350, 694-705 (2004).
45. Harlan, D. M., Kenyon, N. S., Korsgren, O. & Roep, B. O. Current advances and travails in islet transplantation. Diabetes 58, 2175-2184 (2009).
46. Fiorina, P., Shapiro, A. M., Ricordi, C. & Secchi, A. The clinical impact of islet transplantation. Am. J. Transplant. 8, 1990-1997 (2008).
47. Takahashi, K. & Yamanaka, S. Induction of pluripotent stem cells from mouse embryonic and adult fibroblast cultures by defined factors. Cell 126, 663-676 (2006).
48. Zhao, T., Zhang, Z. N., Rong, Z. & Xu, Y. Immunogenicity of induced pluripotent stem cells. Nature 474, 212-215 (2011).
49. U.S. patent application Ser. No. 12/921,001, Publication No. US20110002899 by Lagasse.

9. EXAMPLE 4

The Mouse Lymph Node as an Ectopic Niche for Kidney Organogenesis

Summary

The shortage of organs for kidney transplantation has created the need for new strategies to regenerate renal functions. Here we provide the first evidence that the lymph node permitted mouse metanephroi to engraft, mature and perform glomerular filtration. Host cells likely contributed to this process. Over time, production of waste fluid resulted in some cases in graft degeneration. Indeed, urine-like fluid-containing cysts and glomerular alterations were observed in several grafts after 12 weeks post transplantation. Importantly, the kidney graft adapted in response to a loss of host renal mass, speeding its development. Thus, the lymph node provides a unique tool for studying the mechanisms of renal maturation or cell proliferation and fluid secretion. This innovative system can also be used to validate the differentiation potential of candidate cells in regenerative nephrology and may provide an exclusive site for kidney organogenesis and regeneration.

9.1 Methods

Tissue Collection and Transplantation.

E14.5/15.5 kidneys were retrieved from timed pregnant GFP+ or wild-type C57BL/6 black mice under a dissecting microscope (embryos were considered 0.5 days old when the vaginal plug was detected in the morning). Alternatively, kidneys were isolated from 3-day-old (P3) GFP+C57BL/6 black mice. All kidneys were chopped in PBS and kept on ice until injection. For lymph node transplantation, recipient mice (6-week-old wild-type C57BL/6 black mice, n=52) were anesthetized with 1-3% isoflurane. A small incision was made in the abdomen to expose jejunal lymph nodes. A 1000 μL threaded plunger syringe (Hamilton, 81341) with a removable needle (gauge 20) was used to slowly inject kidney fragments into a single lymph node (paired kidneys from an embryo per mouse were injected). Light cauterization was used to seal the opening. The wound was then closed with surgical sutures. Ketoprofen treatment (2 mg/kg, IM) for postoperative pain relief was initiated right after surgery, and continued for 2 additional consecutive days. After 3, 6, 12 or 16 weeks from transplantation, mice were euthanized for analysis. Mice were bred and housed in the Division of Laboratory Animal Resources facility at the University of Pittsburgh Center for Biotechnology and Bioengineering. Experimental protocols followed US National Institutes of Health guidelines for animal care and were approved by the Institutional Animal Care and Use Committee at the University of Pittsburgh.

Histology and Immunofluorescence/Immunohistochemistry.

Repopulated jejunal lymph nodes and kidneys were fixed 2-4 hours in 4% PFA, and embedded in OCT or paraffin for further analysis. Hematoxylin and eosin (H&E), Periodic acid-Schiff (PAS), Masson's trichrome (TRI), and Picrosirius red (PSR) stains were performed as described elsewhere. Sections were also stained with antibodies against ER-TR7 (Abcam, ab51824), Collagen IV (SB, 1340-01), CD31 (BD, 550274), Podoplanin (Angiobio, 11-033), Claudin-2 (Abcam, ab76032), Keratin-8 (DSHB, TROMA-1), Erythropoietin (SCBT, sc-7956), GFP (Abcam, ab6556), BrdU (SCBT, sc-32323), AQP1 (Abcam, ab15080), NKCC2 (SCBT, sc-133823), AQP2 (Abcam, ab85876), CD45 (BD, 550539), CD106 (SCBT, sc-8304), CD3 (BD, 550275), CD4 (550280), CD8 (BD, 553027), CD45R/B220 (BD, 550286), Ly6C/G (BD, 550291), F4/80 (Caltag Lab, MF48015), WT-1 (SCBT, sc-192) or Epcam (Abcam, ab32392). For BrdU staining, sections were incubated in 2N HCl for 30 minutes in order to denature DNA. Five min incubation in 0.1 M borate buffer pH 8.0 was then carried out to neutralize the acid. Finally, BrdU antibody was added. Alexa Fluor 594 (Invitrogen) or biotinylated (Dako, LSAB2 System-HRP) secondary antibodies were used to detect primary antibodies. Biotin labeling was then revealed using streptavidin-HRP conjugate (Dako, LSAB2 System-HRP) and AEC substrate-chromogen (BioGenex, HK129-5K). Nuclei were counterstained using Hoechst or hematoxylin.

RNA Extraction, cDNA Synthesis, RT-PCR.

Total RNA was isolated from tissues stored in RNAlater® reagent (QIAGEN) using the RNeasy Mini kit (QIAGEN), according to the manufacturer's instructions. Potentially contaminating genomic DNA was digested using DNase (QIAGEN). cDNA was synthesized using the iScript™ Reverse Transcription Supermix for RT-qPCR (Bio-Rad).

PCR was performed using the iTaq DNA Polymerase kit (Bio-Rad). GAPDH transcript levels served as the housekeeping control target. Sequences of primers were as follows: UT-A1,

```
                                        (SEQ ID NO: 1)
Fwd, 5'-GACAGTGAGACGCAGTGAAG-3', (SEQ ID NO: 2)
Rev, 5'-ACGGTCTCAGAGCTCTCTTC-3';

(SEQ ID NO: 3)
UTA2, Fwd, 5'-TTTCTCCAGTCCTATCTGAG-3', (SEQ ID NO: 2)
Rev, 5'-ACGGTCTCAGAGCTCTCTTC-3';

(SEQ ID NO: 4)
UT-A3, Fwd, CCTGACAGTGAGACGCAGTG-3', (SEQ ID NO: 5)
Rev, 5'-AGAGTGGAGGCCACACGGAT-3';

(SEQ ID NO: 6)
UT-B, Fwd, 5'-TCTTCTCAAACAAGGGCGAC-3', (SEQ ID NO: 7)
Rev, TTGCTGAGCACGGAGCTCAA-3';

(SEQ ID NO: 8)
EPO, Fwd, 5'-AAACTGAAGCTGTACACGGGAGA-3', (SEQ ID NO: 9)
Rev, 5'-GGAGCAAGTTCGTCGGTCC-3';

(SEQ ID NO: 10)
GAPDH, Fwd, 5'-GGCATCCTGGGCTACACTGA-3', (SEQ ID NO: 11)
Rev, 5'-GGAGTGGGTGTCGCTGTTG-3'.
```

To enhance EPO production, anemia was induced by a rapid withdrawal of blood for 3 consecutive days before mouse sacrifice and lymph node collection.

Blood Urea Nitrogen (BUN) Test.

BUN test was performed on both serum and lymph node fluid of mice following 16 weeks from embryonic kidney injection (n=5 experimental mice, plus n=1 control mouse). Blood was collected into polyethylene terephthalate serum-gel-separator tubes (Terumo Medical). Tubes were then centrifuged at maximum speed for 10 min, and serum collected. For lymph fluid collection, briefly, the GFP+ area inside each lymph node was isolated under a fluorescent microscope, chopped in very small pieces, centrifuged at maximum speed for 10 min, and supernatant collected. BUN test was performed using the QuantiChrom Urea Assay Kit (Bioassay Systems, DIUR-500) according to the manufacturer's instructions.

Generation of Chimeric Mice.

Bone marrow cells were harvested from tibias and femurs of a GFP+C57BL/6 mouse, as described elsewhere. Subsequently, 6-week-old wild-type C57BL/6 mice (n=11) were lethally irradiated (1000 rad) and immediately retro-orbitally infused with 106 donor cells. Mice were treated with Sulfamethoxazole (SMZ) in the drinking water.

Flow Cytometry.

Whole blood was collected in K2EDTA collection tubes (Terumo Medical). One hundred microliters of blood was added to cold fluorescence-activated cell sorting (FACS) tubes. Three milliliters of Red Blood Cell Lysing Buffer (Sigma) was added to each tube, lightly vortexed and incubated for 15 min. Two milliliters of flow buffer (2% FBS in HBSS) was added to the tubes, mixed and centrifuged at 500 g for 5 min. The supernatant was aspirated. The red blood cell lysis and centrifuge were repeated as described. The final cell pellet was resuspended in 400 µl of flow buffer with Sytox Blue dye. Cells were analyzed for GFP positivity using a Miltenyi MACSQuant and FlowJo software (Tree Star).

Antibodies were added at a dilution of 1/50 in blood and mixed by gentle pipetting. Antibodies used were as follows: PerCP Cy5.5 CD45 (BD, 550994), APC CD3 (BD, 553066), PE CD4 (BD, 553730), APC Cy7 CD8 (BD, 557654), PE CD45R/B220 (BD, 553090), APC CD19 (BD, 550992), PE CD11b (BD, 553311), and APC Ly6G-Ly6C (BD, 553129). Reactions were incubated in the dark in an ice slurry bath for one hour. Three milliliters of Red Blood Cell Lysing Buffer (Sigma) was added to each tube, lightly vortexed and incubated for an additional 15 min. Two milliliters of flow buffer (2% FBS in HBSS) was added to the tubes, mixed and centrifuged at 500 g for 5 min. The supernatant was aspirated. The red blood cell lysis and centrifuge were repeated as described. The final cell pellet was resuspended in 400 µl of flow buffer with Sytox Blue dye. Cells were analyzed using a Miltenyi MACSQuant and FlowJo software (Tree Star).

Proliferation Assay.

To assess proliferation of 6-week ectopic kidneys 1 mg BrdU was dissolved in 200 ul of PBS and intraperitoneally injected 24 hours before mouse sacrifice. To assess ectopic kidney proliferation in response to growth stimuli, embryonic kidneys from GFP+C57BL/6 black mice were transplanted into 9 wild-type C57BL/6 black mice, as described above. Following 12 days from transplantation, 5 of the 9 recipient mice received left nephrectomy (Nx), while the remaining 4 mice received a sham operation. All mice were given drinking water containing 0.8 mg/ml BrdU and 1% sucrose immediately after surgery. BrdUcontaining drinking water was prepared fresh and replaced daily for 9 consecutive days, after which, it was replaced with regular water. After 5 additional days, all mice were euthanized for analysis. The number of BrdU-positive proliferating cells in the recipient kidneys was determined per renal cross-section.

Statistical Analysis.

Data are presented as means±SD. Statistical analysis was performed using Student's t test ($p<0.05$ was considered significant).

Immunofluorescence.

Repopulated jejunal lymph nodes were fixed 2 hours in 4% PFA, and embedded in OCT for further analysis. Sections were stained with antibodies against Podoplanin (Angiobio, 11-033), Claudin-2 (Abcam, ab76032), WT-1 (SCBT, sc-192), CD31 (BD, 550274), Keratin-8 (DSHB, TROMA-1) or Vimentin (SCBT, sc-5565). Alexa Fluor 594 antibodies (Invitrogen) were used to detect primary antibodies. Nuclei were counterstained using Hoechst.

9.2 Results

The Lymph Node is a Permissive Site for Kidney Organogenesis

Figure 23A:
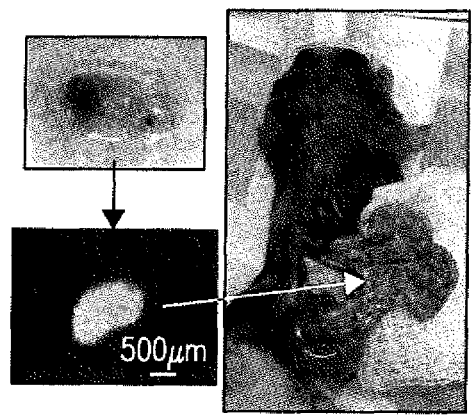
Figure 23B:
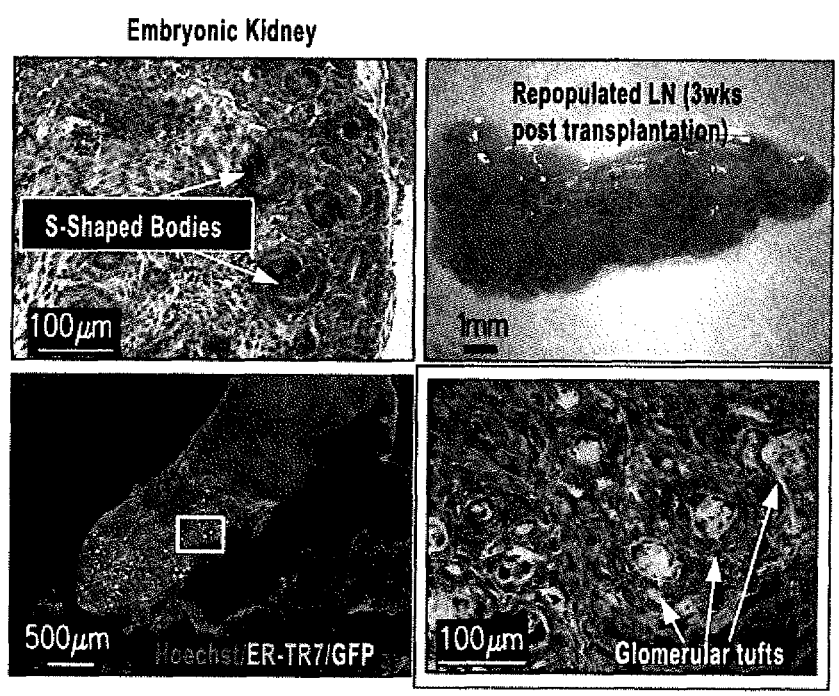
Figure 23D:
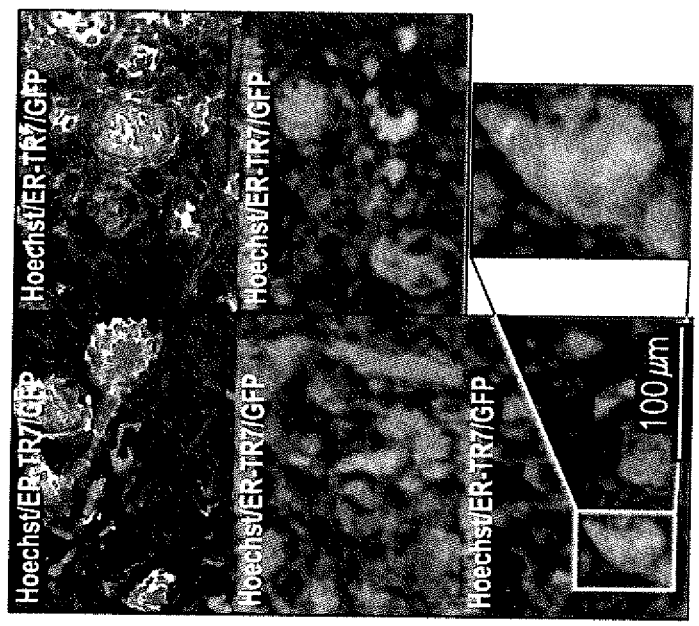
Figure 23C:
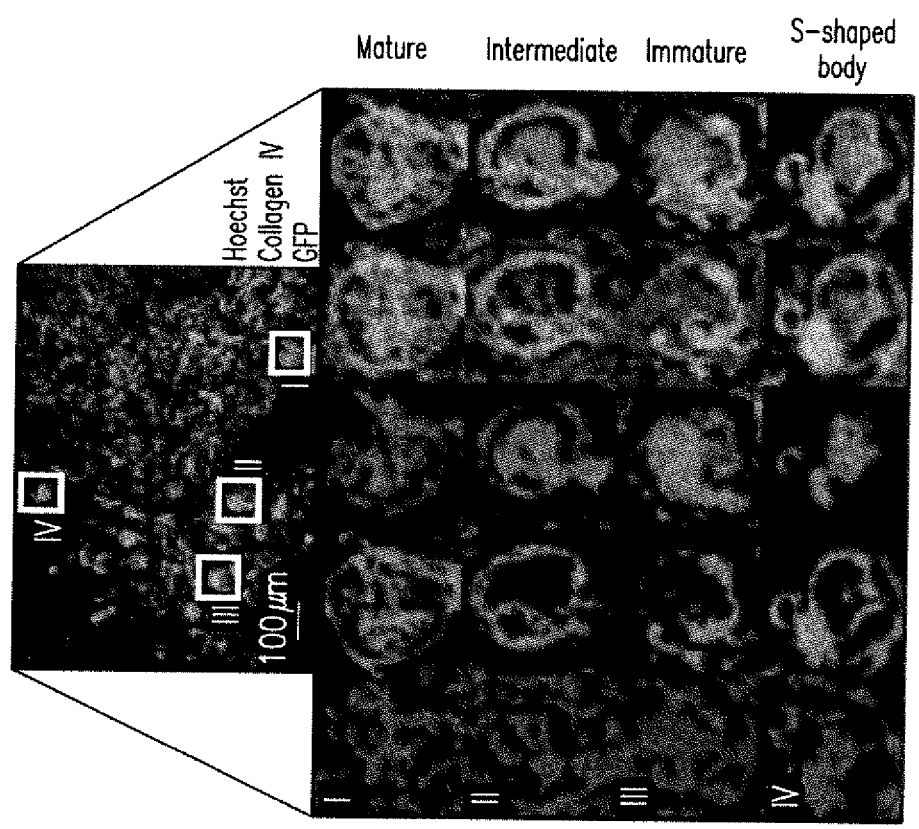

We first investigated whether mid-embryonic mouse kidney fragments could become integrated into a host mouse lymph node, and undergo morphological maturation. Renal tissues were harvested from C57BL/6 GFP+ transgenic embryos, isolated from ureteric buds, minced, and injected directly into a single jejunal lymph node of adult wild-type C57BL/6 mice (FIG. 23a). Following 3 weeks, recipient mice were sacrificed, lymph nodes collected, and histologically examined. Morphogenesis of S-shaped bodies into more mature renal corpuscles was observed in ectopic grafts 3 weeks after embryonic kidney transplantation (FIG. 23b). Developing renal corpuscles expressed type IV collagen in their glomerular basement membranes (GBM) as well in mesangial areas (FIG. 23c). Three stages of glomerulus maturation could be distinguished based on the literature (FIG. 23c) [18]. Briefly, glomeruli with loose structure of the tuft, and capillary loops lined with typical flat epithelia were defined as mature glomeruli. Glomeruli with less than half the circumference of capillary loops lined with cuboidal epithelial cells, but at least five of them adjoining, were defined as intermediate glomeruli. Finally, glomeruli with at least half of the circumference of capillary loops densely lined with cuboidal epithelial cells were defined as immature glomeruli. Ectopic grafts also showed some S-shaped bodies, further indicating that kidney maturation was not completed at the time of lymph node collection. Nevertheless, mature ectopic glomeruli contained different cell types present in the adult glomerulus, including CD31-positive endothelial cells, and podoplaninpositive podocytes (FIG. 23d). Developing kidneys also comprised rudimental claudin-2- and keratin-8-positive tubules (FIG. 23d). Importantly, ectopic grafts showed tubular erythropoietin (Epo) expression, indicating hormonal competence (FIG. 23d).

We also found that kidney organogenesis into the lymph node was critically dependent on the stage of renal development at the time of transplantation. Despite 3-day-old mice (P3) kidneys show glomerular maturity, they failed to efficiently engraft into the lymph node (FIG. 29). Embryonic day (E) 14.5 to 15.5 kidneys generated larger and thicker grafts as compared to P3 kidneys following 3 weeks from transplantation into the lymph node. Moreover, while embryonic kidneys acquired more mature morphological characteristics into the lymph node, newborn kidneys failed to recapitulate their native morphology, resulting in an imperfect glomerulogenesis. Even extending the growth of newborn kidney fragments into the lymph node up to 12 weeks did not result in a better engraftment and maturation, confirming the idea that fetal kidney harbors more regenerative potential than newborn kidney.

Ectopic Grafts Show Well-Defined, and Proliferating Nephrons with Urine Concentrating Ability 6 Weeks after Transplantation Three weeks after transplantation, it was not possible to confirm the presence of mature, functional nephrons. However, some mature nephrons were distinguishable 6 weeks after transplantation (FIG. 24a). Indeed, attached to the developed renal corpuscles, various segments of the renal tubule could be observed. Furthermore, the presence of erythrocytes inside the glomerulus capillary tuft of these elongated structures indicated a probable blood filtration capacity (FIG. 24a). Importantly, such structures were still proliferating at the time of lymph node collection, as indicated by bromodeoxyuridine (BrdU) incorporation, administered to the mouse 24 hours before its sacrifice (FIG. 24b). Importantly, 6-week ectopic grafts showed urine-concentrating ability, as indicated by RT-PCR analysis of different urea transporters (UT-A1, UT-A2, UT-A3, and UT-B) (FIG. 24c). It is not surprising that UT-B mRNA was detected in both control and repopulated lymph nodes, since this urea transporter is known to be expressed in non-renal tissues, as well as in erythrocytes [19]. Erythropoietin production was also confirmed in 6-week ectopic grafts by RT-PCR analysis of mRNA isolated from phlebotomized mice.

Host Cells Vascularize Kidney Ectopic Graft and Likely Integrate into the Developing Tissue In some mice, all nephrons were mature by 12 weeks. These nephrons showed glomerular expression of podoplanin and CD31 (FIG. 25, left). CD31 staining also indicated that ectopic nephrons were vascularized by host arterioles (FIG. 25, right). Collagen IV was localized at GBM and tubules (FIG. 25, left), as well in the mesangial areas in the glomeruli (FIG. 25, right), and it likely had a hybrid origin. Indeed, it did not always colocalize with GFP+ cells. Ectopic nephrons also showed keratin-8- and erythropoietin-positive tubules (FIG. 25, left).

Renal Cysts Develop within Repopulated Lymph Nodes as a Result of Ectopic Kidney's Ability to Filter the Blood and Produce Urine While in some mice the ectopic kidney graft was viable and apparently functional at 12 weeks, in other mice, at the same time point, it comprised fluid-filled cysts. Renal cystic disease has multiple etiologies. Renal cysts can result from defective differentiation of kidney tubules [20]. However, while proliferative activity of the renal tubular epithelium is an essential component of cyst formation, fluid secretion could have a commanding role in cyst development and expansion[21]. We believe in a scenario in which urine-like fluid is produced by ectopic kidneys as a result of their functional maturation into the lymph node. In hepatized lymph nodes, ectopically produced bile juice is transported in the serum, and eventually processed in the native liver without affecting the host (our unpublished data). Similarly, in some cases, fluids and wastes might be successfully drained into the lymphatic vessels, allowing the ectopic graft to better survive. In other cases, kidney products might accumulate inside the tubules, activating a positive loop of epithelial proliferation and vectorial fluid secretion, which eventually leads to cyst appearance. In other words, cyst formation inside the repopulated lymph node could share some traits with multicystic dysplastic kidney (MCDK) and obstructive dysplasia (ORD), where urinary tract obstructive lesions cause urine retention in functioning nephrons and lead to cystogenesis [22].

Figure 26D:
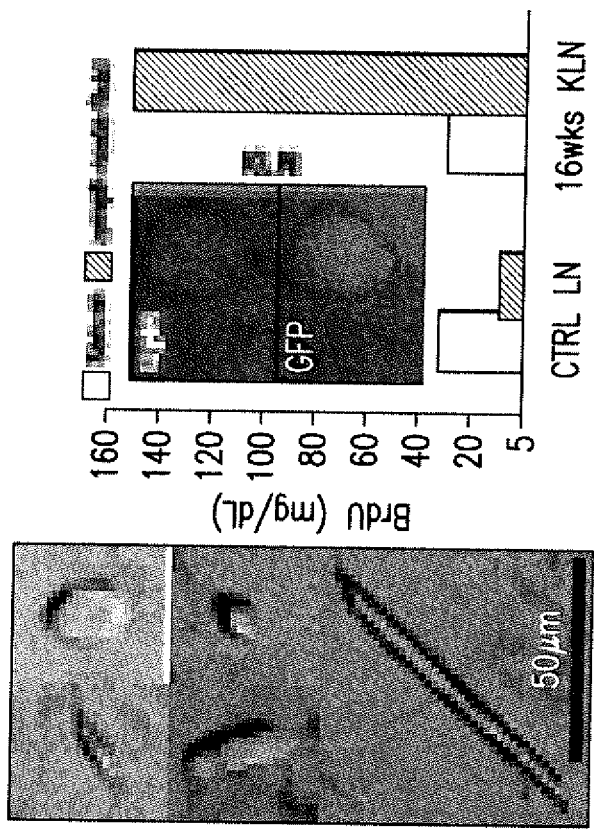
Figure 26C:
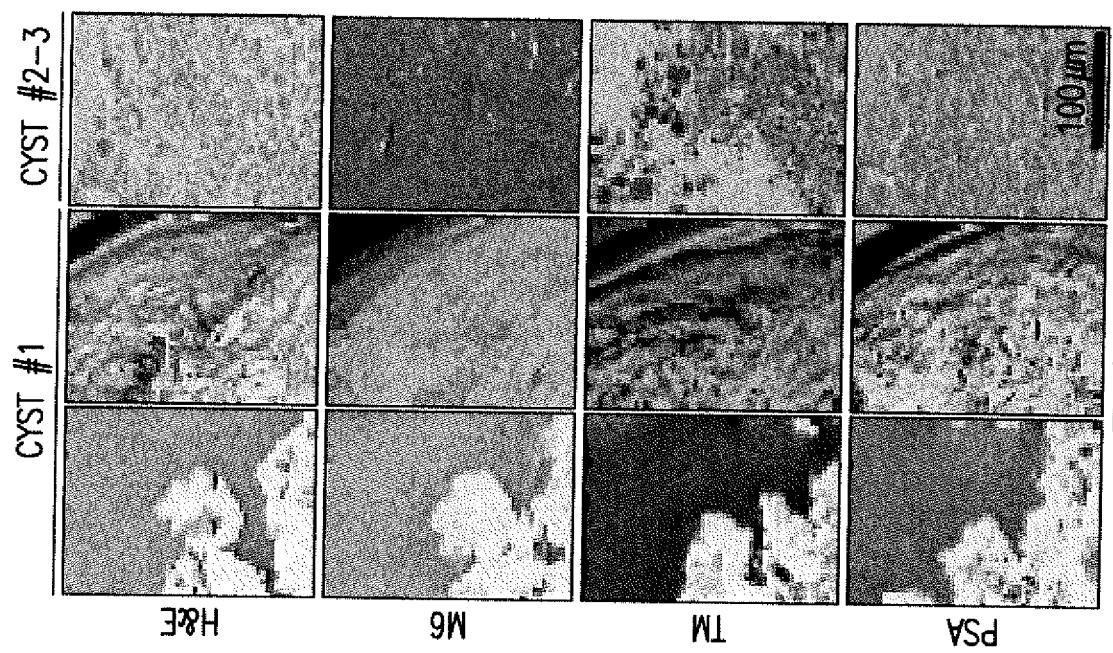

Two main cysts were found in a repopulated lymph node (FIG. 26a). Cyst #1 was lined by a simple squamous epithelium, showing an apical expression of the water channel aquaporin-1 (AQP1) and absence of sodium-potassium-chloride transporter 2 (NKCC2), indicating a possible origin from thin descending limbs of loop of Henle (FIG. 26b, left). The epithelium was negative for BrdU indicating that cystic expansion had already ceased at the time of lymph node collection (FIG. 26b, left). The loop of Henle plays a role in the transport of ions and water, allowing production of urine. Accordingly, cyst #1 contained many oval to round, rhomboid, parallelepiped, and amorphous urinary crystals, with more or less sharply defined contours, some of them reaching 100 μm of length (FIG. 26d, left). Cysts #1 also contained eosinophilic, Periodic acid-Schiff (PAS) positive, acidfuchsinophilic with Masson's trichrome (TRI), and red with picro-sirius red (PSR) staining proteinaceous material, apart from amorphous fibers often containing a periodic banding pattern, and rarely TRI positive (FIG. 26c, left). The presence of urine in repopulated lymph nodes was confirmed by Blood Urea Nitrogen (BUN) test 16 weeks following kidney transplantation. While serum BUN levels were not altered in transplanted mice as compared to control mice, BUN levels were highly increased in lymph node fluid after kidney transplantation and cyst formation (FIG. 26d, right). However, BUN levels were not increased in repopulated lymph nodes where no macroscopic cysts could be observed, further indicating that the time window of ectopic kidney maturation and degeneration differs among mice. Approximately, S-shapes bodies take 6 weeks to be converted into mature nephrons, and these nephrons can degenerate by the 12th week, as well as be still healthy and functional at this stage.

Differently from cyst #1, cyst #2 was lined by a simple tall cuboidal epithelium, showing apical endocytic vacuoles and a PAS positive brush border, indicating an origin from proximal convoluted tubule (FIG. 26b, right). Accordingly, the epithelium stained positive for AQP1 and negative for aquaporin 2 (AQP2) (FIG. 26b, right). Moreover, it showed some positivity for the BrdU marker, indicating cystic expansion process was still active at the time of lymph node collection (FIG. 26b, right). The proximal convoluted tubule reabsorbs large molecules, such as proteins. Accordingly, cyst #2 contained pale eosinophilic, PAS positive, intensely acid-fuchsinophilic with TRI, and yellowish with PSR staining round globules, ranging from 1 to 20 μm diameter, thought to be protein globules (FIG. 26c, right). These structures likely are hyaline casts covered with fat droplets. The accumulation of hyaline droplets is the visible aspect of the damage to the glomerular capillary membrane, which leads to abnormal filtration and reabsorption of plasma proteins.

Figure 26F:
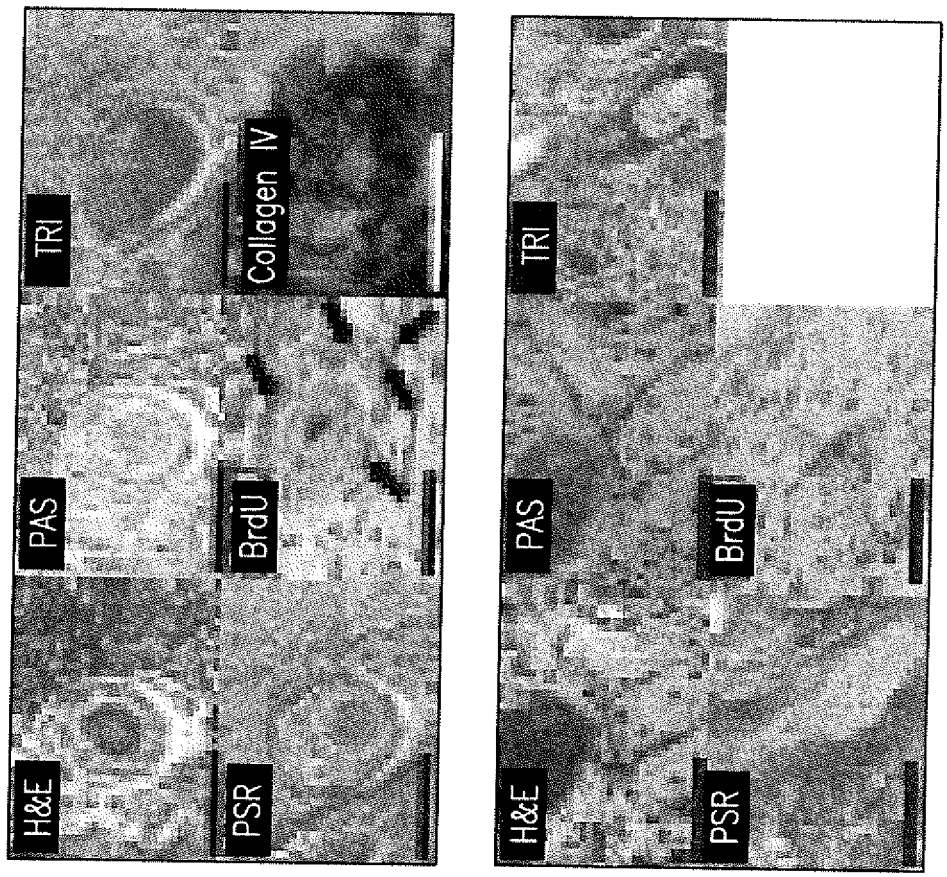
Figure 26E:
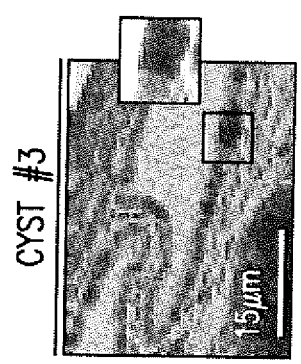

A very small cyst with all the features of cyst #2 was also identified (FIG. 26a, b, c). A mix of GFP positive and negative cells lined this cyst (cyst #3), indicating a hybrid origin (FIG. 26e).

Structural glomerular alterations could be observed in the cyst-containing ectopic renal graft. Specifically, histological analyses often revealed compressed tuft, in the center of the glomerulus, surrounded by a circumferential cellular crescent (H&E) (FIG. 26f, upper). There was a clear space between tuft and the crescent. A mild focal thickening of glomerular basement membrane could be observed (PAS) (FIG. 26f, upper). Basement membrane thickening could be attributed to increased collagen accumulation (TRI and PSR) (FIG. 26f, upper). The cellular crescent contained some BrdU positive cells, indicating active proliferation (FIG. 26f, upper). Expansion of the mesangial matrix in these glomeruli was confirmed by intense staining for collagen IV (FIG. 26f, upper). Hypercellularity within the glomerular tuft, obliterating Bowman's space was also observed (FIG. 26f, bottom). Hypercellular glomeruli can be due to immune cell infiltration. Close to these glomeruli, swelling and vacuolization of proximal tubular cells leading to narrowing of tubular lamina (osmotic nephrosis) were detected (FIG. 26f, bottom). Taken together, although at a certain point, the ectopic graft begins to degenerate, to our knowledge, our study shows the first long-term survival of metanephroi transplanted into an ectopic site.

Bone Marrow-Derived Host Cells Integrate into the Developing Tissue

On the basis of the results shown in FIGS. 3 and 4e, we hypothesized that kidney regeneration inside the lymph node could not only be attributable to transplanted kidney stem/progenitor cells, but could also be attributable to the combination of transplanted kidney stem/progenitor cells and stem cells of host origin such as bone marrow.

To investigate whether bone marrow contributes to ectopic kidney organogenesis into the lymph node, bone marrow chimeras were generated as described in the Methods section. Engraftment was monitored by flow cytometric analysis of the peripheral blood 6 weeks after cell transplantation. All mice except one showed >75% of GFP+ leukocytes in their blood (FIG. 27a). The mouse showing the lowest engraftment (BMT #5) died 8 weeks following transplantation and was therefore not included in the study. Mouse blood was also analyzed for different markers of lymphocytes and granulocytes/monocytes. Gating strategy is indicated in FIG. 30a. Briefly, within the GFP+CD45+ cell population, 13.8%±5.1 were CD3+ cells; in turn this population comprised 61.6%±8.7 CD4+ cells, and 8.7%±1.5 CD8+ cells. When looking at B-lymphocytes, we found 40.2%±9.9 GFP+CD45+ cells to be double reactive for CD19 and B220 (FIG. 30b). Finally, 73.3%±15 of total Ly6G and Ly6C were GFP+(FIG. 30c).

Figure 27C:
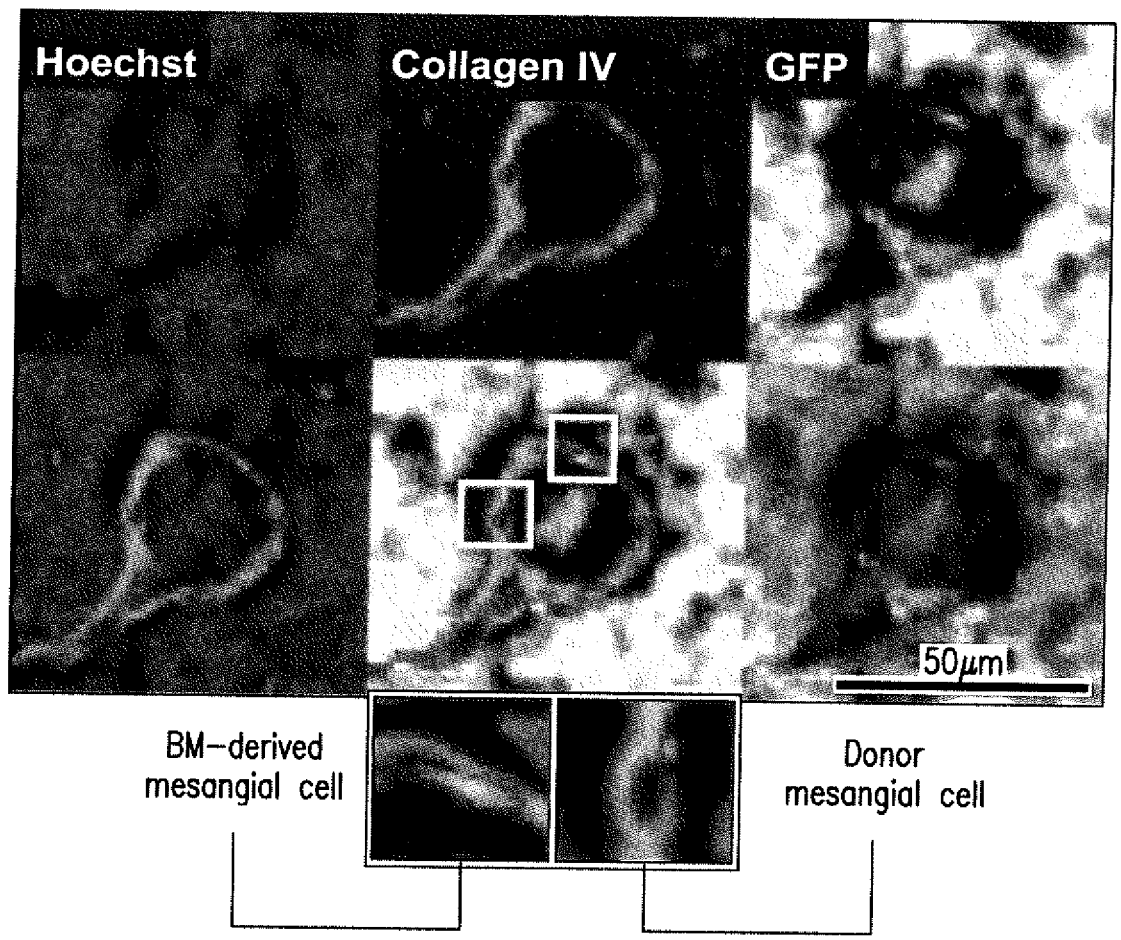
Figure 27D:
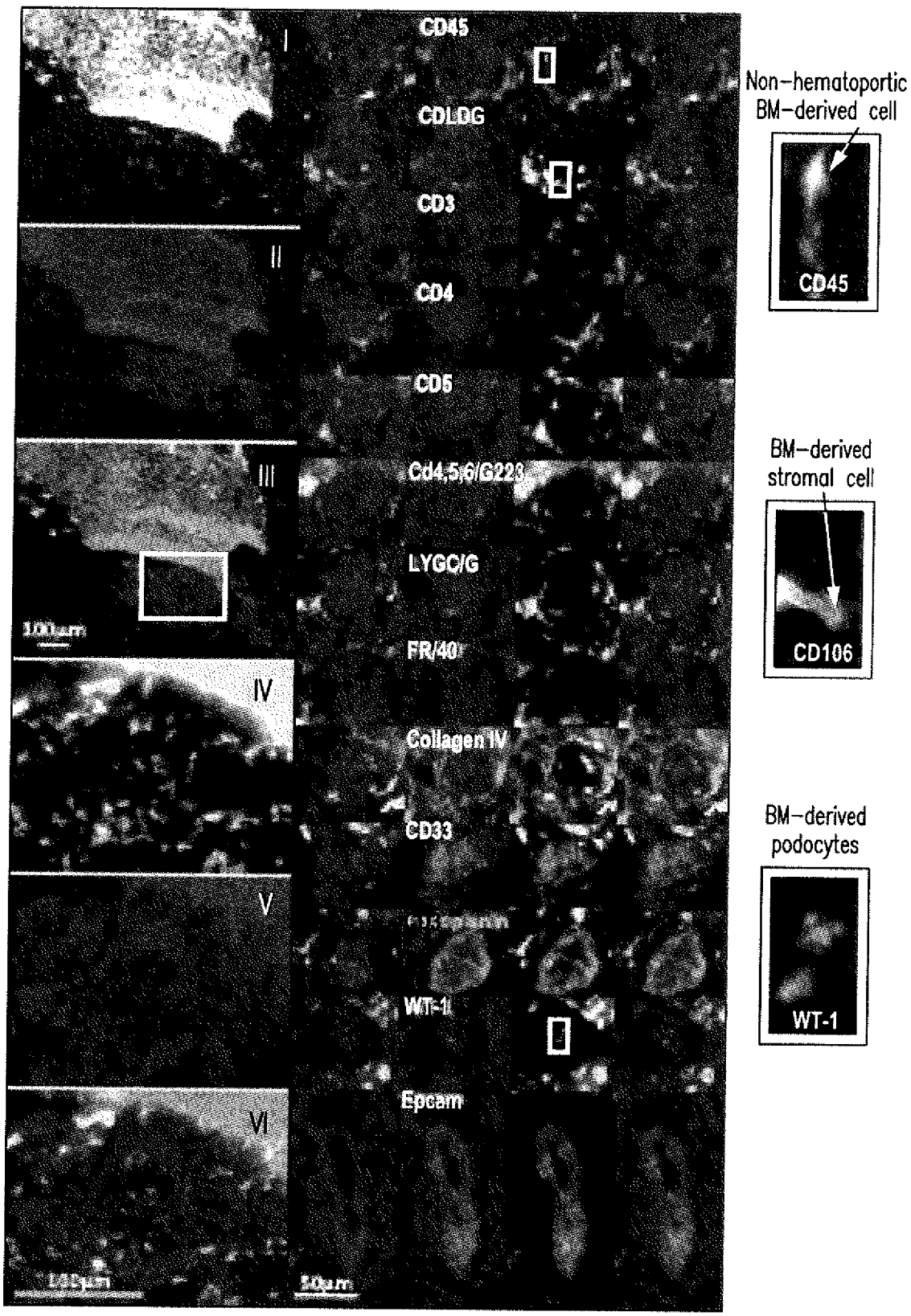

Following 8 weeks from bone marrow transplantation, all mice received injection of wild-type embryonic kidneys (FIG. 27b). Mice were sacrificed 6 or 10 weeks post kidney transplantation (FIG. 27b). Interestingly, bone marrow-derived collagen-producing cells were incorporated in developed renal corpuscles 6 weeks after transplantation (FIG. 27c). Ectopic grafts were also stained for several markers of cells of hematopoietic and nonhematopoietic origin, including CD45, CD106 (VCAM-1), CD3, CD4, CD8, CD45R/B220, Ly6C/G, and F4/80. Immunofluorescence analyses revealed that most GFP+ cells in the glomeruli were neither lymphocytes nor macrophages. Interestingly, both GFP+CD45- and GFP+CD106+ cell subsets localized in ectopic glomeruli, suggesting the participation of bone marrow-derived mesenchymal stromal cells (MSCs) in ectopic kidney organogenesis (FIG. 27d). Moreover, glomerular GFP+WT1+ podocytes were observed, suggesting that BMDCs can contribute to ectopic podocyte regeneration. Nevertheless, it must not be excluded that podocyte generation/replacement could also rely on resident renal cells. Nodular lesions were observed in 10 week-ectopic glomeruli (FIG. 31). Interestingly, cells with immunohistochemical features of parietal epithelial cells (PECs) could be detected at the glomerular tuft. These claudin-2+ cells shared the same location of WT-1+ podocytes (FIG. 31). PECs lining the inner region of Bowman's capsule have been shown to migrate onto the glomerular tuft and differentiate into podocytes [27]. Thus, in the lymph node-grown graft, PECs might transdifferentiate into podocytes. Cellular lesions also expressed the PEC marker keratin-8 and the podocyte marker vimentin (FIG. 31). Interestingly, lesioned glomeruli showed a massive presence of BMDCs. It remains to understand whether BMDCs contribute to regeneration of damaged glomeruli or facilitate extracellular matrix deposition and as a consequence renal failure.

BMDCs did not contribute to vascularization of the ectopic graft, as no GFP+ cells were incorporated in CD31+ vessels (FIG. 27d). Similarly, BMDCs did not contribute to the formation of kidney tubular structures (FIG. 27d, bottom), confirming the idea that tubule regeneration mainly occurs through survival of dedifferentiated epithelial cells which proliferate and redifferentiate into mature functional epithelial cells [28].

Nephrectomy Accelerates Kidney Organogenesis and Degeneration

To assess whether the ectopic kidney tissue could proliferate in response to growth stimuli, we performed unilateral nephrectomy 12 days after embryonic kidney injection into the lymph node, and we added BrdU to the drinking water of the recipient mice as indicated in the Methods section (FIG. 28a). The number of BrdU-positive nuclei per renal cross-section was significantly increased in contralateral kidneys of left nephrectomized animals (FIG. 28b). Ectopic kidneys isolated from both sham-operated and nephrectomized mice showed a variable proliferation rate. Importantly, grafts from mice undergoing left nephrectomy, collected almost 4 weeks after kidney transplantation (26 days, FIG. 28c), were comparable to the 12 week-ectopic grafts shown in FIGS. 3-4. Either grafts comprising fully mature and apparently healthy nephrons or grafts comprising enlarged and swollen glomeruli were in fact observed. Thus, although the stimulus that results in compensatory renal growth following reduction of renal mass is dispensable for kidney organogenesis into the lymph node, nephrectomy accelerates ectopic kidney maturation. To our opinion, this finding further reinforces our hypothesis that ectopic kidney degeneration is a consequence of functionality rather than a result of aberrant kidney development. Moreover, since native renal tissue needs to be removed to successfully grow metanephroi in the omentum [4], our findings suggest that the lymph node could provide a much more better site than omentum for ectopic kidney organogenesis.

9.3 Discussion

In contrast to lower vertebrates, in mammals, nephrogenesis is limited to gestation or early post-natal life. Although the adult kidney cannot make new nephrons, it can regenerate and recover in some circumstances. Indeed, tubular regenerative capacity widely changes going from acute kidney injury (AKI) to chronic kidney disease (CKD), as acute renal insults are handled with successful regeneration, while chronic injuries lead to ineffective or even more damaging cellular responses [29]. More precisely, nephron tubule epithelium is regenerated after AKI, while in the setting of CKD, tubular damage is not repaired, and this is accompanied by a sustained inflammatory response and activation of myofibroblasts, that eventually results in interstitial fibrosis, tubular atrophy, and nephron loss. Although many theories exist on kidney repair, the existence of an intratubular cell source fueling nephron tubule epithelium regeneration after AKI is gaining consensus amongst researchers [30].

A number of experimental evidences have indicated transplantation of embryonic kidney as a potential method for augmentation of kidney function[4, 14-17]. However, various hurdles remain before a clinical therapy can become a reality. Cell culture techniques to produce renal organoids starting from mouse embryonic kidney precursors have been described, but several experimental attempts to develop functional glomeruli have failed, because the avascular in vitro environment is not permissible for glomerulogenesis.

The current studies indicate that the lymph node might be considered as a unique niche to grow several tissues. When embryonic kidneys were transplanted into the lymph node, blood vessels integrated into the glomeruli. Vascularization is likely attributable to migration and proliferation of resident endothelial cells, and does not involve BMDCs. However, both bone marrow hematopoietic and stromal cells were found in the ectopic kidney graft. These cells contributed to mesangial cells and podocyte regeneration. Not only did the lymph node furnish the developing tissue with host cells, but also provided it with growth and homeostatic signals, since a decrease in native renal mass could push maturation of the ectopic graft. In conclusion, the present study provides evidence that ectopic kidney inside the lymph node can sense a stimulus and appropriately respond. This system can also be used to validate in vivo the differentiation potential of candidate cells in regenerative nephrology, including ES or iPS.

REFERENCES FOR EXAMPLE 4

1. Collins A J, Foley R N, Chavers B, Gilbertson D, Herzog C, Johansen K, Kasiske B, Kutner N, Liu J, St Peter W, Guo H, Gustafson S, Heubner B, Lamb K, Li S, Li S, et al. 'United States Renal Data System 2011 Annual Data Report: Atlas of chronic kidney disease & end-stage renal disease in the United States. American journal of kidney diseases: the official journal of the National Kidney Foundation. 2012; 59 (1 Suppl 1):A7, e1-420.
2. Edge A S, Gosse M E and Dinsmore J. Xenogeneic cell therapy: current progress and future developments in porcine cell transplantation. Cell transplantation. 1998; 7(6):525-539.
3. Cascalho M and Platt J L. Xenotransplantation and other means of organ replacement. Nature reviews Immunology. 2001; 1(2): 154-160.
4. Rogers S A, Lowell J A, Hammerman N A and Hammerman M R. Transplantation of developing metanephroi into adult rats. Kidney international. 1998; 54(1):27-37.
5. Bartholomeus K, Jacobs-Tulleneers-Thevissen D, Shouyue S, Suenens K, In't Veld P A, Pipeleers-Marichal M, Pipeleers D G and Hellemans K. Omentum Is Better Site Than Kidney Capsule for Growth, Differentiation, and Vascularization of Immature Porcine beta-Cell Implants in Immunodeficient Rats. Transplantation. 2013.
6. Kim H I, Yu J E, Park C G and Kim S J. Comparison of four pancreatic islet implantation sites. Journal of Korean medical science. 2010; 25(2):203-210.
7. Ellis H. The clinical significance of adhesions: focus on intestinal obstruction. The European journal of surgery Supplement: =Acta chirurgica Supplement. 1997; (577): 5-9.
8. Hoppo T, Komori J, Manohar R, Stolz D B and Lagasse E. Rescue of lethal hepatic failure by hepatized lymph nodes in mice. Gastroenterology. 2011; 140(2):656-666 e652.
9. Komori J, Boone L, DeWard A, Hoppo T and Lagasse E. The mouse lymph node as an ectopic transplantation site for multiple tissues. Nature biotechnology. 2012; 30(10): 976-983.
10. Francipane M G and Lagasse E. Selective targeting of human colon cancer stemlike cells by the mTOR inhibitor Torin-1. Oncotarget. 2013; 4(11):1948-1962.
11. Davidson A J. (2008). Mouse kidney development. StemBook. (Cambridge (Mass.).
12. Kim S S, Gwak S J, Han J, Park H J, Park M H, Song K W, Cho S W, Rhee Y H, Chung H M and Kim B S. Kidney tissue reconstruction by fetal kidney cell transplantation: effect of gestation stage of fetal kidney cells. Stem Cells. 2007; 25(6):1393-1401.
13. Dilworth M R, Clancy M J, Marshall D, Bravery C A, Brenchley P E and Ashton N. Development and functional capacity of transplanted rat metanephroi. Nephrology, dialysis, transplantation: official publication of the European Dialysis and Transplant Association—European Renal Association. 2008; 23(3):871-879.
14. Marshall D, Dilworth M R, Clancy M, Bravery C A and Ashton N. Increasing renal mass improves survival in anephric rats following metanephros transplantation. Experimental physiology. 2007; 92(1):263-271.
15. Clancy M J, Marshall D, Dilworth M, Bottomley M, Ashton N and Brenchley P. Immunosuppression is essential for successful allogeneic transplantation of the metanephros. Transplantation. 2009; 88(2): 151-159.
16. Kim S S, Park H J, Han J, Gwak S J, Park M H, Song K W, Rhee Y H, Min Chung H and Kim B S. Improvement of kidney failure with fetal kidney precursor cell transplantation. Transplantation. 2007; 83(9):1249-1258.
17. Yokote S, Yokoo T, Matsumoto K, Utsunomiya Y, Kawamura T and Hosoya T. The effect of metanephros transplantation on blood pressure in anephric rats with induced acute hypotension. Nephrology, dialysis, transplantation: official publication of the European Dialysis and Transplant Association—European Renal Association. 2012; 27(9):3449-3455.
18. Thony H C, Luethy C M, Zimmermann A, Laux-End R, Oetliker O H and Bianchetti M G. Histological features of glomerular immaturity in infants and small children with normal or altered tubular function. European journal of pediatrics. 1995; 154 (9 Suppl 4):S65-68.
19. Timmer R T, Klein J D, Bagnasco S M, Doran J J, Verlander J W, Gunn R B and Sands J M. Localization of the urea transporter UT-B protein in human and rat erythrocytes and tissues. American journal of physiology Cell physiology. 2001; 281 (4): C1318-1325.
20. Calvet J P. Polycystic kidney disease: primary extracellular matrix abnormality or defective cellular differentiation? Kidney international. 1993; 43(1): 101-108.
21. Mangoo-Karim R, Uchic M, Lechene C and Grantham J J. Renal epithelial cyst formation and enlargement in vitro: dependence on cAMP. Proceedings of the National Academy of Sciences of the United States of America. 1989; 86(15):6007-6011.
22. Nagata M, Shibata S and Shu Y. Pathogenesis of dysplastic kidney associated with urinary tract obstruction in utero. Nephrology, dialysis, transplantation: official publication of the European Dialysis and Transplant Association—European Renal Association. 2002; 17 Suppl 9:37-38.
23. Imasawa T, Utsunomiya Y, Kawamura T, Zhong Y, Nagasawa R, Okabe M, Maruyama N, Hosoya T and Ohno T. The potential of bone marrow-derived cells to differentiate to glomerular mesangial cells. Journal of the American Society of Nephrology: JASN. 2001; 12(7): 1401-1409.
24. Ito T, Suzuki A, Imai E, Okabe M and Hori M. Bone marrow is a reservoir of repopulating mesangial cells during glomerular remodeling. Journal of the American Society of Nephrology: JASN. 2001; 12(12):2625-2635.
25. Lin F, Cordes K, Li L, Hood L, Couser W G, Shankland S J and Igarashi P. Hematopoietic stem cells contribute to the regeneration of renal tubules after renal ischemia-reperfusion injury in mice. Journal of the American Society of Nephrology: JASN. 2003; 14(5):1188-1199.
26. Poulsom R, Forbes S J, Hodivala-Dilke K, Ryan E, Wyles S, Navaratnarasah S, Jeffery R, Hunt T, Alison M, Cook T, Pusey C and Wright N A. Bone marrow contributes to renal parenchymal turnover and regeneration. The Journal of pathology. 2001; 195(2):229-235.
27. Appel D, Kershaw D B, Smeets B, Yuan G, Fuss A, Frye B, Elger M, Kriz W, Floege J and Moeller M J. Recruitment of podocytes from glomerular parietal epithelial cells. Journal of the American Society of Nephrology: JASN. 2009; 20(2):333-343.
28. Duffield J S and Bonventre J V. Kidney tubular epithelium is restored without replacement with bone marrow-derived cells during repair after ischemic injury. Kidney international. 2005; 68(5):1956-1961.
29. Li Y and Wingert R A. Regenerative medicine for the kidney: stem cell prospects & challenges. Clinical and translational medicine. 2013; 2(1):11.
30. Bonventre J V and Yang L. Cellular pathophysiology of ischemic acute kidney injury. The Journal of clinical investigation. 2011; 121(11):4210-4221.
31. Xinaris C, Benedetti V, Rizzo P, Abbate M, Coma D, Azzollini N, Conti S, Unbekandt M, Davies J A, Morigi M, Benigni A and Remuzzi G. In vivo maturation of functional renal organoids formed from embryonic cell suspensions. Journal of the American Society of Nephrology: JASN. 2012; 23(11):1857-1868.
32. Bussolati B, Bruno S, Grange C, Buttiglieri S, Deregibus M C, Cantino D and Camussi G. Isolation of renal progenitor cells from adult human kidney. The American journal of pathology. 2005; 166(2):545-555.
33. Sagrinati C, Netti G S, Mazzinghi B, Lazzeri E, Liotta F, Frosali F, Ronconi E, Meini C, Gacci M, Squecco R, Carini M, Gesualdo L, Francini F, Maggi E, Annunziato F, Lasagni L, et al. Isolation and characterization of multipotent progenitor cells from the Bowman's capsule of adult human kidneys. Journal of the American Society of Nephrology: JASN. 2006; 17(9):2443-2456.
34. Harari-Steinberg O, Metsuyanim S, Omer D, Gnatek Y, Gershon R, Pri-Chen S, Ozdemir D D, Lerenthal Y, Noiman T, Ben-Hur H, Vaknin Z, Schneider D F, Aronow B J, Goldstein R S, Hohenstein P and Dekel B. Identification of human nephron progenitors capable of generation of kidney structures and functional repair of chronic renal disease. EMBO molecular medicine. 2013; 5(10): 1556-1568.
35. Rangel E B, Gomes S A, Dulce R A, Premer C, Rodrigues C O, Kanashiro-Takeuchi R M, Oskouei B, Carvalho D A, Ruiz P, Reiser J and Hare J M. C-kit(+) cells isolated from developing kidneys are a novel population of stem cells with regenerative potential. Stem Cells. 2013; 31(8):1644-1656.
36. Xia Y, Nivet E, Sancho-Martinez I, Gallegos T, Suzuki K, Okamura D, Wu M Z, Dubova I, Esteban C R, Montserrat N, Campistol J M and Izpisua Belmonte J C. Directed differentiation of human pluripotent cells to ureteric bud kidney progenitor-like cells. Nature cell biology. 2013; 15(12):1507-1515.
37. Taguchi A, Kaku Y, Ohmori T, Sharmin S, Ogawa M, Sasaki H and Nishinakamura R. Redefining the in vivo origin of metanephric nephron progenitors enables generation of complex kidney structures from pluripotent stem cells. Cell stem cell. 2014; 14(1):53-67.
38. Takasato M, Er P X, Becroft M, Vanslambrouck J M, Stanley E G, Elefanty A G and Little M H. Directing human embryonic stem cell differentiation towards a renal lineage generates a self-organizing kidney. Nature cell biology. 2014; 16(1):118-126.

10. EXAMPLE 5

The Mouse Lymph Node; A Tool for Studying Functional Maturation

Summary

Our results indicate that it is possible to obtain postnatal development stages for several mid-embryonic tissues including brain, thymus, lung, stomach, and intestine, inside the lymph node (LN). We believe the LN might provide a unique tool to track and monitor stem cell behavior in vivo, in a location far from the native environment, but still responsive to physiologic and homeostatic signals.

10.1 Methods

Tissue Collection and Transplantation.
Embryonic day (E) 14.5 to 15.5 tissues were retrieved from timed pregnant GFP+C57BL/6 black mice under a dissecting microscope (embryos were considered 0.5 days old when the vaginal plug was detected in the morning). All tissue were chopped in PBS and kept on ice until injection. For lymph node transplantation, recipient mice (wild-type C57BL/6 black mice, n=51) were anesthetized with 1-3% isoflurane. A small incision was made in the abdomen to expose jejunal lymph nodes. A 1000 µL, threaded plunger syringe (Hamilton, 81341) with a removable needle (gauge 20) was used to slowly inject tissue fragments into a single lymph node. Light cauterization was used to seal the opening. The wound was then closed with surgical sutures. Ketoprofen (2 mg/kg, IM) treatment for postoperative pain relief was initiated right after surgery and continued for 2 additional consecutive days. Mice were bred and housed in the Division of Laboratory Animal Resources facility at the University of Pittsburgh Center for Biotechnology and Bioengineering. Experimental protocols followed US National Institutes of Health guidelines for animal care and were approved by the Institutional Animal Care and Use Committee at the University of Pittsburgh.

Histology and Immunofluorescence/Immunohistochemistry.

Repopulated jejunal lymph nodes were fixed 2 hours in 4% PFA, and embedded in Optimal Cutting Temperature (OCT) following infiltration with 30% sucrose overnight. Sections were stained with antibodies against GFAPδ (Bioss, bs-11016R), GFP (Abcam, ab6556), Keratin-8 (DSHB, TROMA-1), Keratin-5 (Covance, PRB-160P), GFP (Abcam, ab6556), CD31 (BD, 550274), CD105 (BD, 550546), ER-TR7 (Abcam, ab51824), MUC5AC (Abcam, ab79082), β-catenin (CST, 8480), MUC2 (SCT, sc-15334), or chromogranin A (SCT, sc-18232). Alexa Fluor 594 (Invitrogen) secondary antibodies were then used. Nuclei were counterstained using Hoechst. Donor organs were embedded in paraffin and stained with hematoxylin and eosin (H&E) as described elsewhere.

RNA Extraction, cDNA Synthesis, RT-PCR.

Total RNA was isolated from tissues stored in RNAlater® reagent (QIAGEN) using RNeasy Mini kit (QIAGEN), according to the manufacturer's instructions. Potentially contaminating genomic DNA was digested using DNase (QIAGEN). cDNA was synthesized using the iScript™ Reverse Transcription Supermix for RT-qPCR (Bio-Rad). PCR was performed using the iTaq DNA Polymerase kit (Bio-Rad). GAPDH transcript levels served as the housekeeping control target. Sequences of primers were as follows: GM-CSF, Fwd, 5'-TTCCTGGGCATTGTGGTCT-3' (SEQ ID NO: 12), Rev, 5'-TGGATTCAGAGCTGGCCTGG-3' (SEQ ID NO: 13); GAPDH, Fwd, 5'-GGCATCCTGGGCTACACTGA-3' (SEQ ID NO: 10), Rev, 5'-GGAGTGGGTGTCGCTGTTG-3' (SEQ ID NO: 11). For GM-CSF, PCR mixtures were subjected to different numbers of amplification cycles; 25 cycles were eventually chosen to quantify gene expression.

Flow Cytometry.

Whole blood was collected in K2EDTA collection tubes (Terumo Medical). One hundred microliters of blood was added to cold fluorescence-activated cell sorting (FACS) tubes. Antibodies were added at a dilution of 1/50 in blood and mixed by gentle pipetting. Antibodies used were as follows: PerCP Cy5.5 CD45 (BD, 550994), PECD11b (BD, 553311), and APC Ly6G-Ly6C (BD, 553129). Reactions were incubated in the dark in an ice slurry bath for one hour. Three milliliters of Red Blood Cell Lysing Buffer (Sigma) was added to each tube, lightly vortexed and incubated for an additional 15 min. Two milliliters of flow buffer (2% FBS in HBSS) was added to the tubes, mixed and centrifuged at 500 g for 5 min. The supernatant was aspirated. The red blood cell lysis and centrifuge were repeated as described. The final cell pellet was resuspended in 400 µl of flow buffer with Sytox Blue dye. Cells were analyzed using a Miltenyi MACSQuant and FlowJo software (Tree Star).

Statistical Analysis.

Data are presented as means±SD. Statistical analysis was performed using Student's t test (p<0.05 was considered significant).

10.2 Results

The Lymph Node is a Permissive Site for Tissue Organogenesis.

We first investigated the ability of lymph node to support engraftment of several mouse mid-embryonic tissues including brain, thyroid, thymus, lung, heart, stomach, intestine, liver, and adrenal gland. Tissues were harvested from E14.5/E.15.5 GFP transgenic mice, minced, and injected directly into a single jejunal lymph node of adult wild-type mice (FIG. 32A). Following 3 weeks, recipient mice were sacrificed, lymph nodes collected, and histologically examined. As shown in FIG. 32B, transplants were variably prone to engraft into the lymph node. While the brain showed the highest ability of repopulating the lymph node, the thyroid was unable to engraft in. Although in some cases heart, liver and adrenal gland engrafted, their grafts were very small. We therefore focused our attention on brain, thymus, lung, stomach, and intestine.

Astrogenesis in the Developing Ectopic Brain.

In the developing mouse brain, glial fibrillary acid protein delta (GFAPδ) starts being expressed at E18. Accordingly, we found very low GFAPδ expression in E14.5-E.15.5 mouse brain (FIG. 32C2, upper). Importantly, when transplanted into the LN, E14.5/15.5 brain engrafted (FIG. 32C1) and maturated (FIG. 32C2, lower), as indicated by presence of GFAPδ' cells with complex branching and extended processes, indicative of mature astrocytes.

Figure 33A:
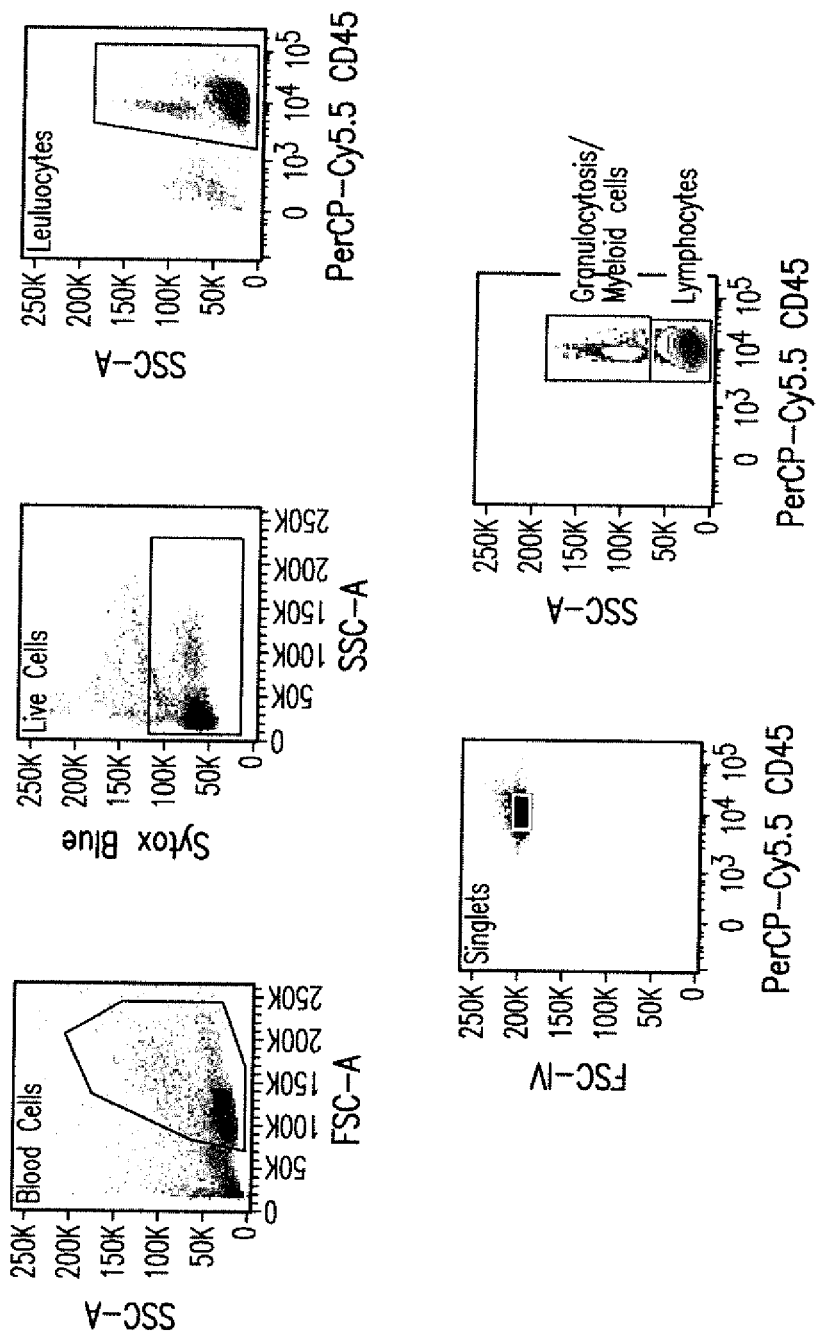
Figure 33B:
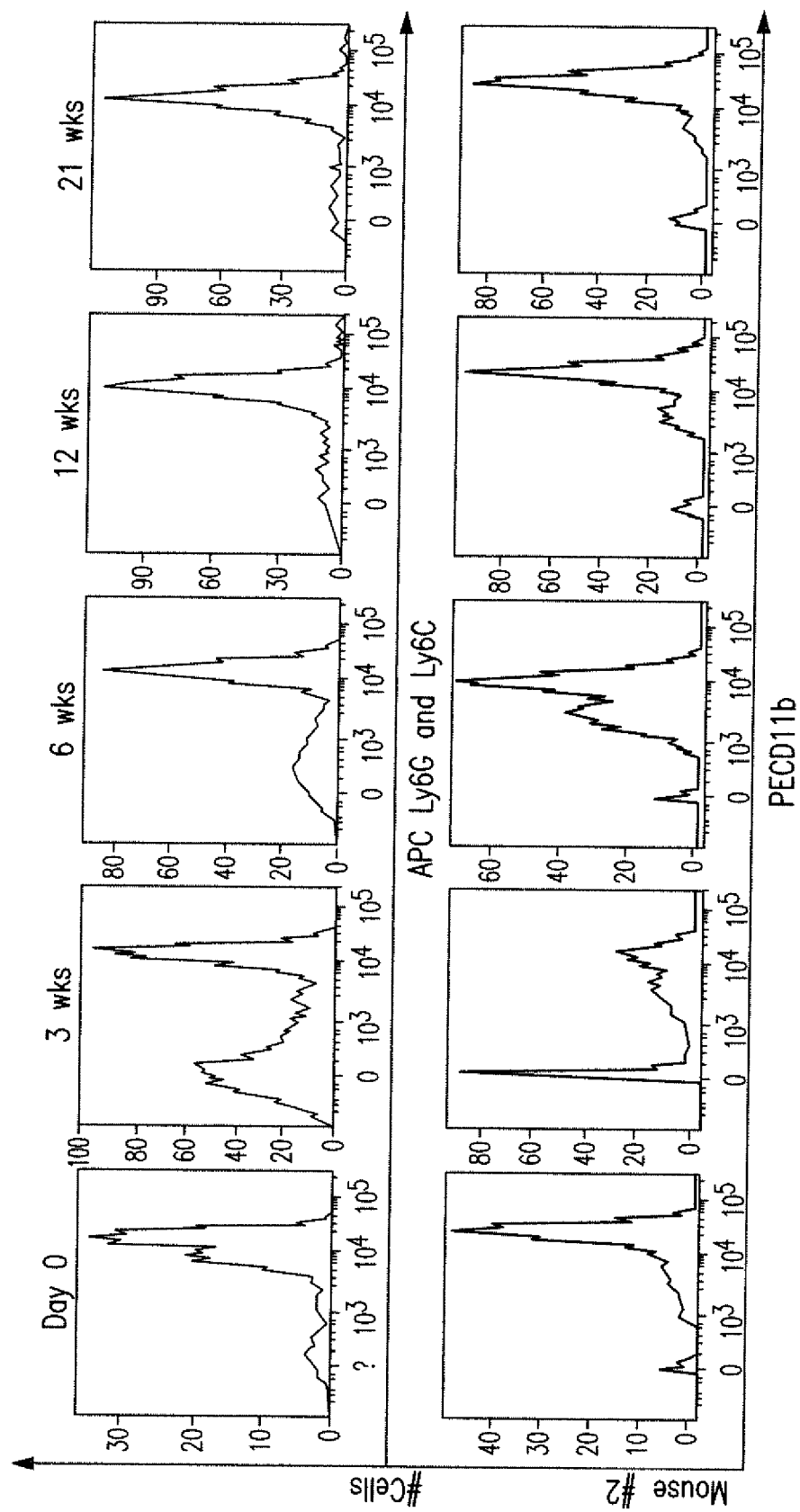
Figure 33C:
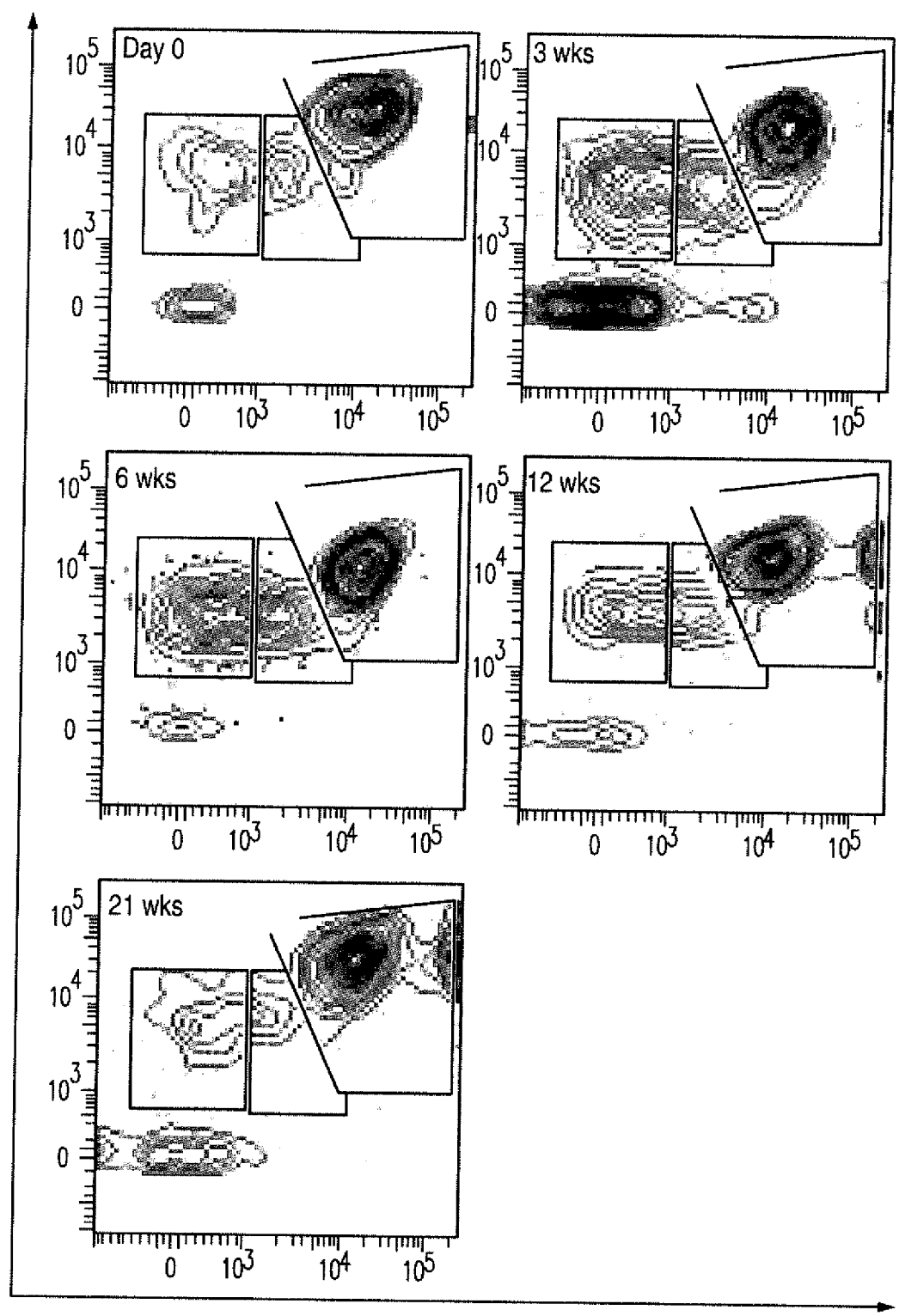
Figure 33D:
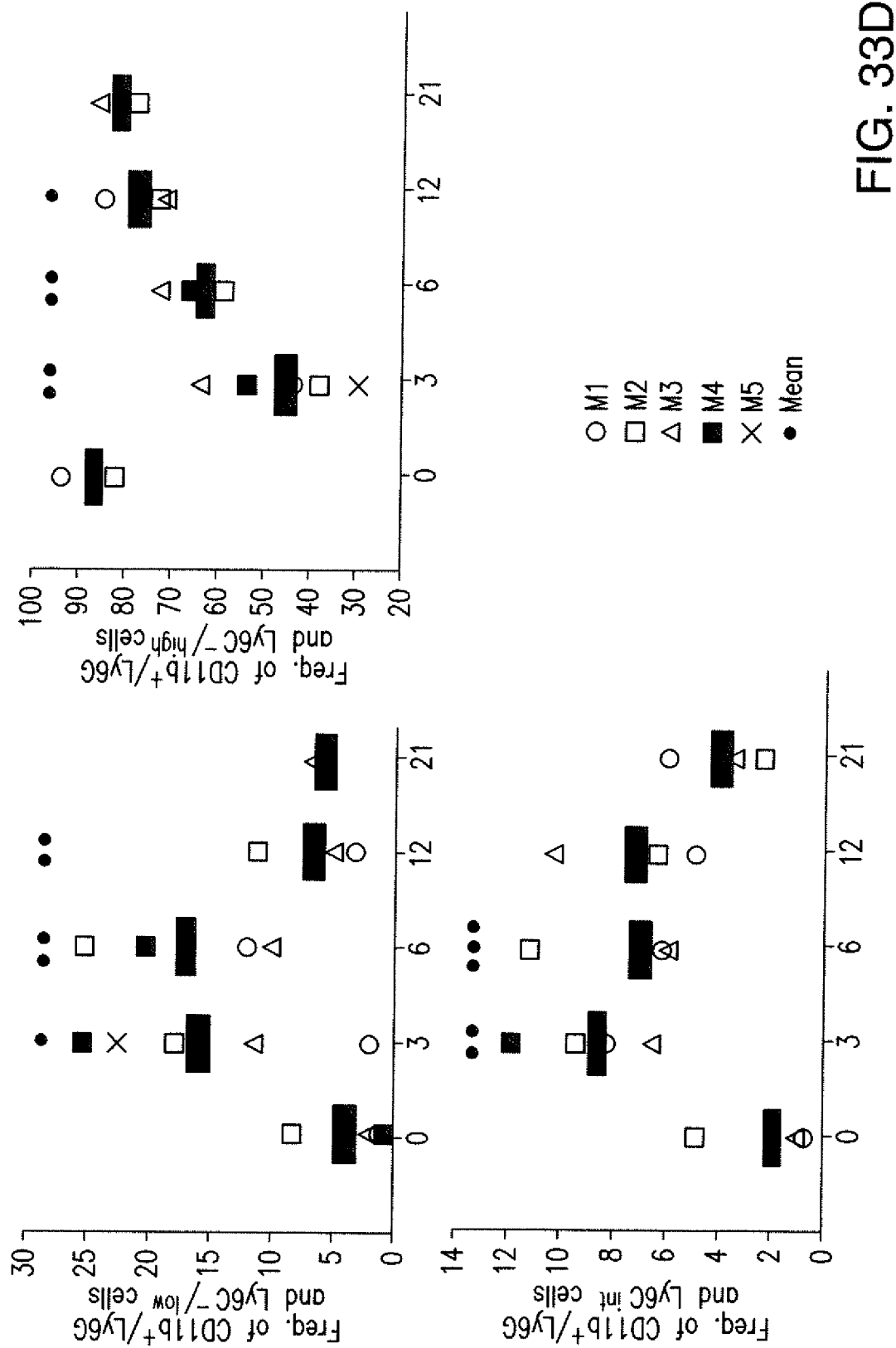

Maturation of the Thymic Epithelium in an Ectopic Site: Contribution of the Host in the Generation of the Thymic Cortex Immune cell percentages were monitored after thymus transplantation. Gating strategy is indicated in FIG. 33A. The CD11b+/Ly6G-Ly6C−/low and CD11b+/Ly6G-Ly6Cint cell populations (mainly comprising immature myeloid cells) were dramatically increased following 3 weeks from thymus transplantation, to the detriment of the CD11b+/Ly6G-Ly6Chigh cell population (mainly comprising mature myeloid cells, such as metamyelocytes/granulocytes) (FIG. 33B-D). All cell populations returned to control levels within 21 weeks (FIG. 33B-D). Slight changes were also observed within the lymphocyte population. Overall, these changes reflect functionality of the ectopic graft. The striking effect on the CD11/Ly6GLy6C phenotype possibly indicates maturation of the ectopic thymic epithelium, and enhanced transcription of the granulocyte-macrophage colony-stimulating factor (GMCSF). Production of this cytokine eventually results in expansion of immature myeloid cells, and as a consequence, in the accumulation of granulocyte/macrophage progenitors. During thymic ontogeny, GM-CSF mRNA reaches its peak level between E19-20; before this stage, it is undetectable during the early amplification cycles of a semi-quantitative PCR (5, 6). We therefore analyzed GM-CSF mRNA levels in the ectopic thymus, as compared to the mid-embryonic thymus used for transplantation. While levels of GMCSF mRNA were very low in E14.5/E.15.5 mouse thymus, GM-CSF mRNA was clearly present in 6-week ectopic grafts, as well as in 21-week grafts, but to a less extent than in the adult thymus (FIG. 34A). Ectopic grafts well varied on size (FIG. 34B, lower). While embryonic thymus had a uniform parenchyma with light staining (FIG. 34B, upper right), 21 week ectopic thymus comprised a meshwork of epithelial cells reactive to antibodies against keratin 8 or keratin 5, indicating a cortical or a medullary identity, respectively (FIG. 34C). Nevertheless, a clear corticomedullary compartmentalization was never observed. Interestingly, most of keratin 8+ cells were of host origin, while most of keratin 5 positive cells were of donor origin (FIG. 34C, right). Ectopic thymic grafts also showed chimeric blood vessels (FIG. 34C, lower right). These vessels were reactive for CD105, a marker for neoangiogenesis (FIG. 34C, lower right).

Overall, our findings reveal that the lymph node might be exploited to understand how and when cortical and medullary lineages diverge. Our results indicate cortical (cTEC) and medullary (mTEC) thymic epithelial progenitors might follow independent differentiation pathways.

Presence of Terminally Differentiated, Mucus-Producing Cells in Ectopic Lung, Stomach and Intestine Tissues.

Embryonic lung fragments arranged in lobe-like structures into the lymph node, and showed sign of differentiation from a pseudoglandular to mixed saccular/alveolar morphology 3 weeks after transplantation. Importantly, ectopic lung comprised a glandular epithelium with MUC5AC-producing goblet cells 10 weeks after transplantation, indicating that it is possible to achieve postnatal stages of mouse lung development inside the lymph node (FIG. 35A).

Similarly, mid-embryonic stomach fragments well engrafted and expanded inside the jejunal lymph node. This ectopic stomach also comprised MUC5AC-producing goblet cells 3 weeks after transplantation (FIG. 35B).

While intestinal development occurs quite early during mammalian embryogenesis, the intestinal maturation takes place during the post-embryonic period. Crypt-like structures developed following injection of intestinal fragments into lymph nodes. Membrane-localized β-catenin was detected all along these crypts. Activity of the Wnt/β-catenin pathway is required for the emergence of secretory cell types in the intestinal epithelium (16). Since both MUC2-reactive goblet-like cells and chromogranin A (CgA)-producing enteroendocrine cells could be detected in intestinal grafts 3 weeks after transplantation, our results likely indicate that Wnt signals were active and supported intestinal epithelium terminal differentiation inside the lymph node (FIG. 4C).

10.3 Discussion

In vivo, stem cells reside in a highly specialized three-dimensional (3D) structure, the so called niche (17). Not only does the niche preserve the stem cell pool, but also promotes progenitor cell expansion and mobilization. Reproducing this dynamic and complex microenvironment in culture is challenging, either because the mechanisms that control stem cell fate in vivo have not yet been fully elucidated, or because of ethical and technical issues. The current study indicates that the lymph node mimic the physiological environment of transplanted tissue and promotes the vascularization of the transplanted tissue. Lymph nodes have ready access to the bloodstream, and can therefore foster cell growth by providing nutrients as well as hormones and growth factors. Accordingly, we here showed the ability of mouse lymph node in supporting organogenesis of different tissues including brain, thymus, lung, stomach and intestine. Lymph node-grown tissues more closely recapitulate in vivo phenotypes under physiological conditions than any other culture system.

REFERENCES FOR EXAMPLE 5

1. Hoppo T, Komori J, Manohar R, Stolz D B, Lagasse E. Rescue of lethal hepatic failure by hepatized lymph nodes in mice. Gastroenterology. 2011; 140:656-66 e2.
2. Komori J, Boone L, DeWard A, Hoppo T, Lagasse E. The mouse lymph node as an ectopic transplantation site for multiple tissues. Nat Biotechnol. 2012; 30:976-83.
3. Francipane M G, Lagasse E. Selective targeting of human colon cancer stem-like cells by the mTOR inhibitor Torin-1. Oncotarget. 2013; 4:1948-62.
4. Mamber C, Kamphuis W, Haring N L, Peprah N, Middeldorp J, Hol E M. GFAPdelta expression in glia of the developmental and adolescent mouse brain. PLoS One. 2012; 7:e52659.
5. Montgomery R A, Dallman M J. Analysis of cytokine gene expression during fetal thymic ontogeny using the polymerase chain reaction. J Immunol. 1991; 147:554-60.
6. Montgomery R A, Dallman M J. Semi-quantitative polymerase chain reaction analysis of cytokine and cytokine receptor gene expression during thymic ontogeny. Cytokine 1997; 9:717-26.
7. Gordon J, Wilson V A, Blair N F, Sheridan J, Farley A, Wilson L, et al. Functional evidence for a single endodermal origin for the thymic epithelium. Nat Immunol. 2004; 5:546-53.
8. Rossi S W, Jenkinson W E, Anderson G, Jenkinson E J. Clonal analysis reveals a common progenitor for thymic cortical and medullary epithelium. Nature. 2006; 441:988-91.
9. Shakib S, Desanti G E, Jenkinson W E, Parnell S M, Jenkinson E J, Anderson G. Checkpoints in the development of thymic cortical epithelial cells. J Immunol. 2009; 182:130-7.
10. Hamazaki Y, Fujita H, Kobayashi T, Choi Y, Scott H S, Matsumoto M, et al. Medullary thymic epithelial cells expressing Aire represent a unique lineage derived from cells expressing claudin. Nat Immunol. 2007; 8:304-11.
11. Zuklys S, Balciunaite G, Agarwal A, Fasler-Kan E, Palmer E, Hollander G A. Normal thymic architecture and negative selection are associated with Aire expression, the gene defective in the autoimmune-polyendocrinopathy-candidiasis-ectodermal dystrophy (APECED). J Immunol. 2000; 165:1976-83.
12. Baik S, Jenkinson E J, Lane P J, Anderson G, Jenkinson W E. Generation of both cortical and Aire(+) medullary thymic epithelial compartments from CD205(+) progenitors. Eur J Immunol. 2013; 43:589-94.
13. Ribeiro A R, Rodrigues P M, Meireles C, Di Santo J P, Alves N L. Thymocyte selection regulates the homeostasis of IL-7-expressing thymic cortical epithelial cells in vivo. J Immunol. 2013; 191:1200-9.
14. Ohigashi I, Zuklys S, Sakata M, Mayer C E, Zhanybekova S, Murata S, et al. Aireexpressing thymic medullary epithelial cells originate from beta5t-expressing progenitor cells. Proc Natl Acad Sci USA. 2013; 110:9885-90.
15. Sun G, Shi Y B. Thyroid hormone regulation of adult intestinal stem cell development: mechanisms and evolutionary conservations. Int J Biol Sci. 2012; 8:1217-24.
16. Pinto D, Gregorieff A, Begthel H, Clevers H. Canonical Wnt signals are essential for homeostasis of the intestinal epithelium. Genes Dev. 2003; 17:1709-13.

17. Spradling A, Drummond-Barbosa D, Kai T. Stem cells find their niche. Nature. 2001; 414:98-104.
18. Baraniak P R, McDevitt T C. Scaffold-free culture of mesenchymal stem cell spheroids in suspension preserves multilineage potential. Cell Tissue Res. 2012; 347:701-11.
19. Langenbach F, Naujoks C, Smeets R, Berr K, Depprich R, Kubler N, et al. Scaffold-free microtissues: differences from monolayer cultures and their potential in bone tissue engineering. Clin Oral Investig. 2013; 17:9-17.
20. Sharma M B, Limaye L S, Kale V P. Mimicking the functional hematopoietic stem cell niche in vitro: recapitulation of marrow physiology by hydrogel-based three dimensional cultures of mesenchymal stromal cells. Haematologica. 2012; 97:651-60.
21. Willerth S M, Sakiyama-Elbert S E. Combining stem cells and biomaterial scaffolds for constructing tissues and cell delivery. StemBook. Cambridge (Mass.); 2008.
22. Liu X, Zhang G, Hou C, Wang H, Yang Y, Guan G, et al. Vascularized bone tissue formation induced by fiber-reinforced scaffolds cultured with osteoblasts and endothelial cells. Biomed Res Int. 2013; 2013:854917.
23. Dalby M J, Gadegaard N, Tare R, Andar A, Riehle M O, Herzyk P, et al. The control of human mesenchymal cell differentiation using nanoscale symmetry and disorder. Nat Mater. 2007; 6:997-1003.
24. Kim J, Kim H N, Lim K T, Kim Y, Seonwoo H, Park S H, et al. Designing nanotopographical density of extracellular matrix for controlled morphology and function of human mesenchymal stem cells. Sci Rep. 2013; 3:3552.
25. Solanki A, Kim J D, Lee K B. Nanotechnology for regenerative medicine: nanomaterials for stem cell imaging. Nanomedicine (Lond). 2008; 3:567-78. 26. Kyrtatos P G, Lehtolainen P, Junemann-Ramirez M, Garcia-Prieto A, Price A N, Martin J F, et al. Magnetic tagging increases delivery of circulating progenitors in vascular injury. JACC Cardiovasc Interv. 2009; 2:794-802.
27. McMurray R J, Gadegaard N, Tsimbouri P M, Burgess K V, McNamara L E, Tare R, et al. Nanoscale surfaces for the long-term maintenance of mesenchymal stem cell phenotype and multipotency. Nat Mater. 2011; 10:637-44.
28. Wu T J, Tzeng Y K, Chang W W, Cheng C A, Kuo Y, Chien C H, et al. Tracking the engraftment and regenerative capabilities of transplanted lung stem cells using fluorescent nanodiamonds. Nat Nanotechnol. 2013; 8:682-9.
29. Solanki A, Shah S, Yin P T, Lee K B. Nanotopography-mediated reverse uptake for siRNA delivery into neural stem cells to enhance neuronal differentiation. Sci Rep. 2013; 3:1553.
30. Rauh J, Milan F, Gunther K P, Stiehler M. Bioreactor systems for bone tissue engineering. Tissue Eng Part B Rev. 2011; 17:263-80.
31. Mabvuure N, Hindocha S, Khan W S. The role of bioreactors in cartilage tissue engineering. Curr Stem Cell Res Ther. 2012; 7:287-92.
32. Berry J L, Steen J A, Koudy Williams J, Jordan J E, Atala A, Yoo J J. Bioreactors for development of tissue engineered heart valves. Ann Biomed Eng. 2010; 38:3272-9.
33. Auger F A, Gibot L, Lacroix D. The pivotal role of vascularization in tissue engineering. Annu Rev Biomed Eng. 2013; 15:177-200.
34. Wang B G, Konig K, Halbhuber K J. Two-photon microscopy of deep intravital tissues and its merits in clinical research. J Microsc. 2010; 238:1-20.

11. EXAMPLE 6

Engineering an Ectopic Thymus in the Lymph Node to Induce Central Tolerance and Allograft Acceptance Summary Allogeneic transplant rejection is one of the major problems plaguing the field of organ transplants today. In the current study, we hypothesized that by conditioning transplant recipients with thymic cells immune-matched to the donor, we will be able to induce long-term tolerance of a subsequent allograft. We were able to achieve long-term allograft acceptance in mice receiving thymic transplants. The allograft acceptance maybe mediated by the increased Treg induction associated with cross-talk between the two thymuses

11.1 Methods

We utilized the FAH−/− mouse model on a 129sv background for our studies. As shown in FIG. 37, We transplanted Balb/c GFP thymuses into the lymph nodes of FAH−/− mice that were transiently immunosuppressed to facilitate acceptance of the thymic grafts. About 6 weeks after the thymus transplant, the animals were further challenged with donor-matched skin grafts or hepatocyte transfer. The recipients were then monitored for long-term allograft acceptance. In addition, we assessed induction of central tolerance and ectopic-native thymus cross-talk by performing mixed lymphocyte reaction assays (MLR), immunostaining of native and ectopic thymus, as well as thymic dendritic cells (tDC)-T cell co-cultures to assess Treg generation.

11.2 Results

As shown in FIG. 38, donor thymus tissue successfully engraftd into recipient lymph node. As shown in FIG. 39, mice with thymus transplants demonstrated long-term acceptance of allografts (skin grafts as well as hepatocyte transfers). Furthermore, as observed in the mixed lymphocyte reaction (MLR) assays, these mice were specifically tolerized to the Balb/c strain, but were reactive against the C57BL/6 strain (FIG. 40). We also observed migration of cells (mostly tDCs) from the ectopic to the native thymus (FIG. 41). Analysis of tDC-T cell co-cultures revealed that the migrating DCs from the ectopic as well as native thymus were instrumental in generating the increased numbers of Tregs observed (FIG. 42).

11.3 Conclusion

We were able to induce long-term acceptance of thymus-matched allografts in immmunocompetant mice. Thymus transplants induced acceptance of allogeneic hepatocytes and rescue of liver function in the 129.Fah−/− mouse model. Migration of antigen-presenting cells to induce Tregs, and cross-talk between the two thymuses appears to be important for induction of central tolerance and allograft acceptance.

Various references are cited herein, the contents of which are hereby incorporated by reference in their entireties.

What is claimed is:

1. A method of producing an ectopic kidney tissue in a lymph node of a subject, comprising:
   introducing embryonic kidney fragments comprising S-shaped bodies into the lymph node, wherein the embryonic kidney fragments in the lymph node are responsive to growth stimuli; and
   producing an ectopic kidney tissue with urine concentrating ability in the lymph node,
   wherein bone marrow-derived stromal cells of the subject integrate into the ectopic kidney tissue.

2. The method of claim 1, wherein the subject is a human subject.

3. The method of claim 1, wherein the subject suffers from renal insufficiency.

4. The method of claim 1, where the lymph node is selected from the group consisting of the splenic hilar lymph node, celiac lymph node, porta hepatis lymph node, iliac lymph node, paraaortic lymph node, retroperitoneal lymph node, and any combinations thereof.

5. The method of claim 1, wherein the embryonic kidney-fragments are syngeneic to the subject.

6. The method of claim 1, wherein the embryonic kidney fragments are allogeneic to the subject.

7. The method of claim 1, wherein the embryonic kidney fragments are introduced into at least two lymph nodes of the subject.

8. The method of claim 1, wherein the subject receives an immunosuppressive treatment.

9. The method of claim 8, wherein the embryonic kidney fragments are human embryonic kidney fragments, and the subject is a non-human subject.

10. The method of claim 1, wherein the ectopic kidney tissue expresses at least one protein selected from the group consisting of podoplanin, urea transporter, claudin-2, vimentin, aquaporin-1, erythropoietin, WT-1, Collagen IV, CD31, CD106, CD45, CD3, CD45R/B220, Ly6C/G, F4/80, and keratin-8.

11. The method of claim 1, wherein the ectopic kidney tissue is hormonally competent.

12. The method of claim 1, wherein the ectopic kidney tissue produces erythropoietin.

13. The method of claim 1, wherein the ectopic kidney tissue is responsive to growth stimuli as determined by accelerated maturation of the ectopic kidney tissue in response to a decrease in native renal mass in the subject.

14. The method of claim 1, wherein the introducing comprises injecting the embryonic kidney fragments into the lymph node.

15. The method of claim 1, wherein the introducing comprises injecting a suspension comprising the embryonic kidney fragments into the lymph node.

16. The method of claim 1, wherein the ectopic kidney tissue expresses at least one protein selected from the group consisting of UT-A1, UT-A2, UT-A3, podoplanin, claudin-2, vimentin, aquaporin 1, erythropoietin, WT-1, and collagen IV.

17. The method of claim 1, wherein the bone marrow derived stromal cells comprise bone marrow-derived collagen-producing cells.

18. The method of claim 1, wherein the ectopic kidney tissue comprises type IV collagen derived from the subject and type IV collagen derived from the embryonic kidney fragments.

19. The method of claim 1, wherein the ectopic kidney tissue comprises type IV collagen localized to glomerular basement membrane, tubules, mesangial areas, or a combination thereof.

20. The method of claim 1, wherein the ectopic kidney tissue comprises podoplanin positive podocytes.

21. The method of claim 1, wherein the ectopic kidney tissue comprises claudin-2 positive tubules.

22. The method of claim 1, where the lymph node is an iliac lymph node.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacagtgaga cgcagtgaag                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acggtctcag agctctcttc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttctccagt cctatctgag                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctgacagtg agacgcagtg                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagtggagg ccacacggat                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcttctcaaa caagggcgac                                                   20

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgctgagca cggagctcaa                                              20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaactgaagc tgtacacggg aga                                          23

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggagcaagtt cgtcggtcc                                               19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcatcctgg gctacactga                                              20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggagtgggtg tcgctgttg                                               19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcctgggca ttgtggtct                                               19
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggattcaga gctggcctgg                                                  20
```